US010041948B2

(12) United States Patent
Garrity-Park et al.

(10) Patent No.: US 10,041,948 B2
(45) Date of Patent: Aug. 7, 2018

(54) MATERIALS AND METHODS FOR DETERMINING CANCER RISK

(75) Inventors: Megan Garrity-Park, Pine Island, MN (US); Thomas C. Smyrk, Rochester, MN (US); Edward V. Loftus, Jr., Rochester, MN (US); William J. Sandborn, LaJolla, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 248 days.

(21) Appl. No.: 13/272,044

(22) Filed: Oct. 12, 2011

(65) Prior Publication Data

US 2012/0094289 A1 Apr. 19, 2012

Related U.S. Application Data

(60) Provisional application No. 61/392,342, filed on Oct. 12, 2010.

(51) Int. Cl.
*C12Q 1/68* (2018.01)
*G01N 33/574* (2006.01)
*C12Q 1/6886* (2018.01)

(52) U.S. Cl.
CPC ..... *G01N 33/57419* (2013.01); *C12Q 1/6886* (2013.01); *C12Q 2600/154* (2013.01); *C12Q 2600/156* (2013.01); *G01N 2800/065* (2013.01); *G01N 2800/50* (2013.01)

(58) Field of Classification Search
None
See application file for complete search history.

(56) References Cited

U.S. PATENT DOCUMENTS 5,552,292 A * 9/1996 Uchida et al. ............... 435/7.23
2003/0224040 A1 12/2003 Baylin et al.
2009/0053706 A1 2/2009 Laird et al.

FOREIGN PATENT DOCUMENTS

WO WO 99/57318 11/1999
WO WO 2008/150962 12/2008
WO WO 2009/037572 3/2009

OTHER PUBLICATIONS

Garrity-Park et al. (2010) Methylation Status of Genes in Non-Neoplastic Mucosa From Patients With Ulcerative Colitis-Associated Colorectal Cancer. The American Journal of Gastroenterology, 105:1610-1619, published online Feb. 16, 2010.*
Weber et al. (2007) Distribution, silencing potential and evolutionary impact of promoter DNA methylation in the human genome. Nature Genetics, 39(4):457-466.*
Xu et al. (2004) Methylation profile of the promoter CpG islands of 31 genes that may contribute to colorectal carcinogenesis. World Journal of Gastroenterology, 10(23):3441-3454.*
Imamura et al. (2005) RUNX3 Promoter Region is Specifically Methylated in Poorly-differentiated Colorectal Cancer. Anticancer Research, 25:2627-2630.*
Agoff et al. (2000) The Role of Cyclooxygenase 2 in Ulcerative Colitis-Associated Neoplasia. American Journal of Pathology, 157(3):737-745.*
Garrity-Park et al. (2008) Tumor Necrosis Factor-Alpha Polymorphisms in Ulcerative Colitis-Associated Colorectal Cancer. American Journal of Gastroenterology, 103:407-415.*
ltzkowitz et al. (2004) Inflammation and Cancer IV. Colorectal cancer in inflammatory bowel disease: the role of inflammation. American Journal of Physiology-Gastrointestinal and Liver Physiology, 287:G7-G17, 11 pages.*
Pepe et al. (2000) Combining diagnostic test results to increase accuracy. Biostatistics, 1(2):123-140.*
Maxwell et al. (2008) Association of the tumour necrosis factor-308 variant with differential response to anti-TNF agents in the treatment of rheumatoid arthritisHuman Molecular Genetics, 17(22):3532-3538.*
Whitehead et al. (2005) Variation in tissue-specific gene expression among natural populations. Genome Biology, 6:R13.1-R13.14, 14 pages.*
Esteller et al. (2002) Cancer as an epigenetic disease: DNA methylation and chromatin alterations in human tumors. Journal of Pathology, 196:1-7.*
The Cleveland Clinic ("How to Prevent Colon Cancer", publicly available on Jan. 5, 2009, obtained from <http://web.archive.org/web/20090105202118/http://my.clevelandclinic.org/disorders/Colorectal_Cancer/hic_How_to_Prevent_Colorectal_Cancer.aspx>, and obtained on Aug. 1, 2013, 4 pages).*
Hegele. (2002) SNP Judgments and Freedom of Association. Arterioscler Thromb Vasc Biol, 22:1058-1061.*
Vogel et al. (2007) Prospective study of interaction between alcohol, NSAID use and polymorphisms in genes involved in the inflammatory response in relation to risk of colorectal cancer. Mutation Research, 624:88-100.*
Ahlquist et al., "Gene methylation profiles of normal mucosa, and benign and malignant colorectal tumors identify early onset markers," *Mol Cancer*, 2008,7:94-104.
Akhtar et al., "Promoter methylation regulates Helicobacter pylori-stimulated cyclooxygenase-2 expression in gastric epithelial cells," *Cancer Res*, Mar. 2001, 61:2399-2403.
Azarschab et al., "Epigenetic control of the E-cadherin gene (CDH1) by CpG methylation in colectomy samples of patients with ulcerative colitis," *Genes Chromosomes Cancer*, 2002, 35:121-126.
Azzoni et al., "Distinct molecular patterns based on proximal and distal sporadic colorectal cancer: arguments for different mechanisms in the tumorigenesis," *Int J Colorectal Dis.*, Feb. 2007, 22(2):115-126.
Bird, "CpG-rich islands and the function of DNA methylation," *Nature*, 1986, 321:209-213.

(Continued)

*Primary Examiner* — Neil P Hammell
(74) *Attorney, Agent, or Firm* — Fish & Richardson P.C.

(57) ABSTRACT

This document relates to materials and methods involved in assessing inflammatory bowel disease patients at risk for developing cancer. For example, materials and methods for monitoring colorectal cancer risk in ulcerative colitis patients are provided.

2 Claims, 40 Drawing Sheets

(56) References Cited

OTHER PUBLICATIONS

Brenner et al., "Loss of Runx3 function in leukocytes is associated with spontaneously developed colitis and gastric mucosal hyperplasia," *Proc Natl Acad Sci USA*, Nov. 2004, 101:16016-16021.
Chow et al., "Aberrant methylation of cyclooxygenase-2 in breast cancer patients," *Biomed Pharmacother*, 2005, 59(Suppl2):S264-267.
Cottrell and Laird, "Sensitive Detection of DNA Methylation," *Ann N Y Acad Sci*, Mar. 2003, 983:120-30.
Cuadrado et al., "Regulatory T cells in patients with inflammatory bowel diseases treated with adacolumn granulocytapheresis," *World J Gastroenterol*, Mar. 2008, 14(10):1521-1527.
D'Incà et al., "Oxidative DNA damage in the mucosa of ulcerative colitis increases with disease duration and dysplasia," *Inflamm Bowel Dis.*, 2004, 10(1):23-27.
Eaden et al., "The risk of colorectal cancer in ulcerative colitis: a meta-analysis," *Gut*, 2001, 48(4):526-535.
Ekbom et al., "Ulcerative Colitis and Colorectal Cancer—A Population-Based Study," *N. Engl. J. Med.*, 1990, 323:1228-1233.
Erdman et al., "Nitric oxide and TNF-alpha trigger colonic inflammation and carcinogenesis in Helicobacter hepaticus infected, Rag2-deficient mice," *Proc Natl Acad Sci U S A*, Jan. 2009, 106(4):1027-32.
Fainaru et al., "Runx3 regulates mouse Tgf-β-mediated dendritic cell function and its absence results in airway inflammation," *EMBO J.*, 2004, 23(4):969-979.
Fantini et al., "Common immunologic mechanisms in inflammatory bowel disease and spondylarthropathies," *World J Gastroenterol.*, May 2009, 15(20):2472-2478.
Fujii et al., "Methylation of the oestrogen receptor gene in non-neoplastic epithelium as a marker of colorectal neoplasia risk in longstanding and extensive ulcerative colitis," *Gut*, 2005, 54: 1287-1292.
Gardiner-Garden and Frommer, "CpG Islands in vertebrate genomes," *J. Mol. Biol.*, 1987, 196:261-282.
Garrity-Park et al., "MHC Class II alleles in ulcerative colitis-associated colorectal cancer," *Gut*, 2009, 58:1226-1233.
Garrity-Park et al., "Myeloperoxidase Immunohistochemistry as a Measure of Disease Activity in Ulcerative Colitis: Association with Ulcerative Colitis-Colorectal Cancer, Tumor Necrosis Factor Polymorphism and RUNX3 Methylation," *Inflamm Bowel Dis.*, 2011, 9 pages.
Geboes et al., "A reproducible grading scale for histological assessment of inflammation in ulcerative colitis," *Gut*, Sep. 2000, 47(3):404-409.
Geboes, "Ulcerative colitis and malignancy," *Acta Gastroenterol Belg.*, 2000, 63:279-283.
GenBank Accession No. AB048818, GI No. 13365764, 2001, 1 page.
GenBank Accession No. AF044206; GI: 3282785, 2004, 3 pages.
GenBank Accession No. AF135501; GI No: 4914684, 1999, 1 page.
GenBank Accession No. AL023096; GI: 3900882, 2012, 21 pages.
Goel et al., "Epigenetic inactivation of RUNX3 in microsatellite unstable sporadic colon cancers," *Int J Cancer*, 2004, 112:754-759.
Gupta et al., "Histologic Inflammation is Risk Factor for Progression to Colorectal Neoplasia in Ulcerative Colitis: A Cohort Study," *Gastroenterol*, 2007, 133(4):1099-1105.
Hoang et al., "Epithelial cells bearing class II molecules stimulate allogeneic human colonic intraepithelial lymphocytes," *Gut*, 1992, 33(8):1089-1093.
Horii et al., "Age-related methylation in normal colon mucosa differs between the proximal and distal colon in patients who underwent colonoscopy," *Br J Cancer*, 2007, 97(10):1425-1431.
Hsieh et al., "Hypermethylation of the p16$^{INK4a}$ promoter in colectomy specimens of patients with long-standing and extensive ulcerative colitis," *Cancer Res.*, Sep. 1998, 58:3942-3945.

Issa et al., "Accelerated age-related CpG island methylation in ulcerative colitis," *Cancer Res.*, May 2001, 61:3573-3577.
Itzkowitz and Present, "Consensus conference: Colorectal cancer screening and surveillance in inflammatory bowel disease," *Inflamm Bowel Dis.*, 2005, 11:314-321.
Jin et al., "A multicenter, double-blinded validation study of methylation biomarkers for progression prediction in Barrett's esophagus," *Cancer Res.*, May 2009, 69:4112-4115.
Kamikozuru et al., "The expression profile of functional regulatory T cells, CD4+CD25$^{high+}$/forkhead box protein P3$^+$, in patients with ulcerative colitis during active and quiescent disease," *Clin. Exp. Immunol.*, 2009, 156(2):320-327.
Karray-Chouayekh et al., "Aberrant methylation of RASSF1A is associated with poor survival in Tunisian breast cancer patients," *J Cancer Res Clin Oncol.*, 2010, 136:203-2010.
Kazi and Qian, "Crocetin Reduces TNBS-Induced Experimental Colitis in Mice by Downregulation of NFkB," *Saudi J Gastronenterol.*, 2009, 15(3):181-187.
Kim et al., "Methylation of RUNX3 in various types of human cancers and premalignant stages of gastric carcinoma," *Lab Invest.*, 2004, 84:479-484.
Klimasauskas et al., "HhaI methyltransferase flips its target base out of the DNA helix," *Cell*, 1994, 76:357-369.
Konishi et al., "Rare CpG island methylator phenotype in ulcerative colitis-associated neoplasias," *Gastroenterol*, 2007, 132: 1254-1260.
Kononen et al., "Tissue microarrays for high-throughput molecular profiling of tumor specimens," *Nat. Med.*, 1998, 4:844-847.
Kundu and Surh, "Inflammation: gearing the journey to cancer," *Mutat Res*, 2008, 659(1-2):15-30.
Langholz et al., "Course of ulcerative colitis: Analysis of changes in disease activity over years," *Gastroenterol.*, 1994, 107:3-11.
Lau et al., "RUNX3 is frequently inactivated by dual mechanisms of protein mislocalization and promoter hypermethylation in breast cancer," *Cancer Res.*, 2006, 66:6512-6520.
Lee et al., "Differences in Immunophenotyping of Mucosal Lymphocytes between Ulcerative Colitis and Crohn's Disease," *Korean J Intern Med.*, Jan. 1997, 12(1):7-15.
Lengauer et al., "DNA methylation and genetic instability in colorectal cancer cells," *Proc. Natl. Acad. Sci. USA*, 1997, 94:2545-2550.
Li et al., "Causal relationship between the loss of RUNX3 expression and gastric cancer," *Cell*, 2002, 109:113-124.
Li et al., "Inflammation-associated cancer: NF-kappaB is the lynchpin," *Trends Immunol.*, 2005, 26:318-325.
Iliopoulos et al., "Correlation of promoter hypermethylation in hTERT, DAPK and MGMT genes with cervical oncogenesis progression," *Oncol Rep.*, 2009, 22:199-204.
Liu et al., "Potential role of Th17 cells in the pathogenesis of inflammatory bowel disease," *World J Gastroenterol.*, Dec. 2009, 15(46):5784-5788.
Loftus Jr, "Epidemiology and risk factors for colorectal dysplasia and cancer in ulcerative colitis," *Gastroenterol Clin North Am.*, 2006, 35:517-531.
MacDonald et al., "Recent developments in the immunology of inflammatory bowel disease," *Scand J Immunol.*, 2000, 51(1):2-9.
Monteleone et al., "Immunoregulation in the gut: success and failures in human disease," *Gut*, 2002, 50(Suppl III):iii60-iii64.
Noronha et al., "Hyperactivated B cells in human inflammatory bowel disease," *J Leukoc Biol.*, Oct. 2009, 86(4):1007-1016.
Olsen et al., "Tissue levels of tumor necrosis factor-alpha correlates with grade of inflammation in untreated ulcerative colitis," *Scand J Gastroenterol.*, 2007, 42(11):1312-1320.
Olson et al., "Genetic variants in SOD2, MPO, and NQO1, and risk of ovarian cancer," *Gynecol Oncol.*, 2004, 93(3):615-620.
Piedrafita et al., "An Alu element in the myeloperoxidase promoter contains a composite SP1-thyroid hormone-retinoic acid response element," *J Biol Chem.*, 1996, 271(24):14412-14420.
Pohl et al., "Chronic inflammatory bowel disease and Cancer," *Hepatogastroenterology*, 2000, 47(31):57-70.
Provenzale and Onken, "Surveillance issues in inflammatory bowel disease:ulcerative colitis," *J Clin Gastroenterol*, 2001, 32(2):99-105.

(56) References Cited

OTHER PUBLICATIONS

Roncucci et al., "Myeloperoxidase-positive cell infiltration in colorectal carcinogenesis as indicator of colorectal cancer risk," *Cancer Epidemiol Biomarkers Prev.*, 2008, 17(9):2291-2297.
Rutter et al., "Severity of inflammation is a risk factor for colorectal neoplasia in ulcerative colitis," *Gastroenterol.*, 2004, 126(2):451-459.
Sandborn et al., "Safety of celecoxib in patients with ulcerative colitis in remission: a randomized, placebo-controlled, pilot study," *Clin Gastroenterol Hepatol.*, 2006, 4(2):203-211.
Sato et al., "Hypermethylation of the $p14^{ARF}$ gene in ulcerative colitis-associated colorectal carcinogenesis," *Cancer Res*, 2002, 62:1148-1151.
Saygili et al., "Enzyme levels and G-463A polymorphism of myeloperoxidase in chronic lymphocytic leukemia and multiple myeloma," *Leuk Lymphoma.*, 2009, 50(12):2030-2037.
Schottenfeld and Beebe-Dimmer, "Chronic inflammation: a common and important factor in the pathogenesis of neoplasia," *CA Cancer J Clin.*, 2006, 56:69-83.
Schulmann et al., "Inactivation of *p16, RUNX3*, and *HPP1* occurs early in Barrett's-associated neoplastic progression and predicts progression risk," *Oncogene*, 2005, 24:4138-4148.
Seidal et al., "Interpretation and quantification of Immunostains," *Am J Surg Pathol.*, Sep. 2001, 25(9):1204-1207.
Shen et al., "Association between DNA methylation and shortened survival in patients with advanced colorectal cancer treated with 5-fluorouracil based chemotherapy," *Clin Cancer Res.*, 2007; 13:6093-6098.
Shimamoto et al., "Selective decrease in colonic $CD56^+$ T and $CD161^+$ T cells in the inflamed mucosa of patients with ulcerative colitis," *World J Gastroenterol.*, Dec. 2007, 13(45):5995-6002.
Silverberg et al., "Toward an integrated clinical, molecular and serological classification of inflammatory bowel disease: Report of a working party of the 2005 Montreal World Congress of Gastroenterology," *Can J Gasteroenterol.*, 2005, 19(Suppl A):5A-36A.
Solomon et al., "Cardiovascular risk associated with celecoxib in a clinical trial for colorectal adenoma prevention," *N Engl J Med.*, 2005, 352(11):1071-1080.
Soo et al., "Overexpression of cyclooxygenase-2 in nasopharyngeal carcinoma and association with epidermal growth factor receptor expression," *Arch Otolaryngol Head Neck Surg.*, 2005, 131:147-152.
Steenport et al., "Association of polymorphisms in myeloperoxidase and catalase genes with precancerous changes in the gastric mucosa of patients at inner-city hospitals in New York," *Oncol Rep.*, 2007, 18(1):235-240.
Subramaniam et al., "Molecular pathology of RUNX3 in human carcinogenesis," *Biochimica et Biophysica Acta*, 2009, 1796:315-331.
Subramaniam et al., "RUNX3 Inactivation in Colorectal Polyps Arising Through Different Pathways of Colonic Carcinogenesis," *Am J Gastroenterol.*, 2009, 104:426-436.
Suter et al., "CpG island methylation is a common finding in colorectal cancer cell lines," *Br J Cancer*, 2003, 88:413-419.
Tahara et al., "Risk prediction of gastric cancer by analysis of aberrant DNA methylation in non-neoplastic gastric epithelium," *Digestion*, 2007, 75:54-61.
Tanemura et al., "CpG island methylator phenotype predicts progression of malignant melanoma," *Clin Cancer Res.*, 2009, 15:1801-1807.
Tominaga et al., "Prediction of colorectal neoplasia by quantitative methylation analysis of estrogen receptor gene in nonneoplastic epithelium from patients with ulcerative colitis," *Clin Cancer Res.*, 2005, 11:8880-8885.
Toyota et al., "CpG island methylator phenotype in colorectal cancer," *Proc Natl Acad Sci USA*, Jul. 1999, 96:8681-8686.
Tucker et al., "Cyclooxygenase-2 expression is up-regulated in human pancreatic cancer," *Cancer Res.*, 1999, 59:987-990.
Ullman et al., "Diagnosis and management of dysplasia in patients with ulcerative colitis and Crohn's disease of the colon," *Inflamm Bowel Dis.*, Apr. 2009, 15(4):630-638.
Underhill et al., "Detection of Numerous Y Chromosome Biallelic Polymorphisms by Denaturing High-Performance Liquid Chromatography," *Genome Res.*, 1997, 7:996-1005.
van Heel et al., "Inflammatory bowel disease susceptibility loci defined by genome scan meta-analysis of 1952 affected relative pairs," *Hum Mol Genet.*, 2004, 13(7):763-770.
Wang et al., "Aberrant DNA methylation in ulcerative colitis without neoplasia," *Hepatogastroenterology*, 2008, 55:62-65.
Wang et al., "Mechanism and clinical significance of cyclooxygenase-2 expression in gastric cancer," *World J Gastroenterol.*, 2005, 11:3240-3244.
Warren, "Genetic risk for colitis-associated colorectal cancer," *Gut*, 2009, 58(9):1177-1179.
Wolff et al., "Expression of cyclooxygenase-2 in human lung carcinoma," *Cancer Res.*, 1998,.58:4997-5001.
Xavier and Podolsky, "Unravelling the pathogenesis of inflammatory bowel disease," *Nature*, Jul.2007, 448(7152):427-434.
Xie and Itzkowitz, "Cancer in inflammatory bowel disease," *World J Gastroenterol.*, Jan. 2008, 21:14(3):378-389.
Yu et al., "Expression and functional characterization of FOXP3+CD4+ regulatory T cells in ulcerative colitis," *Inflamm. Bowel Dis.*, 2007, 13(2):191-199.

\* cited by examiner

Figure 1

```
   1 gctgtctgct tgtgtgtgtg tgtctgggag tgagaacttc ccagtctatc taaggaatgg
  61 agggagggac agagggctca aagggagcaa gagctgtggg gagaacaaaa ggataagggc
 121 tcagagagct tcagggatat gtgatggact caccaggtga ggccgccaga ctgctgcagg
 181 ggaagcaaag gagaagctga gaagatgaag gaaaagtcag ggtctggagg ggcgggggtc
 241 agggagctcc tgggagatat ggccacatgt agcggctctg aggaatgggt tacaggagac
 301 ctctggggag atgtgaccac agcaatgggt aggagaatgt ccagggctat ggaagtcgag
 361 tatggggacc cccccttaac gaagacaggg ccatgtagag ggccccaggg agtgaaagag
 421 cctccaggac ctccaggtat ggaatacagg ggacgtttaa gaagatatgg ccacacactg
 481 gggccctgag aagtgagagc ttcatgaaaa aaatcaggga ccccagagtt ccttggaagc
 541 caagactgaa ccaagcatta tgagtctccg ggtcagaatg aaagaagagg gcctgcccca
 601 gtggggtctg tgaattcccg ggggtgattt cactcccccgg ggctgtccca ggcttgtccc
 661 tgctacccgc acccagcctt tcctgaggcc tcaagcctgc caccaagccc ccagctcctt
 721 ctccccgcag ggcccaaaca caggcctcag gactcaacac agcttttccc tccaacccg
 781 ttttctctcc ctcaacggac tcagcttcct gaagcccctc ccagttctag ttctatcttt
 841 ttcctgcatc ctgtctggaa gttagaagga aacagaccac agacctggtc cccaaaagaa
 901 atggaggcaa taggttttga ggggcatggg gacggggttc agcctccagg gtcctacaca
 961 caaatcagtc agtggcccag aagaccccc tcggaatcag agcagggagg atggggagtg
1021 tgagggtat ccttgatgct tgtgtgtccc c  (SEQ ID NO:1)
```

Figure 2

```
  1 cccgggctgg gtacctggac ctataccttc atagctgcct taggctcaac ttttcggcgg
 61 ggatccctct gcagacgtgc aggtggcggg agagcagagg tagccgcagt aagtgctgag
121 agagcctgaa agaaacacca tgaattttca aactctccca catacattcc cgaagcgcct
181 gtctggcgtc taagagagag caagagaggg ctggagagca ggggagcccg cggggctgag
241 gctctttgtc agcgcctgca cttcctacgt tacaacgcct tcattcagca aaaaccttt
301 gggcgcctgc tgtgcgccag gccaggcgaa gnagaccgag gntgtgaagc tcagagggga
361 gagggaccaa tcgcagtaaa taagctaccg aggtaatctt agatggngat gagggcagga
421 aaagncatca gncgacctct gacctttctc ttaggggtt ttccccttcc gcctgggttc
481 tagaactggg aaganttttc tccagagcgt cgcggggagc gccccggg (SEQ ID NO:51)
```

Figure 3

```
   1 ggtacccagg ctggagtgca ctggtgtgat catagctcac taacctcgaa ctcctgggct
  61 taggcaatcc tcttgccttg gcctcccaaa gtgccaggat tacaggcatg agccaccaca
 121 gtggagctct caattctgat actaataatt tgtgtcttct cttttttcc ttagcctgac
 181 tagagtaatt aactttatgt cttttaaaag aaccacctt ttggttttac ccatttctt
 241 ttttgatttt ctgttttga tttgattgat atctactcta attttattt atttctttc
 301 ctctgcttac tttgaattta attactttc tttttgtag tctcctaaaa tagaagctta
 361 tattattgat tttagatctt tcttctttc tattacagca ctcaatgcta taaatttccc
 421 tctaagcatt gctttcactg catcctacaa tatttcaact ctattgttat ttagctcaaa
 481 agaggttctt aatttctatt gggatttctc tttgacccat gtgttattca gaagtgttcc
 541 gtgtgatctc caaatatttg ggagtttttc agctatcttt ctattaatca tttcttgttt
 601 aattctattg tggcctgaga gcatatattg tatgatttat attcttgtaa atgtgttaag
 661 gtgtgtctta tggtgcagaa tgcggtttat cttgctatat gttccttaga gaataatgta
 721 tgttctgctg ttattggata aagtagtcta tagatgtcag ttacatctcg ttgattaatg
 781 gtgctgttga gttcagctat gtcctaaatg attttctgtc tgctgtatct gtctatttct
 841 gacacaaggc tgttgaagtc tccaaccata ataatgaatt aatctatttt tctttgcagt
 901 tttatcaatt ttgtcttata tatattgatg ctccattgtt tggcacatac acattaagaa
 961 ttgttatgtc ttcttggaga atttaccttt ccataacatg taacatttcc ctttattcct
1021 gataattttt cttgctcaaa agtttgccct gttggaaatt accagaacta ctctggcttt
1081 atttgattag tgttagcatg ctctctcttt ctctattctt acacttttaa tgtatacttg
1141 actttgtatt taaagtgggg ttcttataga aaacatatac ttggtagggt gggaagtaaa
1201 ataaaaagaa atacttgggt attggtttga tccactctaa caatctctat gttttaattg
1261 atgtatttag accattgata cttatttttt tatcctcatc cctgtgatta cccagagagc
1321 tgcttaaatt gattattgat atagacaaat taataattaa tatctaccgt ttgttactgt
1381 tttctatttt tcattgccct tactttctgc tcctatttt tgctcctttt tctgttaatt
1441 taggttttga gttatttat atcattctat tttctctccc ttctcagcat atgaattatc
1501 tttctttttg actttttag tggctgccct gaaggttgca atgtacattt acaaccagtc
1561 ccaatctcct ttcaaaaaac acaatactgt ttcatggcta gtgcaagtac ctaataataa
1621 gaagtcactc ctaatttctt tctctcattc tttgtatctt tactgttatt catttcactt
1681 gtacataagc tgtaatcttt caatacatta ttgctattat tatttcaaaa catgttatct
1741 attatatcta tttaaaataa gaaaaatagg ccaggtgcag tggcttactc atgtaatccc
1801 agcactttgg gagaccgatg gattgctaga gctcaggaat tcgagaccag cctgggcaac
1861 atagtgaaac cctgtctcta ctaaaaatac aaaaaaaaaa attgctgggc atggtggcat
1921 gggcctgtgg tcacagctac tcgggaggct gaggtgagag gattgcttga gcctgggagg
1981 cagaggttgc agtgaaccaa aatcaagcta ctgcactcca gcctaagtga cagagtgaga
2041 ccctgtctca aaaaaaaat gaaagaatta ttttattta tcttcactta tttcttctct
2101 aatgctcttt gtttctttag tatgtagatc caagtttcta acctgtatca ttttttcttat
2161 ctcaataact tcttttaaca tttctcacaa agcagatcta ctggccacag aatgcctcaa
2221 ttttcatttg tctgagaaaa ccttatttct ccttcacttt tgaaagataa ttttgtaggg
2281 tacagaattc taggttgtag gttttttccc ctcaaagtga aatatttcat tccactcttt
2341 tcttcttgt atggtatctg agaagaagtc agatgtaatt cttatcatta ttacttaaaa
2401 gattgcttct gttcctttct ctcttctcct tcccttcttt ccttctctgt atattacacc
2461 ttttatagtt gccccatatt tcttagatat tatgttttgg ttttcttctg tgttttttc
2521 tttgattctc agttttagaa gtctctattt atatatctgc aatcgcaggg attctttcct
2581 ctgccatgtc cagtctacta ataagccctt acagacattg ttgacttctg ttccagtgtt
2641 tttgatctct agcatttctc tgattatttc ttggaattgc catctgtcta cttacattac
2701 caacctattc ttgtgtgttg tcttatcata gtaattgcag ttgttttaat ttcataggta
2761 ttgtaatttc aacatctcta ccatatttga cattgattct gatgcttgct ctgtcttatc
2821 aagctatgtt tttgtctttt agtgtgactt ctaattttt gttgaaagcc aggcatgatg
2881 tactgagtga agaaactca atacattgta atgtgacgat aagagttcag gggaagtgaa
```

Figure 3 (continued)

```
2941 gcattctata gtcctatagc aggtctcggc cttttagtga gcctgtgcct atgaacggtg
3001 actttcaaca agtgcttttc attccactct tttcctgtcc ttaagtggga caagatcact
3061 ggggggggc tagaattggg tatttccctt ctccaatgta gaagctaaag agagggctgg
3121 agttgggtat ttttcttccc ctgtatggaa agctagaggc agttaaattt ggatattttc
3181 cttcttctaa ttcagttagg ctgcgacaaa atcccgaca gtttaggctc taatattata
3241 aaataatttc tcttgagtat aggccttatt aagaacacta tactctgatg gagctgaggg
3301 ggagttttct ctgatattca ctgcgagaac ctcgtagagc tccaggaagc aaaactcaca
3361 aaagtgtggg agtcttccag aattttttcct ttgcagactt atctgcactg aacctccaga
3421 aattcatcaa ttacagttca ggttttccta cccaggtact ggttttcatg gaggtttctg
3481 cctgtgcatt tctgctccag taagttgttc ttcttgtatg gtctgtcttt caaatttttt
3541 aagtagggtt atgacctgtc gcctcacttc tctgacagtt ctgagagtgt tgattttca
3601 gtttgcttag attttactt gttttagga tgaagtgaca atttccaagc tcctccctga
3661 catgccagat cagaaactga aagtcctaag cctcatattc tgtgcgtggg tatgttcaca
3721 tcctgcctgc tccagtgccc ccacctcaca ctctctttcc cttccttgtc ccttgtgag
3781 atttctaggt ccaatacaaa gactgtgttc aactcattca actacttggc tcatctgagt
3841 attataatga acaatcacaa aaaaaatga agtaaagaa aaatccatca aagaattgag
3901 atatttgaga aaagaaagg agatcagtgt tttataaaac ttagaaatag attttttaag
3961 tgtttcttca ttgacttatg tgaaggact ttcttaatt taacaaatta tgtgctttcg
4021 tttatagcct caaaacttct tgtgtagcta agaatggta aataatcagg ctttactaaa
4081 ggactaacgt aaagatcttc tgtaagtaac atttctgcta ctcaaggaag agataaactt
4141 catggcataa ccttgccaaa gtatactaag aataaccctg acacaaagct cttttttcag
4201 ccaacatgcc atgaaagaaa gaagacaagg ggtgatctcc actctctaag tgaaccacta
4261 aacccaccaa agaagaaacg agggaaatag aaagaggacc cttgcctgag ataatggatc
4321 tgtatgtatg agtagtagaa ccctgctcaa agtacaagga agggaaaaaa aagttagttt
4381 atttggaatt ttggacatta agagtcttta ttgttcattt tctttttaact cacatgaatg
4441 gcttatcact tcaattaata aatatttcat ttctttttcaa tctatattca tgaaacaaat
4501 ctgaaatgaa cagtgcaaca tgtgaatgtt tagaacatta taaaattaaa cacaaaatct
4561 gtctggcaat cttcctagca tcttaggaaa aaagttgaca aaatttcaag cagcagaagg
4621 gggcagtaaa actcaacaga aagctctgga agattttaa gattcttcct tattttcttt
4681 tcatgtagag tatttcccaa caaatttcag acgctaatag aaattttgta caacagatcc
4741 atatatttgc ctaaaataga cacagaaaca ttgatatatg caaacatgag agctataagt
4801 tttacatgat caaaaccttt ttttatggt acacaatagt cacagtactt tccatataa
4861 aacaggttta gtggtcttaa tttagtttgg cacatttaat acactcccat gaccagcatc
4921 ccaaatgtac ctatccgttt tatttattg tctcagaatt gtcagttatt taataaatta
4981 tgtaactttt ttccttatgc tcagatttgc acttcttct aaaactctgc ccatccttaa
5041 agtcccagat tctccttgaa cttttttttt tgactttcca agtacatgga actcttcact
5101 ctatcctgct atataagtga cagaatttcc actatgggat agatggagtt caattccttt
5161 gagtttaaaa taatctaaat ataattattc cttatgccct gttttccct cactttgta
5221 tccaaatctc ttttcagaca acagaacaat taatgtctga taaggaagac aatgatgatg
5281 atcacttcaa aataagcttg aattcaggat tgtaatgtaa aatttagta ctctctcaca
5341 gtatggattc taacatggct tctaacccaa actaacatta gtagctctaa ctataaactt
5401 caaatttcag tagatgcaac ctactccttt aaaatgaaac agaagattga aattattaaa
5461 ttatcaaaaa gaaaatgatc cacgctctta gttgaaattt catgtaagat tccatgcaat
5521 aaataggagt gccataaatg gaatgatgaa atatgactag aggaggagaa aggcttccta
5581 gatgagatgg aatttagtc atccgtgtct catgaagaat cagatgtgta cactaagcaa
5641 aacagttaaa aaaaaaacct ccaagtgagt ctcttattta ttttttctt ataagacttc
5701 tacaaattga ggtacctggt gtagttttat ttcaggtttt atgctgtcat ttcctgtaa
5761 tgctaaggac ttaggacata actgaatttt ctattttcca cttcttttct ggtgtgtgtg
5821 tatatatata tgtatatata cacacacaca tatacatata tatattttta gtatctcacc
5881 ctcacatgct cctccctgag cactacccat gatagatgtt aaacaaaagc aaagatgaaa
5941 ttccaactgt taaaatctcc cttccatcta attaattcct catccaacta tgttccaaaa
6001 cgagaataga aaattagccc caataagccc aggcaactga aaagtaaatg ctatgttgta
6061 ctttgatcca tggtcacaac tcataatctt ggaaaagtgg acagaaaaga caaaagagtg
```

Figure 3 (continued)

```
6121 aactttaaaa ctcgaattta ttttaccagt atctcctatg aagggctagt aaccaaaata
6181 atccacgcat cagggagaga aatgccttaa ggcatacgtt ttggacattt agcgtccctg
6241 caaattctgg ccatcgccgc ttcctttgtc catcagaagg caggaaactt tatattggtg
6301 acccgtggag ctcacattaa ctatttacag ggtaactgct taggaccagt attatgagga
6361 gaatttacct ttcccgcctc tctttccaag aaacaaggag ggggtgaagg tacggagaac
6421 agtatttctt ctgttgaaag caacttagct acaaagataa attacagcta tgtacactga
6481 aggtagctat ttcattccac aaaataagag ttttttaaaa agctatgtat gtatgtcctg
6541 catatagagc agatatacag cctattaagc gtcgtcacta aaacataaaa catgtcagcc
6601 tttcttaacc ttactcgccc cagtctgtcc cgacgtgact tcctcgaccc tctaaagacg
6661 tacagaccag acacggcggc ggcggcggga gagggattc cctgcgcccc cggacctcag
6721 ggccgctcag attcctggag aggaagccaa gtgtccttct gccctccccc ggtatcccat
6781 ccaaggcgat cagtccagaa ctggctctcg gaagcgctcg ggcaaagact gcgaagaaga
6841 aaagacatct ggcggaaacc tgtgcgcctg ggcggtgga actcggggag gagagggagg
6901 gatcagacag gagagtgggg actaccccct ctgctcccaa attggggcag cttcctgggt
6961 ttccgatttt ctcatttccg tgggtaaaaa accctgcccc caccgggctt acgcaattt
7021 tttaagggga gaggagggaa aaatttgtgg ggggtacgaa aaggcggaaa gaaacagtca
7081 tttcgtcaca tgggcttggt tttcagtctt ataaaaagga aggttctctc ggttagcgac
7141 caattgtcat acgacttgca gtgagcgtca ggagcacgtc caggaactcc tcagcagcgc
7201 ctccttcagc tccacagcca gacgccctca gacagcaaag cctacccccc gcgccgcgcc
7261 ctgcccgaag ctt (SEQ ID NO: 52)
```

Figure 4

```
   1 gatcacctga ggtcaagagt tggagaccag cctggccatc atggcaaaac cctgtctcta
  61 ctaaaaatac aaaaattagg agggcatggt ggctcatgcc tgtaatccca gctacttggg
 121 aagcagagta ggagaatcac ttgaacctgg gaggtggagg ttgcaatgag ccgagatcgt
 181 gccactgcac tccagcctgg gcgacagagc aatctccatc tcaagaaaaa aaaaaaagaa
 241 aagaaaagaa atgaagattc tttctcccct ttcctcccag tgctctcccc acaggaacga
 301 gacctgcgtg gtgtggggag cagctgaaga cttctcatct gcctttgtga atgccaattg
 361 tacacagcca ctactggaat cttactcatc gcagcaggag gcctggcttc cggcacaggt
 421 ggaatgaatg aaggaaggaa cggatgaatg aaaacaatga agctgtacag agcagtctgt
 481 ctccgagtgg gcagtggatc ctggaaaaca catcttcagc catccagagt gggaagatct
 541 ggatttggga tgtagccgct tcctccctgt gtgacctttg gcagatgtca tttactttt
 601 ggaacttcag tttttccatc cgcaaaaagg ggatgctgcc tgcccagttc atgtcacaga
 661 cctgtgaagg tcaaaacaga aggcaggagg gagcatattc cataaaaggt acagcagccg
 721 ggcagagtgg cccatgcctg gaatcccagc caaggcagga ggattgctgg agaccagaag
 781 tttgagacaa gtatgggcaa aatagcaata cctcatctct aaaaaaaatt atttaaaaaa
 841 tcagctgggg ctgggtgcgg tggctcacct gtaatcccag tactttggga ggccaaggca
 901 ggcggatcac ttgaggccag gagttcaagc ccagcctagc caacatgatg aaacccatc
 961 tctcctaaaa atagaaaaat tagccaggtg tagtggtgca cacctgtagt accactgcac
1021 tccagcctgg gtgacaaagc gagactctgt ctcaacaaac aaacaaacaa acaaacaaaa
1081 aaccagcgga gcatggtggc acacactgta gtcccagata cttgggtggc tgagtgggga
1141 ggatggcttg agcccaggag gtccaggctg cagtgaacca cgatcgcacc actgcactcc
1201 ggcctgggcc acagagtgag actctgtctc tacaaaagaa aataagaaag gaaggaagga
1261 aggaaagaaa aaaaaaataa ataaaaatga aagataaagc atagggacgt tctgagaca
1321 aagagctgag tggaagaatc aagttaggac tcagcagcgc aggatggcga ggcttataat
1381 tttaatcccc tcctcgattt ctttcgatga ggcaaaaaac agtcttggaa attactcacc
1441 aaaccagcag tgggtgccag gagctcattc actttgtgtg tcattataat ttttgtaac
1501 tagaatggat ggagcaacca ctttggtagt gaaaatattt taatatccgc atgtgcataa
1561 agtgacacga ataacagttc ccgtttactg ggctctgatg ctgtagcagg ctgtggggat
1621 ggctactgtg ctcattttac agacaaggaa actgaaaccc aggcaggcga agtggcttgc
1681 ccaggctcac acagccagaa cgggatgaag caggttctga cctccaagca agactgactc
1741 cagtggggaa ttatgggttc ccaaatgaca ctgatcacag caacaacggg caggacagga
1801 caggtgactc agagcagact cctcatgcaa gggagatgt tgcccagtgc cgagggcacc
1861 ggggcagggt tcatgccttc ccctgggaga gcaagaggtt cagagtcaga aagactgggg
1921 cttgtggtcc cagctctgcc actttctggt tgtgtaactt ctgccaaatc ccttcacccc
1981 tccgagcctc aatgtgctca tatgcaaaag gggcgagtaa ccacctacct tgcaggcttg
2041 tgtggactga gtgtgttacg gccatgaaaa caccatgtgc tctataaggt gcgctttatt
2101 cattcctgaa gtgagcattt atcatgcacc cacgttcatg ccaagccctt ctctgggatc
2161 tggggagaca gcagcaaaca cagcagatga ggtcctggtc cctggagtta ctttcaagtg
2221 gttggagcca gataatcaac cgagaaagcc tgacacagtt cagacggcgt tgagtgccgt
2281 ggagaaccca cgccggacag cgtgacggag cggcctcggg gctgggctac tgagcaaggg
2341 aggggcctct ctgactttgt gatgtctgca cagaggctga gcggtgtggt gcaggtcagt
2401 gatggaaagc tgtttatggg aagtgtcaag ggatagcccc aaggaaggga ggagctacag
2461 cgggtgagga acagaaggct agggcaggga aatgggcaa ggggcccacc gggcagtgcc
2521 tgtgcactag aggtggtctc tagaggtggg aatgtctttg tggacacgtg tcctttgctt
2581 aggacagcgg agagaggctt ccaggtctgg gtgggtgaga aagagggagg agctgtcagg
2641 cagaaccatg gaggtaggtg gtaggaggta ggaggtaggt gggagggtga ggcacctgct
2701 ctgagcccct tctccctggg caggaatggg gcatgtgggc agagcagagg gaagcagcgg
2761 tgcaggaatg gccctgacct gcacagatgt gggaggaggt ccgcacgccc agagaggggc
2821 tgagatcata ccaccaggga cctggtgttg gttccacaag aggctcaggg acacacttcc
2881 agaattttga gagcaccct agcagaggca gggacttgga ctggttgacc tggcttttcc
2941 acaccctcaa aacctcaaaa tgtccaatgt ccatccactg atcatgatgg gtctttctag
3001 aatgtcattt tctccccagt gcagttggtg agaggcattc tcacctcctc cctggagagt
```

Figure 4 (continued)

```
3061 ggggttcctc cttaccattg cctggtggtt gagctctagt ccttctgtct ggctggccgt
3121 gtagccttgg gcaagccgct ccatctctct gtgcctctgt tgcctgggct gtaaacagaa
3181 gtgagctaaa ggcaggcaga ccgaggtctg tgaccacgta ataactcata ctcagttcca
3241 gaaatattca cccacagaag tgtctgggac aagcctggaa ggctgatcac accagccctc
3301 cgggtgctgc tcgtggctga gagaacagaa gggagccctg tccaccatgg gaagctgctg
3361 tttccatcac cagcctgggc tgtggtgcag aaagaaggaa ggggagtctg ggtggggcga
3421 gggaggcagc aaagggcctg gaccttcgtg ggagcacgga cacacaggac agccattgtc
3481 gagcttggac tgaccctact tggtgacgtt aagttctcaa gctccaagaa acagcatctg
3541 agttcttgag ctcaatcttc ccaccaaaga aaatcataca caagtcccgg cgcaggggct
3601 tcacagctca aagcatggtc tgtgtccaca tttcctgtgg tgggtcaggc cccactgcag
3661 tcctgagcca gctctgcatt cccaccagag ccccaggaga tcagatgcgg ggtgaactct
3721 gagaagcgct gctctagggc acaggtaggc tcattgcagc cttgtcccca gcgggaaaac
3781 gcggtggacc tgcagcagtc agaggcaagg cacactgcaa gctccaggaa caggcaggac
3841 ccgagaaacg taggtgggtg gaagcaggaa gaaggagaac ccagcgcaaa actgatgatg
3901 catattaaaa acatgcacat ggcggctggg cgtggtggct cacgcctgta atcccaggac
3961 tttgggaggc cgagatgggt ggatcatgag gtcaggattt cgagaccagc ctggccaaga
4021 tggtgaaacc ccatctctac taaaaattca aaaaaattag ccgggcgcgg tggtgggcat
4081 agggagactg aggcaggaga atcacttgag cccaggaggt ggaggttgca gtgagctgag
4141 attgcaccat tgtactccag cctgggagac agagcaagac tcagtctcaa acaaaacaaa
4201 acaaaacaaa acaaaaaaac atgcacatgg caaaatgaca taaggagag tgttgggatg
4261 gtgggagccg tattgtgtca atgtgaactc tcctgaacgt ggttattgtt cctggttatg
4321 taagagcagc tccttgttct caggaggccc acggggaatg tcctgacat gtgtaggtac
4381 ttctatatgg ctcagcaaac aaaatttatg cagatactca gagagaaccc ctggagcaaa
4441 atgttgacaa tctgtgagcc taggtaaagg ggatatggga ggtttgttgt tgttgttttt
4501 tgttttttga gacggagtct cgatctgtca ctgaggctgg agtgcagtgg tacaatctct
4561 gctcgctgca acctctgcct ctcaggttca agtaattctc gtgcctcaac ctcctgagca
4621 tctgggacta caggtgcacg ccactacacc tggctaattt ttgtatttt agtagagacg
4681 gggttttgct gtgttggcta ggttggtctt aaactcctga cctcaagtga tcctcctgct
4741 tcggcctccc aaagtgctgg gattacaggt gtgagccact gtgcctggct aattttata
4801 tttttagtag agatggggtt ttgccatgtt ggccagaact cctggcctca agtgatctgc
4861 ctgcctcggc ctcccaaaat gctgggatta caggcatgag ccactgcacc cagccggata
4921 tgggagttta ttgcactgtc cacagagtga aggtgtggct cctggacttc ctccctcgtc
4981 cagaggagag tcaggctgaa ccagccgggt cccaggagac caaggagac cccccccccc
5041 ccgccgccac taacaaacca cagagatttt tactgaaaat aagttttctt cctctcttct
5101 tgtaattaca aagataaacc aagtttattg taaaaatgtg aaatgactaa gaagtgtata
5161 aagcaaaaag caaagcgttt tttcacctt gccctcccc aattcttaac ctctgtggac
5221 agcttggcag cccctttctag gcattttct ttccaggtga agttctgtc aatctttttt
5281 cctcccagag ggagtcctgc acaatttatt gttcatatat tggggacagg tttccatggc
5341 aaaactcaat ctgattcttt tttacttttt tttttttttt tgagacagag tctcgctctg
5401 ttacccaggt tggaatgcag tgccatgatc tcggctcact gcaacctccg cctcccaggt
5461 tcaagcaatt ctccggcctc agcctcctga gtggttggga ttacaggcac ctgccaccat
5521 gcctggctat ttttgtattt ttagtagaga tgaggtttca ccgtgttggt caggctggtc
5581 tagaactcct gatctcaagc aatccactca cctcggtctc ccaaagtgtt gggattaaag
5641 gcgtgagcca ccgcccctgg ccctttctta ctttttaaat caagaactga aaacgacttt
5701 atttactctt cttgggacat ggccacgccc atggaagtcc caaagtagg ctggacaggc
5761 cacagcagca cccggagcag tggtggcagc tcctgttgag ctgccctcca gaagccagtt
5821 ctgatgcgcg gcctcgccgg gggcctgaga acccctgttt cctgtgaggc tgggccaggg
5881 acaggataac aagggaggca gaaaagagtg ctggcgggga gccaggaggc ctgggttcca
5941 gccccggccc tgccgcttgc ctgctaggag cccttgagaa agtcagttcc cctgcctgaa
6001 cctcagtctc ctcaccttca gatggagatg ccggcccaga gggtaccaga ggcctttcct
6061 ggcttgcaaa caggatgcca gtccacaaag ccacagggtg agggtgcttc ccagttctct
6121 gtgcttcgga acagcgtgct gctccggggg accttggaaa ggtgactggg ctcttctggc
6181 ggtttggggt ggggttgta gtttgtgctc ccggatgttt gcccacgtgg gtggagcctg
6241 cctgtctgtt gccccttaga gggaagttgg cagtaggatg ggttgggggg ccgtggatgt
```

Figure 4 (continued)

```
6301 tgggaggccc taaagctgag cccagactct caggcttggg aaggaccttc ccgatcagcc
6361 ttctgtccat ggcttgaatt cctgtcttgt ggcatcagga aagacttatg tcttttaggg
6421 tccaaccaag aaagcagaaa aacactcagg tgttgcagac agagggcctt catacaggga
6481 gttagtcaca caggttatgg gagagccgag aagccgaaga gggtgtgatg agttaaccca
6541 gagattaaca actgcgagaa accaccaccg ccccaggatg gagaagccag ggaggtggtg
6601 gggttagcag atcctgggat cggggtcacc cagtaccagc caggggcttg tggcagagag
6661 ctggagcaca gaggagacat ggctgctgcc gctgagctca cgaaggaaga cagggaaggg
6721 gagggatacc cagcttctct catcacatgt gccccatctt cagtctcccc cagtgcctcg
6781 ctttggcaga actcgctgaa aaacgcagcc tgcaggtatc agcccccacc ctgccctgaa
6841 cacagagagg aacatatttg aggtcagagg cccaggactg gcccagtgac tgtgtttaaa
6901 tgcttcgggc actggggagc tcactctcta actcttaact gtagaggtgg tggcaacagc
6961 ctgttttgct ggcggctgag catgagcatt tggttcagaa taaggaagaa acattggttt
7021 cctgtgactc cctacagaaa gatgaggggt ttgtcttggg agcagaagcc cccgtgtgtg
7081 ttgctttgtg ctgtcatgtc tgccaggaag gcccttcccg ccctcccatc gcttgagacc
7141 caattctccc agaaaacctt ccggcacctc catgtcgagg gatagtaccg tcatgtccgt
7201 ccacagcacc tgcgcttcct tctctatttta gcagaatgta gcaacatta tgttcaacgt
7261 ggacttctct gtttgttctg cctcattcat aggggcatg gagcttggag aacctgacgt
7321 tgcctaccca gagctggctc taggttaaag agatgctcac taaggcacct atagtgtgcc
7381 aggtctgcca aatgtttggc atgcattatc tagtttaatg ctcccaacaa ctccggaggt
7441 tggtatgatt agcccatgcc tgctcagctg gagaatctga ggctcaaaag gagggtgtcc
7501 aaggccactt ggctagtaag ggcagagcta ggattcgaac acagcctctt aaaggccgcg
7561 ttccttagcc acggggccac gtggtcttgc cacagtgcag ctgggcccag ggtgggattg
7621 tgtgaagtcc ctcactggga atgtttccag ctcagctcct ggtgcctcct ccctgtcct
7681 ctgtccaaga ccacatgtca gcccttgaa ggcgaggcag ccattcccac agccacttct
7741 ctattctgac atgaccaaga agcctggctg ggacagcagg tctgaccaca gattgacaga
7801 tgtttccaca tgtggaagtg aggtttgagc ctcgatgtgc tgtttctgtg gttcccttttt
7861 cacgctttcc ttgggagatg tgtccagaca tggtctcatt gccctaatag gtttccatgt
7921 ctgttgtgca cagtctttag actgtttaac aatcctgttc actggtagag cactgcccag
7981 cttgcacaca gcactttctt atgcattggc tcagtggctc ttcccaacaa tcctgggact
8041 tgggttcatt tactggatgg aggctcagag aggctaagta acaacagtga caaccattag
8101 ttgccttttg cagatctgtc agcatgcctt gctcaaagag agacagaaac tgcccagtgc
8161 acagtgtctc acttgatctt cacaatagcc ctgcaaggta gatattatta caacctctca
8221 ttggaagtag ggaaactgag gctcagagag aataattgac ttacccaagg tcacacagcg
8281 tcaaatccac acctagaacc catctcttgg tcttgactcc tggttcagtg ttccaagcaa
8341 ctgttgagaa catccatcaa acttaaaaat atatatgact atatttcaac aaatctatga
8401 catcattgaa tatagataca ccactctttt atataccca ggaaatagaa atgctgtcag
8461 ctacagtaag acacagtatt tctcatcaca tagaattttt ttattttaga ctaattaaaa
8521 gagctctttc atatctgtat gcatcatata tatataagca ttatatatgc atatatataa
8581 tgcatcatat atgcatcata tataagcata tatgcata tatataatgc atcatata
8641 tgcatcatat atatgcttat atatgatgca tatataagca tatatatgca tatataagca
8701 tatatgcata tatatatgta tctctctcag ttgtctgtac atagaaggaa aatttatctg
8761 aaaataaact tatatgacat gaaatggatt tatgtgaaaa taaacttctt catattcaaa
8821 atctaactga gtaactgggc gtggtggctc atgcctgtgt ccagcacttt gggaggtcaa
8881 ggcaggtgga tcacttgagg ccaggagttt gagaccagct tgggcaacat ggcgaaactc
8941 tgtctctaca aaaatacaa aagttagcca ggtgtggtgg cagaggctgt agccccagct
9001 acttggagg ctggggcagg agagttgctt gaacccggga ggcggaggtt gcagtgagcc
9061 aagattgtgc cactgcactc cagtctgggt gacagagtga gactctgtct taagaaaaaa
9121 aaaaaaaaag acaaactctg agtgagcagt agaagcccag ctctttccca taagattgtt
9181 ctccgcacca gcaaatgctg gcgatgaaga tttctccctc tctcttcaaa aatatgttag
9241 agaggaaaag cgtgtttaca tataacaaag tacataaatt ataagtacac ttgatgaatt
9301 tttatccacg ttaatattca tctagactca ccagtgcgtt ggagctggct cacattagca
9361 ttgttaaaca ctcaggaatt ttgcaaactg gttttttaaat tgttggtcac ttaaaatcag
9421 ctgcgggcca ggcgcagtgg ctcacacctg taattccaac actttgggag gccaaggcag
9481 gaggactgct tgagcccagg agcttgagac cagcctgggc aacataggga gaccctgtct
```

Figure 4 (continued)

```
9541  ctacaaaaat atatatattt ttaaattagc cagatgtggt ggtgtgtgcc tgttaagttc
9601  cagttacttg ggaggattgc ttgagcccag gagattgagg ctgcagtagg ctatgatgga
9661  gctgctgcac tccagcctgt gtgacagagc gagacgccgt ctcaaaaaac aaaaacaaaa
9721  accaaaccct agctgcaatg ggagtatttt acatcatgga aattggcaaa tgctacataa
9781  tccagggctg ttttttttccc ttcagaggtc tggtttactg gcccaccact gagtgtagct
9841  actacccaga tggggagagc ttcccagcat cctagaagcc tcctttgtgg ctgtcccagc
9901  cccttttccac caagggaaca actactggat gcggcatttc ctagaggtgg ctgagggcca
9961  ctggcgctgg gctcctgcga ggggtttgcc attgtgcggg gctggcccac tttcgacgcc
10021 catgggagga atgctgctaa acacgtccga tttaccacct cctccatccc gtacccacag
10081 ccatttggtt cctagaggtt aaaagaacac tcctctattg tctccagggt ttccttccaa
10141 gccgcagaat cccattgtcg atgtgacggt gtaagcgggc tgtgaccact ccctggagag
10201 ggcctcctgc caacaattac tgtaagacac accccctattt cagagacact aaaatgtgaa
10261 aaatcaagcc tcttagagtc accaaaatac agtatattgc cttttgaaga tctttactga
10321 agcagtttcc tctgagaagc agcttgtctc catcattaag ccccggaaag cagatgagac
10381 tgcagttcct ccgggctagc tgtctcagtg gtcacttcgc ccccagacag gtagcttctg
10441 cccacttctc tcatgggcga gccaagtgtt actacctctg gccccggcct ggaataagag
10501 gaccagcagg ccgtgggaaa cctcagctct aataccaggc tgcttctgga cagtcctttc
10561 tgggtgtgga taaagaccag gcttgtgccc tctggggacc gttcaaagca gtcttcaggg
10621 tcggacctca gactcatccc tgtgatgatt gtttcaggtc ctagcgagtt actttcccaa
10681 cctgtgagct tctgcaactg tgttttttttg tttttttgtta ttgttgtttg tttgttttaa
10741 tatttttttc ttttcttttt tttttgagac agagtcttgc tctgttgccc aggctggagt
10801 gcagtggtgc gatctcggct cactgcaacc tccacctcct gggttcaagc gattcttctg
10861 cctcagcctc gcgagtagct gggattacag acgtgtgcca ccacaccagc taatctttgt
10921 attttttagta gagacagggt ttcgccatgt tgcccagact agtctcaaac tcctgacctc
10981 aagtgatcca cccacctcga cctcccaaag tgttggact acaggggtga gccactgtgc
11041 ctggccatgc aactgtgttt taatcacctt tgtgttccca aggccctgac atggaacaag
11101 cacccagtaa gtatttgaat gaatgagcaa atgaaaggcc aggaagggag agcctttatt
11161 ttgaagcctg cccgcgggc tgcccttggg aaagccactt tctgcaaaag tcacaggagc
11221 aaatgagaca aagatgcaaa attgctctgc ctgagctgtg agggcttaac tgtgaatgtc
11281 tttaggtgac cttcttggag acctcaagac caccccctctg tgacttggtt caggctgccc
11341 tgctgtgatg cctgctgggg ccaaggcctg gatccctggg tggggtgggg tggggtgggg
11401 cggggcgggg aggggcgggg cggggcgggg caggagtggc agcaggaagg atccggctga
11461 gacttgccct ggggggccag ggaaggaggg tggcaggagg cagaatccac aaatgaagta
11521 gatctggagc caggcagatc agcccttaga tataatctca gaaggggttg ggagaatgga
11581 aggattttgt tgaggatgga gtgagagggt tggagggttg ggtatgttcc tgagcatatt
11641 tccctgtcta tggggccatt cagagagaag cccacgtgct ccaggccagt ggtggagcct
11701 tcaacgtgga gctggaagac ctgggctcga gtcccacctc tgccatgtcc catcctccct
11761 catgactccc agtagttacc gccttctctg ggcctcagtt tccccaactg gaaattaaag
11821 aaaattaccc tgttcctgca tcagatggtt ggttgtggat atcactgaaa tctcctcacg
11881 tggtattgag ccgctgctct tggccagaca cagagcaatt tacatgaaat gattttcgaa
11941 gtctggtccg ggaccagca gtgtcagcat cacttgggaa ctttgtcaga aatgcaaatt
12001 atcgggctcc accccaacta ctctagaccc aaaaacaatt tttattttta tttttattta
12061 cttttttagga tggagtcttg ctctgtcacc caggctggac tgcagtggtg caatctcagc
12121 tcactgaaac ctctgcctcc tgggttcaag cgattctcct gcctcagcct cctgaatagc
12181 tgggattaca ggcatgcacc acgacgccca gctaaattt tttattttta gaagaggcag
12241 ggtttcacca tgttggccag gtggtctcgc actcctaacc tcaggtgatc cacctgtctc
12301 ggcctccaaa agtgctggga ttacaggcgt gagccacagc gccctgcccc aaggacaatt
12361 tttaaatgat ataattcata tcccataaaa ttaaccttt aaagtgtgca gtgtggtggc
12421 ttttagtatt atccaccagg tcatacaacc tattatcact aattccagaa tatttttcatt
12481 gctctcaaaa gaaaccttgt accatttagc agtgactccc cactcccctg tccctcagcc
12541 cctgcaatca caaacctact tttcatctct atggatttgc ctattctgga cacttcatat
12601 aaatggaatc atagaatatg tggtcttttc tttcacttag cataatgtct tcaaggttca
12661 tccatattgt aatatgtatt agtacatgtt gtactgatgg aacatgtatg ttgtagcatg
```

Figure 4 (continued)

```
12721 tttcaccctt ttaaaaaatc ttcttttttaa attaaaaaca tttttaaaat acattcaaag
12781 attttttag agtcgtttta gtttcacagc aaaattggga ggcaggtatg gagatttccc
12841 tatgttccct gccccacaa catacgcagc ctcccatcat taacatcccc caccagaatg
12901 gaacaatttt aacaaccgat gaactgacat tgacacatca ttatcactgc aaatccatag
12961 tttactttgg ggttcactgt taatgtagta cattctatgg gtttggacaa gcgtataatg
13021 acacgtatct gtcatgatgg tatcatacaa agtattttca ctgccataaa aatcctctgt
13081 gtgccaccta tttcttcctc ccatccccct aatccccggc aaccactgat ctttctacca
13141 tctccacagt tttgccttttt ccagaatgtc attctcttag tccattttct gctgctataa
13201 caaaatacca cagactgggt aatttataaa gaaaagagac ttactaggct cgtggttggg
13261 gaaatccaag gttgaggggt tgcatctggt gagggccttc ttgctgtgtc ataacacggc
13321 agagggcaag cgagctcacg gaacagagag aggaactcag actgaactca tctgtttatc
13381 aggagcccac tcctgcgata actaaccccc tcccctaata atggtattaa tccattcaag
13441 agagcagagc tctcatggcc taatcacctc tttttgttt gtttgttttt gttttcagac
13501 agggtctcac tctgttgctt aggctggagt gcagtggcac aaccatagct cattgcagcc
13561 ttgacctcgc aggctcaagt gatcctccta cctcaggctc caagtagtt gaaactatag
13621 gcatgtacca ccatgcttgg ctaattttga aattttttta gagatgaggg cttgctatgt
13681 ttcctaggct agtcttgaac tcctggactc aagtgatcct tctgcctcag cctcccaaag
13741 tgctgggatt acaggtgtga ggcattgcgc ctggcctaa tcacatccta aaggtcttgt
13801 ctctccacgc tgttacaatg gcaacgaaat ttcaacataa gttttggaaa agacattcaa
13861 gccatagcat tccacctctg gcccaccaaa actcttgtct tccttgcata caaaataaca
13921 ttcatcccat tccaatagcc ccaaagttttt aactcattcc agcaccgact caaaagactg
13981 aagtccagag tctcatctaa atcagatatg gatgagactc aaagcatgac tcatgctgtg
14041 gcaaattcct tccagttgtg agtctgcaaa atcaaaacaa gttatctact tccaaaatac
14101 aatagtggga caggcatagg atagatgttc ccattccgaa agggagcaac aggaaaggag
14161 aaaggagtaa caggcccca agaagtgcaa aacccaaaag ggaaaacaag attaagtctt
14221 aaagctggag aacaatctcc tttgactcca cgaccagcca cctgggcaca ctgggcagcc
14281 ctgcctctac ggctttgcta ggctcagccc acacaatttt cacaggttgg gatctcatgc
14341 ctgcagcttt cccaggctgc catcactcac tggcagctca acagttctgt ggtctggaga
14401 gtggccccac ttccacggct gcagtaggca ttgccctagt gaggactctg tgcagtgcct
14461 ctgatcccac acttccactc ggcatttacc taatagggct ttctgtcatg gctttgcccc
14521 tgtggcaggt ttctgcctgg gcccccttt aaatctagtt gaaggtagcc atgcccccac
14581 agctcttgca ttctgtgagc ttgcagacct aacaccatgt ggatgctgct aaagtttaaa
14641 gcttgtacct cctggagcag caggttgagc tgcacctggg accacttaag ccacagccag
14701 ggaagtcaag aggtgctgca ctggaatgat gggggcagag tcctgagatg gctctgggca
14761 gtgagcctgt ggaggatgtc ccaggcatgt tccctgaaac cattctgctc tcctagagct
14821 ctgggcccgt aataagagaa acagcccgga agagctctga aatgtctttg gagtcttttcc
14881 tccaaaggaa taacacctgg ctttcttcta tctagcctga tcttttaagt aaatggttgc
14941 ttggccacac ccttagtatt cttttccgaa tgttattgct tttcactctt taggaggcca
15001 ggctgtgagt tttcctttgc ttctctttta attataaatt ctgtctttaa gtcattcctt
15061 tccttttgca tctcactgta tgtggttaaa aggagccatg cagcaacctg aatgctctgc
15121 tgcttagctg tttcttccat cagatatccc cgttcattgc tcttcagtcc tgcactctat
15181 aaagcccttta gacataaaca cagttcagcc aaagtctttg ctactttgta acaaagatgg
15241 cctttcctct tagtttccaa taccttgttc ctcatttctg tctgagacct cattagaatg
15301 gcctttactg ttcatatttc tacggacatt ctggtcatga ccacttaaat aatcttcaag
15361 aagatttagg ctgtccttag ttctagggcc ttcttttgag ccctcagcaa aattgctctt
15421 aatgctccat tcacaggaat ctaggctttt tctagcctgc tcctacaaac tcttccagct
15481 tctatccatt acccagttcc aaagcagctt ctacatgttc aagtatttgt catggcaaca
15541 gctcctcttc tgtgcaccaa ttttctgttg ctataacaca ataccacagg ctgggtaatt
15601 ttacgtatat atagaatata tatatagaat atatagaaaa aatatatatg tatgtatttt
15661 atataataat actgagcatt gactcatggt tctacaggct gggaagtcca aggttgagga
15721 actgcatctg gtgaggacct tcttgctgtg ccataacatg gcagaagggc caagagaaag
```

Figure 4 (continued)

```
15781 agaacagaaa tcaggctgaa ctcattcttt ttatcaggag cctacttcct agataactaa
15841 ccaactgtca caataacagc attaatccat tcatgagggc agagctctca taacctaatc
15901 acctttaaa  ggtcttgcct ctcaacagtt actatggcaa ctaaacttca acatcagttt
15961 tttgagggga cttcaaaca atagcagtca tatattggaa tcacacagta tgtagccttt
16021 tctgattggc ttctttcact tagtaatatg gatttaagtt tcctccattc ttttcatggc
16081 ttgatagctc atttctttt  agtgctgaat aatagttcat tgtctggatg taccacagtt
16141 aatccattta cctgctgaag gacatcctgg tttcttcttt tggcagcatg aaaaaagctg
16201 ctataaacat ctgtgtgcag atttttgtgt gaacataagt tttcaactct tttctgtaaa
16261 taccatggag tgtgattgct caatcatatg gtaaaagtat gtttagcttt atagaatgac
16321 aatttacctt tcaaagtgac tgtactatgt gctaagtggg tgtactattt tacatttacg
16381 tttacaacaa tgaaggaaag ttcctgttgc tccatatcct cctcagtgtt tggtgctgtt
16441 tgtattctgt attttggcca ttctaataga tatgtagtat cccgttattt tagttttcat
16501 tcccttgata acatgtgatg tagagtatct tttcttatgc ttatttgaca tctgtatatc
16561 ttttttggtg aggtgtctat taaggtacat ggcccatttt ttaattgggt tgttttttt
16621 cttattgaga gctttaagag ttctttgtat attttggaca actgtctctt atcaaacatg
16681 tcttttgcaa atattttctc ccagtttgtt gcatgtctgg ttattccctt gacattggct
16741 ttcacaaaac agaagtttaa aaattttttt taatgaattc cagctcattc attgtttatt
16801 tcagcaataa tgctttcggt gttatacctg acaagtcatc accataccta aggtcatcta
16861 gacttttttcc tatgttgtct tctcaagagt tttacagttt tgcattttta atttagattt
16921 atgaggtact ttgagttaac tttgtggaa  tgtataatgt ctgtgtctaa attcagtttt
16981 tttggtatat ggatgtccag ttattcatat tttttaaaag atggattttt gcatgatatt
17041 ttgaaaagac tgtctttgct ctattgcatt gtctttgctt ctttgtcaaa gattagttga
17101 ctacatttat gtgggcctat gttgggctct ctattctgtt tattaatcta cttgtttatt
17161 cttttgccaa taccacactg tcttgattag tatagcttta agtcttgaag attactatag
17221 ctttaagtct tgaagactac tatagctagt aagtcttgaa gtcaggtagt gtctgtcctc
17281 caactttgtt cttcctcagt attgtgttga ttattttgat cttccctct  tcatataaac
17341 tttagaatca ttttcaata  tccacaaaat aacatgctgg gattttgatt gggattgcac
17401 tgaatctata gatcaggttg gggaaaactt atatcatgac aattttgaat cttcctatct
17461 gtgaatatgg aatatctctt tatttattta gttcttcttt gattttgttc atcagagttt
17521 tgtagctttc ctcatataaa tcttatatat atttacttag atttatacct aagtactttc
17581 ttttattggg tgctaacgta aatggtattg tgttttaaat ttcaaatttc acttgcccat
17641 tgctggtata taggaaagtg acagacttgt acaacaacct tatatcctac aatcttacta
17701 taatcaccta ttagttccag agattttgt  gttgatttat ttggattttt ctacatagat
17761 aatcatgtca tctacaaagg cagttttatt tcttccttcc caatcagtat aactttatt
17821 tcatttttctt gccttattga gttagcttgg acttccagta tgatgttgaa aaggagtggt
17881 gagaggaaac atccttgact tgttcctgat tttagtggga aagcttctag tttctcacca
17941 taagtatggt gtttgctgta agttttttgt agattttttc atcaaataga ggaagttctc
18001 ctcaattcct agtttactga gagttgttat atgaatgggt gttgaatttt gcgaaattat
18061 ttttcttcat ctattgatat aatcatgggg ttttcttt   ttagcttgtt catgtgatgg
18121 ttatattaat ttattttcaa atcttgaacc agccttatat acccaggata atctcactt
18181 gataatgagg tataattctt tttatacatg gttggatttg atttgctagt aatttgttga
18241 agattttgc  atctgtgttt atgagatata ttggtctgta gttttgtttt ttggtaatgt
18301 ttttttatct ggttttgtta gtgctggact cataggtgaa gttagaaagt atttgctctg
18361 cttctatcct ctgaaagtga ttgtagagaa ttggtataat ttcttcctta aatgtttggt
18421 tgaacttacc agtgaactct tctctgcctg gtgccttctg ttttggaagg ttattaacta
18481 ttgattcaat agatataggc ctattcagat tgtctatttc ttctttatg  agttttggca
18541 aattgtgtct ttcacagagt tggtccattt cacccagatt atcaaatttc tgggcataga
18601 gttcatagta ttcctttctt atcctttcaa tgtccatagg atctgtagtg atgtcccttc
18661 tttaatttct gatattagta atttgtgttc cctctctttt tttcttagtc tggctataga
18721 cttattgatt taattgatct tttcaaagaa tcagcttttg atttcattga ttatttaatt
18781 ttcttttttc aatttcattg atttctgccc taattttac  tattctttt  tttcttctac
18841 ttactttggc cttcttttcc tagtctgtta aggtggaaac ttagattatt gattttagat
18901 ttttcttctt tcctaatata tgcatttgat gctataatct tccctcaaac cactgctttg
```

Figure 4 (continued)

```
18961 gcttatctta cacattttaa taagttgtgt tttaattttc atcaggtaaa aatattaaaa
19021 ttcttttttga gatttcttct ttgacccatg tattatttag aagtgttttg tttaatctcc
19081 acatgttttg gaattttcta gttatctttc tgttattgat ttcttttaat tccattgttg
19141 tctgcgagca gaagttgtat gatttctact cctttttaatt tgttaaggtg ggttttatgg
19201 cccaaaatgt ggtcaaattc tttctgtttt atggcccaat aatattccat tgtatagata
19261 tacaacattt tgtttatcta ctcatgagtt ggtggacatt ggggttgttt tcattttttg
19321 ttaattccat tgtacactga acatacaatt cagtggtatt ttgtatgctc acaatgttgt
19381 gcagccatca cctctatcta actccaaaac atttcatcaa ctcaaaggag atcttgaatc
19441 cattaagcag ccactcctca tgtccctgct ctcaacccct ggcaaccact aatctgcttt
19501 ctgtctccat gaatatagct attttggata cttcatttaa atggaatcat acaatatgtg
19561 atcttttgta tctgacttct tttacttttc ataatgtttt caatgttcat ccatgttgat
19621 agcattcctt tttagggctg aatactgttg tgttgcatgg atatactatg ttgtgtttat
19681 ccattcatct actgatggac gtttgagttg tttccacttt tgctgtgtga atagtgctgc
19741 tatgtatttg tactcattgt acacattgtg tacaaacatt tgttcgaata cctgttttca
19801 attcttttgg agaattattt tcaattctag gagcagaact gctgggttat atggtatcat
19861 tgtgaggaac tgccaagctg tttcccaaag tggctgaacc attttacatc cccaccagca
19921 acatatgaga gttctaatttt ctccacattc tcaccagtgc ttgttttcct ttcctttcct
19981 ttcctttcct ttcctttcct ttcctttcct ttcctttcct ctctctctct ttctgtcttt
20041 taaattatag ccattctagt ggatatgaaa gagtatctca ttgtggtttt gatttggatt
20101 tttcaaatga ctaatgatgt tgagcatctt ttcatgtgct tcttggccat tgtatatctt
20161 ctttgaaaaa atgtctgttc aagcattttg accattttta aattgggtta ttttgtcttt
20221 ctgttgctga attgcaagag tttttttttat atgtcctgga ttctagatgc ttatcagata
20281 aatgatttac aaacattttc tcccattatt cattatttgc tgtcattcca ttttcctttt
20341 tttttttttt ctttcttaga cagggtctta ctctgtcacc caggctggag tgcagtggtg
20401 caatcttggc tcactgccac ctccacctcc ccagctcaag cagtcctccc acctcagcct
20461 ccccagtagc tgggactaca ggtgcacacc accatgctct gctaatttt atatttcttg
20521 tagagatgaa gtttcactat gctgcccagg ctggtctcga actcctgagc tcaagtgatc
20581 ctcctgcctc agcctctaaa agtgttggaa ttacaggcat gagccactgt gcccagcctc
20641 attttatttt cttgatagtg tcttttttttt tttttttgaga caaggtctca ctctgtcacc
20701 caggctggag tacagtgaca tgattatagc tcactgtaac cttgaactct tgggctcaag
20761 caatcctcct gactcagcct ctcaagcagc tagtacaaca ggtgtgtgcc accacgtctg
20821 gctaacttttt acattttttt gtagaggtgg agtcttgctg tgttgcccag gctggatctt
20881 gatagtgttt tgtttttgttt tttttagatg gagtttcact tttgttgccc aggctgaagt
20941 gcaatgtgca attgcgcgat ctcggctcac agcaacctcc atctcccagg ttcaagtgat
21001 tcttctgcct cagcctccca agtagctgtg attacattta tgcaccacca cgcctagcta
21061 attttgcatt tttagtagag atggggtttc accatgttgg ccaggctagt caggtgatcc
21121 gcctgcctca gcctcccaaa gtgctaggat tataggcgtg agccactgtg cctgggtgcc
21181 tggccttgat agtgtttttt gattaactat ctactttat tttgatgaaa tccaagttac
21241 ccatctatgt atatactgag ctgaccctga gacatggcaa aatgtgtgaa gatggtactt
21301 gagtgagtga agtttgggca atgttgtttc tagtgaattc tttctccttg gtggtttcct
21361 ctggcctgtg gatatacttt attcagcaaa agatgccagg gctgagggga tatggcctct
21421 ggtctgccac ccagagggta aacttggcaa gaccccagcc aggctccccc tcctctgctg
21481 ttcctaaaca tgcattcatg gacaaggggt ctctggagca aaggagagtg actccttccc
21541 tctcccgcaa ccttgcccac ttaccttgta gccagccact ccctcctctt tctgtaactg
21601 ggcattggtc cagctgccag gccaggacc tctcccattt agccagatgt agttccaaaa
21661 acaactgcag cagtatttgg atacattttc cagcctgaac tagtggtgtt cctgtccata
21721 gctgggatcc aggtttgttg cctctgggtg gggctacagc tccttacctc ctggaaggtt
21781 gtggaagtgt ggtttccttt ttctcctttc tcttgtggaa cataagcatc tttccaagtc
21841 cttctggcca gatgatgatg gtgtgagcct gtccgtctcc catcagtgct gaggggcctc
21901 agatgctgcc tcttacctat aacccagatg ctcccaggtg tgtttatttc ctagagctgc
21961 tgtgacacag agccacaaac tgggaggctc agaacaacag gcattgttcc ttgcacagtt
```

Figure 4 (continued)

```
22021 ctggaggctg gaagtccaaa atcaaggtgt tggcagggct ggttcctacg ggaggctctg
22081 aggaagaatc tgttccaggc gctctcctgg ctcctggtgg ttgctggcaa tccttggagc
22141 cccttgactt gtagatgcat cactccagtc tctgccttca tcttcacatg gcgttctccc
22201 tttccctctg tctctgtgtc ttcttctcct catcttattg tcatattgga ttaagggcct
22261 accctgcatc agtatggcct cgtcttagct aatttcatct gcagttaccc tatttccaaa
22321 ggtcacattc tcaggttcta agaagtacat gaattttgag caggataatg tatggcccag
22381 tgcaccaggc aatgccaagg gcatcactag gtaggaggct ggagatgact ccatttctgt
22441 gagctcctcc ttggctcctc tgtgtctttg cttctaacag cctgtgcctg ccactctctc
22501 tcgagggctc cccttgagct attagagggg ctttgtgtgc acaaaattca gacacacaca
22561 cacacacacg cacatgcaca tgcacacaca catgcacaca tgcacacaca cacacatata
22621 cacacacaca cagagccaga gtgcctggat attcgtgacc cctggagctg tcttaccatg
22681 gtgatgactg acaggtgggc agggcacggt ggctcacacc tgtaattcca gcactttggg
22741 aggccaaggc aggtggacca cctgaggtta ggagttcaag accagcctaa ccaacatggt
22801 gaaaccttgt ctctactaaa aatagaaaaa aattagttgg gcatggtggc gcatgactgt
22861 aacccagcta cttgggaggc tgaggcagga gaatcacttc aacctgggag gcggaggttg
22921 caatgaaccg agatcacgcc attgcactca agcttgggca acaagagtga aactccatct
22981 caaaaaaaaa aaaaaaaaaa aaaaaaagga atgactgaca ggtgcacatg cagaagcata
23041 gaagcccaga tccctggcct gcagttgggc acaaactctg aggtgtaact tatactccgg
23101 agccccccac aggtcagttt caactggcct caccctccat gtctagctcc ccctactctg
23161 acactggctt gtcctgggag tacttcctta agaaatcact ttcatgtgaa ttctcttctc
23221 aaagtctgct tctgggcagc ccaagctgaa acagatcccc atacctggag cctgctgcag
23281 ccaggactga tatgcaggaa cccagcccag ggagccacaa agggatccac ctcccccggat
23341 ccaggggttc atgattcatg ggcgatggtg ctctgtaaat gggaaggccc tctgtgaaca
23401 ctggggtgtt tgccacgcat tgtgctcaat tgtcccctct atgggcgggc cttccccaac
23461 cacaccatcc aagatattct aatcttgtcc tttcaggctg ctgatcaact agttcaggag
23521 tcactgtgga catgtcacac ttcttcctcc atgagatgga gatgaccaaa tctattcata
23581 gttctgtgtg ccaacctatg aaccagacct gagcccctta cccctctgac agtcggcttc
23641 aggaaatcgc catgaggcta caggtgtgtg ttgaggggtg ggtagagaca caacataagt
23701 gggtggcgtg gggtctggca cacttcttca tgtaacccac ttgtacctgc tggacctgcc
23761 agtctcaatc ccaaatatca ctgtagcatt tctcttttt ttatattatg acaaatactt
23821 atttatttat ttatttattt atttatttat ttattttta atttattttt aagttccagg
23881 gtacatgtgc agaatgtgca ggtttgttac gtaggtaaat gtgtgccatg gtggcttgct
23941 gcacctatca acccatcatc taagcattaa gcccagcatg cattagctat ttatcctgat
24001 gctctccctc cccacgcacc tcctgaaagg ccccagtgtg tgttgttccc ccaccgtgtc
24061 cttgtgttct cattgttcag ctcccactta tgagtgaaaa cacgtggtgt ttggttttct
24121 gttcctgcat tagtttgctg agaataatgg ctcccagttc catccatgtc cctgcaaagg
24181 acataaatatc gttccttttt atggttgtat agtattccat ggtgtatgtg taccacattt
24241 tctttatcca gtctatcatt gatgggtatt tggattgatt tcatgtcttt gctattgtga
24301 atagtgcatt gtagcatttc cattgtacag tgggttactg ctgtgcctgc ctcacattag
24361 gatttggtgg atctggtcat agccagctca cagagggaaa ctcagccagc atagttgctt
24421 gatgtctcat ggtcaggctc tgagtctctg tagggttcag tagcatgcca gcaattgttt
24481 ttcaaaagga gagtagttct ccactgcaga aaattttaga ggtctgtact gggactcttc
24541 tactggggtt tgttaaaggc tccacccaag ttctttatct agcaccataa atcttctcag
24601 tctcatggct agcagagcag ctcacactgc agcttggacc tatgcagcgt tctcttttgc
24661 tttgtctcag aactgaaagc tttctgaatt gcctaataaa taggtcagag tagcattccc
24721 aagtgtggta tatgctgctt tgaaattcaa ggagaacaaa gaaggtgggc ataaaacaac
24781 agaaggacag tttctcgcag ctgggggagat cagaagtctg aaaccaagat gttggcaggg
24841 ctgacacggg caatacacga ggcccgtgta ttgcctcttc ctgcttctct tggctccaga
24901 cattccttgg cttgtggctg catcactcca atctgcgtct gtggtcacat ggcctcctcc
24961 tcttccctat gtgcctctgt tctgtatgtc tcttataagg acatttgcca ttacatttag
25021 gacctgcctg catcatccaa gattacctcc ccatcttgag atccttaact gaattacatc
```

Figure 4 (continued)

```
25081  tgcaaagatc tgttttccaa ataaggtaat atccccatag gttctggaaa ttaggacatg
25141  gacatatctt cgtggtgggg tggggggtg cttttcatc ctactgtatg gtagaggtgc
25201  aaatgcagca acttgtcttt ttttctgaga ggggatggct tggcatgcct cagatcacag
25261  gttccttaag atcttcatca atacggggga ccctgaattt tcagaggctt tatcttccac
25321  tctctggtgt gcatacattt ttgttttgtt ttgttttgag atggagtctc actctgtcac
25381  ccaggctgga gtgcagtggc acgatcttgg ctcactgaaa cctccaactc ctgggttcaa
25441  accattctcc tgcctcagcc tcccaagtag ctgggatgac aggtgcccgc caccatgcat
25501  ggctaatttt tgtatttta gtagagacag ggtttcacca tgttgaccag gctggcctcg
25561  aacgcctcac ctcaggtgat ccacccacct cagcctccca aagtgctggg attacaagcg
25621  taagccactg tgcccagcca tatattttat taaagcatct tgggttcttg ccattttcc
25681  tccttaggtt tagagcagca ggagcatggg agcaactgtc cagtgaaggg ggtctgttga
25741  gaggctcacc cacagcatcc actgcagtgt ccttgatcat cttgacaccc cacgctacca
25801  cccaggtccg tcatgttaac attgtgtgag cattggctgc aaactgctca catctgcccc
25861  cttctctgga gaattgctct ctgccaaaca gtagacatct caccgtggag gttatgctcc
25921  tttgggggtg tggcaagtct tgccaactga cttacctgag gacacaaaaa gtctgctatc
25981  tggaggggac aagtcagtgc tgtaattaat gctccaaagg ccctcatgag accagaatga
26041  ggctggcctc cagcccaggg atgtcataga ttaactttct ttctctgctg tgtcctgctt
26101  ccctctttcc acttcccctg aaagtcctcc ccacaaaaat ccccacctct tgatctgctt
26161  ctagggaaac ctgacctaag agattccttg ggtgtattag tctattctca cgctgctaat
26221  aaaggcatac tcgagactgg gtaatttata aaggaaagag gtttaattga ctcacagttc
26281  ccatggcagg ggaggcctca caatcatggt agaagagcaa ggaatgtctt acatggtggc
26341  aggcaagaga ggatgagagc taagttaaag gggaaactcc ttataaaatc tcgtgagatt
26401  tattcaatat cacaagaaca gtatgaggga aaccacctcc atgattcaat tagctcccac
26461  tgggtccctc ccacaacgta tgggaattat gggagctaca attcaagatg agatttgggt
26521  gaggatacag ccaaaacata tcattccctc cctagcccct cccaaatctt atgtcatcac
26581  atttcaaaat caatcatgcc attccaacag tccctcaaag tcttaactca tttcagcatg
26641  aactcaaaag ttcacagtcc aaagtctcat ctgaaacaag gtaaatccct tctgcctatg
26701  cacctgtaaa atcaaaagca agttagttac ttcctggata aaatgggggt acagggattg
26761  ggtaaataca gctgttccaa atgggagaaa ttggccaaaa caagggact acaggcccca
26821  tgcaagtcca aaatccagtg gggcagtcaa atattaaagt tccaaaatga tctcctttga
26881  ctccatgtct cacatccagg tcacactgat gcaagaggtg ggttcccatg gtcttgggca
26941  gctctgcccc tgtggcttca tggggtagag cctccctcct ggctaatttc acaggctggc
27001  gttgagtatc tatggctttt ccagatgcac agtgcaacct gttggtgggt ctaccattct
27061  gaggtctgga ggatgatggc cctttctcac agctccacta ggcagcaccc cagtggggac
27121  tctatgtggg ggcttcaacc ccacatttct tttctgcact gccctagcag aggttctcca
27181  tgagggcctc accctgcag caaacttctg cctagcatc cagttacatc ctctgaaatc
27241  taagcagagg ttcccaaacc tcaattcttg acttctgtgc acccacaggc acaataccac
27301  atggaagctg ccaaggcttg gggcttccac ctctgaagcc acagcctgag ctgtaccttg
27361  gcccctttta gatatgacta gagcaactgg gatgcagggc accaagtccc taggctgcac
27421  agagcagtgg ggctctggac cccagcccat gaagccattt tgtccttcta agcctctggg
27481  cctgtgatgg gaggggctgc cacaaagtct ctgttatgcc ctggagacat tttccccatt
27541  gtcttggcga ttaacatttg gctcctcatt acttatgcaa atttctgcag caggcttgaa
27601  tttctcctca gaatatggat ttttcttatc tattgcatca tcaggctgca acttttccaa
27661  acttttatgc tctgcttccc cattaaacat aagttccaat tccaaaccat atctttgtga
27721  atgaataaaa ctgaatgctt ttaacagtac ccaagtcacc tcttgaacac tttgctgcct
27781  agaaatttct cccaccagat gccctaaatc atctctctca agttcaaaat gccaccagtc
27841  tctttggtaa aacatagcaa cagtcacctt tgctcttcct ttgtcttctg ccatgactgt
27901  gaggcctccc cagccatgtg aacagagag tcaattaaat gataccatga tggaggatgg
27961  agtgagggag tcctgaggct ggaccatgaa ggtgctctgc tgtccctgcc atgtaaactg
28021  ctctagtgcc tctctgctgt tggatatcag gaagaaagga tttaccaaat tggtagctgc
28081  ataccaaatt ccagagacag tgttgatctg ctgtagtcaa gatgccacaa ctggtacagt
```

Figure 4 (continued)

```
28141 gggtgaaact ggactatgcc tggctatgtt tatgtagtcc acagtcagct cctctgagag
28201 accttccctg accatcttat ctaatgatgc cttccaactc ccagtcttcc tccatcatat
28261 tctcctgttt tattttttg tgtactgatt actgtctgta gccatgtgat ctatttattc
28321 gtttatggcc tttctcccca attagggtgt aggctccagg ggaataagga cattgtgtga
28381 cttgtttgca gctgcatccc aagcacccgc cactgtagta gatgcctaac caatgtgtgt
28441 tgaatgaata aaagagcagg ccaatgttct tttgctcaaa gtagagggga agaaataggg
28501 ttttctgtgg agattccaag gcagaggcca tttctggggg tcactggagt gggagaaggc
28561 aggtcaaggt gggttgtctt ccaggcagtg caaaccccct ggcctctgcc agctgctcac
28621 tggccagtct gcttgttggg tctggcacag gcctcaagga aacataacat ttttaataaa
28681 acctcagagt caataaaggc gaatggtcct gggtgcctct cctgccggcc ccagctgttg
28741 actttagaag tcaagagagt ggggcgttgc ccaattctca tgtagtacag ggagatataa
28801 gctggaaggg cctagcccat tttatatgaa aacaaaacaa aacaaaacaa aactcaccag
28861 gccctggaaa gagtccacca ccagccagaa tcaaaggtcc attcagagcg acagagctcc
28921 tcacattcgc cgctaatgaa aaccaaattt ctcatccctc tgagcatttc cagggctac
28981 aaatggaagg ggctgcagag tctttggcca ccgctcccac caccgaaggg gccccactgt
29041 gttaaaatag ttttatgata atataggcct tgtattttcc taatttcagg cgtcagtgat
29101 ttaggacgga gttgttttca tggaaaaaga aatagaacct gtttgtggcg gggcaagact
29161 gatgcctggg cagatattcc cactgtgggc atatttgggt aggggggtga gcctgccatg
29221 aagaggctca gacctagctc cggggaggcc tcgttcatga agttcccgc cttgggcggg
29281 gaagaatggg ctggggtttt ccagacagat tcagagacag tcacagtgac ttctgttttt
29341 tgatttcatg ctttgtgaaa tcttagaatc acaactcaga aggtagagg catccctctc
29401 agacgcagag aaagggcctc tgttttttta aaaagacatt ttctcatttc ttttcttt
29461 tttcctcccc cttgatcaat ctttataagc aagtatgtgt agaaatgtca tatttttt
29521 ttcttaaagt caacttgatt cttactttga gcctccaata cttttagttg gtaggaaact
29581 taatattttc agcgactgct ctgccttcgt caggatcagg tggaattctg tccttgttc
29641 tcagttttgt tttgttttgt tttcagatgg aatctcactc tgttgtccag gctggagtgc
29701 agtggcacaa actcagctca ctgcaacctc tgcctcctgg attcaagtga ttctcctgcc
29761 tcagcctctt gagtagctgg gattacaggc atgtgccacc atgcctggct aattttgta
29821 tttttagtag agatggggtt tcactatgtt ggccaggctg gtctcgaact cctgacctca
29881 ggtgatcctc ctgcctcagc ctcccaaagt gctgggatta caggcaggag ctaccgcacc
29941 caacctgttt ctcagttttt tttcatctgt aagatgggga gaatgataat acatacctca
30001 atgggctggg ttaaaaaatg gtgaaatatt tagaatagtg cctggcacag agtaagtatt
30061 aactattatt attattattt ttattattcc agagataaag agaaggcatc aaacctagta
30121 tgagggtatc agggaaggct acctggaaga ggtggtgttt cagctaatga cagatgaggt
30181 agtccttgca tgattttgaa ctcctctgct tggacattta tgtctagaat ttgatatgct
30241 ataccctgaa caagtgtgct aattttagaa aactgtaaag aagaaaacag aaaacagcca
30301 taatcccatc tttgcattga tttcattctg gattaatttt atctctattt ttaactatat
30361 taattgataa cctgtatacg cagtgtgtgt ctggctagaa aaatgtttat ttctaaaaag
30421 tatttatata tttataggaa ataaagatct gaatggggga gaaagccta aaaatattaa
30481 cagtggttat ctttggaggg ggggattatg gctcattttt ctcgtgtgtt tgttggtaat
30541 ccggactgtc tactttccct ctcatgatta tatattagtt tgtgtcattt aaaaatgtca
30601 tttagtctgg gcatggtggc tcatcctgta atcccgacac tttgggaggc caaggtggaa
30661 ggtttgcttg aggccaagag tttgaggcca gcctgggaaa cgtaacgagg ccctgcctct
30721 aaaaaaaaaa ttagccaggt gtggtggtgc acacctgtag ttctagctcc ttgagaggcc
30781 aaggcaggag ggaggatcac ttgagcccag gagttggagg ctgcaatgca ctccagtctg
30841 ggtgacagag tgagaccctg tctaaaaata aaaactaaaa atattactta aaatgtaata
30901 tatagaactc aggaaccgca gatggagagt ctcataatct ttatattttc agaccatgaa
30961 ggagagtggg gtagcttggc cggactctga gcgtcctgga cccacaagtc tgagaggaga
31021 ggctgcatgt ggcctctggt atggtcacat ggttctataa ggaaactgag gcaggacata
31081 aggcttcact tgtgaagtgg tggagaggga ggggcaatt gccaactggg tgataataaa
31141 gactattgtt aagaccttgc ccccagtggc acatgaaatg ccactaaccc tgagagattg
```

Figure 4 (continued)

```
31201 agagacattc aaacctgagg tttggggcat ggtgcccttc ctgtgacttt ggtgctaatg
31261 atgtctaaga tacctcttag ctcctccctc tgtcattctg cacaggcttc tcctttgcct
31321 ggactatttt agtagcctgt gaacaggtct ctggaccctc atccccagtc cgcaccatga
31381 tggtgctccc atccaacaca tacatctccg cttggctccc ccgtgccact gacccctgac
31441 atggatcctc tcccacctcc catcaccatt gcgccacttg ccccaccatc ctcccagctc
31501 agcgacacct ggttctccag gcctttgcac atgggattcc ctcctgccac atctctgctt
31561 gatccattcc tactcatctt tccatctgat ctcgggggag agacattttc tctgaggagc
31621 ttggcttgtt tgccctgatc cacactgggc tggcacaacc tgctttcctg tctgtctgcc
31681 ctgtgagatc cctgaggcca tggctgtgac ttgttcacct tgttcttggt gtctggcacc
31741 tgagggtggg gtggggctct gtgtctggtg aatgagtgaa tgaattctgg ccaaggcctc
31801 aaagacaccc agcccaatga gctgagtggg gtggtgtggc ccaaatggtg tgtttggaca
31861 ccagagagcc cacattgctg ccagccgtca gggtgggcac aaaggagggt agtccaggcc
31921 ggctccaggg ctgccgcact ccccttccca tgataggtcc cctgggccag gcccagggca
31981 ggccctttct gtgggtgaat ataaatatat aaaacacaca gcgcactctt agctgcaaaa
32041 ctaaaaatag gaagcgcggg atccggctcc ccaggcttcc ccagccactg gaccacacag
32101 gtgtggctgc ggatgtcggg gcgatgtggc ccctcacccc tcccagctct ggagccctca
32161 tggggaggaa tgagggcat tttggatttc tgccaggaac agttcattct ttcactctgg
32221 cctccctcct gcccccgtcc catttgacag ctcatttcat ttacgacccc aaaatgaacc
32281 gacccactga ggtgtattct ctactcacgt ggccaggctg ggttgtttgg tgcagctgag
32341 agctgccctc tgggccatgc tgggggctg catttatgcg ggggtgcagt ctggagcaga
32401 ggagaggccg gggctgagga gggaggcagg gctgggtctg catccagccc tgccctcccc
32461 tacccacggc actggccca ccccgcgcca tctcctcaag ccctcaccag gccctaacgt
32521 gggaatgtgc catctctggc ctgtagcctc actgccagga catccattgc tcagtgtaaa
32581 agccaaagcc atccccatgg ccacagccca acagtggcag ggctgctcct aggggccggc
32641 aaggcgggtc catctgggcc acttcacccc acaggaggcc acttctggga ccccccaggc
32701 cacagccggc tctctgggtc catcattggg cccatctggg ccaacctcaa gctgtggggg
32761 ctgaagaaac tggagggact caaagtccag cccagatcaa caggactcct agagcctcca
32821 aagcggaatt ctggagtcca ggggctccca ggctgtggaa ctaaatggct tcctcaatct
32881 gaactggctt ctacatgacc taagctcttg ctggtggctc aggggacatg ggtggggctg
32941 ggcccagggt ccaggaggcc agggttgtaa aactatgaaa gtcaaccctg ccttcaagcc
33001 aggtacaccc tgtcccaaag cagacgatta tggggtgtgg ggtcctactc cacacctggc
33061 acacggccgg tgctcattca gcgtatgacc aaaaagggag actcagagag ggacagggac
33121 ctcccactgc cacacggctc gggaagggaa aaccttcccc acatcaagac ctttagctgg
33181 ccctttcggg aatgagtcac ctgaggttgg gaagttcttc ttaataccttt acctgaattc
33241 ttgctgtaac caaggcagcc tctcctcacc cttgtccaaa ggggatgatg tccactctct
33301 ccacctgctg cccagggatg ccgcccccta ttgccacctg caggctgctg tggctactgc
33361 agcacttcct cccgcagccc tgggacctca ggcaagctga gacttctcgg gaccttgagt
33421 ttccccttgg caagctgggt gtgctggttc gtgcctgcta gggtgcaggt gatggagatt
33481 tgagtcagga actctggagg gcacagctcc tctccgatct gctgtggcac caaagtgtgc
33541 ctggtgagga gtgctaccat ccctacaaa gtgacccaa ataaatagaa acagttttgg
33601 ccatgtagat gccgtttcag gaccaaccct ggcagaggct gcccagagca gaccaacaga
33661 gaagttctgt agccacggct gaggtcctgt ccagagatgg acctgctgtc ttttgggtaa
33721 aaggggatgc cgggctaggg aaatggaagc ttcttgttgg gagctgagtt tcaggcagac
33781 caaccaaact gagcagggca aagctttggg agtggttttt gaagtcggtg ggcatcactc
33841 aaaaataagg tctgttttgt aaaaatttcc cttcacaaat cccaactggc caggctctgg
33901 gctgtgtgtt ggtacaaatc ccaagtggac caggcctcct tgctggcaag gtgggagggg
33961 ggctgtcaag ccaggtcccc acaccatcac acccatgcta ccattgttgg gctgtggtcc
34021 cagttcagcc atggacaacc ccagggagac atggaccttg atgacactcc ttctttgcac
34081 cgcagttgtc tcatctgcaa aatgggggca ctgaagttgc cgcttactcc caatccccac
34141 tgctgctagc ttgccacaga tcttgaaaca cgagcctcag aggggggttc tcaccaaggc
34201 acttggactc tccctctgcc tctgcccct cccgaaatgt gaatctgagg aacaggcata
```

Figure 4 (continued)

```
34261 ggaattcctc ccaacacggc tgggaagact cacagcccgc tcatgattgg tggaagggtt
34321 gtggcacttt gaagacctat ttgatgctct cctggggtcc cagccataca ggagcaggcc
34381 tcaccggctg tcctgtggcc agggtggtct ctgcggccat tcctgaagaa gttggaagca
34441 aggagatgaa ggtgctgggt gtctctgttc ctgttcctcc tgggcaacag caggaggtct
34501 ccatcctctc ccccacccca ccccacctcc atgcatagcc ctagaaaccg ggcactggac
34561 tccttccaca catctcagag ttatattatt gtaacaaatc agtcaaaatt ccattttaca
34621 gttaaatagt acagaagaca gtttactgta caagcaagtt gtgcgttaaa aacaaacacc
34681 aagcaaacga tagtgcaaag cagtttccac ccagctccat cctctcgcca gctctgggat
34741 ggttttacat cagatgagtg cagcaggtgt cacacctcag catgacaata tgtcacaaaa
34801 gattggtacc cactactgac aggctcacag taacactata tcaaaacgtc ttcctttcct
34861 cgtgcttcct acatcagtgt gtttgcctag tacaacttta acgcagcctt gtaaataagg
34921 acctactttt accagcccag gctgtctgta cccactttgg gccttacaga ctcagtacgg
34981 ctgccgtcac tttttgtcag gggatggggg atggggtagg aagagcaatt tatttactat
35041 ccctgcctct ccaggatcag gaaggttag taatctggga tgagactaca aagtgctggg
35101 cactgggaac ccaaaggtgc ctcccacgct gacctgggac cagctataac cagagaacag
35161 gagggaagaa actacaagga caatggattc atagctgctt cctaagaagg catggagagg
35221 cccettgggt gcagggagtc agcaactatt ttgaggagat ggagactgtt tttccagtga
35281 ggacaggcca agagaaaccg cagcaggagg gaatggaata ggatcaccag aaggactgcc
35341 taacctgcca gtgtgtctct ggtgtatggt tctggccgtt gtgacaggtt gggtgggac
35401 agtgctctca cagagacaac caatgaagag cattttgtag ggcagatttc tgcatccaca
35461 gaggccgagg cagaaagtta aaataccgca tgctgctagc ctttatgagt tcccttacgc
35521 cttttctaag cctttctagg gccagagaac tctgatgtga gaatccatgc agcctggccc
35581 ttgggcaagc gcccactttc ccattttgca aaattcaggg gcaagacttc acctcggaac
35641 gcagtgcagc tgagctgcgg ctggagagcc ctttacagtg cttctgtcct gccacgcaca
35701 gccagtactc cccacctctc acatcctgcc cacctccgcc cagcctcctg gacagatgtc
35761 ctagagccac agaggagaga tgcccagcgt ctcatcagcg tttccctcgt cctcccaggg
35821 gagcctgtgg tgcaggctgg tgggatgctg cctgatgggg agtgtagccc cttgagaaag
35881 tattgagacc ctaataaccc cacaccctca ggaggcagct ggggtccgc ggggggaga
35941 ggggcgggg atgttgctta taatcacaga gctatcataa tcacggaact atacctgtaa
36001 gagaccttgt gtttgaaaac gttagattaa gcttcttttt ctaaaatcag ttttaaaaac
36061 tgttttgttt ttttttgtt ttttgtttt tttttttttt ttgctcagga ctatttgctt
36121 tcagagcaca aaacaggtta cagacaggtg tgtgccagga gtcgcaagat ttggctggat
36181 cctcccagga ggcttggggg atgggcaca gcttggctgg acccaggggg gacagggaca
36241 ttgatgtctg acccaaaatg atccctcacc tcaatgcctt ctgctaggac ctatctatct
36301 ggccctcctg ttctctccac aaatggaatt atgagaccac ctaggggaaa ggggacctcc
36361 tatccccct cccccgccct gccaagagaa cagagagtgg atgcgttgag ctggtaaagt
36421 gcatggagga gccggtctgt aggtgctttc ctgggtttaa gaacctgatg ccatagactc
36481 atcttctctg gggcctggga cccgtgcggc tgggggaaag ccaacagtta ggaacggagg
36541 ggaagctggg ctgggggac tggcttggat gtgttctcaa accatctctg ccagcagcgt
36601 gctgggtcct gccccatctg tacaatgagg ggaacccgc tcgagggtgg tggggtggg
36661 ggacactttc cagttctgac tcaaatctgt gtaaatgcag aggggctgg acccagggga
36721 tgcaggggct ccaacgaagg tgcagggtc gggaggtttc ccaggcctg aggcttatcc
36781 tgtgggccaa tgctgcctct ctctggaaga gagatggcct ctgtcccagg agacatgggt
36841 cccatgcagc actgggcata gctggagaca gtgaggtcct tccggggggg tggcaggagg
36901 ctgattcccc acagaagtat gggatgagac ggccaggatc tgggccgggg gcagtatccc
36961 gggccgggggt ggggtggta acctatgcct ctgtacaagg atgtggctgc acagatgcag
37021 ccagaggctc ccaccagctg ggaccaccct gggaccgaga ccaccctgga gcgcaggtcc
37081 cattcccgcc cggagcctcg gagccggccc atcactggtc ttgaaggttg ttagggtccc
37141 cgcctccagc gggaggagtc caccagggcg gtcagtaggg ccgcacacg gcctcatcca
37201 tgcggcctgg cgtgctcagg gccgtgggtg agttgctgtg gctgccgtcg gcctccacgc
37261 catcactctg gccgcccagg ctggggttca tgaggttgcc ggcggcgaca gaggcagcgc
```

Figure 4 (continued)

```
37321 tgctggtgca agaggccagc atgcgggtag gtgagcggtc gcccccactg ctgctgccgg
37381 ccaccatgga gaactggtag gagccagagg atgtcccgta gtagaggtgg taggggacg
37441 ggttggcctg gaagggcccg ctctggttct gcggggcccc cgggtagggt ggcgggaggt
37501 aggtatggtg gaagcggctg gtggccggca tgcccgccac gctgaggctg ctgatgctcg
37561 tgcccgaggg cgtggcgctg tagggaagg cagctgacat ggccccggga taatgcatcc
37621 tggggtctgg gaagcggctc tccgtgaggg ttggcagcgt ggggaaggag cggtcaaact
37681 ggcggggtc ggagaatggg ttcagttccg aggtgcctgg aggacagcag ggaagaggtc
37741 agttccagct cgagacaacc caggagggc ttcctgaaga atgaccttgg gctctggttc
37801 ccaaggccca tctgggggac ccctagttct agacctggct ctcctcttcc tgccctaggc
37861 tgcccggggc ctcccccgcc aggactccga acacagacct gccgggaagc tggttggagc
37921 gtgccccggg ccaagagggg ccatgggagc cccccacag cagcaacaga acagaggagg
37981 gggtctattc ttctttttaa atcctccttc ccagcctcgc agaggagagg cctaggatgc
38041 ggtggtgggg ctgagggcag agtcagctca ggcctcccag cagccctgcc caggcaggtt
38101 cctctcccca ccggcccatg ttaacagctg ggaaggccgt ggatgtgtaa agggctccaa
38161 tgaccgtgtg agactgggag ttggaacccg cttttgaaga caagaaaatg gaggcagaga
38221 gagagcaaga ctgagtctct gtggcagaga aaggactggt tctcatcaca aggcctctgc
38281 tggggacaca cgtgcctctc ctgcccaggt gcagcacgcg gaggttctgt gcgctcacac
38341 ctgggttgtg ggcactgagt tcacaggagc tctggcctcc acctcaccct gggcctgtgt
38401 ctctggagcc gactcgtggc cacacagtga ctggatgcca ccctaacctg ccttggcagc
38461 aaagtgagac agcagtcaga caaacttggg gacccagacc caacctggt cacagtgtcc
38521 agcccagact ctgcccctgc tcccccagga atgtggcttc tcaatgggct ccaaggcaag
38581 ggtgttccat cctctgtccc caacttttgt catcacagac ccccaaaacc tcagcattca
38641 aaggggctca gggattgagt ctaacaccct tgatggggaa actgaggccc agacagggtg
38701 aggcacttcc ctcagggtca cacagcacat tggacctggc acacaatcct agggcctctg
38761 gtcctgagcc ccaacacgta cttgagaggg agctgtcccg tctttgaggc agcacaggat
38821 caaggcttac tgtgtggctt ctggagccgg acagttatcc tggtttggac acttactagc
38881 tttgtgtcct tgggcaagtc acttaacctc tctgcgcatc agtttcccca tataaaacat
38941 gagacgataa cagttcatca ggattcagtt aattcacatc gagtacttag aatggcactg
39001 ggcacagagc aggggtccat gaggctttgc aaggccactg tggctgtggt gtctcttact
39061 ctgggtaccc aggagaactg gctcattcag ggccctgcca agttgaggcc ctggtgcagg
39121 gcctcccttc tactctggca gccgggggag gtggatgagc ccccagcagt ggtccagagg
39181 tgcagtctgt ccagcccagc aaccctctg tgtcacccac caaaggataa gggccggtgc
39241 tagccggagt gggctctgcc tgccacgccg aggcttggct gaggacggag agctatgagc
39301 ctgaggtgtg tgtgacttcg gctgggactt ggaacttctc ggggctttgg ggtcttccca
39361 agtcagctgg ggtatgtttc cctcagcagc gtactctggc cctgggcgtg atccgaacg
39421 gagtgatgct cctggcttaa ggtaagaaga tgtggggaca gcagtctggg tggcggggc
39481 cttctgggac atctgggatg ttccctagta ggtcacttgg ctgtcccggc ccttgaggc
39541 cgagagcctc cgaggcacct ggctgccagt tttcatctgg ggagcccctc gggggagag
39601 gtcctgttgc aggtgctggg cacgtcagca cagctgagat gggtggggtg gaagtgggtg
39661 ctggccgcct gatgggaacc ccattctcaa gacgaaggaa acaaatgggg accgcaggat
39721 acaacggcag gactgtgccc ctcagagctc acgcgggctg cagggcgctg ggctgggcct
39781 ccctggacct gccaccatcc cctccagcct cttcctcag ggccaccacc cctcctcgg
39841 ggtggtgggg gaagtacctg ccctcagcac tccctcagac ccccagcag cttccttgga
39901 gctcctgtac ccccaccctg cggcctcgca gccccaggaa acccgagctg cccggggcac
39961 tgtcgagtgg ccaatcccaa cagtggaaag aaatgtttat tttcttctcc agattgtccg
40021 ggctgctgca tggtggctga atgagccctt tcagctgtga gaagcccca ttgtgggcgg
40081 ctgcggctgg gggctggggc tgggtatgg gaggtgctgg ggtctctgca ctgcttgcca
40141 gtgaccaata ttggagggtc aaagcactta acaggcaccg agggaagtgg tggtggggtg
40201 tcccaagggg gatccccagg agggagtccg agggcagagg gaggagggcc tgtgagagtg
40261 acttcccaag cctaggtctg ccagcaaccc ctctttgtca gggacctcct tctccccact
40321 tcacagatga gaaaactgag gctgagttta agtgacttgt ctaagatcat acagccaatg
40381 cctggcagag cctgaattcc tagcctggtc cagctgactg cagagttcat gctcgccctg
```

Figure 4 (continued)

```
40441 tcctggtcat ccgaggccct ttctctcacc caaaggggat gggcctgagg atggagatgc
40501 ctggctgcct gtggcccagt gctgtggggg gctagcgagg gactgggcca ggcctcagga
40561 gggagcaggc agagaagcag aagtcagcca ctgccccaca caggctgggc tcctttcctc
40621 ccagcccagg atggaagcag cagctgtgcc tgccgtgggg ccaggcattg attcccaagc
40681 tgtgcccacc cagcagtgga tgggcagatg tgggctctcc ttccatgggg gctggtggac
40741 aggaagccac tgttcacccc acctcctgga ttctggctcc cccgctgagc ccgatcccc
40801 tggcctggct ctgtccatgg cagagaaagg ctggctctca ggctactgca cctcgacaga
40861 tgctggccca tgggtagcag aagcagaggc agctacgcgg caggggtggg cgtgagcaca
40921 gcgtgcaggg ctccttccgc tacctcttga gagcagacct ccaactcctg ggctcgagag
40981 ctgagagtct caaatgcact agctcctggg ctcagagagg ctgggcctgg ggcttctccc
41041 aaccttggcg tctcagcagg accaaggcca aaagtcctga gcccaggcca gaaggggagg
41101 ggtcctctct tcacactgaa ggcctgcatc cagcccctgg ctgcagcact atgcctggaa
41161 caatgtcagt agagagaccc agtcggcccc cacctcagcg tggcaccgga aaaggggggtg
41221 gggcaggcag accggttggc agccctgttc caggcccctt tatctgtccc ctcagaagta
41281 cagaaagttc ttgggagcag gtactgtgga gactgtggac ctggtcacag atgggctgtg
41341 tgacccgagg gtggctctga acctcttagg cctctcaatt cattcatctg ccaagggggtt
41401 ctaaccaggc tctggggaat tgagaaagaa tgggcacagt ccgtgacggc agccagctgc
41461 ctgcctctgt ccacccggcc accaagcacc cttggcaccc cacttagccc aagggccggc
41521 tgtgcacaca gcctcccatg tccccagctc actgactgag agaacagagg agagatgcag
41581 ccggcagccg tttagtgagc ggctactatg cgccaggcac ctcgatactc cagaagacct
41641 gcctgaggcc tggctgcaac tgtgcttgct gtatccgtct aggcagtgga gatggagacc
41701 ccagctcggt cttcccttcc acctcagctc ctcctgtttg ggaggatgct ctgggcaggg
41761 tgggagacct ttcccaggaa tgctatgtgc ctctctaggg ttggaatgtc acttaacagt
41821 gtgcaaagtt tgtgtgagta cagtaatgtc atttgaatgt catcccagcc ctgggtggag
41881 gcatccgccc caatccactt tcagatgaaa aatcgcaggc tgtggggcag gggtggggaa
41941 actgtacatg gcaggggcga gtctgtcacg gctccttgga caagtcatgc cccaatttta
42001 ataggggcac tatgggggtta accccatttc cccaggcaca gtgaactcct ggtatgcaga
42061 tccctggggc caggcaccag gcatgtgtca gtaatgtcag tgtttgctga gtgaacgaat
42121 gatggctagc acacagaaag cccacaggaa ccgtctgcag gtgccaatga gcaccagcag
42181 ctcctctaca aaacaagggg gtgcagtgac tgatcttcgg acaggctttt ggtctgggggc
42241 agattggacc acatcgaggc cctccacccc cacctcaccc cgctgcagcc cctccctccg
42301 tgccgtacct tggattgggg tctggggctg gctgctgaag tggcttgtgg tgctgagtga
42361 gcctcgggg ctgggtgtgc tcggtgtcac ccgcatgcgc agccgttcca ggtccccaaa
42421 gcggtcaggg aacggcttgg tctggtcctc cagcttctgc cggtgccctg cagagcacag
42481 gaagcccatc agccgttgct tccccagagt ctcagtggag acagaaatgc ctcactctgc
42541 tgggaagttc ttcctgaggt ctgaccttag gcctctgctg ggagaaccct gaggtcaccg
42601 ccagcctctt cacagaggtt ttcaaaagac tttctgaaca gagaatggtc gttatgtgcc
42661 accccacata tctaaacctc tacaacacac ggtgatccaa acctctacaa cacgcggtga
42721 tctaaacctc tacaacacgc ggtgatctaa acctctacaa cacgcggtga tctaaacctc
42781 tacaacacac tgtgatgtaa acctctacaa cacgcggtga tctaaacctc tacaacacac
42841 ggtgatccaa acctctacaa cacgcggtga tctaaacctc tacaacacac ggtgatctaa
42901 acctctacaa cacactgtga tgtaaacctc tacaacacgc ggtgatctaa acctctacaa
42961 cacactgtga tgtaaacctc tacaacacgc ggtgatctaa acctcaacca cacgcggtga
43021 tctaaacctc tacaacacgc ggtgatctaa acctctacaa cacgcggtga tccgaacctc
43081 aaccacacgc ggtgatccga acctctacga cacggtga tccgaacctc tacgacacgc
43141 ggtgatccga acctctacga cacgcggtga tccaaacctc tatgacacgc ggtgatccga
43201 acctctacga cacgcggtga tccgaagctc tacgacacgc ggtgatccga acctctacga
43261 cacgcggtga tctgaacctc tatgacacgc ggtgatctga acctctacga cacgcggtga
43321 tccaaacctc tacgacatgt ggtgatccaa acctctacga cacggtga tccaaacctc
43381 tacaacacac tgtttggcag aagaggaaac tgagggccag gtgcagtggc ttacgcctat
43441 aatctcagca ctttgggaga ctgagatggg aggatcagtt gaacccagga gtttgagatc
```

Figure 4 (continued)

```
43501 agcctgggca actatcgaga cccctgtctg tacaaaaatt aaaaaaaaaa aagaaaaaag
43561 aaaaacttag ccaggtgggg tggcacaagc ctgtagtccc agctactggg atgactgagg
43621 caggaggatc acttgagccc aggaggtgga ggctgcagtg agctgattgt accactgcat
43681 cccagtctgg gcaacggaac aaggaccccta gatctaaaaa aaggaaactg aggcaacaga
43741 catgagaaag tggctcatgc ccccaaggga ggcagggaga taacccagga gcactgccac
43801 cctctgcctc ccagcatccc agcctgcctt gcacactgtc tcccatgtct acaagaacaa
43861 tgggaggtgg ccccaggagg ggactgcagg cttttccagc cctaagtcac tctgggatcc
43921 ccagaacatg ccttcttctc tctgggcctc aggcagaaaa ataactccac caggatgctg
43981 ggcagaggtg taggggcttt gcatgaggga ctagacagcc atctctgcct ggaagctggg
44041 gtcagggac gagatgtcac acctggagaa aactgccagc attttccact ccctatctgc
44101 cagagcccac acaggaagaa tcccagcctc acatccgagg actcagaggt gctgggaggg
44161 tcaaggtggc caggctccca ccctcctgcg gcctgctgag gccgagggac acttctggag
44221 tgatatcaag cttgcaggga cctcccccgc cacacacact tttttaatta ctaattttac
44281 atttcacaag caacacgtga atatttacaa aaataaaagc attacagata aggctctgtc
44341 caccgctcta agctcctctc cagagtcccc accgtgacca gtttctttcc agacattttt
44401 catcttccat gaatggaaaa cgcaaagtag gcttctcatg gaactctctt gaacagcctc
44461 agtccgggtg tgtcattctg taacttgctt tcttagtagc acaccttgga gctcaaactc
44521 agtttcccta tctgcaaaat ggggacagta atccagcccc acagaaatga cggagttccc
44581 ataaaaccct ggggatcctc cctgctacgg aagggattca acaagcatgg cgagaatgac
44641 gctgctctcc ctctttcctg ctggccactg gaggcacagt tcactccgca gtcctctcca
44701 cccacatttc agtccttctc aagcttcccc tttagttccc ttacatgcaa cactcccggg
44761 aacgtccctg ttcgcacccc ctagtggctg cagcttctcc agggctgacc cgaggaaagg
44821 acggctccct tggaggactg tgcactccag ggttcggctg atcaaccta acacggtcac
44881 ggccattcta cctcacgtga cttggtggga ggctgccagt caggcaggggt ggccaggccc
44941 tcttttacaa gtaagagaac tgcaactgcg gagaggcgag gaagcttgtt ggaggccaca
45001 cgccgaacaa ggggtgggat ttcctggacc tgggacccctt tagaaaagat ggaggctagg
45061 catggtggct acgcctgtaa tcccagcgct ttgggaagcc gaggcgggcg gatcacctga
45121 gtgaggtcag gagtttgaaa ccagcctgac caatatggtg aaaccccgtc tctactaaaa
45181 gtacaaaaat tagccgggcg tggtggcggg cgcctatgat cccaactact gggaggctg
45241 aggcaggaga atcgcttgaa cccgggaggc ggaggttgca gtgagccaag atcacaccac
45301 tgcactccag cctaggtgac agagcaagat tccatctcaa aaaaaaaaa aaaaaaaat
45361 gtgggagggg gtaaggggga ggagaaggtt tgcctaaggc cttgggtcta gaatgacatg
45421 tgcgttttct agtttggcag agggagaaga ggcaagatgt aggtgggagg taaaacagaa
45481 ctcactgcgc ttcttgggc ctgaacaagt gattgctggg gactcgaaaa gtgggaaaag
45541 cctgtcgacc actgtagggc atgaggggac agagcccgag gcctcgcatg ggcctgattt
45601 ctgattttca gaatgggaac gcaatggatt ctggtacttg taggccccca agctccctac
45661 gcatccctgt tggaagctca aacaggtatc tgggagcctc agaaagaaag caggggggcct
45721 gggagccaca ggggctcagc cagtcaccaa gaaccaggga gccccacctt ctcctccaat
45781 gaggccccag accaggaatc catgggacac ttggtggcag gaataagacc atttggtctc
45841 tggccaggcc cccactgctg cctcccaggg cccttggcaa caaggggaa aacatgggct
45901 ggggggcgagt ttagctggag ctgggctgc aaactcagat gcccatgggg atgggcaag
45961 tcacgtgaac gaggcaagtg ggatgggtgg ggcctggagc ggatggggag gagatgcctt
46021 gtggaaagca cctgactgct accctgagga gggcaggccc agtacggcca gagcttccaa
46081 ttccagaccg agtcctcagc cctaacaggc cttggaggaa atgttgtcct tgctcctgag
46141 gccactggaa atggcaggga gatgtggatg agctggggga caagtgagca gaagaatctt
46201 aacaggcatg aagcctgccg ggtggacgtg gggaccacag actgatccga caacagcctg
46261 agtgcaaagg atctgggtgt tttagtcagc cacaagcttg aaggagcca ataggggctgg
46321 tgcaaaacct caggccttgt tactttcgtc acaggagaat aaagtcccct gtttctgagt
46381 cacaccatgt acaaagagtg tttacagtta ctcctgcggc ctggcggaag agggcggggt
46441 tgacagccag cctgggttcg aggacgggtc ctgtcacttg cagtctggtg gcctcactca
```

Figure 4 (continued)

```
46501 agtcacactc cttteccccca ccccgagctg cggtgtcccc atcacactgt ctttgtgggt
46561 tgaggtgctg gcctaaggtg tggacacttt ccagtcacgt gggtcaccac catcatgacc
46621 atcgctttta tctctgctca tgcccaaagg aagcagaact atcatcccca tgctggagac
46681 cggggtgtgg aggccaggat gctgaagtcg tgtgaggaac acagagcctg agcagcaagg
46741 caggattcac acccggatcc cccgactcca agcccagggc tcttttcctg cactttccc
46801 ttttgttccc attgtttaga cggggccacc gaggcttcac catgagaccg acgctgagcg
46861 cctgttccgg gaccaggct gtgggtcagg taatctgacc ccggaaccca cgctcccacc
46921 acatgctccc ttgccctccg tagggcagac ttcccggagg aggggagtcc aacagcactt
46981 cggaaatagc ttccttgtta ctgtggaacg ctggagccac tgccagggag gggagagggg
47041 agccaaggcg gccccacgtg gccagggcgc cagagagtct cagagccaca gggccagggc
47101 tctcacactg gaataggac agaagttcca gtgcctgagg aaagaagatg gtcttcagaa
47161 aaagcctctt tcattcggtt acccagagca agagctgcgt ggggagctct ggctctaacc
47221 cactccgtca ccttgggccc agtcctgcta cgcctcagtt tccctctgc acagtctgct
47281 cactgaggcc ccttcctttt gaaagtccct gatttaaggt agcaaagatc agccgctggt
47341 cagaggggcc ccagaaagaa aagaaggcag ggctgctggc cccagggccc acccactacc
47401 acttcttcct gctgctgctg ttcccagtat ttcttgaata ttctctgccc cccactcttc
47461 agagcctcag ctcaggacag cctctgccag caatgctttc tgtcctgtga agcccagtcc
47521 aggagccct cctccaggaa gccccttc tcccacagta gatcccatc acacctctgc
47581 aggctagggc tgtcctttaa agcagtcgcc agcaggagtg gaaatcatca aaacggcagc
47641 agatgcttgc tgggtgcttc ctccacggca gcgtctaagc agctgacaag caccatcttg
47701 tttcgcctgg cagcatcccc ttgagtaatg tctgccacca tcctatcata tgggtgaaaa
47761 aactgaggct ctggacagcc agtgagctca aggtcaagca gaagacacac agccacctgc
47821 tctccctaga gcctgtgaaa acacatctat tgtggcggaa gagggcgggg ttcacagcca
47881 gcctgggttc gatacatcaa tagatgtatc gggactccac aatagatgtt agggccccgt
47941 ccagccccag gcccagagct gctatctgca gcccaggag gataggactt gggagaggaa
48001 gatgagaagg tctcagtgga ctccaccagg ggcccttccc tgctctgaag ctcaggttg
48061 agagtgcaat ttccaatcat accctgctct agaccaccaa gtcactctct gcctctgggc
48121 cacagtttcc acatctgtaa agtggttatc atactgtcta acccctgagg gtgccgatga
48181 gctggaggac aggccacatg cttttaaaag cagaggactg agatggctgg ggaaagcccc
48241 gcgttggccc tcagggcctg tcctggctgc tgtcagcctc cagctgctgg gctcagatca
48301 gacagctcct ccagcatggc ctggattagt gtctatgacc ctcacttatg ggagggcaga
48361 tcccagcctg cccctcccaa gggcccagtg gccccaagct cataccaggc agctctcacc
48421 caccagtggt cactgtcttg ggcaagccac tcttgccttc tgggcctcag ctgtcttatc
48481 tgcaaaatgg ggatcacacc tctaaccccc gagggtcagg aaaggtttca agaattacac
48541 agcccaccag gccttggcct ttgaggaagg tgttctgggt tcccattctg acttggccat
48601 ctgctcctag gcaaacagct cctctctgat gcgtctgtgc agtgggggtg acccacctca
48661 caggcatatg ataaaggcca aagtgggagc aggaatgctg ggccccagcc agtctgggga
48721 ctcaccaggg tcacgcagtg tgggagctag aggaccaggg ctggattctg ggttggcagc
48781 tcctttacca ctgtccccag ggaatccttc cccaccacca gcctggccag cctggggtcc
48841 taccccgcc aggtacctga tgcttctggg ggaaccaaga gaccatcagg gttaccccct
48901 tgcctccatg caggcccaac acaagcccct gtcataggag tggcaaccat tttagcaggc
48961 atccatgatg tgccgggcac tgtgcaaggg gggccatgca tgtcgtctcc aagggtcata
49021 tccctctgac aggctgtgac tatcaccccc gttttacaga tggaaaagtg gaggcacacg
49081 gtcaaggtca cacggtgtgt ggcaccctg agattcaaac ctggaaaggt cacacatgga
49141 gctcagctgc taaggtcatc gcttcccaag acctccatga gagaagagct gggtcacctg
49201 gccgtaaggt ccagctggca agaggccagc tcagtgttca gcctcttggg aaaagcagag
49261 tcgggcaggg ccacaggaac agcatcgtct gctggggaca gtgtgggctc caatgaccag
49321 gcccgtcacc catctgaagc cactcggcag ccttcttggc cgcctggtgc ggctgtgacc
49381 cagacacagc agccactgtc tacccagcag cagggtgggg cgccgggccc gaggccggct
49441 ctgcggcctg tcaggagatt tacacccgac tcttaacagc ctcgcggaat cgcaggcggg
49501 tgccgggcct ggggtggtct gctgtgaatc ggcccctgt gagcagatga aagccgggtc
49561 ggtggctggg cagggaaacg ggctggccgg gggccagcgg gcagggaggc gagcggttcc
```

Figure 4 (continued)

```
49621 ctcccagggc tgcaagtggg gcttccagag gcctggggtt gattaggaga acccaggagg
49681 tctgtggtta accccttccc tcctgctggg cagactccgc tagccctgcc cctagcgcag
49741 gagacactcc tgggggttgt ggggatcttg ggagccaggg acctggagca gctgcctctc
49801 ctcagcccag gaagaaacta cagaaactct aaggccttca aaggcccaac tgcgggctca
49861 gggtcacttc tcctgcccac gccaaaccct cggcagccac actctgctgg ctgctcactt
49921 caggcccctg ctcaaaggtc acctcttcag gaggcctccc cgccccatcc cttgttccat
49981 cccttgcacg ctccactcct tctcccagct ttgttttttct tcataggact tcctactacc
50041 cgaaatgaca ttaatgaatc atttgcttat tcatcaacga tttatggagc agctgtgaag
50101 ggctcctgcc cacattctca gggtctagct ataccagggc ctggcaaacc agagcaaaga
50161 actctgccct tgtagagcat aaacaacagg gggccgggtg cggtggctca cgcctgtagt
50221 cccagcactt tgggaggctg aggtgggcgg atcacttgag gtcgggagtt caagactagc
50281 ctggccaaca tggtgaaacc ctgtctctat taaaaataca aaaattagct gggtgtggtg
50341 gcgtgtgcct gtaatcccag ctcctaggga ggctgaggca agagaatctc ctgaacctgg
50401 gaggcggagg ttgctgtgag ccgagatctt gccactgcac tccagcctgg gcaacagagc
50461 aagactccat ctcaaaaaac aaaacaaaac aaaatgggag aaatgaataa caaatgaaac
50521 aaactatcgg actagatagc accttagaag gtggtagtgg taagtgctcg gggtaacctt
50581 aaagccagga aggaaagggg ggagaggtga ggaaggctgt gtgtgtgcca cttgaaacag
50641 gcgggctgct gagaagtgca gaggctttag ggtgtgaagg agtgtgccat gcatctgggg
50701 gtgtccgggg aggagtgttc cagatagaaa aaagagcagt gcaaaggccc ccgaggcagg
50761 agtgtccctg gcaagttcaa agaccagcca ggataccagg gtggccagag caggatgtgg
50821 gagggagggc agggggtaac gggcacaggc tagggggggcg tgagggcctt tcccccaccg
50881 tggtccatgc cagacttgcc aggtgtcacc gcccctcctg ctgggatcct ggacctggct
50941 cagcaacctg cttcttaacc agcccccagt gactctgagg gacaccagca ctgagaacct
51001 cagaaaccga ggccacacag gcaggaagcc accaagccag ccttcaaacc cagctggcca
51061 cctggctgca ggccgggcac gctctgcagg gcaccagagg ggaacgaccc ggccacagaa
51121 cccacagccg gcctcaggga tctacagatt cccagtcctt ggctcccagg accagcccct
51181 actcccactt caccccacag cgggctcaga tttcagaggg tcggaggtgg caaaacagga
51241 aaaaagccgg gaaggaagt ccaggagcac aaaaggcctg taacaacctg tgaaggttgt
51301 ggggggcactt cctggggcca ggcccggta aactcagtca accttcacag cgactcccct
51361 aggcagacac caataccatc catttgacag ctgagcacac tgaggtgaaa aggcccttcc
51421 aagtggccct cacttcccgc agcccccggg tcggagcccc cagggtgtgc tgacagtcac
51481 cttgggcaaa aggttttgcg ccctggcctc tatcctctcc tggggttgcc caagagatca
51541 gttactgggg actttgcaca gggcctgacg caagggaggg ggttgctcag tgaccaggag
51601 ccgctgagct ggtcccttca ctcttacaga tggggacgct gaggacccga aaggccaagg
51661 atttgtccag ggccaaagac aaaggagtgg ggctgcaacc cagggtatgg gggggaccct
51721 gatctcaggg ccaggatatg ccaggacag gaacaggcag gtcctaagga tgggggacct
51781 agtagactgc cccccgactc catctctgct ctgttctgta aataaaacca ctgatccagc
51841 cgctgccggg gcccagagag ggaggtcacc tgtctcaggt ggtgcagcaa gcctggcttc
51901 tgacgccgtg ggtctccagg cccagcctct gtccctccct cttgttgcct cgtcctgagc
51961 cacgcattta ccttccagct caccccagaa ggggccatct caggtctggg gacccaggc
52021 agggaagagc aggcaggga ttctgctgga atctcccaca ggcagggctg agtctccatg
52081 ctcatccagg ggtcccagca gggcagagtg ggcggctctg gggtggggctg ggctgagcat
52141 ggagggctct cagaggggcc aaccttgccc ggtcccttgg atcttccac caagcgtcaa
52201 gaccccgtcc cgtgcctccc tctttctgga gtggctcccc tctttctgga gtggcttctg
52261 agtgccgcat ccccacccag agcccaactg aggctcctgt ccatgctgac cctgcccctg
52321 gagacatagg gcagggctgc cacctccttc aatggagact tgatacctgc acctctatta
52381 ccaaggcagc cacccagctg ctgcccatga gagagctcac cgttgactaa tggtggtggt
52441 gggagtgcag gaagggggct gggtactgag gacgacaaaa cgctgcggac ccagtgactc
52501 atgggacccc tctgtgctac ggccacgtgc tgtccacatg tcgcccctga tctccaggtc
52561 cgcaggtgg gtggcatcat cacacttcat ggaggaggga gctgaggccc agagaggtca
52621 gtgacttgcc ctaggtcaca ctgcagataa cagccctggc taaagtgacg gatcccttgc
```

Figure 4 (continued)

```
52681 taaccccac cgctaagtgc tttctataga ttaagccact gtttcctcgc aatagcatca
52741 tgaggtagct gcttgtgcga atatcatttt tcagttcagg aaactgaggc acggagatga
52801 ctagcccaag gacccacagc caggaaggct ggcttggaaa ctgctctcta caccatggtg
52861 gtctatggct catgagggct tcccagccat caccaccttg agactcctgg agtcactgat
52921 ccagttctca gatgacaaaa ctgaggccac aagaagaca tgacttgcct agggtcatga
52981 agcccaaggc caagggcatg ggctggtcta tgtctgatct cagcaggagg gaaccagcag
53041 gagtgtggcc agggcaagtg ctggctggga gctgacggtg caggcctgag gatgcgtgcc
53101 ggggctcagg gctggcagag gtgaccctga gagccctgga gggaaactct tccaggcctg
53161 ctggactcag ctccaagcct ttcccaagtg gccagatgct gggatgggcc caggaattgg
53221 atgatggggt gtcaggccca gctgactccc aagaaggag gggccagccc agggctaggc
53281 ctcctgcccc aggcctcctg ccccaggcct gctcagccta gaatcttgcc tctgggaaga
53341 ctgaagcctg gggcgccttc ctgctccttg cacagcatta ggtcctattc aggtacccaa
53401 ctccctcagg cctggattct ctcctcactg gaacttgggt gaccctctg gctctgctgt
53461 catcaagatc ccattcaata gtgactgcta aaaggtcttc taaactacaa agggtcacat
53521 ttctgagaaa gagaggggtg ggccaacctt cagtgcacca agctgaaaat gccttgggga
53581 ggtgggatgg agctcaggaa gctggctggc tctatttcat tcattcattc attcattcag
53641 tcagtcagtc agtcagtcat tcattcattc tgtggacaca gagcctcagc ctaccctccc
53701 acttccccag ccttaatctg accttcagca agcagagaga attaaacaca aactcgcttt
53761 gatggaccag aactccctgc tcatagggtc tgggtgcccg gactctgggt gacctgagca
53821 agtcacatgc taagattcaa agactcagtt ccaaggaag aggcctggcc tcacagccag
53881 accagcccct gacttttgat cactcctgcc ctccatgcat ccctcagcca cccgcagaga
53941 agctggggc agagtaaagc aagcctggct caacctccac ccagaaacac acaagcaccc
54001 gacaaatgcc atatctgaaa gctttctcca tccttttcct ttccttgact ccctcagtag
54061 tctccatgga cagtcatctc cactcccagc ctcctcgctg gcctccacg gtctcaggct
54121 aagcccagag ggtttagggg tttgccagca ggcacgcagt gtgtggggc acagagccaa
54181 ggactgcaac ccccccgagga gggctccatc tgtctgacct agctcgtgtc cttcccgcac
54241 tggaccctcc tccccgcgc aggggctcag ggggctcggt ggcacttacg tctgggctcc
54301 cggggtccgt ccacggtcac cttgatggct cggtggtagg tcgccacttg ggtgggggttg
54361 gtgaacacag tgatggtcag ggtgaaactc ttccctgggg agagtgggga ataggagcag
54421 gtggttggca cctggagctt ccacaatacc ctgctctccc acctgtatct accccctggaa
54481 gccctaact gtcaagaagg ggcactctgt cctctttgaa catgggcaga agatagggct
54541 ctgggtgaag ttcaagctct tgggcttggc attcaaggcc cctgggggtc tgacgccaac
54601 tttgtcaacc ccccgcccca tgccgtgacc accctggctc atgttccct cttcttggcc
54661 tttctgctgt ctcttctatt cagagaccca cacgattttg tggtggggag caggatgggt
54721 atattctatt ttctgaaagt aattggtgat ctttgtagaa aaattcaaga acatacaaaa
54781 tataaataaa gaagaaaaga cacccccccc ccacggttcc actagctgga gatagacacc
54841 gttaccattt ggtgttttcc ctttcagctc ttttttgtatg ggtttgtata tttacacagt
54901 cgcagtggta ctaaaataca gattttcata ctgttttttt tttcatttaa cctcacatca
54961 gaagcacttt cccacgtcat taaaactcca taaacttcgt ttttaatggc tgcaaaatat
55021 ttcaactcaa ggaagcctcc tcatctttta tttatctacc tccttactct cgggtattta
55081 catcgttgct aatttcttat tgatgtgtgc agctggagct gaaaaggac tgatttggga
55141 gctgcagaca tttcttctgt agacacaact gttatttcca gaatgttcta tttttagata
55201 gacatttggc tccaaagtct ccattcaaaa ttcctgagag gggaaaaaac ttttaaaata
55261 ctactttttt ttttttttac catttaaaat aaaatgaaag tgaccttctg tttataaaaa
55321 tctttgtctg catctctgct tatttcctta gaagagattc caagaagcgg tgagtgattt
55381 cacggcagca gagggttggg acatattacg ggcgcggatc cctcttggag tgagatgact
55441 ctccggagag atttagtcgt caccctcgcg tgtgaggctg cgtcacaccc cagggatgtg
55501 tctatcaaga tggaagatct tttacacgct cttgattttg tttgcctttt tttctattac
55561 tagtgagaat gaaactttt atatgattat tatccatcat aatccaacac aaattactgc
55621 ttcatgttct tttactttcc tgtgaaggtt ttagtgcctt taaaaattg ctatatatta
55681 agcttgttaa tactttccat gctgtatttg tggccatcag tttccccggg cacaggcctg
```

Figure 4 (continued)

```
55741 cacattttgc cttcacacgc tgggtggttt ttcattttca cttctatttc tcgttcttct
55801 atcgttttat gttcagacgg gtttctccgt gtagaaagca gtttatgaag atttactttc
55861 gacagtcttc tctctacttt ctacagtgaa ttctctgatg tgtctgggag tttggggtc
55921 tgggtaagag tcctcctctc accctattct ctattacgat ccacagcctc atgctttatg
55981 agattggtgg ccgggagcgg gggagatttg cggatccccc aagccagact ttatccccct
56041 atccctgcct ctggatccca cgtacaggcc tgggaactcc ctgtgggtag gggccaatgg
56101 tctcgcactc tcacctgtac cccagggctg gcacaggatg gtcaaggaga gaggctgccc
56161 aagcgcatcc ctctggtgtc ccccctgacac gcctccaaag tgagcaggta ggtttcaaca
56221 gccccacgtt gcaggtggga gatgaagctc agggtggaga ccagtatctc acagttctct
56281 ttgcatggcc gggtacttgt tagtcaactg atcaagtgaa aattctagcc ccagaggcag
56341 gagaatccgg aacaaaatta aaccagccag gctgccagga gccatgccac aggacccaag
56401 gccctctgag acaccagggg gaatttaaag ctcaagaccc actgagtgtc actccagctg
56461 ggaaatgagg ggcttctctg gaagcctttt cctaagccag tcggctgagg cagggataga
56521 aattctgact gcacttgccc ccggagcccc aggtcagaac agacctggtc tcccactctc
56581 aggtcacagg ggccactttg tatgatttct ggaagcagaa gtgcagatgg tctagggaag
56641 tgccaggcag atgcctcggg ctccctgccc gaccctcct actgcctttc ctcactctga
56701 ggtcatttct ctgctggacc tctttctcct ccaaccagcc cagcactctc ctggggtccc
56761 tgagcctctg accctgccag cattgtccag caccttcttg gttatgacgg ggagtttagg
56821 cagacagccc agagccctag gggccagact ggagacacgg aggactaatg ggtcccagtg
56881 ccctgccaca gggcccgggg cccacagcag catttgaaag cttactaaaa ccctccttca
56941 ggtcgcccac cttctcagtc aggccttccc tggtcacttt atctgaagta ggcatttta
57001 attttaatta attttttttga gacaaggtct tgctctgtca cccaggttgg agtgcagtgg
57061 catgatcata gctcactgca gcctggacct cccgggctca agtgatcctc ctgtctcagc
57121 ctcctgagta gctgggacaa caggtgagcg ccaccatgcc cggctatttc tttttttccc
57181 ttccttcttt tccttccctc ccttccttcc ttccttcct ttcttttctt tctttcctt
57241 ctttcttttt ttttttttttc aagcttttac tatgtgccca ggctggtctt gaactcctgg
57301 gctcaagtga tcctcctgcc ttggcctccc aaagtgttgg gattacagtc gtaaaccact
57361 acacctggaa ggcatttta acttggctcc gtagagttga atgagcctga gaactagggt
57421 aggaaaaaat tacaattgta ttgtccctaa cctctaactg aaatttagca tcactctcaa
57481 gtacgagcgt aggcaacaaa ccacagaggt attatcagcc gtacctgtga ccttgtcacc
57541 aacagacgtc acagatactt acatatcaca ttacagttgc tgcagattgc tctaaatatc
57601 ttttatgctc atcacaactt caaaaccatg gttgtcatta ggcccaatgc tagatcttat
57661 ttaatacatt gaataaagca gcacatttac cacaatttt aaagtatttt gctatgtttt
57721 aatagaaatg gtttctattg taatactttg tatttgattt tataccttaa aaatatcatt
57781 gttctgagaa aggtgtgcgg gcttcaccag ctatcagagg ggcccacagg gcaaaaaaaa
57841 aaaaaaaaaa aaaaaagcg ctaagcagct caacctgaag tatcacaggc cctaccactc
57901 cctttctcta ttccctgcac ctgctggaat tttctcacaa tgcatatgct tttaataatc
57961 catctactca ttttgtctcc ttctactaga ttataacctc cccagggggcc caagttttg
58021 tcttgttcat gcagtgtctc cagcccctag gacggcatcc ggcacagagt aggtgctcaa
58081 caacatttgt taaataaatt aagggcagag ataatggctc ccattttgca cacaggtact
58141 aacgtcccgc tcctgagaag tgagaagccc ccacccatac caggtagcaa accacatgcc
58201 accccctgagg tcaccagcac tcctcggccg cttccaccag cttccacgcc tgtcaccacc
58261 cctcccaggt acaaaggaga ggagtgtggg gcctaagagg aggagtgaga gggaggggca
58321 ggagtcctgg acctcggag acagggagcc tggggagcag gggtgggaga aagctgtctc
58381 cctgagtgcc cctcagctac cccggccctg cccagctctc tctctgcctg gcagtggcaa
58441 acccatccat ccctcctct cagcctctag atataactct gtgcaggagt cccaggcaaa
58501 cctgcaatcc atcaggagcc caggaagtgt aaacccaggc tctctgaggg ctggccctgg
58561 ttgcagggga gaagtcttgg tctgggaaat gggtttcctt tagggctcca gaaactcctc
58621 caggacccat catcaaccag ccggggtggc agcagggcct caggcaagtc cttgagcatt
58681 ctctgcctgg gttcctatgt gtataaggtc cccgccccac ccacaggagc tgcatgggtg
```

Figure 4 (continued)

```
58741 gggggagggg acgtgtctca gtctcagggg acctcggggt tttctcagct tcagccaaga
58801 agccattcat ctctccccca accagcggtt cccctcagcc tgcaccggca cactgcaccc
58861 cgaatctctg tcgacacaca gttgctttt aaccagttga tcacagctcg agagctcatg
58921 tgcttttcat tttcacttag gccagtggcc gcctgctaga ggggcatttt tgggatttgt
58981 ggtggcgtgt ggtcaacata tgttggggt ggcactgcca gcgttagggg tggggtgcgt
59041 gtatgtggtg ggggatgcca gcacccaacg ctgcccaggg tggtgaagat tcaattcttc
59101 ctgggaggga aaaacttgct tataaaagtt ctctggctgg tcgcagtggc tcatgcctgt
59161 aatcccaaca ctttgagagg ctgaggcagg aggatcgctt gagtccagga gttcaagacc
59221 agcctgagca acacagtgaa caacaccccc atctctacaa caaataattt taaaaaatca
59281 gctgagcatg gtggcgcatg cctatagtcc cagctattga ggtgggagga ctgcttgaga
59341 ccaggaggtt gagactgcag tgatcgcacc actgcaccct ggcctgggcg acagagcgag
59401 accttgtccc aaaaaaaagt aaaagaaaaa aaaattatct gagtcatgaa cctaactcag
59461 ttttacataa aacaagggtt ttttttgtac ttttaatatc tactgaattt tccagaagga
59521 aagacagttc tttttttttt tttaattttg ttcagcgctt tgccaacagg tgttgacaac
59581 ttcagaaagt catggtattg gcagcaaggc caggttcaga ttgagccctg ccaccctgcc
59641 tgttccctct gctgtgggct tctgcatgga gggcattcgt ccacctcatg gagtcctgtg
59701 gccccaacgt ttacatattc aaatcagtgt tttattataa attactttcc cttttttct
59761 ccatcatagc tatgaataa catagtttgc aactgcatgt aaataggtag gtttcattat
59821 ttatacattt caacgtagaa tagtaaggct tgatataaaa tatgtattgt aagaaaggct
59881 cctcgtgtct ggcagggcag ggacctcagc cctaatcact gcaggagaca gcaatgacct
59941 ggttttcctc ccttccttt cttggttcac accttcagcc ctgttgttaa gagctctgtg
60001 gtgttactgg gtgcgtgtct ttcatggaaa gccatcttcc tggaattcag acagaatgta
60061 gaactaaaaa ttgaggcaac aagcagaggt ttccatcaga cttcttagtt ctggcagaag
60121 tcaagagacc caggcaaggg ttctgggtcc caacccccag tcttaactcc caaagtgtcc
60181 catctcctaa agtggcccag attgtcactg tcaaccactg actgttctct caggtgggaa
60241 tttcccagtc agcaggatgg gcactgcaga tgtgtgtctg catgccagcg gacccggcac
60301 cctccttcct ccctgccaac cgcctccacc tctcccactc agcagttcac accttctggg
60361 tttccccac ccccgcccaa accacacagt aatcagagaa tcagtggctg tcaccgctca
60421 aagggacctc aaagtcctcc tccagtccca ggcatttgaa gtaacaaaat ctctaacatg
60481 tatccagctc tcaatatgcg ccagctgata cacttgtgtc aatttcccta accttcccaa
60541 aatctcatga ggtaggtacc attatcatcc ccatctcaca gatgaggaaa ctgaggcaca
60601 gagtggttaa gtcatttgcc caatgtcatc cagcaagtca ttagcagagc tgggactcaa
60661 acgcaggtg gctgatacta gaatgcaggc tctcaaagac ctcgagcctc tgaaggctga
60721 acgccttagc cacagttcct cagacatcgg aactcctcct cagatcactt cctgcctccc
60781 aggaccactg agactggtta tggacctctg agaggagatg gatgagagaa tggtttataa
60841 actcagcctc ttgcatctcc cagagccaca gtcccagcct cggccattcc tgctacaagg
60901 acaagctccc aaccaacgcc ttggaaaccc atttcctcc ctgcaggcct ggggagggg
60961 gctcaaggtc tgtgggcatg aaaacccta aaaaaatcat tctcagtgtg cagaatggcc
61021 agacaaggtc tcggtaactc agaaaatcgt cgtctcttct cttctctcg cttcccagga
61081 gagagagtgg gaagggagaa tcaagttcct gatgccttgc tgggctccca gatcgacagc
61141 accttctgcc cgcctcgcaa caggcagcag ctatagtgct cctgacacat acctgggcta
61201 gcagacctgg ccactgcccc gcagtcagca gagctcatca gccttgtctg ccaccgacca
61261 aggaccagtg actgtcctct cagggttggg attaagtcgc aaagggtttg agagattggg
61321 gatgacaaaa gggacttgga gactaattag gagcagcaat gaaagcttaa ttcataaaag
61381 caaacatttt ccatccatca acctgcaacc agttaagggc accgtttgaa agaaatctgt
61441 gtgtgggaa gggagccaac aggaacagga aatgtttgaa agaatgtaaa ctatttcagt
61501 ttcataaaaa gtaacaagta aacagttatt acatgcaaat aatgtcctgg tttaattaa
61561 tgctgaaaag tcaaatatg gctgacattt gtatgtatac atcgaacggc tggaaaggaa
61621 aaaatggtgc ccagatgcct gtttcagagc ggggctggca gctcagaggg aactagaacc
61681 ttgagaaggt cctgtttatt ggtgatgaaa agcacggttc tgcttcagcc acttcagcct
61741 gctgtggagt tggggagcag agggaaccca gcttacttct taacaaagct agaggcgggc
61801 ctggtgcttg ggaagggcga ctcccacttc agccacttct cgtaggcagg ctggtcttaa
```

Figure 4 (continued)

```
61861 agggccagtg gaccctcagg cctccgttcc acaggggcag ggtttccagg actttcccat
61921 ccaggagtta agtgatgatg ggtttcaggt cccagaagcc tcccattcaa cagcccccca
61981 cccccgtccc gccttccttc tgctgctcaa ggtcggtcag acaggcaggg tggcacaccc
62041 gccttgactc tggggcagga gatggcagcc ttcgagctgt gctttccaac attcagctgc
62101 gttagcttcc gttctagacc acctagggct caaaggcgct gggaaactgg gtctgggaga
62161 ccacagctgg agagacagcc tcagagtgtg ggggatattc tgcccctat ggagagagtg
62221 gctggggtgc ttgggcccca cagatcaggg acttgtcctg caaccgcctt gctgaaagac
62281 ctataagctc ccttttttgag cttgttaatc caccatctcc tgccagcatt ttttgtgaga
62341 ccaggtgtgc ttaaccggga aagaggggt ggcatgaacg gtttcaggag ttggtaaacc
62401 ctagaaactg ggagaaaatt gtcttttttct ggcaagagac cataactttc ctcacctcct
62461 caaagcgatc tgtaatatcc tacaggatta caaattgctg tttttagaca gagctgcatc
62521 tggagacctg tttttcggga ttctaaggcc cctctttcaa cctccttccc tgctgccct
62581 gccattgcca atgctgaaat ggcgaggcct ccctcact tacctcgccc actgcggccc
62641 acgaagcgaa ggtcgttgaa cctggccacc tggttcttca tgacggccga ggcattgcgc
62701 agctcagcgg agtagttctc gtcattgcct gccatcacag tcaccaccgt accatccggc
62761 acgtccccca atgccaccac ctgaagacac ggggcggggg gatgcagggg gacagcttag
62821 aaaggaagag ggtgaccagg gaaaggaggg gaggggctgg gctgggcagc tcccccaggt
62881 cccaggcaca ctgagtattt ctccaatgca gggtggagaa gaggcttaaa aacaataaag
62941 accttccccc aaatatcacg aaaacaagaa gatgaatct cgagcttcca caccaaaatc
63001 ctagatcaac tgcttacata aactgtgtcc caagaaatca tcctttcaat gaaatctaag
63061 ccagagctgt gaatcagctc agtcactatg atgtggggtg cagttcccct gttgtcttcg
63121 gctgcagcga aagaggaatc aacatgctcc tagcaacgaa gtctccaaat gagaaagagt
63181 aacaacaata ataacaacag ggctgctacc cccactcaat ttatgcaaga gctgtttagg
63241 gcatgaaatt tggccctgaa atgtggacca ggcccagttt attggcctct gcagagccta
63301 aattcgttat gcagagaaaa tgcagaatgc aaaactcact ggtgttttga aaaaggccac
63361 cagaaaaccc ctttaaagtg agagtggggc ttttgataat ggaaggatgc acctgccggg
63421 aattgcagga tgggggtggc gatgtccccc taaacaccat ctcccccaaa tcccccaccc
63481 ccaggagcac ggagaggcgg atgccttttg aaaaagaatc agactttaaa cagagtcaca
63541 actatttaaa cgtggccgcc gcgtgcaggg actggggatc catatggtaa aaatttcaag
63601 gagaaaatgt ttgggatctg attaagaaga ccagatttcc tgtcaacatc ctgtcttctt
63661 ttaatttcaa agactccttt taagctccaa gtgacagtaa aacctccgat ctgacgatta
63721 aagtcacacg ggcctcccgc ccctcccggc gagatttccc ccactggtat tttaagatgt
63781 caccccggag acctcaaaga gccactcttc cttttttttcc catttagagt cgtcttaatg
63841 ggagcaggga cggcctcagc ttccagccac ctcgggcagc accaccccca gccgccggcc
63901 cttcctgccc tgccctttc tcacggccag tgtgagaggt ttaggggaaa accgaggcgt
63961 tttcgtttca tctcgctgcc cccttaaaaa aatgaaaatg aaacagtcgc ctactccctg
64021 gcataaagaa aaaggtcctc taaatggctg ggggctgcca gggttagggg tcccccaatc
64081 tcaactcgcc attcgggacg cataatatcc ccgagcaaac gtctggagag cagtgccccg
64141 atcccggcct agcgccgtcc ggtaaaattt cggaagcccg agggtgtgag caggaagctt
64201 ttgcgaagcg gcgcgggagg aggggtgctg gaggcggagg gtaggccctt tcaccgttcg
64261 caccccaccc gcggtgtcct tgcccctgtc ccgggatcct cttctccgtt acccgcaggg
64321 ctgtatctga gcgatccggg ttaggggggc gcaaaacccc atccgccat ttccgcacca
64381 acgtctctac gcaaggcgcc ccaaaaccca ggtggagcgg ggcaaccccg ttaaaagtca
64441 ttcctgcagg gcgcatccaa aacggaacgc cgaggtcccg gagccgagcg cgcagccaga
64501 ctgaaccggg tgcccgggtg tcgccgcggc gtctcgggca cctcccatcc ccactgctcc
64561 cgaggctctg gctcccgcag ctcagacgcc cggagcccca gggccggcgc cctcccgccc
64621 cgggtcccgc actcaccttg aaggcgacgg gcagcgtctt gttgcagcgc cagtgcgagg
64681 gcagcacgga gcagaggaag ttggggctgt cggtgcgcac gagctcgcct gcgtggtccg
64741 ccagcacgtc caccatcgag cgcacctcgg gccgggcgcg cctccgggc ccacggccg
64801 cctgcgcgct cagcgcgccg ctgttctcgc ccatcttgcc gccgccgccg ccgcagggga
64861 aggccgggga gggaggtgtg aagcggcggc tggtgcttgg gtctacggga atacgcataa
```

Figure 4 (continued)

```
64921 cagcggccgt cagggcgccg ggcaggcgga gacggcgcgg cttcccccgg gggcggccgg
64981 cgcgggcgcc tcctcggccg ccgctgccgc gagaagcggg aaagcagaag cggcggggcc
65041 cgggcctcag ggcgcagggg gcggcgcccg gccactactc gccagggccc gcccgctgcg
65101 aggcctcgct ggcccgacgg ccgcccgcag cctgccggcc tagtcccgca tcctcggcgc
65161 gcggccccgc gtgcggccgc ccctcgtggc tgtcccggct gcctgggccg cggcggggcc
65221 cgcgcggggc tgtgccgctg ccgccgcctc ccgcccgaa gctcgcccgc ggccgccccg
65281 actccgcggc cgcagcccca gaacaaatcc tccagaatca agtggcgggg ccgcggccgc
65341 ccgcgcgggg ttagtacccc cggggcccgc ggggcggggc tggcggagcg acgcgtcgca
65401 cagccaatcg gcggagcccc catcgcgggc acctcggtgg cgttcgcggg gaggaacggg
65461 gcctgccgga ggccgcccaa cggggagggg cggaaggcgc caccccgcgt aggaggcccc
65521 agtgccacag cccagggccc ccgagagctc tgggagcccg gggcaaatgc tagaaatttg
65581 cttagaacgt ccgggtccca cggaaggcgc ccttgccgcc ctctctcggg tcgtagctcc
65641 ctgacgctgg ggcgcaaccc cttcgctcct cctccccgct ggccgcggcc gggcttcccc
65701 agctcttgct gcttcgggcc tgtgacttct gcaaccccgg gctggggggcc gcggggtctc
65761 agggccggtg acgccgcact gggagccgcc ccaaagaggt tactcacctc cctcgtcccg
65821 cacattattc tgacccaaga gcctccaccc cacacgggat tttgcgcgtc gtccacgccc
65881 ggccggcggc ctttgctgct cccagccctg cgcggctttg gtcccagcct cggtggcccc
65941 tgtgccaaac cggggacagg cggaagggag tctcctaggg accctaagta gcctggggcc
66001 aacaacccct ttcctctctg ctctcccctc aaaacaagtt tcaggatctt gcaggcctcg
66061 cggcgtcgtt cttcgttgtg gcggcctgtg gctctttgaa aaacacgacg aggcctgcaa
66121 aatgcgtttt tcttttttttc ctttacgcat gtaaccacgg tcctgcatcg tgaaacggta
66181 cgcgcgtcgg tggcaaaaga aaaacagcag tggctgcaaa gctaagggcc ctcgctttca
66241 gaggagagaa ttttcttttct ccatgcgggt ggaaagtggc ctctgcgggt ccaaccccac
66301 ttcttcttgg gcccgtgcgc tccggctgcg ccgcagggac cgcggacagc ttcgccaagg
66361 cactgcctgc ccgcccggct ccgggtcccc gctcccactc ccagccgcgt ggcccaacct
66421 ctcctgggct tcactgcaaa tcacccctttc ctctcccgcc tcctaagtct gtcgagcaga
66481 cctaggggcc ggctacagtt ggggagggcaa cgggaaagat caagccacaa tcattccgaa
66541 ttatcgcccc agacacctcc ctagactctg gggaacgaac gcgtgctgag cctccccgcc
66601 gctttggaga cggggctaga ttttcgttgc ctccggctct cgacaggtgc aaaacaatga
66661 attccaagcc tcggaagcaa agaagcttag gatccgacgg tggccgcaag atctcatcat
66721 ggatctgacc cctgctcagc gcgcgccatt tcgtcgttgc caaacgaaat caagccccgc
66781 gtgcgctcca ggggcgaagg actctggact caccccgacc accgggagag ctggccccta
66841 cccacctcgg gacctcacag cacgccctca ggccgtgtcg aaaggaagga cggcaaaggt
66901 cccttactga accttttaag agagcctgcg cctggcagtt gtcgattgcg gacccaggcc
66961 cgcgcgcccct cggacgcgct ggcacgagca gcagaactag aggaaagcga gtgatccagc
67021 ctgggcgctc ccacctccgg gaacgtctcc gagaaggcgc agcgcgtcgt ggccaggtag
67081 ggcctggcc ggggggcgggc aacacgtgct gccctcgagc aggttgcggg accatgaccc
67141 gctgttctag gtggtggtaa attccatttg tcgaatggtt tcggtttgca ccgtgccctt
67201 tgcttgttcc tccgcctgat ttctccctct ccgcttacga tggggttcaca gacaagtttc
67261 cagagaatga gggactcttg tgggcccctgg cacctggcgc agggcccggc acggctccgg
67321 ctctccgtag ggcgctggct ccccgtgggc accagatcca agggaccagg gcggcggggg
67381 gaggggggc gggtgcaggc ccttgggtcc ccagaccaag gtcgcggggc cgcctggcag
67441 gcacagtggc gggagccgcc gctagttggc gcccgcgccc tgccagccgc ggaggtgcgg
67501 gcccggccgg gctacagatg cgcgccagct gcggccccgg gtgcaggcgc ggcgaccgcc
67561 cccgaggagc tgccctttcc ttgccatcca tgcggccagg tctcagacaa accgatggct
67621 ttgtgtcaaa ccaaggccgc cttcctcacc tctgataaga tggacgcctt ctgtcttcgc
67681 gttttcaggc acccggggaa gacccacaga acaggctagc ttgttcccaa tttccacctg
67741 cttcctcccc atcccggacc gacaaaaatt gtcgtctgtt tgatgggagg gagaactccg
67801 actccccccac ctggggcatg cagacaccct cgcccttccc cagttggcat ggaccgtcgt
67861 cttttctccc tcttccatca gatcgatgga caaacaggcc agtttctccc cagtggcccc
67921 cacctaagag cacctaagt tgtccacagc agggctagga agcagaaggt caggacactc
```

Figure 4 (continued)

```
67981 ccctacccta ccttgactta gagctgggta aacccagaac ccatccccgg gcaaatagag
68041 ccagctcctt tgccccagga aggggattcg tctccctctg gcatttagga gtgctctcta
68101 agtgcgttct tggcagtgag ggtgccgcct tcccagggca ggtgtgattc atgtggactc
68161 tgtggcgcct gggcagggat ccccaggtat accagacaag gggcaggtgt gccctgggaa
68221 accgcctaag aggtccatgg gctatggaag gagctgggt ccacagtccc tctgcctgag
68281 cgtgtctttt tccctcaccc acagcgctct agggaaagtt gcctaaacct ctctgagcct
68341 catttctttc atttgtaaag tggggcactc atagtggccc ttcatagaat tgtgtgtaaa
68401 gtgcttagca caggcctggc acatggaggg tgctccagcc tccgggagcc atcactgtca
68461 tgaaaaaata agacctctca atccttgctg ggggcctttg acccacccct cctctctctg
68521 ggcctcacac ttccatctgt gaaatgtcca gttctcatat tcaaagctta ctaggactcc
68581 aagccagtcc atgctgtcct gatccctcaa ttcgcccaca ggctgcctgg gggaggtaag
68641 gactggctgt gacctacctc cacgtggagt cagctcatag cggggtttcc agcaaccatc
68701 acagggcggc cagagctggg tctcgatgat tgcctgtctg accattcctc tcagaacctc
68761 actttcgccc ccagccggcc gccctcctgt gggcagaccc tttcctgagt agcaactggg
68821 cctcagcgga cactgccagg gaccccgttt ccttcccagg aggcctctgt tccccatatc
68881 ccgaatcaca caggagccta gtccagcgaa gagagcagag gactctcttc tagaactgaa
68941 aatttctccc agcctggccc taaatcccct gtccagaggg acccgtggtg aaacctatct
69001 cctgccagt gccctagaac tcaaagggga cattcatgcc cctcactgag cctcaatttc
69061 ctcttctgtc aatggaggtc attctaacca ctccatttca cgggaggggg attaaggatt
69121 ccctctagga ggggagggc atcattgtga ttgatgatcg attgtttgaa gaaacagaaa
69181 gaaaatgctg ctgagtaaac taggactcat ctgcatcctg atttcagata atgatctctg
69241 aatatataag cgagaaatgt taatgaaaaa tggcaatata tctgggttga ggggttgtct
69301 cctgtaggcc ggggggtccag ctccagagag tccagctctg gggtcatcta tcctgggcag
69361 cctctctgga aggattcaga atgtgtggga gcacaaatgt gcttctcaaa ttacagagat
69421 cttttcttcct ttttgaaag ttccagactt ggaggggagg gagaaggagc aagggagagc
69481 agggtggtga gggtgttagg acccagatgc tgcctgtgcg gtctgagact tttgcctggt
69541 gtccacgctc ccctgagcct tggtcccga gggtaaaatg ggaagaacag taacagctgg
69601 gggtgctgag gctttacctt gtgccaggcg ccgcacatgg gcattgctca tggtattcaa
69661 tccccacggc gtcatatgtg gtaggtgtta tgcccatgta agcaaagagg aacgttgtcc
69721 gaggtcagcc aggctagaga gggccagacc cgggttaaaa gtctgctctg gttcaaaatg
69781 tggggcatga acgcatcacc tggccaagca tgtcagcact ctcctcctag tggctgagta
69841 atgggaagag ctagcatcta gatacagagg aaagagctat tgtgatgggg agaggagct
69901 gggtttggta aatcctgcta agcagccctg ggcttggaaa tcagtaaact cttcaaatct
69961 gcagggagtc aggaaggact tgccagggtc attcgggagg gtcctgtgat agtcaaggtg
70021 cacccaccac ctgctctcct ttggcctcag aaccagtctg cgaggaggca ggactggcag
70081 tagtccccag tttacagatg ggaacactga ggcccagaaa ggggaaaggg cgtgatcagg
70141 atctggaatg agctccagca aggccaggag caagcacctc gaggcaaaac gcagttggac
70201 aggacctttg ccttgcagga gactgcagcc cagtcctggg cctcatacac tagcaccctg
70261 atgccacatt cagtgcctct cgcccagggg aagtgctaat cagacgtgtt tccctctggg
70321 cctcagtgtt tgcatctgaa tgcggggtg cactttcaag gcccctctac atgccatgcg
70381 ggttccatag gaccccaggg tttggttgtg acccgaggcc cctcctcccc acccacctcc
70441 tctccacctc ccgcggggcg ccagctccct tgcgtccaca tgacctcgga tccttccacg
70501 cccatcccca ccctgttctg caggtgggtg gtcagagggt gctctgcttt gaggatggga
70561 gagagaaagg gaggcaagga cggagaaaag agacttcttt tgcgggagcg cagagcagaa
70621 aaaccgtctc catcggttac cagggaaggg gtttctggtt tcagatccca tcacttggtg
70681 gggccttcct accaccctcc ctgctactcg ctcttgtcat ctgtaaatca gggaaatact
70741 tctggaagac agttatctgg tctgtgactt tgatcattgg tctatgacta ataattgccc
70801 taattttttg aacacctgcc gcatgctggg agttttccgc caattgtcgc tcaccctcag
70861 gtgcctctga agggcagaga ttttattctt tccatttcac agatggggaa acccaagctc
70921 cgaaagtaaa gagcttttcc tctgtgggcc tcagaatctg agaagttcaa acaggttctc
70981 aggagccctt ccagcacccc actcctcgat cagggagggg ctgtctgcac tctgaccgct
```

Figure 4 (continued)

```
71041 gctctcagcg cagagctctc catccaaagc agcaggtgcg tgcagagcta cctgccagca
71101 gagccatcaa acacggactc ttctactggg agccatggag tggtgagaga gacctgggca
71161 gcttggagcc aaggggggctt ctgggaaaca tgtgcccttc ccccagggtg gggttcagct
71221 ctggcgggca gggagagaaa gggctcttct gagtggctgt tgctttacac acattttttgc
71281 ttcacagtat tcttagggag tagcgacagt tatcactccc attttacagg aaagaaaact
71341 gaggcttaga gagctcaagt aacttgtcca agttggcacc actgggaaac cacaggggta
71401 ggattccaac gaggcagcct ggccccagag cccatgttgc tgcccactac actctactct
71461 tgtggactaa aaccagatgc tcagagttac agtcatggaa tagaattaga atcctggcag
71521 aagaactgtg ggcaggattc ggaattttac aatgtcagac tcgaagggc tctgagatat
71581 caaatccaaa tccccatttc tcaaatgaca gaactgaggc ctaggaagga agagtctcac
71641 tcaaggtcac agccagtgcc aggacagag tctgcacccc ctgcctctcc agctacctcc
71701 cgctgactcc gcaccttcct ctctcgcagg ccctcctctc cccactgccc acccagcagc
71761 ttctgggccc agccaggccc attagggatt ttccacctcc ccaaaaaggt cctgatgact
71821 gtcagtcctt gtgaagcctt aattaatctc agaggccgat ggctcggagg agactggggg
71881 ctttggcctt acgcagatga agattgcggc tctatttcat gtggtggtga aagaacgcct
71941 cagacattcc tgccagcaat aaaagccaca tggctttcca gcatcgccct tggaaaagaa
72001 aaaaaagtgc agcccttttgc ggaaataaat caactatgtg ctgtacgcat ggcatgagat
72061 acaaatgggc atacggaggt gggcaacagt cggtctttta tgccgcctct gatgtccact
72121 gacagtggca gggccagcgg tcatggtccc agctgcaatc ctggggagag ggagtgaccc
72181 ccagtgtggt gggggaagcc tcagcttctc cacctgaact ggatttgagc caccctagat
72241 atcccagagg cagggccggc tttctggcct gtgacccatg cagtcgcaca gggccctggt
72301 ctcagaaggg tcctgagctt gttttaatgc cctgccacca ctgccttgaa cttctgaata
72361 cttgctcaac aaaggtcctg cgttttcatt ttgtactggg ccccccaaat tatatagcca
72421 gtcctgacca caaatccacc cctcatcacc aattgtcacg tctctcctgg cccctgccat
72481 gtacccaatc ccggggagta gggtttcttg agtgcctact agccagtttg cttatatcac
72541 ctgagatgaa cttcagaatg actttgtgaa ttgggcagat gtggaaaatt gaggctcaga
72601 gaggcttcca tatggcaagg aagcctagac ttgaactcag gtctccctga ctccaaagtg
72661 agtgctctta gcagctctac attctgcatt atttcatctt caccatgccc aggggggatgg
72721 ggatacacac agttaggctg ctctattccc agataacaga aggcataact gaggccagag
72781 aagtgaaggt tctcaagtca gtgtcaaacc gagggcctgg gcaacagtgg acctgggcct
72841 ggatccatag ggctggggat ggagtctcag ttttatagtt gtttgtgcca cttgtaaatt
72901 tattagctct ttccatgcag gtcactgcct tgagtctggt ctggaatgtg gctggagccc
72961 taccctgtcc ccctccccca cagctctcca ttctaaacat ctggaagtcc ttccttgtgt
73021 cttcttccac tctttcacgc tgcagttttc ctctgccacc ctcactggtt gggaagcagt
73081 tggatctggc accttgataa actcaaaaga gtccaaattc ttgatgaaag ttgggggctga
73141 acagagccca tagattgcca tgtcctataa ccaggcctgg gcctaaggct catagagcca
73201 actgctagat ccagggcagc catttccttg ttccttgctg ggtaaccttg agcaagtccc
73261 ttccctctct ggccctcaga ctccccttca gggagataaa tgcattggac cacacctgag
73321 ccccaggagg cctctctgtc ttcaacattc tagaattcca tattaatcta caacaggtct
73381 gttcatttcc gcatctaata gctggggaaa ccgaggccca ggaaggatca gagatttgcc
73441 caccgtcaca gaaggtgctt attgacaagt ggacttgact ctgaggctcc tgtcagctgg
73501 cccggttgcc tctgcacaaa cttttcggagg atctggcctc agcatcagct cagcttgccc
73561 ttgtcccgcc gcctttagcc caggtggtct gtcaggcacc ctcagtgtcc aggcctggaa
73621 atcacagcta agagtccttg gcaggcaata aagttcctct tctatggctt gaatgtctcc
73681 caaaagtcat acattaaaac ttcaccccca ttgtgatggt attaagaggc agtgggggggc
73741 ctttcgggaa gtgattaagt ggtgaaggct ctgccctcat gaatggatta ggccctcttt
73801 gcccttctga cttcaggaca caatgttctg tgtcctccgg aggacacagc cagaagacac
73861 tgccttggaa acagggagtc caggacctca ccagatgcgg aacctgccag agccttgatc
73921 ttggacttcc cagtctccag aaccatgtgt agtaagtttc tatttctcta tttataaatt
73981 atcccgtctc aggtattttg ttacagcgac acagagtgaa ctaagacact ctctttagac
74041 aaaagtgggc caggggatgg cagcaaccct tttctcccca atcgcatttg ggctgtgtca
```

Figure 4 (continued)

```
74101 gtgtttccgt aataaaggcc ccttttccag gggttataat ttggctggaa aatgaggagg
74161 aaagaccaga ctccaggact ggaggggcac atgaagtagg aggctaggat gggaaaagtc
74221 tccactggac cctgggcacg cagagtgcac acacacacgc acacacatct atacccctaca
74281 tgtgtgcact cacacacagc acccacgctc atgggcacag tctctcacac attcactggc
74341 agctcacacc cacatggaca agccctcatg gaggacagca ttgttacagt gcagccacag
74401 gtgcaaacag ttaagtgcag gtgtgtgcaa agatgctcct aggagatgcc tctgtctgca
74461 tcatcatgca tggacctatt ggtatagatg cgcagataga tgcacagata ggccccatta
74521 tatgagtggt gtggacacac acatgggcag aaacccacat cacagctgtg taaacagcag
74581 accattgtgt ggacaaatct ttacacacag aggcaggcat ggaatcaggg ctcagagctt
74641 tggatttgtt ctacagagca gctctgggag gagtcgaacc ctggctctgg aagtttctgc
74701 ttctcctcaa ttcagaggca tggactttct gggtggtttg cccccctggg gcttccaaac
74761 cattccccag catctgagtt taacccgctc cctcattgtt cgatggggac aaggagagcc
74821 tgtcttcctg gtccagagaa aggcagtggg aggggagaag tgggagggtt gcagctaggg
74881 tgccccacgg cagcatgggt ggaagggcag ggcactagcc taggggccca gagacctgag
74941 tttgggttta ggttgagatg ccctaggcca acacatggcc tctctgggct tcatcctgag
75001 cccctctgt tagggccatg tgacaccccc aggggcctca gcatggggaa gagcactgaa
75061 accatgtcac atgatgaact attaaagcaa ctggagactt tgccctggag gagagcaggc
75121 ttgggggta agagctcctc tggcagatct atgaagagct cccaggtggc agggaccata
75181 tggatgctgg gggctccata ccaggaatag aaatattgag agctggcttg gaatagggac
75241 acgtcccctc agaggtagag atcaagttga gaccaggata ttgtgcaggg agttcgagtg
75301 ttagatgggg cagggggccgg accagatact agtgtctcaa acgctcagct catagcaaac
75361 acgtattgaa caaatgagag agcgactgca gagctccatt tctgagccaa tcatccgtga
75421 ttcagagcat accagctctg ggttcccacc ttgccatctg catgaccttg gccctctcca
75481 aacctcagtt tcctcatcta tgaaatgggg agaacaaatt atttccaaga gctccagcaa
75541 gtcacatccc ctattgttgg tctttcaggt catcccagaa tttctgctct tataaataga
75601 aaatgacatt gaaggtgaaa agcagacaga caagcaagag aatagttaat acaaaaatca
75661 tagctaggcg tggtaacttg tgtctgtaat ctcagctact tggaagggtg aggtgggggg
75721 atctacttga ggcctagagt tcaagactag cctgggcaac aaagtgagac tctgtatcta
75781 ccaaaaaaaa aaaaaaaaat caggagagtg gtccccacca cttgccacct gtgatgagta
75841 gggagaggga tgcagtcagg gaagggacac tggtgggagc cctaaggtcc cattagtgct
75901 ttgtttttta aagccaggtg gtaggtagat agatgtctgc tttattcttc ttctttaaac
75961 aatacttata ttttatacat tcttctgtac atgtatttta catgtttaaa aatatttaa
76021 aggaaagcaa aagataaaat atagaaaag ttccctgcc ccaaacctct gaaaaatgg
76081 acaatatgct caaatgtgca taatatcgta caattattca tgatgcagca aagctgcact
76141 gtttcatccg gatggtcctg tgtaccatca cactctcagt tgaatctctg caggcccttg
76201 cagctgtcct catcatggca accccacct aggtaagcac ttctaggtaa cagcccctgc
76261 tgagcacgct ccccaagcac tcctcatggc cgaccagtag cccttcaggt atgtgtcagt
76321 gggcccactt tacaggcaag gaagtccctt gcacctacat aggaaggggc agagctggga
76381 tttgaaccag ctctgtcaat gccaaagttg tgcagcaacc tcacccgagg agccaggccc
76441 cttgattata gtaactagcg ttatgtacac tcacacatgc tgttgaatcc ccggagccac
76501 ttttgtatta ggtacattta tcatcatccc cattgtaaca gtaggacaac ggaggcatag
76561 caaggtcagg aacgtgttca agttcacacc ctaggtgagt atcagagctg agccttgaac
76621 ctcagcagcc tgatcccaga ttgtgtttcc tggcctggct gtgtggggag ctcagacttc
76681 atggaaacaa aagacagaac ggtggctcca gggtccacag cggatcccaa gggaccagag
76741 gccagcaggg gggttggctg gggttggagg atgctgccta ggagatctgc tcccagagtg
76801 atgctagccc tgtgtgatga cctgagtccc cgcctcctta cagggtcatg gctgctgggg
76861 aggtgctgag gctgtgggta cagccaaacg gagctagagc aggctttgga ctccctgcct
76921 ggcaagtcca ggtgacaggc tcagacactg ggcactctgt catttgctgt tggcataagt
76981 ttccactggc aggaatgtga catttatcac ctgagtgggc ttccagaagc ccactgaatg
77041 tcctcagacc tggggtgggg ggccctctca ctgcctcacc tctgagcctt aatcaaatcc
77101 agggtggctg gatgatctga aggccctttt agctcacgga ggcctgggct tgccccctgcc
```

Figure 4 (continued)

```
77161 cccatccgtg tcctcagggg aaaaggttcc cagtcctgcc cttagcagct ctgagcttag
77221 atgagggggg gagatgagat ggaaaggaaa aggagaagta agaaacagac agaggaaaag
77281 gagttggcac tagattgaag cagtcaacac acacttatta ggcacctagg gctattttag
77341 gtgctgggga tacaagcaat ggaccagaaa gccatggagc tccttggggg ctttgattcc
77401 agcagggcag acagaagaca gacaaggagg caaataaata agcacgccaa tatttgatag
77461 tgtcttggga cactcaagaa aacagatggg ggtaaagtca gagagagtga ctgggtggat
77521 ggggagagag gggctcttgg caatacttta gacagggtgg tcagggaagg tctgtcggag
77581 caggtgacat gcgagctgag accagagggt tgagagggac ccaggaaggg agaaggggc
77641 tggtaggagg gcccactgca cagtggaact ggctttaccc acctgccttc tccccactcc
77701 tctgcactgc tagtatcccc agttcctaaa actcttactg cccttctct ctgttgcttc
77761 tcccacaaca gccctgagag ccagatgggg tgagcctaag tagcctgacc tgcagtgcag
77821 gaaactgagg ctagagtggg gagggtcagc atcagcggtg ccctaatgcc aggacctgac
77881 ccgggctccc gcctcccagc ctggtgctcc tcggagcctg cccattgcct ggcatgttat
77941 tcaaccaccc cagtccaggc aggctgcagc cactgtggag ccagccgtg ggcaccgctc
78001 ctgagaggtc acaggctgga aatgtgggca gctgggtagg gtctaggagg gggcagcggc
78061 tcaggactgg gcgggggtcc ggagcggaag gcgcccagcc ctgattggaa caaggtggca
78121 gcaccgggag ccgagccggg tgtcattgat cttgcccggt gttccagcca ccaggcggga
78181 ccagcgccgg gcagactgcc ggttttccca ggtgtgggga cccctgagg gaatgacttt
78241 tcatgtggtt gtggggcagg catgccaccc agcacgtggg ggaggccagg gctttgggag
78301 catgctggca gcagggtgga gggggtgtc tggagactca gaatcccaca gccagcaaat
78361 gtgaggctcc tggagacagg gtcatggact tgaggctctg agaccctgag gatgttagaa
78421 tcttcatcgc agtagctccc actgatggtg tgctcacggt gccaggcacg gttctgagaa
78481 ctcacacagc ttaactcttc atccttgctc catcctaaga gggggttctg tgatcatccc
78541 cacttacagt tggggaaact gaggctcggc aaggttaagt agcctgccaa acacacagct
78601 accaggtttt tgtcttagga aataagagcc ctggaacagt tggccagtgc ggagaggacc
78661 cccgaagatc tctgaggcta gtccccttgt gtcggaaaaa caggtctgga gaggggatgt
78721 gacgtgctgg ggcccagggg agtccaaagt caggactcat tcttccccca ggtcatcgtg
78781 ggacctccgc tggtccctga atgtcaggcc cctgagggc agggtcctca gccaggacct
78841 aggctcccag atgttaccaa ccttaactga cagttttctg ctagcacaca ggaagttctt
78901 ttgaacatct aacctgaatc cctcgtttgc agggaaagcc tcttccttct catcttgcag
78961 tactctaaga agagtttggc ctttgatgtt agggaagatc accagttccc tggtgttgtg
79021 ggaggtgaga ctgtgcccct ctctgccata aaatatctct ttactgtcca tcgctgggcc
79081 taaacattag cgacttagcc cttgggcct tacagagttt cttattaaaa tgtgagtact
79141 cctggaatgg gtgtcagctt agcaggacag ggtggtactt caggggcagg gcttggggc
79201 cgttgagggg caggagagag ctgattctcc ccttctagcc aggcttgatg gggtctacat
79261 gacctgccac cctccacctc tctgacctca tctgcttcca ctctgcccct ccctcaccct
79321 gctccagcca ccctgccttc aaatatgccc atcatactcc caccacaggg cctttgtctg
79381 tgctgccctt tacctggaaa accctttccca ttctgtctgc ctggctcagc tacccacttc
79441 attcaggtcc ctgctgcctc ctccaagagg ccttctctgg tctcctgtgg taggcagaat
79501 aatggccaca gagatgtcca catcctaatc cccaaacctg tggctatgtt accttatatg
79561 gcaaaaggga cttcgcagat gtgatgaagg ataaagactt tcagatggga gattatcctg
79621 gattccccag gtgggcccca tatgatcaca aggatcctca cacatggaat agggaggcag
79681 aaaaggacag tcggagggag atggggtgtg gaaactgatt agggaacctg agagatggca
79741 gcgtgggaaa aacatggctc aaagctgtgg gctttgaagg tggaggaagg ggctatgagc
79801 catggaaagc agacagcctt taggagctgg acaagacaag gaaacaaatt ctccaccaga
79861 gcctccagca aggaacacag ccctgcctg accttgatct tggccaaggg agactcatag
79921 agaatttctg atccctggaa ctgtaagatt ataatgcat gttttttta aggcactaaa
79981 agtgggttaa tttatgatgg caggcatagg aaacgaatat gtctcccttc cttgattgac
80041 agttcctcag cacatttatt agtgcctgat acacaatagc ttgacttatg aattgtctct
80101 tttctctcac agaaggtcag ctgcaggagg gcaggatttt tttgcttgct tggtgttaca
80161 ttcgcagata gagttgtcac atttaacaaa tggaaatata aacacccag ttaaattgaa
80221 tttcagataa ataatgaact ccttttagt ataagttgc cccaaatatt gcaattattt
```

Figure 4 (continued)

```
80281 atcgtttatc tgaaattaaa ataatttagg agtcttgtat tttatctggc gaattcatcc
80341 ccaacacata aaaccattcc tgggtatgta ttaggatctc aataaatgtc tgttgaatga
80401 gtgaaataga taagcaaatg aattcacatt aacttctagc ttaaaaaccc tctttggctc
80461 ccagaatgcc tacagggtaa agtgtaaatc atagcaaatg ataaaagcag acagtttcat
80521 agccgcttca atatgccaga cccgggctga gtgctttaca cttattaact cactcggttc
80581 ttgcaataac ccaatgaggt ggttagccca ttttccagat gaggaaactg aggcccagga
80641 ggcttagtaa cttgttcaaa gtcacataac cattgagcag cagagccagg caattccagg
80701 cctttgaaaa cttggctcat ggaatgttct aatgttatct ccctacccat tcccctgaac
80761 actgtggatc ctctctctct aacagccccc ggttccttt cagggtatgt gcttccgcat
80821 tctctgactg ctgaactcct cctcatacat caaagccctg tcctacttt ctctctttgt
80881 gagaccatct ctaaaactcc caggaggact tggcccctc tcttcccct ccccaccatg
80941 gccccttgtc tgaatgcgtt gtaaggactt gctattgtgt cctttacgtt ccctgactgt
81001 gacctccctg agaacggaga tgggcccctt tcagctcttt ggcatgggc ttcaaactga
81061 gtctggcttt aggggggttc ccagaagcat ttgagaatga atgaatgaat gaatgaatga
81121 gtgagtgaat gaatggctga gtgaatgaac gaatgctgtt tgtttccact ctgggcctca
81181 gtttcagagt ctataaaagg ggaagaacaa tcctgaaccg ccccccattc cttaaaacaa
81241 aacacatttt tttctgatta taaaaataat acacattcat taaagaaaaa ttggaaaata
81301 ataaaattat gaagaagaaa attaaaacca tccataatcc tgccacccag aacaatggtt
81361 cccactgggt gttcagcctt ctgctcttct tactgtatgt atagatttat tatcttcttc
81421 tcttccccgc cctccctccc ttctctcctt ccttttttt ttgagtgttg ggaacataca
81481 gtatgggtc ctttaaacct gcttttgaaa tccccaaca tgtgtgtatg tgtgttctcc
81541 tgttttctta aagcctccct gatggcaggg gacaagtggc tgctagacaa gcctggtagg
81601 ggccagggtg tggaaagccc attcccccc tactcatgga ccaccatagt tcccttgtga
81661 tgggctgttt aggggtttc cagatttctg tcaggaaca ccctgcgtgg atgtcttagc
81721 tgcatccctg gttccttcct taggacagat tctgggactg gggttgctga gaccagtata
81781 gacactgaga ggctccggac accgccccac atcctcccca cagctgctct ccagccccac
81841 tcccactggc agcctggact tctcagcttg gcagaaagcc gggggcagta ttccacctcc
81901 tccagagaaa agccttgtct cacccaagg cctcactgat tccatccaac gctgaaaata
81961 cccatttact cagctatttc tccacgttat ggtctaaggc ccagatgctt agttccaacc
82021 aaaatagcca cagaggtcac tgtggtctga gggtcctctg gacctcaggc ctgtgtagac
82081 atcatacttg gtaataatta acccacggag ctcaccacgt gccagaccct ctgcgtctct
82141 gtgtgtcctc acggtaaccc tgaagctagg gatggctgtc tcccatctta caggtgagaa
82201 cactgagggt gctccagaga gctgtgggcc ctaggccttg tcacctgggg gtgcaaaggc
82261 gctgccccag tagtccggct gcctgctacc tggctgcctg ctacccaatg gggcaaagtc
82321 ccagcactac cccgaaacaa ggacaagctt tggcctagaa gctgggcagc caggtcctgt
82381 gcctgttttt tctccatatg tgccctgggc agctcaccct ctccgtctgt gaaatgggag
82441 agcagggagt cagagacagc ctcctaggcc tgtggcggct ctgagcacag tgggtgcaga
82501 tactcagtgc tgagtcaaag agagagagaa ccctgccaga tgggccagct caccacaagc
82561 agccaagccc ggtctttgag gggttggagt gggcaggcct ttgaccaagg ctgagctagg
82621 agggacctga cggccccaga tggaggctgg cccaccctgc cccagcagat gggaggctat
82681 tttttaaccc cacaggaaga agaggacaga aatgattgca gggggttaac ctaggcccct
82741 ggggacgctc cctgtttgca tcctcctttc cccacaaccc agagagctat gtgggcttca
82801 cctggagttc cctgaatcct tctggagctc cccgcagatc acagccggag ctgcagggc
82861 ctgagtggcc cctgtctgcc aggcgaggga cccagagccc agagaagttt gaccaggact
82921 ggcttcctct gccctctctg ctgtgtgctt ccaccaggtg aggctgcctc ctccgcttct
82981 acctttcttc ctggggtgac ctggggaggc cccaccttct cccgggccag tttccccatc
83041 tgtcagacaa tgggaccctc cagacatcac tgaggcttct cccagctggg aaacctcctt
83101 ctgagctggg gccctgactc tgtcacatca gtcctggatt cctggaggcc tcagccctcc
83161 agaagcatcc acccagtgga caggagctcg tggcaggtgt ctggggaccc ccaggaagag
83221 gaaggatttc ctggccagag ataagaagag cagcgtgggt aggggttaag catcctcccc
83281 ctgcagcctc cctcagacca cgccaccagg tggcccttgg tcccccaaa aggagttcct
```

Figure 4 (continued)

```
83341 gaaaagtctg tgtctgttgc agcaggtgcg gcctgtgaag tgtgtgtatg cttgtgtgag
83401 ggtggtgtgt gttcacatgc acatggtggg ggtgggcaca caaggcggga ggcctaacat
83461 ggtggcaggg acagactttg gttgctgagc tgggacagcc tgtgacagag gccccagcac
83521 acccgcaggt cttaccagaa accctcagat ggtgctggtc tgacctgaag gtgggcacat
83581 gcagggaagg ggtacatgca ggacagggt gcatgtgggg gagggccatg tacagggcag
83641 gggtgcatgt ggaggagggg tacatgcagg atgggtgcat gtcggggagg gtcatgtgca
83701 ggacgggtg catgtggggg gtgcgtgcaa gacagaggtg catgggagag aagggtttgt
83761 acatggcagg ggtgcattgg gggtgcatgc agggcaggtg tgcatgtggg ggagggcat
83821 atccaggaca agggtacatg tggggaggcc acagggctca aatgctgtca gggcctctgg
83881 gaagctggga ccccagtgaa tgcttgaggg gagccaactc tgcctgacct cctcttatga
83941 ttgtctattt aaacaatact gtaaattaat cacattaatc gaacccacct ccctgcctcc
84001 tgctgcttgc ccctgtgata caaataatat gagcacaatg aaaaatcttg gaaaatacag
84061 aaaacacata aaaaatgtta aagcctgaag tcttataacc acagtgaaca ctgcgagtgt
84121 ctttgagggg atgggggtct gcaggtcttc ttgatacaat cacattcatt cccacatact
84181 ggagcatttc ccacgggcgg ctgtggagct gagcacttca ggtttgtctt agtgaattct
84241 ctaacagcct gagagggagg tactgttatt ctccccattg tatggctgaa gaaacagcaa
84301 aaaggaggtt aaatatcccc ctcagggtgt aagaagcaga gccaagattt gaatccaagt
84361 ctggctaaat ggaaagtgca aatcgtccag cgtccagggc tgcactccag ccatgccccg
84421 cccccgtga gcagaccact catttattca ttcctccagg agcatttact gagcacctcc
84481 tgtgactcag accctgccca gcacccacac caaggacttg gcggatgtga acgagacaga
84541 gagaggcccc aacctgactc cccaagcggc cacaaactga gtcccaacct tgaccacagc
84601 ttgatttcta gtccaagttg tcactgaccc ccactggcct tcatcactga ctgaactgtg
84661 acctggcctc ctgcactctg cagtggcctc tgtgagcttt tcattccccg tgatgtgtgt
84721 gaaagccaag gccagcagcc cacctcaccc agcctatcat ccacgcggcc tgggccaggg
84781 aggccgtcag gagcccaccc accacctctg gcctgccact ctgggccagg cctctctgga
84841 gcgggggttt ggccttgcc cttggcaccc tgcttggcag aagggtgggc cttggctcag
84901 agcatggggc caccccagga ggggtcagca tagctgagct cagggtacct gtgggcgggg
84961 cttccatgtc ccagggtcct cacactgcag cctcctcttt ttgcctgggc cctggaaccc
85021 caggagaccc caggagccgt tgctccctcc tctcacttgc agaaactcaa cagggcagct
85081 catctgagct cccccgatgc ctgcactgta tttctggggg tcctgcatgt ctctccaatc
85141 ctcaggcagg gccagttacc tactttatag gacccagtgc aaaagaaaa tacaggaccc
85201 cttttcaaaa tgcaggaaca aaagtttttc cttcttctg tggactctca acccacggtg
85261 gtgtttttta tttgctgttc aatgtcacac gtacttggac ctggggagac ttgtgcagaa
85321 agtgcagacc ctcacagatg ctcaggggcc accccaaaac ttggtgtgca gattccaacc
85381 ccttttctcct ccccatgcct gcctcagtgg agggcggcag tgcaggtagt gggctgctga
85441 gaacccatcc ctggaggcag caggaggcag actggacccg ggccccaagt ccccaggcat
85501 gctgcactag cccatcaggc ttcatttaca acacactaat tcagagcgaa aatgatccag
85561 catttcaata tggcaactgc tgagcgttaa attcaagcac aggaggtggg ggggccaggt
85621 agccctggaa catagcagtc tcacaggtgg ctgggcgtgg ggtggatctc tgttcttgga
85681 gtagagggat gtggagtacc tccctctgct tggagtatct ggggtacctg gacaagcaca
85741 gggggccatg aacagggcca tgcctgtgtg cctgcccctc gctcagaaga gggcacctga
85801 cgggaatacc agggcatatc tgcaccatgc ccgggcagta ggcctgggca tgaccctgga
85861 tcaggcagac ctgtagtagg tggaagggcc caggagagc tgaggagcct aggggagagg
85921 aacccagagg tccctgccaa agtgcttgat gtgctgccgt aagaagggca gcataggccg
85981 ggcgtggtgg ctcacgcctg taatcctagc accttgggag gctgaggtgg gtggatcacg
86041 aggtcaggag attgagaccc tcctggataa catgggaaa ccctgtctct actaaaaata
86101 caaaaattag ccggttgtgg tggtgcgtgc ctgtaatccc agctactcgg aaggctgagg
86161 tagaagaatt gcttgaacca gggagttgga ggttgcagtg agccaagatc atgccactgc
86221 actccagtct ggcaacagag agagactcca tctcaaaaaa aaaaaaaaa aaataaggca
86281 gcatggggtgc ctgctgagag agagagaaag aagctctttc cctgcatgtg ttgccatggg
```

Figure 4 (continued)

```
86341 attctggccc agctccctgg ggtgctctct gagctcagct ttggccctgt ccctctctct
86401 ctgtgcctca atttctctaa ctatgcactg agcaaggaga agaccaccac acctcaagta
86461 ccttctgcat gggccataca ctgagtttta tgaatctccc ctctcttgtt ccacaaatga
86521 ttactggccc atttctcaga cgaggaaact gaagcccaga ggaggcaatg actcacccag
86581 taagaaggtg gtggagctgg ttctgcctgg cttcccttca ccccttgagt cgctccagcc
86641 tctctaggtt tgggtggagg acgtgggaac caagctcgtg ggggcaccac cagctcttgc
86701 cagaaatggg gccaagagaa gaccaaggat gctccttgac ctgaggaaac gtccattaat
86761 tcatagctac tgtgctttgg cgagccacgc aggctctgga tgcaggctgc ctgggtgggt
86821 gacctgagca gatgccttaa tctctctggg gttcagtttt ctcatctgta aaataggcct
86881 cataagagct tttgtcttat agggttgtga ggattaaatg agctaaggta tatcacttga
86941 gcctgggagg cagagacttt agtgagcaag attatgccac tgcactccag cctggaagac
87001 agagccagaa cctgtctcaa atacatatat aaacaaaatg agcaaggta tggaaaacac
87061 ttagacagtg gctgacatag agttaagagc tatgtaaatg tttactgcta atggaactat
87121 ttaaaagttg agtcataatt tatattttct agactgtcaa ttacgaattg attcatttca
87181 atgttgtgct tttcccttt gtatttagga tccagcaaat tttcctttga aatctcaata
87241 caatttccta ggtccttgag aagataattt ccccgccccc acagtgctta tagcccatgg
87301 tggatccaat agctctctct agagcagctt ttccaaaagt ggactttgca cacaccagcc
87361 ccttccagat gcatcatctc accccaagag ataactcaat aaacagttga gcatacacta
87421 ttttagatct ccatggccca acaaggtagc cattagcata tcaaagactc tgacaagtcc
87481 tgcagcaaaa caccattgaa cattgtttga acaaccaat cccaatcttg tttgaccaca
87541 gagttccatt atttctgctc aacagctgat aacatctgaa cacacgttgg gagatgccac
87601 cctcatttcc tgctttctag gaaatggcaa ggggagtcag agctgtgagg aacaccctct
87661 cgcagggatg agtggctcca cctctacaga aatcatctcc agtcatgtgc accatcgcta
87721 ggccattcct cctgttctca ccttccttgt ctgattcagc ccccacagcg gcctggagag
87781 gtcactagca tcaatgtctc catcatacag atgaggaaat tgaggttcac aaaggttaag
87841 tgggcacata gccagtaagt ggcagatccg gtagacaaac ccacagcttc tgattctaaa
87901 ccccacattc gttcttctgt atgttgactg aaaagtaaa aatagatcct attctaacag
87961 gatcaatctc cccccatcat aggcttttaa aaaactcagg tattttttt ttccggtagc
88021 attgaatgct ttaaaaactt aaaatttta ctatctttct tttgattact aaagcagtac
88081 gtgcttgtta tgtataaaac ttttcaaaca ttttgagttg aaaaatgaaa aaaaggcagg
88141 gcgcggtggc tcaagcctgc aatcccatca ctttgggagg ctgaggcggg cggatcacga
88201 ggtcaggaga tcgagaccat cctggctaac acagtgaaac cccgtctcta ctaaaaatac
88261 aaaaattagc caggcgtagt ggcgggcacc tgtagtccca gctactcgag aggctgaggc
88321 aggagaatgg cgtgaaccca ggaggcggag cttgcagtga gtgcgattgc gccactgcac
88381 gccagcctgg gcgacagagc cagactccgt ctgaaaaaa aaaaaaaag aaaagaaaag
88441 aaaagaaaaa tgaaaaaaaa aaaaaacag atctgcatag ccctacaaag tagccattag
88501 cttttaaatg aaaatactta aatgctatct aaatgaaaat agttaaaatg aaataagata
88561 aaaaattcag ttcctcagtt acagtagcca cgtttcaagc gctcgggatt cacgtgcccc
88621 tggtggctac tgtgttgggc agcacagaca tgggacatta ctatcatcac agagaatcct
88681 acgggacggt gccgttctag attcttctta gacatatcct aacacctata caggttgatt
88741 atccctaatt caaaaatcta aatctgaaa tgctccaaaa tccaaaactt ttttagggcc
88801 aacatggtac tcaaaggaaa tgctcattgg agaattttgg attttggact gaagtataat
88861 ccaactattc cgaaatctga caaaatcaga agtcctaaat ttgaatgctt ctggtcccag
88921 ccatcttggg taagggatgt tcaacctgta atgactgtta atgtgtggtt ttttttttg
88981 gagaccaggt cttgctctgt cgcccaagct agagtgcagt ggcacgatca tagttcactg
89041 cagccttcac ctcttgagct caagttatcc tcctgcctca gcctcccaaa gtgttgggat
89101 tacaggcggg agccgccatg ccccagccta ttgatattct tgttgaggtt ctcagacata
89161 tctgcatggc ctcacacatg gaggaaagag acccacagag gcaaaaacaa gacatgggt
89221 aaaaatagac tggaaggaaa cacaccgaat gatagtggtt ttttctgggt gttgagatta
89281 ccgagcttat ttttaaattt cttagatcct tcaggtgttc tacaacgtaa aatgcagaca
89341 gggtggggac gttggttgga gtcatgtttt ccctaatgtt cttactggtt ctaaaatctt
89401 caagctatgc tctcacccaa ggcttcactt attattattt taacactgtg gattcataaa
```

Figure 4 (continued)

```
89461 gaatggaagc ccacacaagt ccagggaagg aaggaaaggc agacagaggc ttattttcag
89521 gcctgggcag ttgcacaggg tcccttgctt agaagggcct catgcttggt ttcgtgttct
89581 gtggtcgctg tcctgaaatt cttactgatt tttgaacaag ggatcctgta ttttcatttt
89641 gcactgtgcc ctgaaaatca tgccgccgtc actagccctg ggattctccc caggacaggt
89701 ttcccttcag ctgctctaag ccttcgccct tgtccttgtc caaccacgga cgtggccatc
89761 cacggagccc tctacgtgcc tcagagcaag tgtgcttcgg ctgctcaggt gtgtgtctag
89821 agactgataa aaacagggct cgtgagtggg tgcgggaggc ccctgtggtc tctgttcaca
89881 cacgtaccta ccctcaaggc catgtctaca ctggcctatt tcagagaacc gccctgtgca
89941 tcatgggatg ctttgcccca catcacggcc cagcttggtt cagtcctgga gccctgtgtc
90001 ctgaagccat gaccaacccc aggcctggcc caccttcttc ctcagtctcc tctccctcaa
90061 gccctccaca ggacccataa accttccatc tccatgtaat ccttttgtgt gatccttctt
90121 ccatacccttt gcccatgctg ttcactctgc ttgtaccagc aaggttcctt cctccccaga
90181 tctgcccttt ctagacccat ctcagattcc acccttttcta gaaagacttc aggaagtatt
90241 tgagaagggc ctgaagatgc tgtggttgca tagaggagga tatgaatcac ctcgcttaga
90301 ggtatcgggg agggctccat ggaggtggtg ccctcaggcc aaggaagaga agatatcttc
90361 cgggcagaag ggagagtttg acgggctggt ttgatgtcag acagaccaca ggatgactca
90421 aggtcctctt tcctcttctt aaacattagt tgcagcaagt cccaccatct gcctgagtct
90481 gttttcatct ccacaatgga ggtggtgatg cccagcacac ggagctgtga tgaggattta
90541 atggggaatc cagagcattt atggaagtgc caggaggcca agattctgca taggtaggaa
90601 ggacctaagc cagagggtg tgggtggcca gaggagagag cctaccttag tagggcttgg
90661 taggctaagg tctgggctga atctcgaggc tctggagctt agaacagcat ctgcaactcc
90721 ctggctgtcg gggttcaggc aaggactgcc tcctctctga gtgtcagttt ccccatctat
90781 aaatggaaag ctgggacact gaaaaacact ggggggggagg gtggttcctg aggcagtctc
90841 tctccacaca tcacaggaat gtggcgcccc agggagaagg catctttgtc cattgtgttc
90901 acttctgcat ctccagtgcc cagaacagtg cttgcatgca gtagatgctc aataaatgtt
90961 cattgaatga atcagcagca accaattcgc ccacctcaca tcctaagtcc gctggggacg
91021 taggcccacc tctccaggga aactgtctgc agattgggac cacacctcag gtcacaagca
91081 tttcctgagc acctactgta tgcatggctc tgcgcagccc ggggcagacc cttgctccac
91141 agcccgacag ggcagagcca aggaggcagg tgacagacac agtgatttgg gaagaagaac
91201 agagagcagg gtggccagca gggccttgcc tgggtgggag caggccgttc ccaggctgga
91261 gctcaggctg atgggagccc cagcttgcct gttcctggga gggtgggact gcctcttcct
91321 cttttcttct ctgaaaacaa aaattgtttt cccttaaatt tacaagtatt aaaagtttgg
91381 aaaatacaca ataatcaaaa gaatataaaa taaaggttac ctgccatcat ggcggaccac
91441 acagtattaa ctactatgga cttttcagtg tttccctcta gtctttttc tgaggtggct
91501 ttgctctcag aggtggcttt ctctccccct gggaagggat atagctgctc tgtaggagat
91561 gtgggggcac caggctctct ccatgggctc tttatcactt ctgacttgga ggtccttttct
91621 ccaccccccc tggacctagc acctcttccc gagacacagg ggtgcgaaga gctgggggag
91681 gtacgtcagc aggcctcccc tcctgcccct gcttacccca cggaggtggg gtgggacaga
91741 actcaggctt gaggaaggag cactggaggc caagccacag gtgctggtcc tcagccctgg
91801 tgcccaggca agttgggttt gggaataggg gcatgaccaa aatggacccc tcctttcctc
91861 cccaccccttt tccactccat ccgccttttcc ctttgcgttc tccaagcgtt ccgtccccca
91921 gatgccctct gtttcctctg ctccagcctt ttaactcctc tcaacaaagg ccaaggaatc
91981 aggcagactg tggacactca ggtgtgcatg atgggaaggg acctgcattt acaaaagctc
92041 cccccacag ggactgcatg tgctggtgga atctcagtca ccatgtccca cgttaagga
92101 tgtttggagg gggctgactt tggtcaccct tcaaatcata agttatatgc gtctgcccttt
92161 tccgcccaca cgtaagtctg aaccttttgc caaaaacact tttcccagac tcgaaagaaa
92221 accccaaaga ggaacctaaa ccttcacgct gcctgcaccg attggaccgg agtgctcagg
92281 ctcgcgccaa caagtgtttc aaagaagaag ccagacagtg aagggggaag tgagggagaa
92341 gctggaaaac tctcaggctg accaatcgtc agcccattca ttcgttcatc catccatcca
92401 tccatccatc catccatcca tccatccatc cattcttttct ttcttttcctc tatccattca
92461 gtgagaaggg ctgaatatca cctgtgagcc tgcccctgct cccaagaaca cccttttggac
92521 acctgtgggg tgagtagtga ggggcagcaa tggcagagca cccccaccgc ctggagggga
```

Figure 4 (continued)

```
92581 gaaagggaag ggctgggaag gctccccaag ggggcggcca tgaagctggg ccttgagaag
92641 acaggccagg gtttctcacc ttccacatcc tgcttagagt cagacagaag gcttttgcag
92701 aggaggagga acattaaata gtagtaattt ctggcattcc atgagggctt gtctgtgccg
92761 ggccctgtgc tgtgcacgtg atacacacta cctcattaaa cctacccaac atgccttgag
92821 ggggtgctat tcattttctc cattttacag gtaagaaaat gaaacacaga gaggtgaggc
92881 acctctccca acgccacaca gcgaggaagt ggcagagcct ggctgcagct gaggcttata
92941 gccgcatttt acattgcttt ctctccgaag agtgccttcc tttatccctg ggagccattg
93001 acaaggggtc tgacagtccc tctagtcttg tgcctgctca gccctctcta gccctgaaaa
93061 aaccagggct tggcgctgga gaaagagcag gagggtgaga tgtggaaaca tctgttgagt
93121 ggcaggggat cacgctggcg cagagggcc cgagccgatc aggaggccgg cctgtgccag
93181 gccagtgctc cctgtgtacc aggtgccaca tgcggggctc agggtagggc cacagttgct
93241 cctcccaacc acccttttgag gtcagtgtta ctagcccatt ttacagagga ggaaactgag
93301 accttaagag gtgaattaac atgtcaggtc acccagctac catgcagttt aagcctagat
93361 tgttctgact cctaaactgt gtgcaaggcg gatgattgga ccccagggag gcaaggaaag
93421 tcagttttcc tgctgctgaa ttcaatgttt tacaagacca cacacctctt tagacctcag
93481 tttcgtcatg tatgaaatga ggaggggaac tctctgcctc cgggctctga tatgctcctg
93541 gactgattca ctgttccttg ttcttgtgac ttctcaaagc aagaccagag tcccactccc
93601 agccctaggc ccgagattcc catccccact gtgtccaggg gcttcaggag gtgctatttt
93661 agggcagatg gcaaaggcct gggctgtaga tccactgagg gctaaaggca atctttcttc
93721 cctccacccc tcccttcctt ccttccttct ctttacttcc actaagcaag gtagggaact
93781 actcgctgag tctcagggca ggcccacgga ctgaagctca ggaggacagg gctcccagt
93841 ggctgcaggt gtcccagcac tgactcctag cagaggggt gtttgggttc agtctggaag
93901 attgggtgag attccccaac tacgggggt ggggcacac tctgggtggc agatttgagg
93961 aagagtctgc agataaggca tccccaggag atggcaataa gagctggtgt tggggctgcc
94021 ccactgaacc cagagcccag gcctgtttcc ccacccatgg aggagtccgg actggctcag
94081 tggcaaggcc ggggtcagag gctgccactc tcctcctgcc tctcacagcc cgctggaagg
94141 tcaggttttc aggctctgct tatccgtctc ccggcctcct ccctccaggt aaccgaggga
94201 gcctccgctt tgatgcggcc acctccaggc ccaggcgtca atgagccctc tatatgacca
94261 gtgggctgc tggggcctc cagcccgcca gagtgggtgc ggtgaggcct ggacacacag
94321 tcccgctgtg tggggtcggc tcatgcctgc ctagaccctg tgggcagtgg ggggctccta
94381 ggaatgcttt tccagcctgg ggggcacttt ggacaggcag ggtggtctgg ggagacgggt
94441 gtgtgcaggg cagcctcaga agccgccatc aaaggggacct agcagacgtg gcgccaggca
94501 agcgccatag tgggcacgga agggctggcg gtcagtctgt tcctctccca gggatggcgg
94561 ggaggggag gccccatgga cacatgtgct cagggtgacc agccatcagg ggttgcctgg
94621 gatgaagggg tttcctggga cgtggagctt tcagtgctaa aacagagagt ccctgttat
94681 tggaacttcc tggaccttcg gaaaggatac agtgactgac ctctctggtc tgggcagcct
94741 cctccctgtc cggtgacctc tgagtcagac catctcggcc agacctgccc agggccattt
94801 tgtccacccc ctgcctccac acaggcctgc ctcatacccca agagtccact ttccatttct
94861 cccaggcatc ttcaggggag gagctgccgg ccaactccaa ccactgctag ggggacctcg
94921 gccagaccca caccacgctc ccagccctcc ctgtggctcc cgagccagct catactttcc
94981 tgcttccaca cctttgccca ggacgttcct tctgcctgga acatccttttc cctgtctttg
95041 ttacctcttt acccttaggg acccagtttc caagtcactc ctccagagga cttgttctct
95101 ctttcccaag gctgggctag tacccctctt tgaactcaca gccctggttc ttctcccaaa
95161 aaacctttgt cacgccccag ggcaatttttc tgttgaccca tcttttctca caccagatgg
95221 tgagctctta ggatggagat c (SEQ ID NO:53)
```

ACCTGGTCCCCAAAAGAAATGGAGGCAATAGGTTTTGAGGGGCATG(G)GGACGGGGTTCAGCCT
CCAGGGTCCTACACACAAATCAGTCAGTGGCCCAGAAGACCCCCCTCGGAATCA(G)AGCAGGGA
GGATGGGGAGTGTGAGGGGTATCCTTGATGCTTGTGTGTCCCCAACTTTCCAAATCCCCG
(SEQ ID NO:4)

Receiver Operating Characteristic Curves for Combined Marker Analysis

SEQUENCE LISTING

<160> NUMBER OF SEQ ID NOS: 87

<210> SEQ ID NO 1
<211> LENGTH: 1051
<212> TYPE: DNA
<213> ORGANISM: Homo sapiens

<400> SEQUENCE: 1

| | | | | | |
|---|---|---|---|---|---|
| gctgtctgct | tgtgtgtgtg | tgtctgggag | tgagaacttc | ccagtctatc | taaggaatgg | 60 |
| agggagggac | agagggctca | aagggagcaa | gagctgtggg | gagaacaaaa | ggataagggc | 120 |
| tcagagagct | tcagggatat | gtgatggact | caccaggtga | ggccgccaga | ctgctgcagg | 180 |
| ggaagcaaag | gagaagctga | gaagatgaag | gaaaagtcag | ggtctggagg | ggcgggggtc | 240 |
| agggagctcc | tgggagatat | ggccacatgt | agcggctctg | aggaatgggt | tacaggagac | 300 |
| ctctggggag | atgtgaccac | agcaatgggt | aggagaatgt | ccagggctat | ggaagtcgag | 360 |
| tatggggacc | ccccctaac | gaagacaggg | ccatgtagag | ggcccaggg | agtgaaagag | 420 |
| cctccaggac | ctccaggtat | ggaatacagg | ggacgtttaa | gaagatatgg | ccacacactg | 480 |
| gggccctgag | aagtgagagc | ttcatgaaaa | aaatcaggga | ccccagagtt | ccttggaagc | 540 |
| caagactgaa | ccaagcatta | tgagtctccg | ggtcagaatg | aaagaagagg | gcctgcccca | 600 |
| gtggggtctg | tgaattcccg | ggggtgattt | cactccccgg | ggctgtccca | ggcttgtccc | 660 |
| tgctacccgc | acccagcctt | tcctgaggcc | tcaagcctgc | caccaagccc | ccagctcctt | 720 |
| ctccccgcag | ggcccaaaca | caggcctcag | gactcaacac | agcttttccc | tccaaccccg | 780 |
| ttttctctcc | ctcaacggac | tcagctttct | gaagcccctc | ccagttctag | ttctatcttt | 840 |
| ttcctgcatc | ctgtctggaa | gttagaagga | aacagaccac | agacctggtc | cccaaaagaa | 900 |
| atggaggcaa | taggttttga | ggggcatggg | gacggggttc | agcctccagg | gtcctacaca | 960 |
| caaatcagtc | agtggcccag | aagacccccc | tcggaatcag | agcagggagg | atggggagtg | 1020 |
| tgaggggtat | ccttgatgct | tgtgtgtccc | c | | | 1051 |

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acctggtccc caaaaga                                                  17

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cggggatttg gaaagttg                                                 18

<210> SEQ ID NO 4

-continued

```
<211> LENGTH: 186
<212> TYPE: DNA
<213> ORGANISM: Homo sapiens

<400> SEQUENCE: 4
acctggtccc caaaagaaat ggaggcaata ggttttgagg ggcatgggga cggggttcag      60
cctccagggt cctacacaca aatcagtcag tggcccagaa gaccccctc ggaatcagag     120 cagggaggat ggggagtgtg aggggtatcc ttgatgcttg tgtgtcccca actttccaaa   180
tccccg                                                                186

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggggcggat cgcgtgcgtt                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgaccccgaa ccgcgacggt                                                  20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggggtggat tgtgtgtgtt tggt                                             24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccacctccaa caatacccat acct                                             24

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcggcgaga atatggtgc                                                   19
```

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgacgaacg gccctaacg                                              19

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttggtgttaa agggtggt                                               18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaaaaccctc actcacaa                                               18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13 aggggattt ttgcgttttc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgcaatcttt acccgaacgc                                             20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaggggattt tttgtgttttt t                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tctttaccca aacacttcca a                                              21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ttagagggtt atcgcgttta tgc                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
accaaataaa ccccgaaaca cgg                                            23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
taattttagg ttagagggtt attgt                                          25

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cacaaccaat caacaacaca                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cgttcggttt tatcggattc                                                20

<210> SEQ ID NO 22

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaaactcaa aaaccgacga                                                   20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgagttggag tttttgaatt gttt                                              24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acacattaac aacaaccaca                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttcggcgta gttttttagc                                                   20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actaaacatc ccgcgaacg                                                    19

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggtgtagtt ttttagtgga tg                                                22

<210> SEQ ID NO 28
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acaataacaa taacacccaa ca                                           22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tttcgaagcg tttgtttggc                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caaaaaacct caaccccggg                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tggagagtag gggagtttgt                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aacctaacac acaacaaaca                                              20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tattcgattt atttcgtc                                                18

<210> SEQ ID NO 34
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 34
ctacgaaaaa taaacacg                                                   18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gattttaatt ttttgtggtg gt                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctaaaaccat cacccctaaa ca                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgtttgcgtg gttcgttagt ac                                              22

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgacgacga cgacgaca                                                   18

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttgggtttta tggttgtttg tgt                                             23

<210> SEQ ID NO 40
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 40
acccaacacc ctaacaacca c                                              21

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acggggtatc ggtattttc                                                 19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tacgatcatt ctacgaccg                                                 19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggttattttg gttgttatt                                                 19

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaacactac aatcattcta ca                                             22

<210> SEQ ID NO 45
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
cgtttgcgtg gttcgttagt acgtttatta tcgagcgtat ttcgggtcgg gcgcgttttt    60
cgggttttac ggtcgtttgc gcgtttagcg cgtcgttgtt ttcgtttatt ttgtcgtcgt   120
cgtcgtcgt                                                           129

<210> SEQ ID NO 46
```

```
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
ttgggtttta tggttgtttg tgtgtttagt gtgttgttgt ttttgtttat tttgttgttg      60
ttgttgttgt aggggaaggt tgggtaggga ggtgtgaagt ggtggttggt gtttgggttt     120
atgggaatat gtataatagt ggttgttagg gtgttgggt                            159

<210> SEQ ID NO 47
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tttcgaagcg tttgtttggc gtttaagaga gagtaagaga gggttggaga gtagggagt      60 tcgcggggtt gaggttt                                                    77

<210> SEQ ID NO 48
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
tggagagtag gggagtttgt ggggttgagg ttttttgtta gtgtttgtat tttttatgtt      60
ataatgtttt tatttagtaa aaattttttg ggtgtttgtt gtgtgttagg tt              112

<210> SEQ ID NO 49
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
aggggatttt ttgcgttttc ggattttagg gtcgtttaga ttttttggaga ggaagttaag    60 tgttttttttg ttttttttcg gtatttttatt taaggcgatt agtttagaat tggttttcgg   120
aagcgttcgg gtaaagattg cg                                              142

<210> SEQ ID NO 50
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gaggggattt tttgtgtttt tggattttag ggttgtttag atttttggag aggaagttaa      60 gtgtttttttt gttttttttt ggtatttttat ttaaggtgat tagtttagaa ttggttttttg   120 gaagtgtttg ggtaaaga                                                   138
```

```
<210> SEQ ID NO 51
<211> LENGTH: 528
<212> TYPE: DNA
<213> ORGANISM: Homo sapiens
<220> FEATURE:
<221> NAME/KEY: modified_base
<222> LOCATION: (332)..(332)
<223> OTHER INFORMATION: a, c, t, g, unknown or other
<220> FEATURE:
<221> NAME/KEY: modified_base
<222> LOCATION: (342)..(342)
<223> OTHER INFORMATION: a, c, t, g, unknown or other
<220> FEATURE:
<221> NAME/KEY: modified_base
<222> LOCATION: (407)..(407)
<223> OTHER INFORMATION: a, c, t, g, unknown or other
<220> FEATURE:
<221> NAME/KEY: modified_base
<222> LOCATION: (425)..(425)
<223> OTHER INFORMATION: a, c, t, g, unknown or other
<220> FEATURE:
<221> NAME/KEY: modified_base
<222> LOCATION: (432)..(432)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other

<400> SEQUENCE: 51
cccgggctgg gtacctggac ctataccttc atagctgcct taggctcaac ttttcggcgg      60
ggatccctct gcagacgtgc aggtggcggg agagcagagg tagccgcagt aagtgctgag     120
agagcctgaa agaaacacca tgaattttca aactctccca catacattcc cgaagcgcct     180
gtctggcgtc taagagagag caagagaggg ctggagagca ggggagcccg cggggctgag     240
gctctttgtc agcgcctgca cttcctacgt tacaacgcct tcattcagca aaaacctttt     300
gggcgcctgc tgtgcgccag gccaggcgaa gnagaccgag gntgtgaagc tcagagggga     360
gagggaccaa tcgcagtaaa taagctaccg aggtaatctt agatggngat gagggcagga     420
aaagncatca gncgacctct gacctttctc ttaggggggtt ttccccttcc gcctgggttc     480
tagaactggg aagantttc tccagagcgt cgcggggagc gccccggg                   528

<210> SEQ ID NO 52
<211> LENGTH: 7273
<212> TYPE: DNA
<213> ORGANISM: Homo sapiens

<400> SEQUENCE: 52
ggtacccagg ctggagtgca ctggtgtgat catagctcac taacctcgaa ctcctgggct      60
taggcaatcc tcttgccttg gcctcccaaa gtgccaggat tacaggcatg agccaccaca     120
gtggagctct caattctgat actaataatt tgtgtcttct cttttttcc ttagcctgac      180 tagagtaatt aactttatgt cttttaaaag aaccacctt ttggttttac ccattttctt      240
ttttgatttt ctgtttttga tttgattgat atctactcta attttttatt atttcttttc     300
ctctgcttac tttgaattta attacttttc ttttttgtag tctcctaaaa tagaagctta     360
tattattgat tttagatctt tcttcttttc tattacagca ctcaatgcta taaatttccc     420
tctaagcatt gctttcactg catcctacaa tatttcaact ctattgttat ttagctcaaa     480
agaggttctt aatttctatt gggatttctc tttgacccat gtgttattca gaagtgttcc     540
gtgtgatctc caaatatttg ggagtttttc agctatcttt ctattaatca tttcttgttt     600
aattctattg tggcctgaga gcatatattg tatgatttat attcttgtaa atgtgttaag     660
```

```
gtgtgtctta tggtgcagaa tgcggtttat cttgctatat gttccttaga gaataatgta    720
tgttctgctg ttattggata agtagtcta tagatgtcag ttacatctcg ttgattaatg     780
gtgctgttga gttcagctat gtcctaaatg attttctgtc tgctgtatct gtctatttct    840
gacacaaggc tgttgaagtc tccaaccata ataatgaatt aatctatttt tctttgcagt    900
tttatcaatt ttgtcttata tatattgatg ctccattgtt tggcacatac acattaagaa    960
ttgttatgtc ttcttggaga atttaccttt ccataacatg taacatttcc ctttattcct   1020
gataattttt cttgctcaaa agtttgccct gttggaaatt accagaacta ctctggcttt   1080
atttgattag tgttagcatg ctctctcttt ctctattctt acacttttaa tgtatacttg   1140
actttgtatt taaagtgggg ttcttataga aaacatatac ttggtagggt gggaagtaaa   1200
ataaaaagaa atactgggt attggtttga tccactctaa caatctctat gttttaattg    1260
atgtatttag accattgata cttattttt tatcctcatc cctgtgatta cccagagagc    1320
tgcttaaatt gattattgat atagacaaat taataattaa tatctaccgt tgttactgt    1380 tttctatttt tcattgccct tactttctgc tcctattttt tgctcctttt tctgttaatt   1440
taggttttga gttatttat atcattctat tttctctccc ttctcagcat atgaattatc    1500 tttcttttg actttttag tggctgccct gaaggttgca atgtacattt acaaccagtc    1560
ccaatctcct ttcaaaaaac acaatactgt ttcatggcta gtgcaagtac ctaataataa   1620
gaagtcactc ctaatttctt tctctcattc tttgtatctt tactgttatt catttcactt   1680
gtacataagc tgtaatcttt caatacatta ttgctattat tatttcaaaa catgttatct   1740
attatatcta tttaaaataa gaaaaatagg ccaggtgcag tggcttactc atgtaatccc   1800
agcactttgg gagaccgatg gattgctaga gctcaggaat tcgagaccag cctgggcaac   1860
atagtgaaac cctgtctcta ctaaaaatac aaaaaaaaaa attgctgggc atggtggcat   1920
gggcctgtgg tcacagctac tcgggaggct gaggtgagag gattgcttga gcctgggagg   1980
cagaggttgc agtgaaccaa aatcaagcta ctgcactcca gcctaagtga cagagtgaga   2040
ccctgtctca aaaaaaaaat gaaagaatta tttttattta tcttcactta tttcttctct   2100
aatgctcttt gtttctttag tatgtagatc caagttctaa cctgtatca ttttctttat    2160 ctcaataact tcttttaaca tttctcacaa agcagatcta ctggccacag aatgcctcaa   2220
ttttcatttg tctgagaaaa ccttatttct ccttcacttt tgaaagataa ttttgtaggg   2280
tacagaattc taggttgtag gttttttccc ctcaaagtga aatatttcat tccactcttt   2340
tcttctttgt atggtatctg agaagaagtc agatgtaatt cttatcatta ttacttaaaa   2400
gattgcttct gttcctttct ctcttctcct tcccttcttt ccttctctgt atattacacc   2460
ttttatagtt gccccatatt tcttagatat tatgttttgg ttttcttctg tgttttttc    2520 tttgattctc agtttagaa gtctctattt atatatctgc aatcgcaggg attctttcct   2580
ctgccatgtc cagtctacta ataagccctt acagacattg ttgacttctg ttccagtgtt   2640
tttgatctct agcatttctc tgattatttc ttggaattgc catctgtcta cttacattac   2700
caacctattc ttgtgtgttg tcttatcata gtaattgcag ttgttttaat ttcataggta   2760
ttgtaatttc aacatctcta ccatatttga cattgattct gatgcttgct ctgtcttatc   2820
aagctatgtt tttgtctttt agtgtgactt ctaattttttt gttgaaagcc aggcatgatg   2880
tactgagtga aagaaactca atacattgta atgtgacgat aagagttcag gggaagtgaa   2940
gcattctata gtcctatagc aggtctcggc ctttagtga gcctgtgcct atgaacggtg    3000
```

```
actttcaaca agtgctttc attccactct tttcctgtcc ttaagtggga caagatcact    3060
ggggggggc tagaattggg tatttcctt ctccaatgta gaagctaaag agagggctgg    3120
agttgggtat ttttcttccc ctgtatggaa agctagaggc agttaaattt ggatattttc    3180
cttcttctaa ttcagttagg ctgcgacaaa atcccgaca gtttaggctc taatattata    3240
aaataatttc tcttgagtat aggccttatt aagaacacta tactctgatg gagctgaggg    3300
ggagttttct ctgatattca ctgcgagaac ctcgtagagc tccaggaagc aaaactcaca    3360
aaagtgtggg agtcttccag aattttttcct ttgcagactt atctgcactg aacctccaga    3420
aattcatcaa ttacagttca ggttttccta cccaggtact ggttttcatg gaggtttctg    3480
cctgtgcatt tctgctccag taagttgttc ttcttgtatg gtctgtcttt caaattttttt    3540
aagtagggtt atgacctgtc gcctcacttc tctgacagtt ctgagagtgt tgatttttca    3600
gtttgcttag attttttactt gttttaggga tgaagtgaca atttccaagc tcctccctga    3660
catgccagat cagaaactga aagtcctaag cctcatattc tgtgcgtggg tatgttcaca    3720
tcctgcctgc tccagtgccc ccacctcaca ctctctttcc cttccttgtc cccttgtgag    3780
atttctaggt ccaatacaaa gactgtgttc aactcattca actacttggc tcatctgagt    3840
attataatga acaatcacaa aaaaaaatga agtaaaagaa aaatccatca agaattgag    3900
atatttgaga aaagaaagg agatcagtgt tttataaaac ttagaaatag attttttaag    3960
tgtttcttca ttgacttatg tgaaaggact tttcttaatt taacaaatta tgtgctttcg    4020
tttatagcct caaaacttct tgtgtagcta agaatgggta aataatcagg ctttactaaa    4080
ggactaacgt aaagatcttc tgtaagtaac atttctgcta ctcaaggaag agataaactt    4140
catggcataa ccttgccaaa gtatactaag aataaccctg acacaaagct cttttttcag    4200
ccaacatgcc atgaaagaaa gaagacaagg ggtgatctcc actctctaag tgaaccacta    4260
aacccaccaa agaagaaacg agggaaatag aaagaggacc cttgcctgag ataatggatc    4320
tgtatgtatg agtagtagaa ccctgctcaa agtacaagga agggaaaaaa aagttagttt    4380
atttggaatt ttggacatta agagtcttta ttgttcattt tcttttaact cacatgaatg    4440
gcttatcact tcaattaata aatatttcat ttcttttcaa tctatattca tgaaacaaat    4500
ctgaaatgaa cagtgcaaca tgtgaatgtt tagaacatta taaaattaaa cacaaaatct    4560
gtctggcaat cttcctagca tcttaggaaa aaagttgaca aaatttcaag cagcagaagg    4620
gggcagtaaa actcaacaga aagctctgga agattttttaa gattcttcct tatttctttt    4680
tcatgtagag tatttcccaa caaatttcag acgctaatag aaattttgta caacagatcc    4740
atatatttgc ctaaaataga cacagaaaca ttgatatatg caaacatgag agctataagt    4800
tttacatgat caaaaccttt tttttatggt acacaatagt cacagtactt ttccatataa    4860
aacaggttta gtggtcttaa tttagtttgg cacatttaat acactcccat gaccagcatc    4920
ccaaatgtac ctatccgttt tatttttattg tctcagaatt gtcagttatt taataaatta    4980
tgtaactttt ttccttatgc tcagatttgc acttctttct aaaactctgc ccatccttaa    5040
agtcccagat tctccttgaa ctttttttttt tgactttcca agtacatgga actcttcact    5100
ctatcctgct atataagtga cagaatttcc actatgggat agatggagtt caattccttt    5160
gagtttaaaa taatctaaat ataattattc cttatgccct gttttccct cacttttgta    5220
tccaaatctc ttttcagaca acagaacaat taatgtctga taaggaagac aatgatgatg    5280
atcacttcaa aataagcttg aattcaggat tgtaatgtaa aatttagta ctctctcaca    5340
gtatggattc taacatggct tctaacccaa actaacatta gtagctctaa ctataaactt    5400
```

```
caaatttcag tagatgcaac ctactccttt aaaatgaaac agaagattga aattattaaa    5460
ttatcaaaaa gaaaatgatc cacgctctta gttgaaattt catgtaagat tccatgcaat    5520
aaataggagt gccataaatg gaatgatgaa atatgactag aggaggagaa aggcttccta    5580
gatgagatgg aattttagtc atccgtgtct catgaagaat cagatgtgta cactaagcaa    5640
aacagttaaa aaaaaaacct ccaagtgagt ctcttattta ttttttttctt ataagacttc    5700 tacaaattga ggtacctggt gtagttttat ttcaggtttt atgctgtcat ttcctgtaa     5760 tgctaaggac ttaggacata actgaatttt ctattttcca cttcttttct ggtgtgtgtg    5820
tatatatata tgtatatata cacacacaca tatacatata tatattttta gtatctcacc    5880
ctcacatgct cctccctgag cactacccat gatagatgtt aaacaaaagc aaagatgaaa    5940
ttccaactgt taaaatctcc cttccatcta attaattcct catccaacta tgttccaaaa    6000
cgagaataga aaattagccc caataagccc aggcaactga aaagtaaatg ctatgttgta    6060
ctttgatcca tggtcacaac tcataatctt ggaaaagtgg acagaaaaga caaagagtg     6120 aactttaaaa ctcgaattta ttttaccagt atctcctatg aagggctagt aaccaaaata    6180
atccacgcat cagggagaga aatgccttaa ggcatacgtt ttggacattt agcgtccctg    6240
caaattctgg ccatcgccgc ttcctttgtc catcagaagg caggaaactt tatattggtg    6300
acccgtggag ctcacattaa ctatttacag ggtaactgct taggaccagt attatgagga    6360
gaatttacct ttcccgcctc tctttccaag aaacaaggag ggggtgaagg tacggagaac    6420
agtatttctt ctgttgaaag caacttagct acaaagataa attacagcta tgtacactga    6480
aggtagctat ttcattccac aaaataagag ttttttaaaa agctatgtat gtatgtcctg    6540
catatagagc agatatacag cctattaagc gtcgtcacta aaacataaaa catgtcagcc    6600
tttcttaacc ttactcgccc cagtctgtcc cgacgtgact tcctcgaccc tctaaagacg    6660
tacagaccag acacggcggc ggcggcggga gaggggattc cctgcgcccc cggacctcag    6720
ggccgctcag attcctggag aggaagccaa gtgtccttct gccctccccc ggtatcccat    6780
ccaaggcgat cagtccagaa ctggctctcg gaagcgctcg ggcaaagact gcgaagaaga    6840
aaagacatct ggcggaaacc tgtgcgcctg gggcggtgga actcggggag gagagggagg    6900
gatcagacag gagagtgggg actacccct ctgctcccaa attggggcag cttcctgggt     6960
ttccgatttt ctcatttccg tgggtaaaaa accctgcccc caccgggctt acgcaatttt    7020
tttaagggga gaggagggaa aaatttgtgg ggggtacgaa aaggcggaaa gaaacagtca    7080
tttcgtcaca tgggcttggt tttcagtctt ataaaaagga aggttctctc ggttagcgac    7140
caattgtcat acgacttgca gtgagcgtca ggagcacgtc caggaactcc tcagcagcgc    7200
ctccttcagc tccacagcca gacgccctca gacagcaaag cctaccccc gcgccgcgcc     7260 ctgcccgaag ctt                                                      7273
```

<210> SEQ ID NO 53
<211> LENGTH: 95241
<212> TYPE: DNA
<213> ORGANISM: Homo sapiens

<400> SEQUENCE: 53

```
gatcacctga ggtcaagagt tggagaccag cctggccatc atggcaaaac cctgtctcta      60
ctaaaaatac aaaaattagg agggcatggt ggctcatgcc tgtaatccca gctacttggg     120
aagcagagta ggagaatcac ttgaacctgg gaggtggagg ttgcaatgag ccgagatcgt     180
```

```
gccactgcac tccagcctgg gcgacagagc aatctccatc tcaagaaaaa aaaaaaagaa    240
aagaaaagaa atgaagattc tttctcccct ttcctcccag tgctctcccc acaggaacga    300
gacctgcgtg gtgtggggag cagctgaaga cttctcatct gcctttgtga atgccaattg    360
tacacagcca ctactggaat cttactcatc gcagcaggag gcctggcttc cggcacaggt    420
ggaatgaatg aaggaaggaa cggatgaatg aaaacaatga agctgtacag agcagtctgt    480
ctccgagtgg gcagtggatc ctggaaaaca catcttcagc catccagagt gggaagatct    540
ggatttggga tgtagccgct tcctccctgt gtgacctttg gcagatgtca tttacttttt    600
ggaacttcag tttttccatc cgcaaaaagg ggatgctgcc tgcccagttc atgtcacaga    660
cctgtgaagg tcaaaacaga aggcaggagg gagcatattc cataaaaggt acagcagccg    720
ggcagagtgg cccatgcctg gaatcccagc caaggcagga ggattgctgg agaccagaag    780
tttgagacaa gtatgggcaa aatagcaata cctcatctct aaaaaaaatt atttaaaaaa    840
tcagctgggg ctgggtgcgg tggctcacct gtaatcccag tactttggga ggccaaggca    900
ggcggatcac ttgaggccag gagttcaagc ccagcctagc caacatgatg aaaccccatc    960
tctcctaaaa atagaaaaat tagccaggtg tagtggtgca cacctgtagt accactgcac   1020
tccagcctgg gtgacaaagc gagactctgt ctcaacaaac aaacaaacaa acaaacaaaa   1080
aaccagcgga gcatggtggc acacactgta gtcccagata cttgggtggc tgagtgggga   1140
ggatggcttg agcccaggag gtccaggctg cagtgaacca cgatcgcacc actgcactcc   1200
ggcctgggcc acagagtgag actctgtctc tacaaaagaa aataagaaag gaaggaagga   1260
aggaaagaaa aaaaaataa ataaaaatga aagataaagc atagggacgt ctctgagaca   1320
aagagctgag tggaagaatc aagttaggac tcagcagcgc aggatggcga ggcttataat   1380
tttaatcccc tcctcgattt ctttcgatga ggcaaaaaac agtcttggaa attactcacc   1440
aaaccagcag tgggtgccag gagctcattc actttgtgtg tcattataat ttttgtaac   1500 tagaatggat ggagcaacca ctttggtagt gaaaatattt taatatccgc atgtgcataa   1560
agtgacacga ataacagttc ccgtttactg ggctctgatg ctgtagcagg ctgtggggat   1620
ggctactgtg ctcattttac agacaaggaa actgaaaccc aggcaggcga agtggcttgc   1680
ccaggctcac acagccagaa cgggatgaag caggttctga cctccaagca agactgactc   1740
cagtggggaa ttatgggttc ccaaatgaca ctgatcacag caacaacggg caggacagga   1800
caggtgactc agagcagact cctcatgcaa ggggagatgt tgcccagtgc cgagggcacc   1860
ggggcagggt tcatgccttc ccctgggaga gcaagaggtt cagagtcaga aagactgggg   1920
cttgtggtcc cagctctgcc actttctggt tgtgtaactt ctgccaaatc ccttcacccc   1980
tccgagcctc aatgtgctca tatgcaaaag gggcgagtaa ccacctacct tgcaggcttg   2040
tgtggactga gtgtgttacg gccatgaaaa caccatgtgc tctataaggt gcgctttatt   2100
cattcctgaa gtgagcattt atcatgcacc cacgttcatg ccaagcccct tctctgggatc   2160 tggggagaca gcagcaaaca cagcagatga ggtcctggtc cctggagtta ctttcaagtg   2220
gttggagcca gataatcaac cgagaaagcc tgacacagtt cagacggcgt tgagtgccgt   2280
ggagaaccca cgccggacag cgtgacggag cggcctcggg gctgggctac tgagcaaggg   2340
aggggcctct ctgactttgt gatgtctgca cagaggctga gcggtgtggt gcaggtcagt   2400
gatggaaagc tgtttatggg aagtgtcaag ggatagcccc aaggaaggga ggagctacag   2460
cgggtgagga acagaaggct agggcaggga gaatgggcaa gggggcccacc gggcagtgcc   2520 tgtgcactag aggtggtctc tagaggtggg aatgtctttg tggacacgtg tcctttgctt   2580
```

```
aggacagcgg agagaggctt ccaggtctgg gtgggtgaga aagagggagg agctgtcagg    2640
cagaaccatg gaggtaggtg gtaggaggta ggaggtaggt gggagggtga ggcacctgct    2700
ctgagcccct tctccctggg caggaatggg gcatgtgggc agagcagagg gaagcagcgg    2760
tgcaggaatg gccctgacct gcacagatgt gggaggaggt ccgcacgccc agagaggggc    2820
tgagatcata ccaccaggga cctggtgttg gttccacaag aggctcaggg acacacttcc    2880
agaattttga gagcacccct agcagaggca gggacttgga ctggttgacc tggctttccc    2940
acaccctcaa aacctcaaaa tgtccaatgt ccatccactg atcatgatgg gtctttctag    3000
aatgtcattt tctccccagt gcagttggtg agaggcattc tcacctcctc cctggagagt    3060
ggggttcctc cttaccattg cctggtggtt gagctctagt ccttctgtct ggctggccgt    3120
gtagccttgg gcaagccgct ccatctctct gtgcctctgt tgcctgggct gtaaacagaa    3180
gtgagctaaa ggcaggcaga ccgaggtctg tgaccacgta ataactcata ctcagttcca    3240
gaaatattca cccacagaag tgtctgggac aagcctggaa ggctgatcac accagccctc    3300
cgggtgctgc tcgtggctga gagaacagaa gggagccctg tccaccatgg gaagctgctg    3360
tttccatcac cagcctgggc tgtggtgcag aaagaaggaa ggggagtctg ggtggggcga    3420
gggaggcagc aaagggcctg gaccttcgtg ggagcacgga cacacaggac agccattgtc    3480
gagcttggac tgaccctact tggtgacgtt aagttctcaa gctccaagaa acagcatctg    3540
agttcttgag ctcaatcttc ccaccaaaga aaatcataca caagtcccgg cgcaggggct    3600
tcacagctca aagcatggtc tgtgtccaca tttcctgtgg tgggtcaggc cccactgcag    3660
tcctgagcca gctctgcatt cccaccagag ccccaggaga tcagatgcgg ggtgaactct    3720
gagaagcgct gctctagggc acaggtaggc tcattgcagc cttgtcccca gcgggaaaac    3780
gcggtggacc tgcagcagtc agaggcaagg cacactgcaa gctccaggaa caggcaggac    3840
ccgagaaacg taggtgggtg gaagcaggaa gaaggagaac ccagcgcaaa actgatgatg    3900
catattaaaa acatgcacat ggcggctggg cgtggtggct cacgcctgta atcccaggac    3960
tttgggaggc cgagatgggt ggatcatgag gtcaggattt cgagaccagc ctggccaaga    4020
tggtgaaacc ccatctctac taaaaattca aaaaaattag ccgggcgcgg tggtgggcat    4080
agggagactg aggcaggaga atcacttgag cccaggaggt ggaggttgca gtgagctgag    4140
attgcaccat tgtactccag cctgggagac agagcaagac tcagtctcaa acaaaacaaa    4200
acaaaacaaa acaaaaaaac atgcacatgg caaaatgaca taaggagag tgttgggatg     4260 gtgggagccg tattgtgtca atgtgaactc tcctgaacgt ggttattgtt cctggttatg    4320
taagagcagc tccttgttct caggaggccc acggggaatg gtcctgacat gtgtaggtac    4380
ttctatatgg ctcagcaaac aaaatttatg cagatactca gagagaaccc ctggagcaaa    4440
atgttgacaa tctgtgagcc taggtaaagg ggatatggga ggtttgttgt tgttgttttt    4500
tgttttttga gacggagtct cgatctgtca ctgaggctgg agtgcagtgg tacaatctct    4560
gctcgctgca acctctgcct ctcaggttca agtaattctc gtgcctcaac ctcctgagca    4620
tctgggacta caggtgcacg ccactacacc tggctaattt ttgtattttt agtagagacg    4680
gggttttgct gtgttggcta ggttggtctt aaactcctga cctcaagtga tcctcctgct    4740
tcggcctccc aaagtgctgg gattacaggt gtgagccact gtgcctggct aatttttata    4800
tttttagtag atatggggtt ttgccatgtt ggccagaact cctggcctca gtgatctgc     4860 ctgcctcggc ctcccaaaat gctgggatta caggcatgag ccactgcacc cagccggata    4920
```

```
tgggagttta ttgcactgtc cacagagtga aggtgtggct cctggacttc ctccctcgtc   4980
cagaggagag tcaggctgaa ccagccgggt cccaggagac caaaggagac cccccccccc   5040
ccgccgccac taacaaacca cagagatttt tactgaaaat aagttttctt cctctcttct   5100
tgtaattaca aagataaacc aagtttattg taaaaatgtg aaatgactaa gaagtgtata   5160
aagcaaaaag caaagcgttt tttcaccttt gcccctcccc aattcttaac ctctgtggac   5220
agcttggcag ccccttctag gcattttttct ttccaggtga aagttctgtc aatctttttt   5280
cctcccagag ggagtcctgc acaatttatt gttcatatat tggggacagg tttccatggc   5340
aaaactcaat ctgattcttt tttactttt ttttttttt tgagacagag tctcgctctg   5400
ttacccaggt tggaatgcag tgccatgatc tcggctcact gcaacctccg cctcccaggt   5460
tcaagcaatt ctccggcctc agcctcctga gtggttggga ttacaggcac ctgccaccat   5520
gcctggctat ttttgtattt ttagtagaga tgaggtttca ccgtgttggt caggctggtc   5580
tagaactcct gatctcaagc aatccactca cctcggtctc ccaaagtgtt gggattaaag   5640
gcgtgagcca ccgcccctgg ccctttctta cttttttaaat caagaactga aaacgacttt   5700
atttactctt cttgggacat ggccacgccc atggaagtcc ccaaagtagg ctggacaggc   5760
cacagcagca cccggagcag tggtggcagc tcctgttgag ctgccctcca gaagccagtt   5820
ctgatgcgcg gcctcgccgg gggcctgaga acccctgttt cctgtgaggc tgggccaggg   5880
acaggataac aagggaggca gaaaagagtg ctggcgggga gccaggaggc ctgggttcca   5940
gccccggccc tgccgcttgc ctgctaggag cccttgagaa agtcagttcc cctgcctgaa   6000
cctcagtctc ctcaccttca gatggagatg ccggcccaga gggtaccaga ggcctttcct   6060
ggcttgcaaa caggatgcca gtccacaaag ccacagggtg aggtgcttc ccagttctct   6120 gtgcttcgga acagcgtgct gctccggggg accttggaaa ggtgactggg ctcttctggc   6180
ggtttggggt gggggttgta gtttgtgctc ccggatgttt gcccacgtgg gtggagcctg   6240
cctgtctgtt gccccttaga gggaagttgg cagtaggatg ggttggggg ccgtggatgt   6300 tgggaggccc taaagctgag cccagactct caggcttggg aaggaccttc ccgatcagcc   6360
ttctgtccat ggcttgaatt cctgtcttgt ggcatcagga aagacttatg tcttttaggg   6420
tccaaccaag aaagcagaaa aacactcagg tgttgcagac agagggcctt catacaggga   6480
gttagtcaca caggttatgg gagagccgag aagccgaaga gggtgtgatg agttaaccca   6540
gagattaaca actgcgagaa accaccaccg ccccaggatg gagaagccag ggaggtggtg   6600
gggttagcag atcctgggat cggggtcacc cagtaccagc caggggcttg tgcagagag   6660 ctggagcaca gaggagacat ggctgctgcc gctgagctca cgaaggaaga cagggaaggg   6720
gagggatacc cagcttctct catcacatgt gccccatctt cagtctcccc cagtgcctcg   6780 cttttggcaga actcgctgaa aaacgcagcc tgcaggtatc agccccacc ctgccctgaa   6840 cacagagagg aacatatttg aggtcagagg cccaggactg gcccagtgac tgtgtttaaa   6900
tgcttcgggc actggggagc tcactctcta actcttaact gtagaggtgg tggcaacagc   6960
ctgttttgct ggcggctgag catgagcatt tggttcagaa taaggaagaa acattggttt   7020
cctgtgactc cctacagaaa gatgaggggt ttgtcttggg agcagaagcc cccgtgtgtg   7080
ttgctttgtg ctgtcatgtc tgccaggaag gcccttcccg ccctcccatc gcttgagacc   7140
caattctccc agaaaacctt ccggcacctc catgtcgagg gatagtaccg tcatgtccgt   7200
ccacagcacc tgcgcttcct tctctatttta gcagaatgta gcgaacatta tgttcaacgt   7260
ggacttctct gtttgttctg cctcattcat aggggggcatg gagcttggag aacctgacgt   7320
```

```
tgcctaccca gagctggctc taggttaaag agatgctcac taaggcacct atagtgtgcc    7380
aggtctgcca aatgtttggc atgcattatc tagtttaatg ctcccaacaa ctccggaggt    7440
tggtatgatt agcccatgcc tgctcagctg gagaatctga ggctcaaaag gagggtgtcc    7500
aaggccactt ggctagtaag ggcagagcta ggattcgaac acagcctctt aaaggccgcg    7560
ttccttagcc acggggccac gtggtcttgc cacagtgcag ctgggcccag ggtgggattg    7620
tgtgaagtcc ctcactggga atgtttccag ctcagtcct ggtgcctcct ccctgtcct    7680 ctgtccaaga ccacatgtca gcccttgaa ggcgaggcag ccattcccac agccacttct    7740
ctattctgac atgaccaaga agcctggctg ggacagcagg tctgaccaca gattgacaga    7800
tgtttccaca tgtggaagtg aggtttgagc ctcgatgtgc tgtttctgtg gttccctttt    7860
cacgctttcc ttgggagatg tgtccagaca tggtctcatt gccctaatag gtttccatgt    7920
ctgttgtgca cagtctttag actgtttaac aatcctgttc actggtagag cactgcccag    7980
cttgcacaca gcactttctt atgcattggc tcagtggctc ttcccaacaa tcctgggact    8040
tgggttcatt tactggatgg aggctcagag aggctaagta acaacagtga caaccattag    8100
ttgccttttg cagatctgtc agcatgcctt gctcaaagag agacagaaac tgcccagtgc    8160
acagtgtctc acttgatctt cacaatagcc ctgcaaggta gatattatta caacctctca    8220
ttggaagtag ggaaactgag gctcagagag aataattgac ttacccaagg tcacacagcg    8280
tcaaatccac acctagaacc catctcttgg tcttgactcc tggttcagtg ttccaagcaa    8340
ctgttgagaa catccatcaa acttaaaaat atatatgact atatttcaac aaatctatga    8400
catcattgaa tatagataca ccactctttt atatacccca ggaaatagaa atgctgtcag    8460
ctacagtaag acacagtatt tctcatcaca tagaattttt ttattttaga ctaattaaaa    8520
gagctctttc atatctgtat gcatcatata tatataagca ttatatatgc atatatataa    8580
tgcatcatat atgcatcata tataagcata tatgcata tataatgc atcatatata    8640 tgcatcatat atatgcttat atatgatgca tataagca tatatgca tatataagca    8700 tatatgcata tatatgta tctctctcag ttgtctgtac atagaaggaa aatttatctg    8760
aaaataaact tatatgacat gaaatggatt tatgtgaaaa taaacttctt catattcaaa    8820
atctaactga gtaactgggc gtggtggctc atgcctgtgt ccagcacttt gggaggtcaa    8880
ggcaggtgga tcacttgagg ccaggagttt gagaccagcc tggcaacat ggcgaaactc    8940 tgtctctaca aaaatacaa agttagcca ggtgtggtgg cagaggctgt agccccagct    9000
acttgggagg ctggggcagg agagttgctt gaacccggga ggcggaggtt gcagtgagcc    9060
aagattgtgc cactgcactc cagtctgggt gacagagtga gactctgtct taagaaaaaa    9120
aaaaaaaaag acaaactctg agtgagcagt agaagcccag ctctttccca taagattgtt    9180
ctccgcacca gcaaatgctg gcgatgaaga tttctccctc tctcttcaaa aatatgttag    9240
agaggaaaag cgtgtttaca tataacaaag tacataaatt ataagtacac ttgatgaatt    9300
tttatccacg ttaatattca tctagactca ccagtgcgtt ggagctggct cacattagca    9360
ttgttaaaca ctcaggaatt ttgcaaactg gtttttaaat tgttggtcac ttaaaatcag    9420
ctgcgggcca ggcgcagtgg ctcacacctg taattccaac actttgggag gccaaggcag    9480
gaggactgct tgagcccagg agcttgagac cagcctgggc aacatagga gaccctgtct    9540 ctacaaaaat atatatattt ttaaattagc cagatgtggt ggtgtgtgcc tgttaagttc    9600
cagttacttg ggaggattgc ttgagcccag gagattgagg ctgcagtagg ctatgatgga    9660
```

```
gctgctgcac tccagcctgt gtgacagagc gagacgccgt ctcaaaaaac aaaaacaaaa    9720
accaaaccct agctgcaatg ggagtatttt acatcatgga aattggcaaa tgctacataa    9780
tccagggctg ttttttttcc ttcagaggtc tggtttactg gcccaccact gagtgtagct    9840
actacccaga tggggagagc ttcccagcat cctagaagcc tcctttgtgg ctgtcccagc    9900 cccttttccac caagggaaca actactggat gcggcatttc ctagaggtgg ctgagggcca    9960
ctggcgctgg gctcctgcga ggggtttgcc attgtgcggg gctggcccac tttcgacgcc   10020
catgggagga atgctgctaa acacgtccga tttaccacct cctccatccc gtacccacag   10080
ccatttggtt cctagaggtt aaaagaacac tcctctattg tctccagggt ttccttccaa   10140
gccgcagaat cccattgtcg atgtgacggt gtaagcgggc tgtgaccact ccctggagag   10200
ggcctcctgc caacaattac tgtaagacac acccctattt cagagacact aaaatgtgaa   10260
aaatcaagcc tcttagagtc accaaaatac agtatattgc cttttgaaga tctttactga   10320
agcagtttcc tctgagaagc agcttgtctc catcattaag ccccggaaag cagatgagac   10380
tgcagttcct ccgggctagc tgtctcagtg gtcacttcgc cccagacag gtagcttctg    10440 cccacttctc tcatggggca gccaagtgtt actacctctg gccccggcct ggaataagag   10500
gaccagcagg ccgtgggaaa cctcagctct aataccagge tgcttctgga cagtccttc    10560 tgggtgtgga taaagaccag gcttgtgccc tctgggacc gttcaaagca gtcttcaggg    10620
tcggacctca gactcatccc tgtgatgatt gtttcaggtc ctagcgagtt actttcccaa   10680
cctgtgagct tctgcaactg tgttttttttg ttttttgtta ttgttgtttg tttgttttaa   10740
tatttttttc ttttctttt tttttgagac agagtcttgc tctgttgccc aggctggagt    10800
gcagtggtgc gatctcggct cactgcaacc tccacctcct gggttcaagc gattcttctg   10860
cctcagcctc gcgagtagct gggattacag acgtgtgcca ccacaccagc taatctttgt   10920 attttagta gagacagggt ttcgccatgt tgcccagact agtctcaaac tcctgacctc    10980
aagtgatcca cccaccctcga cctcccaaag tgttgggact acaggggtga gccactgtgc   11040
ctggccatgc aactgtgttt taatcacctt tgtgttccca aggccctgac atggaacaag   11100
cacccagtaa gtatttgaat gaatgagcaa atgaaaggcc aggaagggag gcctttatt    11160 ttgaagcctg cccgccgggc tgcccttggg aaagccactt tctgcaaaag tcacaggagc   11220
aaatgagaca aagatgcaaa attgctctgc ctgagctgtg agggcttaac tgtgaatgtc   11280
tttaggtgac cttcttggag acctcaagac cacccctctg tgacttggtt caggctgccc   11340
tgctgtgatg cctgctgggg ccaaggcctg gatccctggg tggggtgggg tgggtgggg   11400 cggggcgggg aggggcgggg cggggcgggg caggagtggc agcaggaagg atccggctga   11460
gacttgccct gggggggccag ggaaggaggg tggcaggagg cagaatccac aaatgaagta   11520
gatctggagc caggcagatc agcccttaga tataatctca gaaggggttg ggagaatgga   11580
aggattttgt tgaggatgga gtgagagggt tggagggttg ggtatgttcc tgagcatatt   11640
tccctgtcta tgggggccatt cagagagaag cccacgtgct ccaggccagt ggtggagcct   11700
tcaacgtgga gctggaagac ctgggctcga gtcccacctc tgccatgtcc catcctccct   11760
catgactccc agtagttacc gccttctctg ggcctcagtt tccccaactg gaaattaaag   11820
aaaattaccc tgttcctgca tcagatggtt ggttgtggat atcactgaaa tctcctcacg   11880
tggtattgag ccgctgctct tggccagaca cagagcaatt tacatgaaat gattttcgaa   11940
gtctggtccg ggaccagca gtgtcagcat cacttgggaa ctttgtcaga aatgcaaatt    12000
atcgggctcc accccaacta ctctagaccc aaaaacaatt tttatttta tttttattta   12060
```

```
cttttttagga tggagtcttg ctctgtcacc caggctggac tgcagtggtg caatctcagc   12120
tcactgaaac ctctgcctcc tgggttcaag cgattctcct gcctcagcct cctgaatagc   12180
tgggattaca ggcatgcacc acgacgccca gctaaatttt tttattttta gaagaggcag   12240
ggtttcacca tgttggccag gtggtctcgc actcctaacc tcaggtgatc cacctgtctc   12300
ggcctccaaa agtgctggga ttacaggcgt gagccacagc gccctgcccc aaggacaatt   12360
tttaaatgat ataattcata tcccataaaa ttaacccttt aaagtgtgca gtgtggtggc   12420
ttttagtatt atccaccagg tcatacaacc tattatcact aattccagaa tattttcatt   12480
gctctcaaaa gaaaccttgt accatttagc agtgactccc cactcccctg tccctcagcc   12540
cctgcaatca caaacctact tttcatctct atggatttgc ctattctgga cacttcatat   12600
aaatggaatc atagaatatg tggtcttttc tttcacttag cataatgtct tcaaggttca   12660
tccatattgt aatatgtatt agtacatgtt gtactgatgg aacatgtatg ttgtagcatg   12720 tttcacccctt ttaaaaaatc ttcttttttaa attaaaaaca ttttttaaaat acattcaaag   12780 attttttttag agtcgtttta gtttcacagc aaaattggga ggcaggtatg gagatttccc   12840
tatgttccct gcccccacaa catacgcagc ctcccatcat taacatcccc caccagaatg   12900 gaacaattttt aacaaccgat gaactgacat tgacacatca ttatcactgc aaatccatag   12960 tttacttttgg ggttcactgt taatgtagta cattctatgg gtttgacaa gcgtataatg   13020 acacgtatct gtcatgatgg tatcatacaa agtattttca ctgccataaa aatcctctgt   13080
gtgccaccta tttcttcctc ccatcccct aatccccggc aaccactgat ctttctacca   13140
tctccacagt tttgccttttt ccagaatgtc attctcttag tccattttct gctgctataa   13200
caaaatacca cagactgggt aatttataaa gaaaagagac ttactaggct cgtggttggg   13260
gaaatccaag gttgagggggt tgcatctggt gagggccttc ttgctgtgtc ataacacggc   13320
agagggcaag cgagctcacg gaacagagag aggaactcag actgaactca tctgtttatc   13380
aggagcccac tcctgcgata actaaccccc tcccctaata atggtattaa tccattcaag   13440
agagcagagc tctcatggcc taatcacctc ttttttgttt gtttgttttt gttttcagac   13500
agggtctcac tctgttgctt aggctggagt gcagtggcac aaccatagct cattgcagcc   13560
ttgacctcgc aggctcaagt gatcctccta cctcaggctc ccaagtagtt gaaactatag   13620
gcatgtacca ccatgcttgg ctaattttga aattttttta gagatgaggg cttgctatgt   13680
ttcctaggct agtcttgaac tcctggactc aagtgatcct tctgcctcag cctcccaaag   13740
tgctgggatt acaggtgtga ggcattgcgc ctggccctaa tcacatccta aaggtcttgt   13800
ctctccacgc tgttacaatg caacgaaat ttcaacataa gttttggaaa agacattcaa   13860
gccatagcat tccacctctg gcccaccaaa actcttgtct tccttgcata caaataaca   13920 ttcatcccat tccaatagcc ccaaagtttt aactcattcc agcaccgact caaaagactg   13980
aagtccagag tctcatctaa atcagatatg gatgagactc aaagcatgac tcatgctgtg   14040
gcaaattcct tccagttgtg agtctgcaaa atcaaaacaa gttatctact tccaaaatac   14100
aatagtggga caggcatagg atagatgttc ccattccgaa agggagcaac aggaaaggag   14160
aaaggagtaa caggcccaa agaagtgcaa acccaaaag ggaaaacaag attaagtctt   14220
aaagctggag aacaatctcc tttgactcca cgaccagcca cctgggcaca ctgggcagcc   14280
ctgcctctac ggctttgcta ggctcagccc acacaatttt cacaggttgg gatctcatgc   14340
ctgcagcttt cccaggctgc catcactcac tggcagctca acagttctgt ggtctggaga   14400
```

-continued

```
gtggccccac ttccacggct gcagtaggca ttgccctagt gaggactctg tgcagtgcct    14460
ctgatcccac acttccactc ggcatttacc taatagggct ttctgtcatg gctttgcccc    14520
tgtggcaggt ttctgcctgg gccccttttt aaatctagtt gaaggtagcc atgccccac     14580 agctcttgca ttctgtgagc ttgcagacct aacaccatgt ggatgctgct aaagtttaaa    14640
gcttgtacct cctggagcag caggttgagc tgcacctggg accacttaag ccacagccag    14700
ggaagtcaag aggtgctgca ctggaatgat gggggcagag tcctgagatg gctctgggca    14760
gtgagcctgt ggaggatgtc ccaggcatgt tccctgaaac cattctgctc tcctagagct    14820
ctgggcccgt aataagagaa acagcccgga agagctctga atgtctttg gagtctttcc     14880 tccaaaggaa taacacctgg ctttcttcta tctagcctga tcttttaagt aaatggttgc    14940
ttggccacac ccttagtatt cttttccgaa tgttattgct tttcactctt taggaggcca    15000
ggctgtgagt tttcctttgc ttctcttta attataaatt ctgtctttaa gtcattcctt     15060
tccttttgca tctcactgta tgtggttaaa aggagccatg cagcaacctg aatgctctgc    15120
tgcttagctg tttcttccat cagatatccc cgttcattgc tcttcagtcc tgcactctat    15180
aaagccctta gacataaaca cagttcagcc aaagtctttg ctactttgta caaagatgg     15240 cctttcctct tagtttccaa taccttgttc ctcattctg tctgagacct cattagaatg     15300
gcctttactg ttcatatttc tacggacatt ctggtcatga ccacttaaat aatcttcaag    15360
aagatttagg ctgtccttag ttctagggcc ttcttttgag ccctcagcaa aattgctctt    15420
aatgctccat tcacaggaat ctaggctttt tctagcctgc tcctacaaac tcttccagct    15480
tctatccatt acccagttcc aaagcagctt ctacatgttc aagtatttgt catggcaaca    15540
gctcctcttc tgtgcaccaa ttttctgttg ctataacaca ataccacagg ctgggtaatt    15600
ttacgtatat atagaatata tatatagaat atatagaaaa aatatatatg tatgtatttt    15660
atataataat actgagcatt gactcatggt tctacaggct gggaagtcca aggttgagga    15720
actgcatctg gtgaggacct tcttgctgtg ccataacatg gcagaagggc caagagaaag    15780
agaacagaaa tcaggctgaa ctcattcttt ttatcaggag cctacttcct agataactaa    15840
ccaactgtca caataacagc attaatccat tcatgagggc agagctctca taacctaatc    15900 acctttaaa ggtcttgcct ctcaacagtt actatggcaa ctaaacttca acatcagttt     15960
tttgagggga ctttcaaaca atagcagtca tatattggaa tcacacagta tgtagccttt    16020
tctgattggc ttctttcact tagtaatatg gatttaagtt tcctccattc ttttcatggc    16080
ttgatagctc atttctttt agtgctgaat aatagttcat tgtctggatg taccacagtt     16140
aatccattta cctgctgaag gacatcctgg ttcttctt tggcagcatg aaaaaagctg      16200
ctataaacat ctgtgtgcag attttttgtgt gaacataagt tttcaactct tttctgtaaa   16260
taccatggag tgtgattgct caatcatatg gtaaaagtat gtttagcttt atagaatgac    16320
aatttacctt tcaaagtgac tgtactatgt gctaagtggg tgtactattt tacatttacg    16380
tttacaacaa tgaaggaaag ttcctgttgc tccatatcct cctcagtgtt tggtgctgtt    16440
tgtattctgt attttggcca ttctaataga tatgtagtat cccgttattt tagttttcat    16500
tcccttgata acatgtgatg tagagtatct tttcttatgc ttatttgaca tctgtatatc    16560 tttttggtg aggtgtctat taaggtacat ggcccatttt ttaattgggt tgttttttt      16620 cttattgaga gctttaagag ttctttgtat attttggaca actgtctctt atcaaacatg    16680
tcttttgcaa atattttctc ccagtttgtt gcatgtctgg ttattccctt gacattggct    16740
ttcacaaaac agaagtttaa aaaattttt taatgaattc cagctcattc attgtttatt     16800
```

```
tcagcaataa tgctttcggt gttatacctg acaagtcatc accataccta aggtcatcta    16860 gacttttcc  tatgttgtct tctcaagagt tttacagttt tgcatttta  atttagattt    16920 atgaggtact ttgagttaac ttttgtggaa tgtataatgt ctgtgtctaa attcagtttt    16980
tttggtatat ggatgtccag ttattcatat tttttaaaag atggatttt  gcatgatatt    17040 ttgaaaagac tgtctttgct ctattgcatt gtctttgctt ctttgtcaaa gattagttga    17100
ctacatttat gtgggcctat gttgggctct ctattctgtt tattaatcta cttgtttatt    17160
cttttgccaa taccacactg tcttgattag tatagcttta agtcttgaag attactatag    17220
ctttaagtct tgaagactac tatagctagt aagtcttgaa gtcaggtagt gtctgtcctc    17280
caactttgtt cttcctcagt attgtgttga ttattttgat cttccctct  tcatataaac    17340 tttagaatca tttttcaata tccacaaaat aacatgctgg gattttgatt gggattgcac    17400
tgaatctata gatcaggttg gggaaaactt atatcatgac aattttgaat cttcctatct    17460
gtgaatatgg aatatctctt tatttattta gttcttcttt gattttgttc atcagagttt    17520
tgtagctttc ctcatataaa tcttatatat atttacttag atttatacct aagtactttc    17580
ttttattggg tgctaacgta aatggtattg tgttttaaat ttcaaatttc acttgcccat    17640
tgctggtata taggaaagtg acagacttgt acaacaacct tatatcctac aatcttacta    17700
taatcaccta ttagttccag attttttgt  gttgatttat ttggattttt ctacatagat    17760
aatcatgtca tctacaaagg cagttttatt tcttccttcc caatcagtat aactttatt    17820 tcattttctt gccttattga gttagcttgg acttccagta tgatgttgaa aaggagtggt    17880
gagaggaaac atccttgact tgttcctgat tttagtggga aagcttctag tttctcacca    17940
taagtatggt gtttgctgta agttttttgt agattttttc atcaaataga ggaagttctc    18000
ctcaattcct agtttactga gagttgttat atgaatgggt gttgaatttt gcgaaattat    18060
ttttcttcat ctattgatat aatcatgggg ttttctttt  ttagcttgtt catgtgatgg    18120
ttatattaat ttattttcaa atcttgaacc agccttatat acccaggata aatctcactt    18180
gataatgagg tataattctt tttatacatg gttggatttg atttgctagt aatttgttga    18240 agattttgc  atctgtgttt atgagatata ttggtctgta gttttgtttt ttggtaatgt    18300 tttttatct  ggttttgtta gtgctggact catagggtga gttagaaagt atttgctctg    18360
cttctatcct ctgaaagtga ttgtagagaa ttggtataat ttcttcctta aatgtttggt    18420
tgaacttacc agtgaactct tctctgcctg gtgccttctg ttttggaagg ttattaacta    18480
ttgattcaat agatataggc ctattcagat tgtctatttc ttcttttatg agttttggca    18540
aattgtgtct ttcacagagt tggtccattt cacccagatt atcaaatttc tgggcataga    18600
gttcatagta ttcctttctt atcctttcaa tgtccatagg atctgtagtg atgtcccttc    18660
tttaatttct gatattagta atttgtgttc cctctctttt tttcttagtc tggctataga    18720
cttattgatt taattgatct tttcaaagaa tcagcttttg atttcattga ttatttaatt    18780 ttctttttc  aatttcattg atttctgccc taatttttac tattcttttt tttcttctac    18840
ttactttggc cttcttttcc tagtctgtta aggtggaaac ttagattatt gattttagat    18900
ttttcttctt tcctaatata tgcatttgat gctataatct tccctcaaac cactgctttg    18960
gcttatctta cacattttaa taagttgtgt tttaatttc  atcaggtaaa aatattaaaa    19020 ttcttttga  gatttcttct ttgacccatg tattatttag aagtgttttg tttaatctcc    19080
acatgttttg gaattttcta gttatctttc tgttattgat ttcttttaat tccattgttg    19140
```

```
tctgcgagca gaagttgtat gatttctact cctttaatt tgttaaggtg ggttttatgg    19200
cccaaaatgt ggtcaaattc tttctgtttt atggcccaat aatattccat tgtatagata    19260
tacaacattt tgtttatcta ctcatgagtt ggtggacatt ggggttgttt tcattttttg    19320
ttaattccat tgtacactga acatacaatt cagtggtatt ttgtatgctc acaatgttgt    19380
gcagccatca cctctatcta actccaaaac atttcatcaa ctcaaaggag atcttgaatc    19440
cattaagcag ccactcctca tgtccctgct ctcaaccct ggcaaccact aatctgcttt    19500
ctgtctccat gaatatagct attttggata cttcatttaa atggaatcat acaatatgtg    19560
atcttttgta tctgacttct tttacttttc ataatgtttt caatgttcat ccatgttgat    19620
agcattcctt tttagggctg aatactgttg tgttgcatgg atatactatg ttgtgtttat    19680
ccattcatct actgatggac gtttgagttg tttccacttt tgctgtgtga atagtgctgc    19740
tatgtatttg tactcattgt acacattgtg tacaaacatt tgttcgaata cctgttttca    19800
attcttttgg agaattattt tcaattctag gagcagaact gctgggttat atggtatcat    19860
tgtgaggaac tgccaagctg tttcccaaag tggctgaacc attttacatc cccaccagca    19920
acatatgaga gttctaattt ctccacattc tcaccagtgc ttgttttcct ttccttcct    19980 ttcctttcct ttcctttcct ttcctttcct ttcctttcct ctctctctct ttctgtcttt    20040
taaattatag ccattctagt ggatatgaaa gagtatctca ttgtggtttt gatttggatt    20100
tttcaaatga ctaatgatgt tgagcatctt ttcatgtgct tcttggccat tgtatatctt    20160
ctttgaaaaa atgtctgttc aagcattttg accatttta aattgggtta ttttgtcttt    20220
ctgttgctga attgcaagag tttttttat atgtcctgga ttctagatgc ttatcagata    20280
aatgatttac aaacattttc tcccattatt cattatttgc tgtcattcca ttttcctttt    20340 ttttttttt ctttcttaga cagggtctta ctctgtcacc caggctggag tgcagtggtg    20400
caatcttggc tcactgccac ctccacctcc ccagctcaag cagtcctccc acctcagcct    20460
ccccagtagc tgggactaca ggtgcacacc accatgctct gctaattttt atatttcttg    20520
tagagatgaa gtttcactat gctgcccagg ctggtctcga actcctgagc tcaagtgatc    20580
ctcctgcctc agcctctaaa agtgttggaa ttacaggcat gagccactgt gcccagcctc    20640
attttatttt cttgatagtg tcttttttttt tttttgaga caaggtctca ctctgtcacc    20700
caggctggag tacagtgaca tgattatagc tcactgtaac cttgaactct tgggctcaag    20760
caatcctcct gactcagcct ctcaagcagc tagtacaaca ggtgtgtgcc accacgtctg    20820
gctaactttt acatttttt gtagaggtgg agtcttgctg tgttgcccag gctggatctt    20880
gatagtgttt tgttttgttt ttttagatg gagtttcact tttgttgccc aggctgaagt    20940
gcaatgtgca attgcgcgat ctcggctcac agcaacctcc atctcccagg ttcaagtgat    21000
tcttctgcct cagcctccca gtagctgtg attacattta tgcaccacca cgcctagcta    21060
attttgcatt tttagtagag atgggggttc accatgttgg ccaggctagt caggtgatcc    21120
gcctgcctca gcctcccaaa gtgctaggat tataggcgtg agccactgtg cctgggtgcc    21180
tggccttgat agtgttttt gattaactat ctactttat tttgatgaaa tccaagttac    21240
ccatctatgt atatactgag ctgaccctga gacatggcaa aatgtgtgaa gatggtactt    21300
gagtgagtga agtttgggca atgttgtttc tagtgaattc tttctccttg gtggtttcct    21360
ctggcctgtg gatatacttt attcagcaaa agatgccagg gctgagggga tatggcctct    21420
ggtctgccac ccagagggta aacttggcaa gaccccagcc aggctccccc tcctctgctg    21480
ttcctaaaca tgcattcatg gacaaggggt ctctggagca aaggagagtg actccttccc    21540
```

```
tctcccgcaa ccttgcccac ttaccttgta gccagccact ccctcctctt tctgtaactg    21600
ggcattggtc cagctgccag gcccaggacc tctcccattt agccagatgt agttccaaaa    21660
acaactgcag cagtatttgg atacattttc cagcctgaac tagtggtgtt cctgtccata    21720
gctgggatcc aggtttgttg cctctgggtg gggctacagc tccttacctc ctggaaggtt    21780
gtggaagtgt ggtttccttt ttctcctttc tcttgtggaa cataagcatc tttccaagtc    21840
cttctggcca gatgatgatg gtgtgagcct gtccgtctcc catcagtgct gaggggcctc    21900
agatgctgcc tcttacctat aacccagatg ctcccaggtg tgtttatttc ctagagctgc    21960
tgtgacacag agccacaaac tgggaggctc agaacaacag gcattgttcc ttgcacagtt    22020
ctggaggctg gaagtccaaa atcaaggtgt tggcagggct ggttcctacg ggaggctctg    22080
aggaagaatc tgttccaggc gctctcctgg ctcctggtgg ttgctggcaa tccttggagc    22140
cccttgactt gtagatgcat cactccagtc tctgccttca tcttcacatg gcgttctccc    22200
tttccctctg tctctgtgtc ttcttctcct catcttattg tcatattgga ttaagggcct    22260
accctgcatc agtatggcct cgtcttagct aatttcatct gcagttaccc tatttccaaa    22320
ggtcacattc tcaggttcta agaagtacat gaattttgag caggataatg tatggcccag    22380
tgcaccaggc aatgccaagg gcatcactag gtaggaggct ggagatgact ccatttctgt    22440
gagctcctcc ttggctcctc tgtgtctttg cttctaacag cctgtgcctg ccactctctc    22500
tcgagggctc cccttgagct attagagggg ctttgtgtgc acaaaattca gacacacaca    22560
cacacacacg cacatgcaca tgcacacaca catgcacaca tgcacacaca cacacatata    22620
cacacacaca cagagccaga gtgcctggat attcgtgacc cctggagctg tcttaccatg    22680
gtgatgactg acaggtgggc agggcacggt ggctcacacc tgtaattcca gcactttggg    22740
aggccaaggc aggtggacca cctgaggtta ggagttcaag accagcctaa ccaacatggt    22800
gaaaccttgt ctctactaaa aatagaaaaa aattagttgg gcatggtggc gcatgactgt    22860
aacccagcta cttgggaggc tgaggcagga gaatcacttc aacctgggag gcggaggttg    22920
caatgaaccg agatcacgcc attgcactca agcttgggca acaagagtga aactccatct    22980
caaaaaaaaa aaaaaaaaa aaaaaaagga atgactgaca ggtgcacatg cagaagcata    23040
gaagcccaga tccctggcct gcagttgggc acaaactctg aggtgtaact tatactccgg    23100 agcccccac aggtcagttt caactggcct caccctccat gtctagctcc ccctactctg    23160
acactggctt gtcctgggag tacttcctta agaaatcact ttcatgtgaa ttctcttctc    23220
aaagtctgct tctgggcagc ccaagctgaa acagatcccc atacctggag cctgctgcag    23280
ccaggactga tatgcaggaa cccagcccag ggagccacaa agggatccac ctccccggat    23340
ccaggggttc atgattcatg ggcgatggtg tctgtaaat gggaaggccc tctgtgaaca    23400
ctggggtgtt tgccacgcat tgtgctcaat tgtcccctct atgggcgggc cttccccaac    23460
cacaccatcc aagatattct aatcttgtcc tttcaggctg ctgatcaact agttcaggag    23520
tcactgtgga catgtcacac ttcttcctcc atgagatgga gatgaccaaa tctattcata    23580
gttctgtgtg ccaacctatg aaccagacct gagcccctta cccctctgac agtcggcttc    23640
aggaaatcgc catgaggcta caggtgtgtg ttgaggggtg ggtagagaca caacataagt    23700
gggtggcgtg gggtctggca cacttcttca tgtaacccac ttgtacctgc tggacctgcc    23760
agtctcaatc ccaaatatca ctgtagcatt tctcttttt ttatattatg acaaatactt    23820
atttatttat ttatttattt atttatttat ttattttta attttatttt aagttccagg    23880
```

-continued

```
gtacatgtgc agaatgtgca ggtttgttac gtaggtaaat gtgtgccatg gtggcttgct    23940
gcacctatca acccatcatc taagcattaa gcccagcatg cattagctat ttatcctgat    24000
gctctccctc cccacgcacc tcctgaaagg ccccagtgtg tgttgttccc ccaccgtgtc    24060
cttgtgttct cattgttcag ctcccactta tgagtgaaaa cacgtggtgt ttggttttct    24120
gttcctgcat tagtttgctg agaataatgg ctcccagttc catccatgtc cctgcaaagg    24180
acataatatc gttccttttt atggttgtat agtattccat ggtgtatgtg taccacattt    24240
tctttatcca gtctatcatt gatgggtatt tggattgatt tcatgtcttt gctattgtga    24300
atagtgcatt gtagcatttc cattgtacag tgggttactg ctgtgcctgc ctcacattag    24360
gatttggtgg atctggtcat agccagctca cagagggaaa ctcagccagc atagttgctt    24420
gatgtctcat ggtcaggctc tgagtctctg tagggttcag tagcatgcca gcaattgttt    24480
ttcaaaagga gagtagttct ccactgcaga aaatttttaga ggtctgtact gggactcttc    24540 tactgggggtt tgttaaaggc tccacccaag ttctttatct agcaccataa atcttctcag    24600
tctcatggct agcagagcag ctcacactgc agcttggacc tatgcagcgt tctcttttgc    24660
tttgtctcag aactgaaagc tttctgaatt gcctaataaa taggtcagag tagcattccc    24720
aagtgtggta tatgctgctt tgaaattcaa ggagaacaaa gaaggtgggc ataaaacaac    24780
agaaggacag tttctcgcag ctggggagat cagaagtctg aaaccaagat gttggcaggg    24840
ctgacacggg caatacacga ggcccgtgta ttgccttctc ctgcttctct tggctccaga    24900
cattccttgg cttgtggctg catcactcca atctgcgtct gtggtcacat ggcctcctcc    24960
tcttccctat gtgcctctgt tctgtatgtc tcttataagg acatttgcca ttacatttag    25020
gacctgcctg catcatccaa gattacctcc ccatcttgag atccttaact gaattacatc    25080
tgcaaagatc tgtttttccaa ataaggtaat atccccatag gttctggaaa ttaggacatg    25140
gacatatctt cgtggtgggg tgggggggtg cttttttcatc ctactgtatg gtagaggtgc    25200
aaatgcagca acttgtcttt ttttctgaga ggggatggct tggcatgcct cagatcacag    25260
gttccttaag atcttcatca atacgggggga ccctgaattt tcagaggctt tatcttccac    25320
tctctggtgt gcatacattt ttgttttgtt ttgttttgag atggagtctc actctgtcac    25380
ccaggctgga gtgcagtggc acgatcttgg ctcactgaaa cctccaactc ctgggttcaa    25440
accattctcc tgcctcagcc tcccaagtag ctgggatgac aggtgcccgc caccatgcat    25500 ggctaattttt tgtattttta gtagagacag ggtttcacca tgttgaccag ctggcctcg    25560 aacgcctcac ctcaggtgat ccacccacct cagcctccca aagtgctggg attacaagcg    25620
taagccactg tgcccagcca tatatttttat taaagcatct tgggttcttg ccatttttcc    25680
tccttaggtt tagagcagca ggagcatggg agcaactgtc cagtgaaggg ggtctgttga    25740
gaggctcacc cacagcatcc actgcagtgt ccttgatcat cttgacaccc cacgctacca    25800
cccaggtccg tcatgttaac attgtgtgag cattggctgc aaactgctca catctgcccc    25860
cttctctgga gaattgctct ctgccaaaca gtagacatct caccgtggag ttatgctcc    25920 tttggggggtg tggcaagtct tgccaactga cttacctgag gacacaaaaa gtctgctatc    25980 tggagggggac aagtcagtgc tgtaattaat gctccaaagg ccctcatgag accagaatga    26040
ggctggcctc cagcccaggg atgtcataga ttaactttct ttctctgctg tgtcctgctt    26100 ccctcttttcc acttcccctg aaagtcctcc ccacaaaaat ccccacctct tgatctgctt    26160
ctagggaaac ctgacctaag agattccttg ggtgttattag tctattctca cgctgctaat    26220
aaaggcatac tcgagactgg gtaattata aaggaaagag gtttaattga ctcacagttc    26280
```

```
ccatggcagg ggaggcctca caatcatggt agaagagcaa ggaatgtctt acatggtggc   26340
aggcaagaga ggatgagagc taagttaaag gggaaactcc ttataaaatc tcgtgagatt   26400
tattcaatat cacaagaaca gtatgaggga aaccacctcc atgattcaat tagctcccac   26460
tgggtccctc ccacaacgta tgggaattat gggagctaca attcaagatg agatttgggt   26520
gaggatacag ccaaaacata tcattccctc cctagcccct cccaaatctt atgtcatcac   26580
atttcaaaat caatcatgcc attccaacag tccctcaaag tcttaactca tttcagcatg   26640
aactcaaaag ttcacagtcc aaagtctcat ctgaacaag gtaaatccct tctgcctatg   26700
cacctgtaaa atcaaaagca agttagttac ttcctggata aaatggggt acagggattg   26760 ggtaaataca gctgttccaa atgggagaaa ttggccaaaa caagggact acaggcccca   26820 tgcaagtcca aaatccagtg gggcagtcaa atattaaagt tccaaaatga tctcctttga   26880
ctccatgtct cacatccagg tcacactgat gcaagaggtg ggttcccatg gtcttgggca   26940
gctctgcccc tgtggcttca tggggtagag cctccctcct ggctaatttc acaggctggc   27000
gttgagtatc tatggctttt ccagatgcac agtgcaacct gttggtgggt ctaccattct   27060
gaggtctgga ggatgatggc cctttctcac agctccacta gcagcaccc cagtggggac   27120 tctatgtggg ggcttcaacc ccacatttct tttctgcact gccctagcag aggttctcca   27180
tgagggcctc accccctgcag caaacttctg cctagacatc cagttacatc ctctgaaatc   27240
taagcagagg ttcccaaacc tcaattcttg acttctgtgc acccacaggc acaataccac   27300
atggaagctg ccaaggcttg gggcttccac ctctgaagcc acagcctgag ctgtaccttg   27360 gccccttta gatatgacta gagcaactgg gatgcagggc accaagtccc taggctgcac   27420
agagcagtgg ggctctggac cccagcccat gaagccattt tgtccttcta agcctctggg   27480
cctgtgatgg gaggggctgc cacaaagtct ctgttatgcc ctggagacat tttccccatt   27540
gtcttggcga ttaacatttg gctcctcatt acttatgcaa atttctgcag caggcttgaa   27600
tttctcctca gaatatggat ttttcttatc tattgcatca tcaggctgca acttttccaa   27660
acttttatgc tctgcttccc cattaaacat aagttccaat tccaaaccat atctttgtga   27720
atgaataaaa ctgaatgctt ttaacagtac ccaagtcacc tcttgaacac tttgctgcct   27780
agaaatttct cccaccagat gccctaaatc atctctctca agttcaaaat gccaccagtc   27840
tctttggtaa aacatagcaa cagtcacctt tgctcttcct ttgtcttctg ccatgactgt   27900
gaggcctccc cagccatgtg aacagagag tcaattaaat gataccatga tggaggatgg   27960
agtgagggag tcctgaggct ggaccatgaa ggtgctctgc tgtccctgcc atgtaaactg   28020
ctctagtgcc tctctgctgt tggatatcag gaagaagga tttaccaaat tggtagctgc   28080
ataccaaatt ccagagacag tgttgatctg ctgtagtcaa gatgccacaa ctggtacagt   28140
gggtgaaact ggactatgcc tggctatgtt tatgtagtcc acagtcagct cctctgagag   28200
accttccctg accatcttat ctaatgatgc cttccaactc ccagtcttcc tccatcatat   28260
tctcctgttt tatttttttg tgtactgatt actgtctgta gccatgtgat ctatttattc   28320
gtttatggcc tttctcccca attagggtgt aggctccagg ggaataagga cattgtgtga   28380
cttgtttgca gctgcatccc aagcacccgc cactgtagta gatgcctaac caatgtgtgt   28440
tgaatgaata aaagagcagg ccaatgttct tttgctcaaa gtagagggga agaaataggg   28500
ttttctgtgg agattccaag gcagaggcca tttctggggg tcactggagt gggagaaggc   28560
aggtcaaggt gggttgtctt ccaggcagtg caaaccccct ggcctctgcc agctgctcac   28620
```

```
tggccagtct gcttgttggg tctggcacag gcctcaagga acataacat ttttaataaa    28680 acctcagagt caataaaggc gaatggtcct gggtgcctct cctgccggcc ccagctgttg    28740
actttagaag tcaagagagt ggggcgttgc ccaattctca tgtagtacag ggagatataa    28800
gctggaaggg cctagcccat tttatatgaa acaaaacaa acaaaacaa aactcaccag    28860 gccctggaaa gagtccacca ccagccagaa tcaaaggtcc attcagagcg acagagctcc    28920
tcacattcgc cgctaatgaa aaccaaattt ctcatccctc tgagcatttc caggggctac    28980
aaatggaagg ggctgcagag tctttggcca ccgctcccac caccgaaggg gccccactgt    29040
gttaaaatag ttttatgata atataggcct tgtattttcc taatttcagg cgtcagtgat    29100
ttaggacgga gttgttttca tggaaaaaga aatagaacct gtttgtggcg gggcaagact    29160
gatgcctggg cagatattcc cactgtgggc atatttgggt aggggggtga gcctgccatg    29220
aagaggctca gacctagctc cggggaggcc tcgttcatga agttcccgc cttgggcggg    29280 gaagaatggg ctgggggttt ccagacagat tcagagacag tcacagtgac ttctgttttt    29340
tgatttcatg ctttgtgaaa tcttagaatc acaactcaga aaggtagagg catccctctc    29400
agacgcagag aaagggcctc tgttttttta aaaagacatt ttctcatttc ttttttcttt    29460
tttcctcccc cttgatcaat cttttataagc aagtatgtgt agaaatgtca tatttttttt    29520
ttcttaaagt caacttgatt cttactttga gcctccaata cttttagttg gtaggaaact    29580 taatatttc agcgactgct ctgccttcgt caggatcagg tggaattctg tccttgtttc    29640
tcagttttgt tttgttttgt tttcagatgg aatctcactc tgttgtccag gctggagtgc    29700
agtggcacaa actcagctca ctgcaacctc tgcctcctgg attcaagtga ttctcctgcc    29760
tcagcctctt gagtagctgg gattacaggc atgtgccacc atgcctggct aattttttgta    29820 tttttagtag agatggggtt tcactatgtt ggccaggctg gtctcgaact cctgacctca    29880
ggtgatcctc ctgcctcagc ctcccaaagt gctgggatta caggcaggag ctaccgcacc    29940
caacctgttt ctcagttttt tttcatctgt aagatgggga gaatgataat acatacctca    30000
atgggctggg ttaaaaaatg gtgaaatatt tagaatagtg cctggcacag agtaagtatt    30060
aactattatt attattattt ttattattcc agagataaag agaaggcatc aaacctagta    30120
tgagggtatc agggaaggct acctggaaga ggtggtgttt cagctaatga cagatgaggt    30180
agtccttgca tgattttgaa ctcctctgct tggacattta tgtctagaat ttgatatgct    30240
ataccctgaa caagtgtgct aattttagaa aactgtaaag aagaaaacag aaaacagcca    30300
taatcccatc tttgcattga tttcattctg gattaatttt atctctattt ttaactatat    30360
taattgataa cctgtatacg cagtgtgtgt ctggctagaa aaatgtttat ttctaaaaag    30420
tatttatata tttataggaa ataaagatct gaatggggga gaaaagccta aaatattaa    30480 cagtggttat ctttggaggg ggggattatg gctcattttt ctcgtgtgtt tgttggtaat    30540
ccggactgtc tactttccct ctcatgatta tatattagtt tgtgtcattt aaaaatgtca    30600
tttagtctgg gcatggtggc tcatcctgta atcccgacac tttgggaggc caaggtgaa    30660 ggtttgcttg aggccaagag tttgaggcca gcctgggaaa cgtaacgagg ccctgcctct    30720
aaaaaaaaaa ttagccaggt gtggtggtgc acacctgtag ttctagctcc ttgagaggcc    30780
aaggcaggag ggaggatcac ttgagcccag gagttggagg ctgcaatgca ctccagtctg    30840
ggtgacagag tgagaccctg tctaaaaata aaaactaaaa atattactta aaatgtaata    30900
tatagaactc aggaaccgca gatggagagt ctcataatct ttatattttc agaccatgaa    30960
ggagagtggg gtagcttggc cggactctga gcgtcctgga cccacaagtc tgagaggaga    31020
```

```
ggctgcatgt ggcctctggt atggtcacat ggttctataa ggaaactgag gcaggacata   31080
aggcttcact tgtgaagtgg tggagaggga gggggcaatt gccaactggg tgataataaa   31140
gactattgtt aagaccttgc ccccagtggc acatgaaatg ccactaaccc tgagagattg   31200
agagacattc aaacctgagg tttgggcat ggtgcccttc ctgtgacttt ggtgctaatg    31260
atgtctaaga tacctcttag ctcctccctc tgtcattctg cacaggcttc tcctttgcct   31320
ggactatttt agtagcctgt gaacaggtct ctggaccctc atccccagtc cgcaccatga   31380
tggtgctccc atccaacaca tacatctccg cttggctccc ccgtgccact gaccctgac    31440 atggatcctc tcccacctcc catcaccatt gcgccacttg ccccaccatc ctcccagctc   31500
agcgacacct ggttctccag gcctttgcac atgggattcc ctcctgccac atctctgctt   31560
gatccattcc tactcatctt tccatctgat ctcgggggag agacattttc tctgaggagc   31620
ttggcttgtt tgccctgatc cacactgggc tggcacaacc tgctttcctg tctgtctgcc   31680
ctgtgagatc cctgaggcca tggctgtgac ttgttcacct tgttcttggt gtctggcacc   31740
tgagggtggg gtggggctct gtgtctggtg aatgagtgaa tgaattctgg ccaaggcctc   31800
aaagacaccc agcccaatga gctgagtggg gtggtgtggc ccaaatggtg tgtttggaca   31860
ccagagagcc cacattgctg ccagccgtca gggtgggcac aaaggagggt agtccaggcc   31920
ggctccaggg ctgccgcact ccccttccca tgataggtcc cctggccag cccagggca    31980 ggccctttct gtgggtgaat ataaatatat aaaacacaca gcgcactctt agctgcaaaa   32040
ctaaaaatag gaagcgcggg atccggctcc ccaggcttcc ccagccactg gaccacacag   32100
gtgtggctgc ggatgtcggg gcgatgtggc ccctcaccc tccagctct ggagccctca    32160 tggggaggaa tgaggggcat tttggatttc tgccaggaac agttcattct ttcactctgg   32220
cctccctcct gccccgtcc catttgacag ctcatttcat ttacgacccc aaaatgaacc    32280
gacccactga ggtgtattct ctactcacgt ggccaggctg ggttgtttgg tgcagctgag   32340
agctgccctc tgggccatgc tggggggctg catttatgcg ggggtgcagt ctggagcaga   32400
ggagaggccg gggctgagga gggaggcagg gctgggtctg catccagccc tgccctcccc   32460
tacccacggc actggcccca ccccgcgcca tctcctcaag ccctcaccag gcctaacgt    32520 gggaatgtgt catctctggc ctgtagcctc actgccagga catccattgc tcagtgtaaa   32580
agccaaagcc atcccatgg ccacagccca acagtggcag ggctgctcct aggggccggc    32640
aaggcgggtc catctgggcc acttcacccc acaggaggcc acttctggga gcccccaggc   32700
cacagccggc tctctgggtc catcattggg cccatctggg ccaacctcaa gctgtggggg   32760
ctgaagaaac tggagggact caaagtccag cccagatcaa caggactcct agagcctcca   32820
aagcggaatt ctgagtcca ggggctccca ggctgtggaa ctaaatggct tcctcaatct    32880
gaactggctt ctacatgacc taagctcttg ctggtggctc aggggacatg ggtgggctg    32940 ggcccagggt ccaggaggcc agggttgtaa aactatgaaa gtcaaccctg ccttcaagcc   33000
aggtacaccc tgtcccaaag cagacgatta tgggtgtgg ggtcctactc cacacctggc    33060
acacggccgg tgctcattca gcgtatgacc aaaaagggag actcagagag gacagggac    33120 ctcccactgc cacacggctc gggaagggaa aaccttcccc acatcaagac ctttagctgg   33180
ccctttcggg aatgagtcac ctgaggttgg gaagttcttc ttaataccttt acctgaattc  33240 ttgctgtaac caaggcagcc tctcctcacc cttgtccaaa ggggatgatg tccactctct   33300
ccacctgctg cccagggatg ccgcccccta ttgccacctg caggctgctg tggctactgc   33360
```

```
agcacttcct cccgcagccc tgggacctca ggcaagctga gacttctcgg gaccttgagt    33420
ttccccttgg caagctgggt gtgctggttc gtgcctgcta gggtgcaggt gatggagatt    33480
tgagtcagga actctggagg gcacagctcc tctccgatct gctgtggcac caaagtgtgc    33540
ctggtgagga gtgctaccat cccctacaaa gtgaccccaa ataaatagaa acagttttgg    33600
ccatgtagat gccgtttcag gaccaaccct ggcagaggct gcccagagca gaccaacaga    33660
gaagttctgt agccacggct gaggtcctgt ccagagatgg acctgctgtc ttttgggtaa    33720 aagggatgc cgggctaggg aaatggaagc ttcttgttgg gagctgagtt tcaggcagac    33780
caaccaaact gagcagggca aagctttggg agtggttttt gaagtcggtg ggcatcactc    33840
aaaaataagg tctgttttgt aaaaatttcc cttcacaaat cccaactggc caggctctgg    33900
gctgtgtgtt ggtacaaatc ccaagtggac caggcctcct tgctggcaag gtgggagggg    33960
ggctgtcaag ccaggtcccc acaccatcac acccatgcta ccattgttgg gctgtggtcc    34020
cagttcagcc atggacaacc caggggagac atggaccttg atgacactcc ttctttgcac    34080
cgcagttgtc tcatctgcaa aatgggggca ctgaagttgc cgcttactcc caatcccac    34140 tgctgctagc ttgccacaga tcttgaaaca cgagcctcag aggggggttc tcaccaaggc    34200
acttggactc tccctctgcc tctgccccct cccgaaatgt gaatctgagg aacaggcata    34260
ggaattcctc ccaacacggc tgggaagact cacagcccgc tcatgattgg tggaagggtt    34320
gtggcacttt gaagacctat ttgatgctct cctggggtcc cagccataca ggagcaggcc    34380
tcaccggctg tcctgtggcc agggtggtct ctgcggccat tcctgaagaa gttggaagca    34440
aggagatgaa ggtgctgggt gtctctgttc ctgttcctcc tgggcaacag caggaggtct    34500
ccatcctctc ccccaccccca ccccacctcc atgcatagcc ctagaaaccg ggcactggac    34560
tccttccaca catctcagag ttatattatt gtaacaaatc agtcaaaatt ccattttaca    34620
gttaaatagt acagaagaca gtttactgta caagcaagtt gtgcgttaaa aacaaacacc    34680
aagcaaacga tagtgcaaag cagttttccac ccagctccat cctctcgcca gctctgggat    34740
ggttttacat cagatgagtg cagcaggtgt cacacctcag catgacaata tgtcacaaaa    34800
gattggtacc cactactgac aggctcacag taacactata tcaaaacgtc ttcctttcct    34860
cgtgcttcct acatcagtgt gtttgcctag tacaacttta acgcagcctt gtaaataagg    34920
acctactttt accagcccag gctgtctgta cccactttgg gccttacaga ctcagtacgg    34980
ctgccgtcac tttttgtcag gggatggggg atggggtagg aagagcaatt tatttactat    35040
ccctgcctct ccaggatcag gaagggttag taatctggga tgagactaca aagtgctggg    35100
cactgggaac ccaaaggtgc ctcccacgct gacctgggac cagctataac cagagaacag    35160
gagggaagaa actacaagga caatggattc atagctgctt cctaagaagg catggagagg    35220
ccccttgggt gcagggagtc agcaactatt ttgaggagat ggagactgtt tttccagtga    35280
ggacaggcca agagaaaccg cagcaggagg gaatggaata ggatcaccag aaggactgcc    35340
taacctgcca gtgtgtctct ggtgtatggt tctggccgtt gtgacaggtt gggtggggac    35400
agtgctctca cagagacaac caatgaagag cattttgtag ggcagatttc tgcatccaca    35460
gaggccgagc cagaaagtta aaataccgca tgctgctagc ctttatgagt tcccttacgc    35520
cttttctaag cctttctagg gccagagaac tctgatgtga gaatccatgc agcctggccc    35580
ttgggcaagc gcccactttc ccattttgca aaattcaggg gcaagacttc acctcggaac    35640
gcagtgcagc tgagctgcgg ctggagagcc ctttacagtg cttctgtcct gccacgcaca    35700
gccagtactc cccacctctc acatcctgcc cacctccgcc cagcctcctg gacagatgtc    35760
```

```
ctagagccac agaggagaga tgcccagcgt ctcatcagcg tttccctcgt cctcccaggg    35820
gagcctgtgg tgcaggctgg tgggatgctg cctgatgggg agtgtagccc cttgagaaag    35880
tattgagacc ctaataaccc cacaccctca ggaggcagct gggggtccgc ggggggagga    35940
gggggcgggg atgttgctta taatcacaga gctatcataa tcacggaact atacctgtaa    36000
gagaccttgt gtttgaaaac gttagattaa gcttcttttt ctaaaatcag ttttaaaaac    36060
tgttttgttt ttttttttgtt ttttttgtttt tttttttttt ttgctcagga ctatttgctt    36120
tcagagcaca aaacaggtta cagacaggtg tgtgccagga gtcgcaagat ttggctggat    36180
cctcccagga ggcttggggg atggggcaca gcttggctgg acccaggggg gacagggaca    36240
ttgatgtctg acccaaaatg atccctcacc tcaatgcctt ctgctaggac ctatctatct    36300
ggccctcctg ttctctccac aaatggaatt atgagaccac ctaggggaaa ggggacctcc    36360 tatccccct cccccgccct gccaagagaa cagagagtgg atgcgttgag ctggtaaagt    36420
gcatggagga gccggtctgt aggtgctttc ctgggtttaa gaacctgatg ccatagactc    36480
atcttctctg gggcctggga cccgtgcggc tgggggaaag ccaacagtta ggaacggagg    36540
ggaagctggg ctgggggggac tggcttggat gtgttctcaa accatctctg ccagcagcgt    36600
gctgggtcct gccccatctg tacaatgagg ggaacccgc tcgagggtgg tgggggtggg    36660
ggacactttc cagttctgac tcaaatctgt gtaaatgcag agggggctgg acccagggga    36720
tgcaggggct ccaacgaagg tgcaggggtc gggaggtttc ccagggcctg aggcttatcc    36780
tgtgggccaa tgctgcctct ctctggaaga gagatggcct ctgtcccagg agacatgggt    36840
cccatgcagc actgggcata gctggagaca gtgaggtcct tccggggggg tggcaggagg    36900
ctgattcccc acagaagtat gggatgagac ggccaggatc tgggccgggg gcagtatccc    36960 gggccgggt gggggtggta acctatgcct ctgtacaagg atgtggctgc acagatgcag    37020
ccagaggctc ccaccagctg gaccaccct gggaccgaga ccaccctgga gcgcaggtcc    37080
cattcccgcc cggagcctcg gagccggccc atcactggtc ttgaaggttg ttagggtccc    37140
cgcctccagc gggaggagtc caccagggcg gtcagtaggg ccgccacacg gcctcatcca    37200
tgcggcctgg cgtgctcagg gccgtgggtg agttgctgtg gctgccgtcg gcctccacgc    37260
catcactctg gccgcccagg ctggggttca tgaggttgcc ggcggcgaca gaggcagcgc    37320
tgctggtgca agaggccagc atgcgggtag gtgagcggtc gccccactg ctgctgccgg    37380 ccaccatgga gaactggtag gagccagagg atgtcccgta gtagaggtgg tagggggacg    37440
ggttggcctg gaagggcccg ctctggttct gcggggcccc cggtagggt ggcgggaggt    37500 aggtatggtg gaagcggctg gtggccggca tgcccgccac gctgaggctg ctgatgctcg    37560
tgcccgaggg cgtggcgctg taggggaagg cagctgacat ggccccggga taatgcatcc    37620
tggggtctgg gaagcggctc tccgtgaggg ttggcagcgt ggggaaggag cggtcaaact    37680
ggcgggggtc ggagaatggg ttcagttccg aggtgcctgg aggacagcag ggaagaggtc    37740
agttccagct cgagacaacc ccaggagggc ttcctgaaga atgaccttgg gctctggttc    37800
ccaaggccca tctgggggac ccctagttct agacctggct ctcctcttcc tgccctaggc    37860
tgcccggggc ctcccccgcc aggactccga acacagacct gccgggaagc tggttggagc    37920
gtgccccggg ccaagagggg ccatgggagc ccccccacag cagcaacaga acagaggagg    37980
gggtctattt ttcttttttaa atcctccttc ccagcctcgc agaggagagg cctaggatgc    38040
ggtggtgggg ctgagggcag agtcagctca ggcctcccag cagccctgcc caggcaggtt    38100
```

```
cctctcccca ccggcccatg ttaacagctg ggaaggccgt ggatgtgtaa agggctccaa   38160
tgaccgtgtg agactgggag ttggaacccg cttttgaaga caagaaaatg gaggcagaga   38220
gagagcaaga ctgagtctct gtggcagaga aaggactggt tctcatcaca aggcctctgc   38280
tggggacaca cgtgcctctc ctgcccaggt gcagacgcg gaggttctgt gcgctcacac    38340
ctgggttgtg ggcactgagt tcacaggagc tctggcctcc acctcaccct gggcctgtgt   38400
ctctggagcc gactcgtggc cacacagtga ctggatgcca ccctaacctg ccttggcagc   38460
aaagtgagac agcagtcaga caaacttggg gacccagacc ccaacctggt cacagtgtcc   38520
agcccagact ctgcccctgc tcccccagga atgtggcttc tcaatgggct ccaaggcaag   38580
ggtgttccat cctctgtccc caacttttgt catcacagac ccccaaaacc tcagcattca   38640
aaggggctca gggattgagt ctaacaccct tgatggggaa actgaggccc agacagggtg   38700
aggcacttcc ctcagggtca cacagcacat tggacctggc acacaatcct agggcctctg   38760
gtcctgagcc ccaacacgta cttgagaggg agctgtcccg tctttgaggc agcacaggat   38820
caaggcttac tgtgtggctt ctggagccgg acagttatcc tggtttggac acttactagc   38880
tttgtgtcct tgggcaagtc acttaacctc tctgcgcatc agtttcccca tataaaacat   38940
gagacgataa cagttcatca ggattcagtt aattcacatc gagtacttag aatggcactg   39000
ggcacagagc aggggtccat gaggctttgc aaggccactg tggctgtggt gtctcttact   39060
ctgggtaccc aggagaactg gctcattcag ggccctgcca agttgaggcc ctggtgcagg   39120
gcctcccttc tactctggca gccggggag gtggatgagc cccagcagt ggtccagagg      39180 tgcagtctgt ccagcccagc aacccctctg tgtcacccac caaaggataa gggccggtgc   39240
tagccggagt gggctctgcc tgccacgccg aggcttggct gaggacggag agctatgagc   39300
ctgaggtgtg tgtgacttcg gctgggactt ggaacttctc ggggctttgg ggtcttccca   39360
agtcagctgg ggtatgtttc cctcagcagc gtactctggc cctgggcgtg gatccgaacg   39420
gagtgatgct cctggcttaa ggtaagaaga tgtggggaca gcagtctggg tggcggggc    39480 cttctgggac atctgggatg ttccctagta ggtcacttgg ctgtcccggc cccttgaggc   39540
cgagagcctc cgaggcacct ggctgccagt tttcatctgg ggagccctc ggggggagag    39600 gtcctgttgc aggtgctggg cacgtcagca cagctgagat gggtggggtg gaagtgggtg   39660
ctggccgcct gatgggaacc ccattctcaa gacgaaggaa acaaatgggg accgcaggat   39720
acaacggcag gactgtgccc ctcagagctc acgcgggctg cagggcgctg ggctgggcct   39780
ccctggacct gccaccatcc cctccagcct cttttcctcag gccaccacc cctcctccgg    39840 ggtggtgggg gaagtacctg ccctcagcac tccctcagac ccccagcag cttccttgga    39900 gctcctgtac ccccacccctg cggcctcgca gccccaggaa acccgagctg cccggggcac   39960
tgtcgagtgg ccaatcccaa cagtggaaag aaatgtttat tttcttctcc agattgtccg   40020
ggctgctgca tggtggctga atgagccctt tcagctgtga gaagccccca ttgtgggcgg   40080
ctgcggctgg gggctggggc tggggtatgg gaggtgctgg ggtctctgca ctgcttgcca   40140
gtgaccaata ttggagggtc aaagcactta acaggcaccg agggaagtgg tggtggggtg   40200
tcccaagggg gatccccagg agggagtccg agggcagagg gaggagggcc tgtgagagtg   40260
acttcccaag cctaggtctg ccagcaaccc ctctttgtca gggacctcct tctccccact   40320
tcacagatga gaaaactgag gctgagttta agtgacttgt ctaagatcat acagccaatg   40380
cctggcagag cctgaattcc tagcctggtc cagctgactg cagagttcat gctcgccctg   40440
tcctggtcat ccgaggccct ttctctcacc caaaggggat gggcctgagg atggagatgc   40500
```

```
ctggctgcct gtggcccagt gctgtggggg gctagcgagg gactgggcca ggcctcagga   40560
gggagcaggc agagaagcag aagtcagcca ctgccccaca caggctgggc tcctttcctc   40620
ccagcccagg atggaagcag cagctgtgcc tgccgtgggg ccaggcattg attcccaagc   40680
tgtgcccacc cagcagtgga tgggcagatg tgggctctcc ttccatgggg gctggtggac   40740
aggaagccac tgttcacccc acctcctgga ttctggctcc cccgctgagc ccgatcccc    40800 tggcctggct ctgtccatgg cagagaaagg ctggctctca ggctactgca cctcgacaga   40860
tgctggccca tgggtagcag aagcagaggc agctacgcgg caggggtggg cgtgagcaca   40920
gcgtgcaggg ctccttccgc tacctcttga gagcagacct ccaactcctg ggctcgagag   40980
ctgagagtct caaatgcact agctcctggg ctcagagagg ctgggcctgg ggcttctccc   41040
aaccttggcg tctcagcagg accaaggcca aaagtcctga gcccaggcca gaaggggagg   41100
ggtcctctct tcacactgaa ggcctgcatc cagcccctgg ctgcagcact atgcctggaa   41160
caatgtcagt agagagaccc agtcggcccc cacctcagcg tggcaccgga aaaggggtg    41220 gggcaggcag accggttggc agccctgttc caggcccctt tatctgtccc ctcagaagta   41280
cagaaagttc ttgggagcag gtactgtgga gactgtggac ctggtcacag atgggctgtg   41340
tgacccgagg gtggctctga acctcttagg cctctcaatt cattcatctg ccaagggtt    41400 ctaaccaggc tctggggaat tgagaaagaa tgggcacagt ccgtgacggc agccagctgc   41460
ctgcctctgt ccacccggcc accaagcacc cttggcaccc cacttagccc aagggccggc   41520
tgtgcacaca gcctcccatg tccccagctc actgactgag agaacagagg agagatgcag   41580
ccggcagccg tttagtgagc ggctactatg cgccaggcac ctcgatactc cagaagacct   41640
gcctgaggcc tggctgcaac tgtgcttgct gtatccgtct aggcagtgga gatggagacc   41700
ccagctcggt cttcccttcc acctcagctc ctcctgtttg ggaggatgct ctgggcaggg   41760
tgggagacct ttcccaggaa tgctatgtgc ctctctaggg ttggaatgtc acttaacagt   41820
gtgcaaagtt tgtgtgagta cagtaatgtc atttgaatgt catcccagcc ctgggtggag   41880
gcatccgccc caatccactt tcagatgaaa aatcgcaggc tgtggggcag gggtggggaa   41940
actgtacatg gcagggcga gtctgtcacg gctccttgga caagtcatgc cccaatttta    42000
ataggggcac tatggggtta accccatttc cccaggcaca gtgaactcct ggtatgcaga   42060
tccctggggc caggcaccag gcatgtgtca gtaatgtcag tgtttgctga gtgaacgaat   42120
gatggctagc acacagaaag cccacaggaa ccgtctgcag gtgccaatga gcaccagcag   42180
ctcctctaca aaacaagggg gtgcagtgac tgatcttcgg acaggctttt ggtctggggc   42240
agattggacc acatcgaggc cctccacccc cacctcaccc cgctgcagcc cctccctccg   42300
tgccgtacct tggattgggg tctggggctg gctgctgaag tggcttgtgg tgctgagtga   42360
gcctcggggg ctgggtgtgc tcggtgtcac ccgcatgcgc agccgttcca ggtccccaaa   42420
gcggtcaggg aacggcttgg tctggtcctc cagcttctgc cggtgccctg cagagcacag   42480
gaagcccatc agccgttgct tccccagagt ctcagtggag acagaaatgc ctcactctgc   42540
tgggaagttc ttcctgaggt ctgaccttag gcctctgctg ggagaaccct gaggtcaccg   42600
ccagcctctt cacagaggtt ttcaaaagac tttctgaaca gagaatggtc gttatgtgcc   42660
accccacata tctaaaccct tacaacacac ggtgatccaa acctctacaa cacgcggtga   42720
tctaaacctc tacaacacgc ggtgatctaa acctctacaa cacgcggtga tctaaacctc   42780
tacaacacac tgtgatgtaa acctctacaa cacgcggtga tctaaacctc tacaacacac   42840
```

```
ggtgatccaa acctctacaa cacacggtga tctaaacctc tacaacacac ggtgatctaa   42900
acctctacaa cacactgtga tgtaaacctc tacaacacgc ggtgatctaa acctctacaa   42960
cacactgtga tgtaaacctc tacaacacgc ggtgatctaa acctcaacca cacgcggtga   43020
tctaaacctc tacaacacgc ggtgatctaa acctctacaa cacgcggtga tccgaacctc   43080
aaccacacgc ggtgatccga acctctacga cacgcggtga tccgaacctc tacgacacgc   43140
ggtgatccga acctctacga cacgcggtga tccaaacctc tatgacacgc ggtgatccga   43200
acctctacga cacgcggtga tccgaagctc tacgacacgc ggtgatccga acctctacga   43260
cacgcggtga tctgaacctc tatgacacgc ggtgatctga acctctacga cacgcggtga   43320
tccaaacctc tacgacatgt ggtgatccaa acctctacga cacacggtga tccaaacctc   43380
tacaacacac tgtttggcag aagaggaaac tgagggccag gtgcagtggc ttacgcctat   43440
aatctcagca ctttgggaga ctgagatggg aggatcagtt gaacccagga gtttgagatc   43500
agcctgggca actatcgaga ccctgtctg tacaaaaatt aaaaaaaaa aagaaaaaag   43560 aaaaacttag ccaggtgggg tggcacaagc ctgtagtccc agctactggg atgactgagg   43620
caggaggatc acttgagccc aggaggtgga ggctgcagtg agctgattgt accactgcat   43680
cccagtctgg gcaacggaac aaggacccta gatctaaaaa aaggaaactg aggcaacaga   43740
catgagaaag tggctcatgc ccccaaggga ggcagggaga taacccagga gcactgccac   43800
cctctgcctc ccagcatccc agcctgcctt gcacactgtc tcccatgtct acaagaacaa   43860
tgggaggtgg ccccaggagg ggactgcagg cttttccagc cctaagtcac tctgggatcc   43920
ccagaacatg ccttcttctc tctgggcctc aggcagaaaa ataactccac caggatgctg   43980
ggcagaggtg tagggggctt gcatgaggga ctagacagcc atctctgcct ggaagctggg   44040
gtcaggggac gagatgtcac acctggagaa aactgccagc attttccact ccctatctgc   44100
cagagcccac acaggaagaa tcccagcctc acatccgagg actcagaggt gctgggaggg   44160
tcaaggtggc caggctccca ccctcctgcg gcctgctgag gccgagggac acttctggag   44220
tgatatcaag cttgcaggga cctcccccgc cacacacact tttttaatta ctaattttac   44280
atttcacaag caaacgtga atatttacaa aaataaaagc attacagata aggctctgtc   44340
caccgctcta agctcctctc cagagtcccc accgtgacca gtttctttcc agacattttt   44400
catcttccat gaatggaaaa cgcaaagtag gcttctcatg gaactctctt gaacagcctc   44460
agtccgggtg tgtcattctg taacttgctt tcttagtagc acaccttgga gctcaaactc   44520
agtttcccta tctgcaaaat ggggacagta atccagcccc acagaaatga cggagttccc   44580
ataaaaccct ggggatcctc cctgctacgg aagggattca acaagcatgg cgagaatgac   44640
gctgctctcc ctctttcctg ctggccactg gaggcacagt tcactccgca gtcctctcca   44700
cccacatttc agtccttctc aagcttcccc tttagttccc ttacatgcaa cactcccggg   44760
aacgtccctg ttcgcacccc ctagtggctg cagcttctcc agggctgacc cgaggaaagg   44820
acggctccct tggaggactg tgcactccag ggttcggctg atcaaccta acacggtcac   44880 ggccattcta cctcacgtga cttggtggga ggctgccagt caggcagggt ggccaggccc   44940
tcttttacaa gtaagagaac tgcaactgcg gagaggcgag gaagcttgtt ggaggccaca   45000
cgccgaacaa ggggtgggat ttcctggacc tgggacccctt tagaaaagat ggaggctagg   45060
catggtggct acgcctgtaa tcccagcgct ttgggaagcc gaggcgggcg gatcacctga   45120
gtgaggtcag gagtttgaaa ccagcctgac caatatggtg aaaccccgtc tctactaaaa   45180
gtacaaaaat tagccgggcg tggtggcggg cgcctatgat cccaactact tgggaggctg   45240
```

```
aggcaggaga atcgcttgaa cccgggaggc ggaggttgca gtgagccaag atcacaccac    45300
tgcactccag cctaggtgac agagcaagat tccatctcaa aaaaaaaaaa aaaaaaaaat    45360
gtgggagggg gtaagggggga ggagaaggtt tgcctaaggc cttgggtcta gaatgacatg    45420
```

```
aggctagggc tgtcctttaa agcagtcgcc agcaggagtg gaaatcatca aaacggcagc    47640
agatgcttgc tgggtgcttc ctccacggca gcgtctaagc agctgacaag caccatcttg    47700
tttcgcctgg cagcatcccc ttgagtaatg tctgccacca tcctatcata tgggtgaaaa    47760
aactgaggct ctggacagcc agtgagctca aggtcaagca aagacacac agccacctgc     47820 tctccctaga gcctgtgaaa acacatctat tgtggcggaa gagggcgggg ttcacagcca    47880
gcctgggttc gatacatcaa tagatgtatc gggactccac aatagatgtt agggcccgt     47940 ccagccccag gcccagagct gctatctgca ggcccaggag ataggactt gggagaggaa     48000 gatgagaagg tctcagtgga ctccaccagg ggcccttccc tgctctgaag ctcagggttg    48060
agagtgcaat ttccaatcat accctgctct agaccaccaa gtcactctct gcctctgggc    48120
cacagtttcc acatctgtaa agtggttatc atactgtcta accctgagg gtgccgatga     48180 gctggaggac aggccacatg cttttaaaag cagaggactg agatggctgg ggaaagcccc    48240
gcgttggccc tcagggcctg tcctggctgc tgtcagcctc cagctgctgg gctcagatca    48300
gacagctcct ccagcatggc ctggattagt gtctatgacc ctcacttatg ggagggcaga    48360
tcccagcctg cccctcccaa gggcccagtg gccccaagct cataccaggc agctctcacc    48420
caccagtggt cactgtcttg ggcaagccac tcttgccttc tgggcctcag ctgtcttatc    48480
tgcaaaatgg ggatcacacc tctaaccccc gagggtcagg aaaggtttca agaattacac    48540
agcccaccag gccttggcct ttgaggaagg tgttctgggt tcccattctg acttggccat    48600
ctgctcctag gcaaacagct cctctctgat gcgtctgtgc agtgggggtg acccacctca    48660
caggcatatg ataaaggcca aagtgggagc aggaatgctg ggcccagcc agtctgggga     48720 ctcaccaggg tcacgcagtg tgggagctag aggaccaggg ctggattctg ggttggcagc    48780
tcctttacca ctgtccccag ggaatccttc cccaccacca gctggccag cctggggtcc     48840 tacccccgcc aggtacctga tgcttctggg ggaaccaaga gaccatcagg gttaccccct    48900
tgcctccatg caggcccaac acaagcccct gtcataggag tggcaaccat tttagcaggc    48960
atccatgatg tgccgggcac tgtgcaaggg gggccatgca tgtcgtctcc aagggtcata    49020
tccctctgac aggctgtgac tatcaccccc gttttacaga tggaaaagtg gaggcacacg    49080
gtcaaggtca cacggtgtgt ggcaccctg agattcaaac ctggaaaggt cacacatgga     49140
gctcagctgc taaggtcatc gcttcccaag acctccatga gagaagagct gggtcacctg    49200
gccgtaaggt ccagctggca agaggccagc tcagtgttca gcctcttggg aaaagcagag    49260
tcgggcaggg ccacaggaac agcatcgtct gctggggaca gtgtgggctc caatgaccag    49320
gcccgtcacc catctgaagc cactcggcag ccttcttggc cgcctggtgc ggctgtgacc    49380
cagacacagc agccactgtc tacccagcag cagggtgggg cgccgggccc gaggccggct    49440
ctgcggcctg tcaggagatt tacacccgac tcttaacagc ctcgcggaat cgcaggcggg    49500
tgccgggcct ggggtggtct gctgtgaatc ggccccctgt gagcagatga aagccgggtc    49560
ggtggctggg cagggaaacg ggctggccgg gggcagcgg gcaggaggc gagcggttcc      49620 ctcccagggc tgcaagtggg gcttccagag gcctggggtt gattaggaga acccaggagg    49680
tctgtggtta accccttccc tcctgctggg cagactccgc tagccctgcc cctagcgcag    49740
gagacactcc tgggggttgt ggggatcttg ggagccaggg acctggagca gctgcctctc    49800
ctcagcccag gaagaaacta cagaaactct aaggccttca aaggcccaac tgcgggctca    49860
gggtcacttc tcctgcccac gccaaaccct cggcagccac actctgctgg ctgctcactt    49920
caggcccctg ctcaaaggtc acctcttcag gaggcctccc cgccccatcc cttgttccat    49980
```

```
cccttgcacg ctccactcct tctcccagct ttgtttttct tcataggact tcctactacc   50040
cgaaatgaca ttaatgaatc atttgcttat tcatcaacga tttatggagc agctgtgaag   50100
ggctcctgcc cacattctca gggtctagct ataccagggc ctggcaaacc agagcaaaga   50160
actctgccct tgtagagcat aaacaacagg gggccgggtg cggtggctca cgcctgtagt   50220
cccagcactt tgggaggctg aggtgggcgg atcacttgag gtcgggagtt caagactagc   50280
ctggccaaca tggtgaaacc ctgtctctat taaaaataca aaaattagct gggtgtggtg   50340
gcgtgtgcct gtaatcccag ctcctaggga ggctgaggca agagaatctc ctgaacctgg   50400
gaggcggagg ttgctgtgag ccgagatctt gccactgcac tccagcctgg gcaacagagc   50460
aagactccat ctcaaaaaac aaaacaaaac aaaatgggag aaatgaataa caaatgaaac   50520
aaactatcgg actagatagc accttagaag gtggtagtgg taagtgctcg gggtaacctt   50580
aaagccagga aggaaagggg ggagaggtga ggaaggctgt gtgtgtgcca cttgaaacag   50640
gcgggctgct gagaagtgca gaggctttag ggtgtgaagg agtgtgccat gcatctgggg   50700
gtgtccgggg aggagtgttc cagatagaaa aaagagcagt gcaaaggccc ccgaggcagg   50760
agtgtccctg gcaagttcaa agaccagcca ggataccagg gtggccagag caggatgtgg   50820
gagggagggc aggggtaac gggcacaggc taggggggcg tgagggcctt tcccccaccg   50880
tggtccatgc cagacttgcc aggtgtcacc gcccctcctg ctgggatcct ggacctggct   50940
cagcaacctg cttcttaacc agcccccagt gactctgagg gacaccagca ctgagaacct   51000
cagaaaccga ggccacacag gcaggaagcc accaagccag ccttcaaacc cagctggcca   51060
cctggctgca ggccgggcac gctctgcagg gcaccagagg ggaacgaccc ggccacagaa   51120
cccacagccg gcctcaggga tctacagatt cccagtcctt ggctcccagg accagcccct   51180
actcccactt caccccacag cgggctcaga tttcagaggg tcggaggtgg caaaacagga   51240
aaaaagccgg gaaggaagt ccaggagcac aaaaggcctg taacaacctg tgaaggttgt   51300
gggggcactt cctggggcca ggccccggta aactcagtca accttcacag cgactcccct   51360
aggcagacac caataccatc catttgacag ctgagcacac tgaggtgaaa aggcccttcc   51420
aagtggccct cacttcccgc agcccccggg tcggagcccc cagggtgtgc tgacagtcac   51480
cttgggcaaa aggttttgcg ccctggcctc tatcctctcc tggggttgcc caagagatca   51540
gttactgggg actttgcaca gggcctgacg caagggaggg ggttgctcag tgaccaggag   51600
ccgctgagct ggtcccttca ctcttacaga tggggacgct gaggacccga aaggccaagg   51660
atttgtccag ggccaaagac aaaggagtgg ggctgcaacc cagggtatgg ggggggacct   51720
gatctcaggg ccaggatatg ccagggacag gaacaggcag gtcctaagga tggggacct   51780
agtagactgc cccccgactc catctctgct ctgttctgta aataaaacca ctgatccagc   51840
cgctgccggg gcccagagag ggaggtcacc tgtctcaggt ggtgcagcaa gcctggcttc   51900
tgacgccgtg ggtctccagg cccagcctct gtccctccct cttgttgcct cgtcctgagc   51960
cacgcattta ccttccagct cacccccagaa ggggccatct caggtctggg agacccaggc   52020
agggaagagc aggcagggga ttctgctgga atctcccaca ggcagggctg agtctccatg   52080
ctcatccagg ggtcccagca gggcagagtg gcggctctg gggtgggctg ggctgagcat   52140
ggagggctct cagaggggcc aaccttgccc ggtcccttgg atcttcccac caagcgtcaa   52200
gaccccgtcc cgtgcctccc tctttctgga gtggctcccc tctttctgga gtggcttctg   52260
agtgccgcat ccccacccag agcccaactg aggctcctgt ccatgctgac cctgcccctg   52320
```

```
gagacatagg gcagggctgc cacctccttc aatggagact tgatacctgc acctctatta    52380
ccaaggcagc cacccagctg ctgcccatga gagagctcac cgttgactaa tggtggtggt    52440
gggagtgcag gaagggggct gggtactgag gacgacaaaa cgctgcggac ccagtgactc    52500
atgggacccc tctgtgctac ggccacgtgc tgtccacatg tcgcccctga tctccaggtc    52560
cgcagggtgg gtggcatcat cacacttcat ggaggaggga gctgaggccc agagaggtca    52620
gtgacttgcc ctaggtcaca ctgcagataa cagccctggc taaagtgacg gatcccttgc    52680
taaccccac cgctaagtgc tttctataga ttaagccact gtttcctcgc aatagcatca    52740
tgaggtagct gcttgtgcga atatcatttt tcagttcagg aaactgaggc acggagatga    52800
ctagcccaag gacccacagc caggaaggct ggcttggaaa ctgctctcta caccatggtg    52860
gtctatggct catgagggct tcccagccat caccaccttg agactcctgg agtcactgat    52920
ccagttctca gatgacaaaa ctgaggccac aaagaagaca tgacttgcct agggtcatga    52980
agcccaaggc caagggcatg ggctggtcta tgtctgatct cagcaggagg gaaccagcag    53040
gagtgtggcc agggcaagtg ctggctggga gctgacggtg caggcctgag gatgcgtgcc    53100
ggggctcagg gctggcagag gtgaccctga gagccctgga gggaaactct tccagggctg    53160
ctggactcag ctccaagcct ttcccaagtg gccagatgct gggatgggcc caggaattgg    53220
atgatggggt gtcaggccca gctgactccc aagaagggag gggccagccc agggctaggc    53280
ctcctgcccc aggcctcctg ccccaggcct gctcagccta gaatcttgcc tctgggaaga    53340
ctgaagcctg gggcgccttc ctgctccttg cacagcatta ggtcctattc aggtacccaa    53400
ctccctcagg cctggattct ctcctcactg gaacttgggt gaccccctctg gctctgctgt    53460
catcaagatc ccattcaata gtgactgcta aaaggtcttc taaactacaa agggtcacat    53520
ttctgagaaa gagaggggtg ggccaacctt cagtgcacca agctgaaaat gccttgggga    53580
ggtgggatgg agctcaggaa gctggctggc tctatttcat tcattcattc attcattcag    53640
tcagtcagtc agtcagtcat tcattcattc tgtggacaca gagcctcagc ctaccctccc    53700
acttccccag ccttaatctg accttcagca agcagagaga attaaacaca aactcgcttt    53760
gatgaccag aactccctgc tcatagggtc tgggtgcccg gactctgggt gacctgagca    53820
agtcacatgc taagattcaa agactcagtt tccaaggaag aggcctggcc tcacagccag    53880
accagcccct gacttttgat cactcctgcc ctccatgcat ccctcagcca cccgcagaga    53940
agctggggc agagtaaagc aagcctggct caacctccac ccagaaacac acaagcaccc    54000
gacaaatgcc atatctgaaa gctttctcca tccttttcct ttccttgact ccctcagtag    54060
tctccatgga cagtcatctc cactcccagc ctcctcgctg gcctcccacg gtctcaggct    54120
aagcccagag ggtttagggg tttgccagca ggcacgcagt gtgtgggggc acagagccaa    54180
ggactgcaac ccccgagga gggctccatc tgtctgacct agctgctgtc cttcccgcac    54240
tggaccctcc tcccccgcgc aggggctcag ggggctcggt ggcacttacg tctgggctcc    54300
cggggtccgt ccacggtcac cttgatggct cggtggtagg tcgccacttg ggtgggttg    54360
gtgaacacag tgatggtcag ggtgaaactc ttccctgggg agagtgggga atagaggcag    54420
gtggttggca cctggagctt ccacaatacc ctgctctccc acctgtatct accccctggaa    54480
gccctaact gtcaagaagg ggcactctgt cctctttgaa catgggcaga agatagggct    54540
ctgggtgaag ttcaagctct tgggcttggc attcaaggcc cctgggggtc tgacgccaac    54600
tttgtcaacc ccccgcccca tgccgtgacc accctggctc atgttcccct cttcttggcc    54660
tttctgctgt ctcttctatt cagagaccca cacgattttg tggtggggag caggatgggt    54720
```

```
atattctatt ttctgaaagt aattggtgat ctttgtagaa aaattcaaga acatacaaaa    54780
tataaataaa gaagaaaaga cacccccccc ccacggttcc actagctgga gatagacacc    54840
gttaccattt ggtgttttcc ctttcagctc tttttgtatg ggtttgtata tttacacagt    54900
cgcagtggta ctaaaataca gattttcata ctgtttttt  tttcatttaa cctcacatca    54960
gaagcacttt cccacgtcat taaaactcca taaacttcgt ttttaatggc tgcaaaatat    55020
ttcaactcaa ggaagcctcc tcatctttta tttatctacc tccttactct cgggtattta    55080
catcgttgct aatttcttat tgatgtgtgc agctggagct gaaaaaggac tgatttggga    55140
gctgcagaca tttcttctgt agacacaact gttatttcca gaatgttcta tttttagata    55200
gacatttggc tccaaagtct ccattcaaaa ttcctgagag gggaaaaaac ttttaaaata    55260
ctactttttt tttttttttac catttaaaat aaaatgaaag tgaccttctg tttataaaaa    55320
tctttgtctg catctctgct tatttcctta gaagagattc caagaagcgg tgagtgattt    55380
cacggcagca gagggttggg acatattacg ggcgcggatc cctcttggag tgagatgact    55440
ctccggagag atttagtcgt caccctcgcg tgtgaggctg cgtcacaccc cagggatgtg    55500
tctatcaaga tggaagatct tttacacgct cttgattttg tttgccttt  tttctattac    55560 tagtgagaat gaaacttttt atatgattat tatccatcat aatccaacac aaattactgc    55620
ttcatgttct tttactttcc tgtgaaggtt ttagtgcctt ttaaaaattg ctatatatta    55680
agcttgttaa tactttccat gctgtatttg tggccatcag tttccccggg cacaggcctg    55740
cacattttgc cttcacacgc tgggtggttt ttcattttca cttctatttc tcgttcttct    55800
atcgttttat gttcagacgg gtttctccgt gtagaaagca gtttatgaag atttactttc    55860
gacagtcttc tctctacttt ctacagtgaa ttctctgatg tgtctgggag tttgggggtc    55920
tgggtaagag tcctcctctc accctattct ctattacgat ccacagcctc atgctttatg    55980
agattggtgg ccgggagcgg gggagatttg cggatccccc aagccagact ttatcccct     56040 atccctgcct ctggatccca cgtacaggcc tgggaactcc ctgtgggtag gggccaatgg    56100
tctcgcactc tcacctgtac cccagggctg gcacaggatg gtcaaggaga gaggctgccc    56160
aagcgcatcc ctctggtgtc cccctgacac gcctccaaag tgagcaggta ggtttcaaca    56220
gccccacgtt gcaggtggga gatgaagctc agggtggaga ccagtatctc acagttctct    56280
ttgcatggcc gggtacttgt tagtcaactg atcaagtgaa aattctagcc ccagaggcag    56340
gagaatccgg aacaaaatta aaccagccag gctgccagga gccatgccac aggacccaag    56400
gccctctgag acaccagggg gaatttaaag ctcaagaccc actgagtgtc actccagctg    56460
ggaaatgagg ggcttctctg gaagcctttt cctaagccag tcggctgagg cagggataga    56520
aattctgact gcacttgccc ccggagcccc aggtcagaac agacctggtc tcccactctc    56580
aggtcacagg ggccactttg tatgatttct ggaagcagaa gtgcagatgg tctagggaag    56640
tgccaggcag atgcctcggg ctccctgccc gaccctcct  actgcctttc ctcactctga    56700
ggtcatttct ctgctggacc tctttctcct ccaaccagcc cagcactctc ctggggtccc    56760
tgagcctctg accctgccag cattgtccag caccttcttg gttatgacgg ggagtttagg    56820
cagacagccc agagccctag gggccagact ggagacacgg aggactaatg ggtcccagtg    56880
ccctgccaca gggccccggg cccacagcag catttgaaag cttactaaaa ccctccttca    56940
ggtcgcccac cttctcagtc aggccttccc tggtcacttt atctgaagta ggcatttta     57000 atttaaatta attttttga  gacaaggtct tgctctgtca cccaggttgg agtgcagtgg    57060
```

```
catgatcata gctcactgca gcctggacct cccgggctca agtgatcctc ctgtctcagc    57120
ctcctgagta gctgggacaa caggtgagcg ccaccatgcc cggctatttc ttttttttcc    57180
ttccttcttt tccttccctc ccttccttcc ttcctttcct ttcttttctt tctttccttt    57240
ctttcttttt ttttttttc aagcttttac tatgtgccca ggctggtctt gaactcctgg    57300
gctcaagtga tcctcctgcc ttggcctccc aaagtgttgg gattacagtc gtaaaccact    57360
acacctggaa ggcatttta acttggctcc gtagagttga atgagcctga gaactagggt    57420
aggaaaaaat tacaattgta ttgtccctaa cctctaactg aaatttagca tcactctcaa    57480
gtacgagcgt aggcaacaaa ccacagaggt attatcagcc gtacctgtga ccttgtcacc    57540
aacagacgtc acagatactt acatatcaca ttacagttgc tgcagattgc tctaaatatc    57600
ttttatgctc atcacaactt caaaaccatg gttgtcatta ggcccaatgc tagatcttat    57660
ttaatacatt gaataaagca gcacatttac cacaatttt aaagtattt gctatgtttt    57720 aatagaaatg gtttctattg taatactttg tatttgattt tataccttaa aaatatcatt    57780
gttctgagaa aggtgtgcgg gcttcaccag ctatcagagg ggcccacagg gcaaaaaaaa    57840
aaaaaaaaaa aaaaaaagcg ctaagcagct caacctgaag tatcacaggc cctaccactc    57900
cctttctcta ttccctgcac ctgctggaat tttctcacaa tgcatatgct tttaataatc    57960
catctactca ttttgtctcc ttctactaga ttataacctc cccaggggcc caagttttg    58020 tcttgttcat gcagtgtctc cagccccag acggcatcc ggcacagagt aggtgctcaa    58080
caacatttgt taaataaatt aagggcagag ataatggctc ccatttgca cacaggtact    58140 aacgtcccgc tcctgagaag tgagaagccc ccacccatac caggtagcaa accacatgcc    58200 accctgagg tcaccagcac tcctcggccg cttccaccag cttcacgcc tgtcaccacc    58260 cctcccaggt acaaaggaga ggagtgtggg gcctaagagg aggagtgaga gggaggggca    58320
ggagtcctgg acctcgggag acagggagcc tggggagcag gggtgggaga agctgtctc    58380 cctgagtgcc cctcagctac cccggccctg cccagctctc tctctgcctg gcagtggcaa    58440
acccatccat ccctctctct cagcctctag atataactct gtgcaggagt cccaggcaaa    58500
cctgcaatcc atcaggagcc caggaagtgt aaacccaggc tctctgaggg ctggccctgg    58560
ttgcagggga gaagtcttgg tctgggaaat gggtttcctt tagggctcca gaaactcctc    58620
caggacccat catcaaccag ccggggtggc agcagggcct caggcaagtc cttgagcatt    58680
ctctgcctgg gttcctatgt gtataaggtc cccgccccac ccacaggagc tgcatgggtg    58740
gggggagggg acgtgtctca gtctcagggg acctcggggt tttctcagct tcagccaaga    58800
agccattcat ctctccccca accagcggtt cccctcagcc tgcaccggca cactgcaccc    58860
cgaatctctg tcgacacaca gttgcttttt aaccagttga tcacagctcg agagctcatg    58920
tgcttttcat tttcacttag gccagtggcc gcctgctaga ggggcatttt tgggatttgt    58980
ggtggcgtgt ggtcaacata tgttggggt ggcactgcca gcgttagggg tggggtgcgt    59040
gtatgtggtg ggggatgcca gcacccaacg ctgcccaggg tggtgaagat tcaattcttc    59100
ctgggaggga aaaacttgct tataaaagtt ctctggctgg tcgcagtggc tcatgcctgt    59160
aatcccaaca ctttgagagg ctgaggcagg aggatcgctt gagtccagga gttcaagacc    59220
agcctgagca acacagtgaa caacaccccc atctctacaa caataatttt taaaaaatca    59280
gctgagcatg gtggcgcatg cctatagtcc cagctattga ggtgggagga ctgcttgaga    59340
ccaggaggtt gagactgcag tgatcgcacc actgcaccct ggcctgggcg acagagcgag    59400
accttgtccc aaaaaaaagt aaaagaaaaa aaattatct gagtcatgaa cctaactcag    59460
```

```
ttttacataa aacaaggggtt ttttttgtac ttttaatatc tactgaattt tccagaagga   59520
aagacagttc tttttttttt tttaattttg ttcagcgctt tgccaacagg tgttgacaac   59580
ttcagaaagt catggtattg gcagcaaggc caggttcaga ttgagccctg ccaccctgcc   59640
tgttccctct gctgtgggct tctgcatgga gggcattcgt ccacctcatg gagtcctgtg   59700
gccccaacgt ttacatattc aaatcagtgt tttattataa attactttcc cttttttct    59760 ccatcatagc tatggaataa catagtttgc aactgcatgt aaataggtag gtttcattat   59820
ttatacattt caacgtagaa tagtaaggct tgatataaaa tatgtattgt aagaaaggct   59880
cctcgtgtct ggcagggcag ggacctcagc cctaatcact gcaggagaca gcaatgacct   59940
ggttttcctc ccttccttt cttggttcac accttcagcc ctgttgttaa gagctctgtg    60000
gtgttactgg gtgcgtgtct ttcatggaaa gccatcttcc tggaattcag acagaatgta   60060
gaactaaaaa ttgaggcaac aagcagaggt ttccatcaga cttcttagtt ctggcagaag   60120
tcaagagacc caggcaaggg ttctgggtcc caacccccag tcttaactcc caaagtgtcc   60180
catctcctaa agtggcccag attgtcactg tcaaccactg actgttctct caggtgggaa   60240
tttcccagtc agcaggatgg gcactgcaga tgtgtgtctg catgccagcg gacccggcac   60300
cctccttcct ccctgccaac cgcctccacc tctcccactc agcagttcac accttctggg   60360
tttcccccac ccccgcccaa accacacagt aatcagagaa tcagtggctg tcaccgctca   60420
aagggacctc aaagtcctcc tccagtccca ggcatttgaa gtaacaaaat ctctaacatg   60480
tatccagctc tcaatatgcg ccagctgata cacttgtgtc aatttcccta accttcccaa   60540
aatctcatga ggtaggtacc attatcatcc ccatctcaca gatgaggaaa ctgaggcaca   60600
gagtggttaa gtcatttgcc caatgtcatc cagcaagtca ttagcagagc tgggactcaa   60660
acgcagggtg gctgatacta gaatgcaggc tctcaaagac ctcgagcctc tgaaggctga   60720
acgccttagc cacagttcct cagacatcgg aactcctcct cagatcactt cctgcctccc   60780
aggaccactg agactggtta tggacctctg agaggagatg gatgagagaa tggtttataa   60840
actcagcctc ttgcatctcc cagagccaca gtcccagcct cggccattcc tgctacaagg   60900
acaagctccc aaccaacgcc ttggaaaccc atttccctcc ctgcaggcct ggggagggg    60960 gctcaaggtc tgtgggcatg aaaacccta aaaaaatcat tctcagtgtg cagaatggcc    61020
agacaaggtc tcggtaactc agaaaatcgt cgtctcttct ctttctctcg cttcccagga   61080
gagagagtgg gaagggagaa tcaagttcct gatgccttgc tgggctccca gatcgacagc   61140
accttctgcc cgcctcgcaa caggcagcag ctatagtgct cctgacacat acctgggcta   61200
gcagacctgg ccactgcccc gcagtcagca gagctcatca gccttgtctg ccaccgacca   61260
aggaccagta actgtcctct cagggttggg attaagtcgc aaagggtttg agagattggg   61320
gatgacaaaa gggacttgga gactaattag gagcagcaat gaaagcttaa ttcataaaag   61380
caaacatttt ccatccatca acctgcaacc agttaagggc accgtttgaa agaaatctgt   61440
gtgtggggaa gggagccaac aggaacagga aatgtttgaa agaatgtaaa ctatttcagt   61500
ttcataaaaa gtaacaagta aacagttatt acatgcaaat aatgtcctgg ttttaattaa   61560
tgctgaaaag tcaaaatatg gctgacattt gtatgtatac atcgaacggc tggaaaggaa   61620
aaaatggtgc ccagatgcct gtttcagagc ggggctggca gctcagaggg aactagaacc   61680
ttgagaaggt cctgttttatt ggtgatgaaa agcacggttc tgcttcagcc acttcagcct  61740
gctgtggagt tggggagcag agggaaccca gcttacttct taacaaagct agaggcgggc   61800
```

```
ctggtgcttg ggaagggcga ctcccacttc agccacttct cgtaggcagg ctggtcttaa    61860
agggccagtg gaccctcagg cctccgttcc acagggcagg gtttccagg actttcccat     61920 ccaggagtta agtgatgatg ggtttcaggt cccagaagcc tcccattcaa cagcccccca    61980
cccccgtccc gccttccttc tgctgctcaa ggtcggtcag acaggcaggg tggcacaccc    62040
gccttgactc tggggcagga gatggcagcc ttcgagctgt gctttccaac attcagctgc    62100
gttagcttcc gttctagacc acctagggct caaaggcgct gggaaactgg gtctgggaga    62160
ccacagctgg agagacagcc tcagagtgtg ggggatattc tgcccccctat ggagagagtg   62220 gctggggtgc ttgggcccca cagatcaggg acttgtcctg caaccgcctt gctgaaagac    62280
ctataagctc ccttttttgag cttgttaatc caccatctcc tgccagcatt ttttgtgaga   62340
ccaggtgtgc ttaaccggga aagagggggt ggcatgaacg gtttcaggag ttggtaaacc    62400
ctagaaactg ggagaaaatt gtcttttttct ggcaagagac cataactttc ctcacctcct   62460
caaagcgatc tgtaatatcc tacaggatta caaattgctg tttttagaca gagctgcatc    62520
tggagacctg tttttcggga ttctaaggcc cctctttcaa cctccttccc tgctgcccct    62580
gccattgcca atgctgaaat ggcgaggcct cccttccact tacctcgccc actgcggccc    62640
acgaagcgaa ggtcgttgaa cctggccacc tggttcttca tgacggccga ggcattgcgc    62700
agctcagcgg agtagttctc gtcattgcct gccatcacag tcaccaccgt accatccggc    62760
acgtccccca atgccaccac ctgaagacac ggggcggggg gatgcagggg gacagcttag    62820
aaaggaagag ggtgaccagg gaaaggaggg gaggggctgg gctgggcagc tcccccaggt    62880
cccaggcaca ctgagtattt ctccaatgca gggtggagaa gaggcttaaa aacaataaag    62940
accttccccc aaatatcacg aaaacaagaa gatggaatct cgagcttcca caccaaaatc    63000
ctagatcaac tgcttacata aactgtgtcc caagaaatca tcctttcaat gaaatctaag    63060
ccagagctgt gaatcagctc agtcactatg atgtggggtg cagttcccct gttgtcttcg    63120
gctgcagcga aagaggaatc aacatgctcc tagcaacgaa gtctccaaat gagaaagagt    63180
aacaacaata ataacaacag ggctgctacc cccactcaat ttatgcaaga gctgtttagg    63240
gcatgaaatt tggccctgaa atgtggacca ggcccagttt attggcctct gcagagccta    63300
aattcgttat gcagagaaaa tgcagaatgc aaaactcact ggtgttttga aaaaggccac    63360
cagaaacccc ctttaaagtg agagtggggc ttttgataat ggaaggatgc acctgccggg    63420
aattgcagga tgggggtggc gatgtccccc taaacaccat ctcccccaaa tccccacccc    63480
ccaggagcac ggagaggcgg atgccttttg aaaaagaatc agactttaaa cagagtcaca    63540
actatttaaa cgtggccgcc gcgtgcaggg actggggatc catatggtaa aaatttcaag    63600
gagaaaatgt ttgggatctg attaagaaga ccagatttcc tgtcaacatc ctgtcttctt    63660
ttaatttcaa agactccttt taagctccaa gtgacagtaa aacctccgat ctgacgatta    63720
aagtcacacg ggcctcccgc ccctcccggc gagatttccc ccactggtat tttaagatgt    63780 caccccgggag acctcaaaga gccactcttc cttttttttcc catttagagt cgtcttaatg   63840
ggagcaggga cggcctcagc ttccagccac ctcgggcagc accaccccca gccgccggcc    63900
cttcctgccc tgcccttttc tcacggcagc tgtgagaggt ttaggggaaa accgaggcgt    63960
tttcgtttca tctcgctgcc cccttaaaaa aatgaaaatg aaacagtcgc ctactccctg    64020
gcataaagaa aaaggtcctc taaatggctg ggggctgcca gggttagggg tcccccaatc    64080
tcaactcgcc attcgggacg cataatatcc ccgagcaaac gtctggagag cagtgccccg    64140
atcccggcct agcgccgtcc ggtaaaattt cggaagcccg agggtgtgag caggaagctt    64200
```

```
ttgcgaagcg gcgcgggagg aggggtgctg gaggcggagg gtaggccctt tcaccgttcg    64260
caccccaccc gcggtgtcct tgccctgtc ccgggatcct cttctccgtt acccgcaggg     64320
ctgtatctga gcgatccggg ttaggggggc gcaaaacccc atccgcccat ttccgcacca    64380
acgtctctac gcaaggcgcc ccaaaaccca ggtggagcgg ggcaacccg ttaaaagtca     64440 ttcctgcagg gcgcatccaa aacggaacgc cgaggtcccg gagccgagcg cgcagccaga    64500
ctgaaccggg tgcccgggtg tcgccgcggc gtctcgggca cctcccatcc ccactgctcc    64560
cgaggctctg gctcccgcag ctcagacgcc cggagcccca gggccggcgc cctcccgccc    64620
cgggtcccgc actcaccttg aaggcgacgg gcagcgtctt gttgcagcgc cagtgcgagg    64680
gcagcacgga gcagaggaag ttggggctgt cggtgcgcac gagctcgcct gcgtggtccg    64740
ccagcacgtc caccatcgag cgcacctcgg gccgggcgcg ccctccgggc cccacggcc     64800 cctgcgcgct cagcgcgccg ctgttctcgc ccatcttgcc gccgccgccg ccgcaggga     64860 aggccgggga gggaggtgtg aagcggcggc tggtgcttgg gtctacggga atacgcataa    64920
cagcggccgt cagggcgccg ggcaggcgga gacgcgcgg cttcccccgg gggcggccgg     64980
cgcgggcgcc tcctcggccg ccgctgccgc gagaagcggg aaagcagaag cggcggggcc    65040
cgggcctcag ggcgcagggg gcggcgcccg gccactactc gccagggccc gcccgctgcg    65100
aggcctcgct ggcccgacgg ccgcccgcag cctgcccggc tagtcccgca tcctcggcgc    65160
gcggccccgc gtgcggccgc ccctcgtggc tgtcccggct gcctgggccg cggcggggcc    65220
cgcgcggggc tgtgccgctg ccgccgcctc ccgccccgaa gctcgcccgc ggccgccccg    65280
actccgcggc cgcagcccca gaacaaatcc tccagaatca agtggcgggg ccgcggccgc    65340
ccgcgcgggg ttagtacccc cggggcccgc ggggcggggc tggcggagcg acgcgtcgca    65400
cagccaatcg gcggagcccc catcgcgggc acctcggtgg cgttcgcggg gaggaacggg    65460
gcctgccgga ggccgcccaa cggggagggg cggaaggcgc caccccgcgg aggaggcccc    65520
agtgccacag cccagggccc ccgagagctc tgggagcccg gggcaaatgc tagaaatttg    65580
cttagaacgt ccgggtccca cggaaggcgc ccttgccgcc ctctctcggg tcgtagctcc    65640
ctgacgctgg ggcgcaaccc cttcgctcct cctccccgct ggccgcggcc gggcttcccc    65700
agctcttgct gcttcgggcc tgtgacttct gcaaccccgg gctggggggcc gcgggtctc    65760 agggccggtg acgccgcact gggagccgcc ccaaagaggt tactcacctc cctcgtcccg    65820
cacattattc tgacccaaga gcctccaccc cacacgggat tttgcgcgtc gtccacgccc    65880
ggccggcggc ctttgctgct cccagccctg cgcggctttg gtcccagcct cggtggcccc    65940
tgtgccaaac cggggacagg cggaagggag tctcctaggg accctaagta gcctggggcc    66000
aacaacccct ttcctctctg ctctcccctc aaaacaagtt tcaggatctt gcaggcctcg    66060
cggcgtcgtt cttcgttgtg gcggcctgtg gctctttgaa aaacacgacg aggcctgcaa    66120
aatgcgtttt tcttttttc ctttacgcat gtaaccacgg tcctgcatcg tgaaacggta    66180
cgcgcgtcgg tggcaaaaga aaaacagcag tggctgcaaa gctaagggcc ctcgctttca    66240
gaggagagaa ttttctttct ccatgcgggt ggaaagtggc ctctgcgggt ccaacccac     66300 ttcttcttgg gcccgtgcgc tccggctgcg ccgcaggac cgcggacagc ttcgccaagg     66360
cactgcctgc ccgccggct ccgggtcccc gctcccactc ccagccgcgt ggcccaacct     66420 ctcctggct tcactgcaaa tcacccctcc ctctcccgcc tcctaagtct gtcgagcaga     66480
cctaggggcc ggctacagtt gggagggcaa cgggaaagat caagccacaa tcattccgaa    66540
```

```
ttatcgcccc agacacctcc ctagactctg gggaacgaac gcgtgctgag cctcccgcc    66600 gctttggaga cggggctaga ttttcgttgc ctccggctct cgacaggtgc aaaacaatga    66660
attccaagcc tcggaagcaa agaagcttag gatccgacgg tggccgcaag atctcatcat    66720
ggatctgacc cctgctcagc gcgcgccatt tcgtcgttgc caaacgaaat caagcccgc     66780 gtgcgctcca ggggcgaagg actctggact caccccgacc accgggagag ctggccccta    66840
cccacctcgg gacctcacag cacgccctca ggccgtgtcg aaaggaagga cggcaaaggt    66900
cccttactga acctttttaag agagcctgcg cctggcagtt gtcgattgcg gacccaggcc    66960
cgcgcgccct cggacgcgct ggcacgagca gcagaactag aggaaagcga gtgatccagc    67020
ctgggcgctc ccacctccgg gaacgtctcc gagaaggcgc agcgcgtcgt ggccaggtag    67080
ggccctggcc gggggcgggc aacacgtgct gccctcgagc aggttgcggg accatgaccc    67140
gctgtttcag gtggtggtaa attccatttg tcgaatggtt tcggtttgca ccgtgccctt    67200
tgcttgttcc tccgcctgat ttctccctct ccgcttacga tgggttcaca gacaagtttc    67260
cagagaatga gggactcttg tgggccctgg cacctgcgc agggcccggc acggctccgg    67320
ctctccgtag ggcgctggct ccccgtgggc accagatcca agggaccagg gcggcggggg    67380
gagggggggc gggtgcaggc ccttgggtcc ccagaccaag gtcgcggggc cgcctggcag    67440
gcacagtggc gggagccgcc gctagttggc gcccgcgccc tgccagccgc ggaggtgcgg    67500
gcccggccgg gctacagatg cgcgccagct gcggccccgg gtgcaggcgc ggcgaccgcc    67560
cccgaggagc tgccctttcc ttgccatcca tgcggccagg tctcagacaa accgatggct    67620
ttgtgtcaaa ccaaggccgc cttcctcacc tctgataaga tggacgcctt ctgtcttcgc    67680
gttttcaggc acccggggaa gacccacaga acaggctagc ttgttcccaa tttccacctg    67740
cttcctcccc atcccggacc gacaaaaatt gtcgtctgtt tgatgggagg gagaactccg    67800 actccccac ctggggcatg cagacaccct cgcccttccc cagttggcat ggaccgtcgt    67860 ctttttctccc tcttccatca gatcgatgga caaacaggcc agtttctccc cagtggccc     67920 cacctaagag caccctaagt tgtccacagc agggctagga agcagaaggt caggacactc    67980
ccctacccta ccttgactta gagctgggta aacccagaac ccatccccgg gcaaatagag    68040
ccagctcctt tgccccagga aggggattcg tctccctctg gcatttagga gtgctctcta    68100
agtgcgttct tggcagtgag ggtgccgcct tcccagggca ggtgtgattc atgtggactc    68160
tgtggcgcct gggcagggat ccccaggtat accagacaag gggcaggtgt gccctgggaa    68220
accgcctaag aggtccatgg gctatggaag gagctgggt ccacagtccc tctgcctgag    68280
cgtgtctttt tccctcaccc acagcgctct agggaaagtt gcctaaacct ctctgagcct    68340
catttctttc atttgtaaag tgggcactc atagtggccc ttcatagaat tgtgtgtaaa     68400
gtgcttagca caggcctggc acatggaggg tgctccagcc tccgggagcc atcactgtca    68460
tgaaaaaata agacctctca atccttgctg ggggcctttg acccacccct cctctctctg    68520
ggcctcacac ttccatctgt gaaatgtcca gttctcatat tcaaagctta ctaggactcc    68580
aagccagtcc atgctgtcct gatccctcaa ttcgcccaca ggctgcctgg gggaggtaag    68640
gactggctgt gacctacctc cacgtggagt cagctcatag cggggtttcc agcaaccatc    68700
acagggcggc cagagctggg tctcgatgat tgcctgtctg accattcctc tcagaacctc    68760
actttcgccc ccagccggcc gccctcctgt gggcagaccc tttcctgagt agcaactggg    68820
cctcagcgga cactgccagg gacccgtttt ccttcccagg aggcctctgt tccccatatc    68880
ccgaatcaca caggagccta gtccagcgaa gagagcagag gactctcttc tagaactgaa    68940
```

```
aatttctccc agcctggccc taaatcccct gtccagaggg acccgtggtg aaacctatct   69000
cctgcccagt gccctagaac tcaaagggga cattcatgcc cctcactgag cctcaatttc   69060
ctcttctgtc aatggaggtc attctaacca ctccatttca cgggaggggg attaaggatt   69120
ccctctagga ggggagggc atcattgtga ttgatgatcg attgtttgaa gaaacagaaa    69180
gaaaatgctg ctgagtaaac taggactcat ctgcatcctg atttcagata atgatctctg   69240
aatatataag cgagaaatgt taatgaaaaa tggcaatata tctgggttga ggggttgtct   69300
cctgtaggcc gggggtccag ctccagagag tccagctctg gggtcatcta tcctgggcag   69360
cctctctgga aggattcaga atgtgtggga gcacaaatgt gcttctcaaa ttacagagat   69420
cttcttcct tttggaaag ttccagactt ggagggagg gagaaggagc aagggagagc     69480
agggtggtga gggtgttagg acccagatgc tgcctgtgcg gtctgagact tttgcctggt   69540
gtccacgctc ccctgagcct tggtccccga gggtaaaatg ggaagaacag taacagctgg   69600
gggtgctgag gctttacctt gtgccaggcg ccgcacatgg gcattgctca tggtattcaa   69660
tccccacggc gtcatatgtg gtaggtgtta tgcccatgta agcaaagagg aacgttgtcc   69720
gaggtcagcc aggctagaga gggccagacc cgggttaaaa gtctgctctg gttcaaaatg   69780
tggggcatga acgcatcacc tggccaagca tgtcagcact ctcctcctag tggctgagta   69840
atgggaagag ctagcatcta gatacagagg aaagagctat tgtgatgggg agagggagct   69900
gggtttggta atcctgcta agcagccctg ggcttggaaa tcagtaaact cttcaaatct    69960
gcagggagtc aggaaggact tgccagggtc attcgggagg gtcctgtgat agtcaaggtg   70020
cacccaccac ctgctctcct ttggcctcag aaccagtctg cgaggaggca ggactggcag   70080
tagtccccag tttacagatg ggaacactga ggcccagaaa ggggaaaggg cgtgatcagg   70140
atctggaatg agctccagca aggccaggag caagcacctc gaggcaaaac gcagttggac   70200
aggacctttg ccttgcagga gactgcagcc cagtcctggg cctcatacac tagcaccctg   70260
atgccacatt cagtgcctct cgcccagggg aagtgctaat cagacgtgtt tccctctggg   70320
cctcagtgtt tgcatctgaa tgcgggggtg cactttcaag gccctctac atgccatgcg    70380
ggttccatag gaccccaggg tttggttgtg acccgaggcc cctcctcccc acccacctcc   70440
tctccacctc ccgcggggcg ccagctccct tgcgtccaca tgacctcgga tccttccacg   70500
cccatcccca ccctgttctg caggtgggtg gtcagagggt gctctgcttt gaggatggga   70560
gagagaaagg gaggcaagga cggagaaaag agacttcttt tgcgggagcg cagagcagaa   70620
aaaccgtctc catcggttac cagggaaggg gtttctggtt tcagatccca tcacttggtg   70680
gggccttcct accaccctcc ctgctactcg ctcttgtcat ctgtaaatca gggaaatact   70740
tctgaaagac agttatctgg tctgtgactt tgatcattgg tctatgacta ataattgccc   70800
taattttttg aacacctgcc gcatgctggg agttttccgc caattgtcgc tcaccctcag   70860
gtgcctctga aggcagaga tttattctt tccatttcac agatggggaa acccaagctc      70920
cgaaagtaaa gagcttttcc tctgtgggcc tcagaatctg agaagttcaa acaggttctc   70980
aggagccctt ccagcacccc actcctcgat cagggagggg ctgtctgcac tctgaccgct   71040
gctctcagcg cagagctctc catccaaagc agcaggtgcc tgcagagcta cctgccagca   71100
gagccatcaa acacggactc ttctactggg agccatggag tggtgagaga gacctgggca   71160
gcttggagcc aaggggcctt ctgggaaaca tgtgccctc ccccagggtg gggttcagct     71220
ctggcgggca gggagagaaa gggctcttct gagtggctgt tgctttacac acattttgc    71280
```

```
ttcacagtat tcttagggag tagcgacagt tatcactccc attttacagg aaagaaaact    71340
gaggcttaga gagctcaagt aacttgtcca agttggcacc actgggaaac cacagggta     71400 ggattccaac gaggcagcct ggccccagag cccatgttgc tgcccactac actctactct    71460
tgtggactaa aaccagatgc tcagagttac agtcatggaa tagaattaga atcctggcag    71520
aagaactgtg ggcaggattc ggaattttac aatgtcagac tcgaaagggc tctgagatat    71580
caaatccaaa tccccatttc tcaaatgaca gaactgaggc ctaggaagga agagtctcac    71640
tcaaggtcac agccagtgcc agggacagag tctgcacccc ctgcctctcc agctacctcc    71700
cgctgactcc gcaccttcct ctctcgcagg ccctcctctc cccactgccc acccagcagc    71760
ttctgggccc agccaggccc attagggatt ttccacctcc ccaaaaaggt cctgatgact    71820
gtcagtcctt gtgaagcctt aattaatctc agaggccgat ggctcggagg agactggggg    71880
ctttggcctt acgcagatga agattgcggc tctatttcat gtggtggtga aagaacgcct    71940
cagacattcc tgccagcaat aaaagccaca tggctttcca gcatcgccct tggaaaagaa    72000 aaaaagtgc agcccttgc ggaaataaat caactatgtg ctgtacgcat ggcatgagat      72060
acaaatgggc atacggaggt gggcaacagt cggtctttta tgccgcctct gatgtccact    72120
gacagtggca gggccagcgg tcatggtccc agctgcaatc ctggggagag ggagtgaccc    72180
ccagtgtggt gggggaagcc tcagcttctc cacctgaact ggatttgagc caccctagat    72240
atcccagagg cagggccggc tttctggcct gtgacccatg cagtcgcaca gggccctggt    72300
ctcagaaggg tcctgagctt gttttaatgc cctgccacca ctgccttgaa cttctgaata    72360
cttgctcaac aaaggtcctg cgttttcatt ttgtactggg ccccccaaat tatatagcca    72420
gtcctgacca caaatccacc cctcatcacc aattgtcacg tctctcctgg cccctgccat    72480
gtacccaatc ccgggggagta gggtttcttg agtgcctact agccagtttg cttatatcac    72540
ctgagatgaa cttcagaatg actttgtgaa ttgggcagat gtggaaaatt gaggctcaga    72600
gaggcttcca tatggcaagg aagcctagac ttgaactcag gtctccctga ctccaaagtg    72660
agtgctctta gcagctctac attctgcatt atttcatctt caccatgccc agggggatgg    72720
ggatacacac agttaggctg ctctattccc agataacaga aggcataact gaggccagag    72780
aagtgaaggt tctcaagtca gtgtcaaacc gagggcctgg gcaacagtgg acctgggcct    72840
ggatccatag ggctggggat ggagtctcag ttttatagtt gtttgtgcca cttgtaaatt    72900
tattagctct ttccatgcag gtcactgcct tgagtctggt ctggaatgtg gctggagccc    72960
taccctgtcc ccctccccca cagctctcca ttctaaacat ctggaagtcc ttccttgtgt    73020
cttcttccac tctttcacgc tgcagttttc ctctgccacc ctcactggtt gggaagcagt    73080
tggatctggc accttgataa actcaaaaga gtccaaattc ttgatgaaag ttggggctga    73140
acagagccca tagattgcca tgtcctataa ccaggcctgg gcctaaggct catagagcca    73200
actgctagat ccagggcagc catttccttg ttccttgctg ggtaaccttg agcaagtccc    73260
ttccctctct ggccctcaga ctccccttca gggagataaa tgcattggac cacacctgag    73320
ccccaggagg cctctctgtc ttcaacattc tagaattcca tattaatcta caacaggtct    73380
gttcatttcc gcatctaata gctggggaaa ccgaggccca ggaaggatca gagatttgcc    73440
caccgtcaca gaaggtgctt attgacaagt ggacttgact ctgaggctcc tgtcagctgg    73500
cccggttgcc tctgcacaaa ctttcggagg atctggcctc agcatcagct cagcttgccc    73560
ttgtcccgcc gcctttagcc caggtggtct gtcaggcacc ctcagtgtcc aggcctgaa     73620 atcacagcta agagtccttg gcaggcaata aagttcctct tctatggctt gaatgtctcc    73680
```

```
caaaagtcat acattaaaac ttcaccccca ttgtgatggt attaagaggc agtgggggc    73740
ctttcgggaa gtgattaagt ggtgaaggct ctgccctcat gaatggatta ggccctcttt   73800
gcccttctga cttcaggaca caatgttctg tgtcctccgg aggacacagc cagaagacac   73860
tgccttggaa acagggagtc caggacctca ccagatgcgg aacctgccag agccttgatc   73920
ttggacttcc cagtctccag aaccatgtgt agtaagtttc tatttctcta tttataaatt   73980
atcccgtctc aggtattttg ttacagcgac acagagtgaa ctaagacact ctctttagac   74040
aaaagtgggc caggggatgg cagcaaccct tttctcccca atcgcatttg ggctgtgtca   74100
gtgtttccgt aataaaggcc ccttttccag gggttataat ttggctggaa aatgaggagg   74160
aaagaccaga ctccaggact ggaggggcac atgaagtagg aggctaggat gggaaaagtc   74220
tccactggac cctgggcacg cagagtgcac acacacacgc acacacatct atacccctaca  74280
tgtgtgcact cacacacagc acccacgctc atgggcacag tctctcacac attcactggc   74340
agctcacacc cacatggaca agccctcatg gaggacagca ttgttacagt gcagccacag   74400
gtgcaaacag ttaagtgcag gtgtgtgcaa agatgctcct aggagatgcc tctgtctgca   74460
tcatcatgca tggacctatt ggtatagatg cgcagataga tgcacagata ggccccatta   74520
tatgagtggt gtggacacac acatgggcag aaacccacat cacagctgtg taaacagcag   74580
accattgtgt ggacaaatct ttacacacag aggcaggcat ggaatcaggg ctcagagctt   74640
tggatttgtt ctacagagca gctctgggag gagtcgaacc ctggctctgg aagtttctgc   74700
ttctcctcaa ttcagaggca tggactttct gggtggtttg ccccctggg gcttccaaac    74760
cattccccag catctgagtt taacccgctc cctcattgtt cgatggggac aaggagagcc   74820
tgtcttcctg gtccagagaa aggcagtggg aggggagaag tgggagggtt gcagctaggg   74880
tgccccacgg cagcatgggt ggaagggcag ggcactagcc tagggcccca gagacctgag   74940
tttgggttta ggttgagatg ccctaggcca acacatggcc tctctgggct tcatcctgag   75000
cccccctctgt tagggccatg tgacaccccc aggggcctca gcatgggaa gagcactgaa   75060
accatgtcac atgatgaact attaaagcaa ctggagactt tgccctggag gagagcaggc   75120
ttgggggta agagctcctc tggcagatct atgaagagct cccaggtggc agggaccata    75180
tggatgctgg gggctccata ccaggaatag aaatattgag agctggcttg gaatagggac   75240
acgtcccctc agaggtagag atcaagttga gaccaggata ttgtgcaggg agttcgagtg   75300
ttagatgggg caggggccgg accagatact agtgtctcaa acgctcagct catagcaaac   75360
acgtattgaa caaatgagag agcgactgca gagctccatt tctgagccaa tcatccgtga   75420
ttcagagcat accagctctg ggttcccacc ttgccatctg catgaccttg gccctctcca   75480
aacctcagtt tcctcatcta tgaaatgggg agaacaaatt atttccaaga gctccagcaa   75540
gtcacatccc ctattgttgg tcttttcaggt catcccagaa tttctgctct tataaataga   75600
aaatgacatt gaaggtgaaa agcagacaga caagcaagag aatagttaat acaaaaatca   75660
tagctaggcg tggtaacttg tgtctgtaat ctcagctact tggaagggtg aggtgggggg   75720
atctacttga ggcctagagt tcaagactag cctgggcaac aaagtgagac tctgtatcta   75780
ccaaaaaaaa aaaaaaaat caggagagtg gtccccacca cttgccacct gtgatgagta   75840
gggagaggga tgcagtcagg gaagggacac tggtgggagc cctaaggtcc cattagtgct   75900
ttgttttttta aagccaggtg gtaggtagat agatgtctgc tttattcttc ttctttaaac   75960
aatacttata ttttatacat tcttctgtac atgtatttta catgtttaaa aatattttaa   76020
```

```
aggaaagcaa aagataaaat atagaaaaag ttcccctgcc ccaaacctct gaaaaaatgg   76080
acaatatgct caaatgtgca taatatcgta caattattca tgatgcagca aagctgcact   76140
gtttcatccg gatggtcctg tgtaccatca cactctcagt tgaatctctg caggcccttg   76200
cagctgtcct catcatggca accccacct aggtaagcac ttctaggtaa cagcccctgc    76260
tgagcacgct ccccaagcac tcctcatggc cgaccagtag cccttcaggt atgtgtcagt   76320
gggcccactt tacaggcaag gaagtccctt gcacctacat aggaaggggc agagctggga   76380
tttgaaccag ctctgtcaat gccaaagttg tgcagcaacc tcacccgagg agccaggccc   76440
cttgattata gtaactagcg ttatgtacac tcacacatgc tgttgaatcc ccggagccac   76500
ttttgtatta ggtacattta tcatcatccc cattgtaaca gtaggacaac ggaggcatag   76560
caaggtcagg aacgtgttca agttcacacc ctaggtgagt atcagagctg agccttgaac   76620
ctcagcagcc tgatcccaga ttgtgtttcc tggcctggct gtgtgggag ctcagacttc     76680 atggaaacaa aagacagaac ggtggctcca gggtccacag cggatcccaa gggaccagag   76740
gccagcaggg gggttggctg gggttggagg atgctgccta ggagatctgc tcccagagtg   76800
atgctagccc tgtgtgatga cctgagtccc cgcctcctta cagggtcatg gctgctgggg   76860
aggtgctgag gctgtgggta cagccaaacg gagctagagc aggctttgga ctccctgcct   76920
ggcaagtcca ggtgacaggc tcagacactg gcactctgt catttgctgt tggcataagt    76980
ttccactggc aggaatgtga catttatcac ctgagtgggc ttccagaagc ccactgaatg   77040
tcctcagacc tggggtgggg ggccctctca ctgcctcacc tctgagcctt aatcaaatcc   77100
agggtggctg gatgatctga aggccctttt agctcacgga ggcctgggct tgcccctgcc   77160
cccatccgtg tcctcagggg aaaaggttcc cagtcctgcc cttagcagct ctgagcttag   77220
atgagggggg gagatgagat ggaaaggaaa aggagaagta agaaacagac agaggaaaag   77280
gagttggcac tagattgaag cagtcaacac acacttatta ggcacctagg gctattttag    77340
gtgctgggga tacaagcaat ggaccagaaa gccatgagc tccttgggg ctttgattcc      77400 agcagggcag acagaagaca gacaaggagg caaataaata agcacgccaa tatttgatag   77460
tgtcttggga cactcaagaa aacagatggg ggtaaagtca gagagagtga ctgggtggat   77520
ggggagagag gggctcttgg caatacttta gacagggtgg tcagggaagg tctgtcggag   77580
caggtgacat gcgagctgag accagagggt tgagagggac ccaggaaggg agaagggggc   77640
tggtaggagg gcccactgca cagtggaact ggctttaccc acctgccttc tccccactcc   77700
tctgcactgc tagtatcccc agttcctaaa actcttactg ccctttctct ctgttgcttc   77760
tcccacaaca gccctgagag ccagatgggg tgagcctaag tagcctgacc tgcagtgcag   77820
gaaactgagg ctagagtggg gagggtcagc atcagcggtg ccctaatgcc aggacctgac   77880
ccgggctccc gcctcccagc ctggtgctcc tcggagcctg cccattgcct ggcatgttat   77940
tcaaccaccc cagtccaggc aggctgcagc cactgtggag ccagcccgtg ggcaccgctc   78000
ctgagaggtc acaggctgga aatgtgggca gctgggtagg gtctaggagg gggcagcggc   78060
tcaggactgg gcgggggtcc ggagcggaag gcgcccagcc ctgattggaa caaggtggca   78120
gcaccgggag ccgagccggg tgtcattgat cttgcccggt gttccagcca ccaggcggga   78180
ccagcgccgg gcagactgcc ggttttccca ggtgtgggga cacccctgagg gaatgacttt  78240 tcatgtggtt gtgggcagg catgccaccc agcacgtggg ggaggccagg gctttgggag    78300
catgctggca gcagggtgga ggggggtgtc tggagactca gaatcccaca gccagcaaat   78360
gtgaggctcc tggagacagg gtcatggact tgaggctctg agaccctgag gatgttagaa   78420
```

```
tcttcatcgc agtagctccc actgatggtg tgctcacggt gccaggcacg gttctgagaa    78480
ctcacacagc ttaactcttc atccttgctc catcctaaga gggggttctg tgatcatccc    78540
cacttacagt tggggaaact gaggctcggc aaggttaagt agcctgccaa acacacagct    78600
accaggtttt tgtcttagga aataagagcc ctggaacagt tggccagtgc ggagaggacc    78660
cccgaagatc tctgaggcta gtcccttgt gtcggaaaaa caggtctgga gagggatgt    78720 gacgtgctgg ggcccagggg agtccaaagt caggactcat tcttccccca ggtcatcgtg    78780
ggacctccgc tggtccctga atgtcaggcc ccctgagggc agggtcctca gccaggacct    78840
aggctcccag atgttaccaa ccttaactga cagttttctg ctagcacaca ggaagttctt    78900
ttgaacatct aacctgaatc cctcgtttgc agggaaagcc tcttccttct catcttgcag    78960
tactctaaga agagtttggc ctttgatgtt agggaagatc accagttccc tggtgttgtg    79020
ggaggtgaga ctgtgcccct ctctgccata aaatatctct ttactgtcca tcgctgggcc    79080
taaacattag cgacttagcc cttggggcct tacagagttt cttattaaaa tgtgagtact    79140
cctggaatgg gtgtcagctt agcaggacag ggtggtactt caggggcagg gcttggggc    79200 cgttgagggg caggagagag ctgattctcc ccttctagcc aggcttgatg gggtctacat    79260
gacctgccac cctccacctc tctgacctca tctgcttcca ctctgcccct ccctcaccct    79320
gctccagcca ccctgccttc aaatatgccc atcatactcc caccacaggg cctttgtctg    79380
tgctgccctt tacctggaaa accctcccca ttctgtctgc ctggctcagc tacccacttc    79440
attcaggtcc ctgctgcctc ctccaagagg ccttctctgg tctcctgtgg taggcagaat    79500
aatggccaca gagatgtcca catcctaatc cccaaacctg tggctatgtt accttatatg    79560
gcaaagggga cttcgcagat gtgatgaagg ataaagactt tcagatggga gattatcctg    79620
gattccccag gtgggcccca tatgatcaca aggatcctca cacatggaat agggaggcag    79680
aaaaggacag tcggagggag atggggtgtg gaaactgatt agggaacctg agagatggca    79740
gcgtgggaaa aacatggctc aaagctgtgg gctttgaagg tggaggaagg ggctatgagc    79800
catgaaaagc agacagcctt taggagctgg acaagacaag gaaacaaatt ctccaccaga    79860
gcctccagca aggaacacag ccctgccctg accttgatct tggccaaggg agactcatag    79920
agaatttctg atccctggaa ctgtaagatt ataaatgcat gttttttta aggcactaaa    79980 agtgggttaa tttatgatgg caggcatagg aaacgaatat gtctcccttc cttgattgac    80040
agttcctcag cacatttatt agtgcctgat acacaatagc ttgacttatg aattgtctct    80100
tttctctcac agaaggtcag ctgcaggagg gcagggattt tttgcttgct tggtgttaca    80160
ttcgcagata gagttgtcac atttaacaaa tggaaatata aaacacccag ttaaattgaa    80220
tttcagataa ataatgaact cctttttagt ataaagttgc cccaaatatt gcaattattt    80280
atcgtttatc tgaaattaaa ataatttagg agtcttgtat tttatctggc gaattcatcc    80340
ccaacacata aaaccattcc tgggtatgta ttaggatctc aataaatgtc tgttgaatga    80400
gtgaaataga taagcaaatg aattcacatt aacttctagc ttaaaaaccc tctttggctc    80460
ccagaatgcc tacagggtaa agtgtaaatc atagcaaatg ataaaagcag acagtttcat    80520
agccgcttca atatgccaga cccgggctga gtgctttaca cttattaact cactcggttc    80580
ttgcaataac ccaatgaggt ggttagccca ttttccagat gaggaaactg aggcccagga    80640
ggcttagtaa cttgttcaaa gtcacataac cattgagcag cagagccagg caattccagg    80700
cctttgaaaa cttggctcat ggaatgttct aatgttatct ccctacccat tccctgaac    80760
```

```
actgtggatc ctctctctct aacagccccc ggttcctttt cagggtatgt gcttccgcat   80820
tctctgactg ctgaactcct cctcatacat caaagccctg tcctacttt tctctctttgt   80880 gagaccatct ctaaaactcc caggaggact tggcccccctc tctttcccct ccccaccatg   80940
gccccttgtc tgaatgcgtt gtaaggactt gctattgtgt cctttacgtt ccctgactgt   81000
gacctccctg agaacggaga tgggccccctt tcagctcttt ggcatggggc ttcaaactga   81060
gtctggcttt aggggggttc ccagaagcat ttgagaatga atgaatgaat gaatgaatga   81120
gtgagtgaat gaatggctga gtgaatgaac gaatgctgtt tgtttccact ctgggcctca   81180
gtttcagagt ctataaaagg ggaagaacaa tcctgaaccg cccccattc cttaaaacaa   81240 aacacatttt tttctgatta taaaataat acacattcat taaagaaaaa ttggaaaata   81300
ataaaattat gaagaagaaa attaaaacca tccataatcc tgccacccag aacaatggtt   81360
cccactgggt gttcagcctt ctgctcttct tactgtatgt atagatttat tatcttcttc   81420
tcttccccgc cctccctccc ttctctcctt ccttttttt ttgagtgttg ggaacataca   81480
gtatggggtc cttttaaacct gcttttgaaa tcccccaaca tgtgtgtatg tgtgttctcc   81540
tgttttctta aagcctccct gatggcaggg gacaagtggc tgctagacaa gcctggtagg   81600
ggccagggtg tggaaagccc attcccccc tactcatgga ccaccatagt tcccttgtga   81660
tgggctgttt aggggtttc cagatttctg tcagggaaca ccctgcgtgg atgtcttagc   81720
tgcatccctg gttccttcct taggacagat tctgggactg gggttgctga ccagtata   81780 gacactgaga ggctccggac accgccccac atcctcccca cagctgctct ccagccccac   81840
tcccactggc agcctggact tctcagcttg gcagaaagcc gggggcagta ttccacctcc   81900
tccagagaaa agccttgtct acacccaagg cctcactgat tccatccaac gctgaaaata   81960
cccatttact cagctatttc tccacgttat ggtctaaggc ccagatgctt agttccaacc   82020
aaaatagcca cagaggtcac tgtggtctga gggtcctctg gacctcaggc ctgtgtagac   82080
atcatacttg gtaataatta acccacggag ctccaccacgt gccagaccct ctgcgtctct   82140
gtgtgtcctc acggtaaccc tgaagctagg gatggctgtc tcccatctta caggtgagaa   82200
cactgagggt gctccagaga gctgtgggcc ctaggccttg tcacctgggg gtgcaaaggc   82260
gctgccccag tagtccggct gcctgctacc tggctgcctg ctacccaatg gggcaaagtc   82320
ccagcactac cccgaaacaa ggacaagctt tggcctagaa gctgggcagc caggtcctgt   82380
gcctgttttt tctccatatg tgccctgggc agctcaccct ctccgtctgt gaaatgggag   82440
agcagggagt cagagacagc ctcctaggcc tgtggcggct ctgagcacag tgggtgcaga   82500
tactcagtgc tgagtcaaag agagagagaa ccctgccaga tgggccagct caccacaagc   82560
agccaagccc ggtctttgag gggttggagt gggcaggcct ttgaccaagg ctgagctagg   82620
agggacctga cggccccaga tggaggctgg cccacccctgc cccagcagat gggaggctat   82680
ttttaacccc cacaggaaga agaggacaga aatgattgca gggggttaac ctaggccccct   82740 ggggacgctc cctgtttgca tcctcctttc cccacaaccc agagagctat gtgggcttca   82800
cctggagttc cctgaatcct tctggagctc cccgcagatc acagccggag ctggcagggc   82860
ctgagtggcc cctgtctgcc aggcgaggga cccagagccc agagaagttt gaccaggact   82920
ggcttcctct gccctctctg ctgtgtgctt ccaccaggtg aggctgcctc ctccgcttct   82980
acctttcttc ctggggtgac ctggggaggc cccaccttct cccgggccag tttccccatc   83040
tgtcagacaa tgggaccctc cagacatcac tgaggcttct cccagctggg aaacctcctt   83100
ctgagctggg gccctgactc tgtcacatca gtcctggatt cctggaggcc tcagccctcc   83160
```

```
agaagcatcc acccagtgga caggagctcg tggcaggtgt ctggggaccc ccaggaagag    83220
gaaggatttc ctggccagag ataagaagag cagcgtgggt aggggttaag catcctcccc    83280
ctgcagcctc cctcagacca cgccaccagg tggcccttgg tccccccaaa aggagttcct    83340
gaaaagtctg tgtctgttgc agcaggtgcg gcctgtgaag tgtgtgtatg cttgtgtgag    83400
ggtggtgtgt gttcacatgc acatggtggg ggtgggcaca caaggcggga ggcctaacat    83460
ggtggcaggg acagactttg gttgctgagc tgggacagcc tgtgacagag gccccagcac    83520
acccgcaggt cttaccagaa accctcagat ggtgctggtc tgacctgaag gtgggcacat    83580
gcagggaagg ggtacatgca ggacaggggt gcatgtgggg gagggccatg tacagggcag    83640
gggtgcatgt ggaggagggg tacatgcagg atgggtgcat gtcggggagg gtcatgtgca    83700 ggacgggtg catgtggggg gtgcgtgcaa gacagaggtg catgggagag aagggtttgt    83760
acatggcagg ggtgcattgg gggtgcatgc agggcaggtg tgcatgtggg ggaggggcat    83820
atccaggaca agggtacatg tggggaggcc acagggctca aatgctgtca gggcctctgg    83880
gaagctggga ccccagtgaa tgcttgaggg gagccaactc tgcctgacct cctcttatga    83940
ttgtctattt aaacaatact gtaaattaat cacattaatc gaacccacct ccctgcctcc    84000
tgctgcttgc ccctgtgata caaataatat gagcacaatg aaaaatcttg gaaaatacag    84060
aaaacacata aaaaatgtta aagcctgaag tcttataacc acagtgaaca ctgcgagtgt    84120 cttttgagggg atgggggtct gcaggtcttc ttgatacaat cacattcatt cccacatact    84180
ggagcatttc ccacgggcgg ctgtggagct gagcacttca ggtttgtctt agtgaattct    84240
ctaacagcct gagagggagg tactgttatt ctccccattg tatggctgaa gaaacagcaa    84300
aaaggaggtt aaatatcccc ctcagggtgt aagaagcaga gccaagattt gaatccaagt    84360
ctggctaaat ggaaagtgca aatcgtccag cgtccagggc tgcactccag ccatgccccg    84420
ccccccgtga gcagaccact catttattca ttcctccagg agcatttact gagcacctcc    84480
tgtgactcag accctgccca gcacccacac caaggacttg gcggatgtga acgagacaga    84540
gagaggcccc aacctgactc cccaagcggc cacaaactga gtcccaacct tgaccacagc    84600
ttgatttcta gtccaagttg tcactgaccc ccactggcct tcatcactga ctgaactgtg    84660
acctggcctc ctgcactctg cagtggcctc tgtgagcttt tcattccccg tgatgtgtgt    84720
gaaagccaag gccagcagcc cacctcaccc agcctatcat ccacgcggcc tgggccaggg    84780
aggccgtcag gagcccaccc accacctctg gcctgccact ctgggccagg cctctctgga    84840 gcggggttt ggccttggcc cttggcaccc tgcttggcag aagggtgggc cttggctcag    84900
agcatggggc caccccagga ggggtcagca tagctgagct cagggtacct gtgggcgggg    84960
cttccatgtc ccagggtcct cacactgcag cctcctctttt tgcctgggc cctggaaccc    85020 caggagaccc caggagccgt tgctccctcc tctcacttgc agaaactcaa caggcagct    85080 catctgagct cccccgatgc ctgcactgta tttctggggg tcctgcatgt ctctccaatc    85140
ctcaggcagg gccagttacc tactttatag gacccagtgc aaaaagaaaa tacaggaccc    85200
cttttcaaaa tgcaggaaca aaagtttttc ctttcttctg tggactctca acccacggtg    85260
gtgtttttta tttgctgttc aatgtcacac gtacttggac ctggggagac ttgtgcagaa    85320
agtgcagacc ctcacagatg ctcagggcc accccaaaac ttggtgtgca gattccaacc    85380
cctttctcct ccccatgcct gcctcagtgg agggcggcag tgcaggtagt gggctgctga    85440
gaacccatcc ctggaggcag caggaggcag actggacccg ggccccaagt ccccaggcat    85500
```

-continued

```
gctgcactag cccatcaggc ttcatttaca acacactaat tcagagcgaa aatgatccag    85560
catttcaata tggcaactgc tgagcgttaa attcaagcac aggaggtggg ggggccaggt    85620
agccctggaa catagcagtc tcacaggtgg ctgggcgtgg ggtggatctc tgttcttgga    85680
gtagagggat gtggagtacc tccctctgct tggagtatct ggggtacctg acaagcaca    85740 gggggccatg aacagggcca tgcctgtgtg cctgcccctc gctcagaaga gggcacctga    85800
cgggaatacc agggcatatc tgcaccatgc ccgggcagta ggcctgggca tgaccctgga    85860
tcaggcagac ctgtagtagg tggaagggcc ccaggagagc tgaggagcct aggggagagg    85920
aacccagagg tccctgccaa agtgcttgat gtgctgccgt aagaagggca gcataggccg    85980
ggcgtggtgg ctcacgcctg taatcctagc accttgggag gctgaggtgg gtggatcacg    86040
aggtcaggag attgagaccc tcctggataa catgggaaa ccctgtctct actaaaaata    86100
caaaaattag ccggttgtgg tggtgcgtgc ctgtaatccc agctactcgg aaggctgagg    86160
tagaagaatt gcttgaacca gggagttgga ggttgcagtg agccaagatc atgccactgc    86220
actccagtct ggcaacagag agagactcca tctcaaaaaa aaaaaaaaa aataaggca    86280 gcatgggtgc ctgctgagag agagagaaag aagctctttc cctgcatgtg ttgccatggg    86340
attctggccc agctccctgg ggtgctctct gagctcagct ttggccctgt ccctctctct    86400
ctgtgcctca atttctctaa ctatgcactg agcaaggaga agaccaccac acctcaagta    86460
ccttctgcat gggccataca ctgagttta tgaatctccc ctctcttgtt ccacaaatga    86520
ttactggccc atttctcaga cgaggaaact gaagcccaga ggaggcaatg actcacccag    86580
taagaaggtg gtggagctgg ttctgcctgg cttcccttca cccttgagt cgctccagcc    86640 tctctaggtt tgggtggagg acgtgggaac caagctcgtg ggggcaccac cagctcttgc    86700
cagaaatggg gccaagagaa gaccaaggat gctccttgac ctgaggaaac gtccattaat    86760
tcatagctac tgtgctttgg cgagccacgc aggctctgga tgcaggctgc ctgggtgggt    86820
gacctgagca gatgccttaa tctctctggg gttcagtttt ctcatctgta aaataggcct    86880
cataagagct tttgtcttat agggttgtga ggattaaatg agctaaggta tatcacttga    86940
gcctgggagg cagagacttt agtgagcaag attatgccac tgcactccag cctggaagac    87000
agagccagaa cctgtctcaa atacatatat aaacaaaatg agcaaaggta tggaaaacac    87060
ttagacagtg gctgacatag agttaagagc tatgtaaatg tttactgcta atggaactat    87120
ttaaaagttg agtcataatt tatatttctct agactgtcaa ttacgaattg attcatttca    87180
atgttgtgct tttcccttt gtatttagga tccagcaaat tttcctttga aatctcaata    87240
caatttccta ggtccttgag aagataattt ccccgccccc acagtgctta tagcccatgg    87300
tggatccaat agctctctct agagcagctt ttccaaaagt ggactttgca cacaccagcc    87360
ccttccagat gcatcatctc accccaagag ataactcaat aaacagttga gcatacacta    87420
ttttagatct ccatggccca acaaggtagc cattagcata tcaaagactc tgacaagtcc    87480
tgcagcaaaa caccattgaa cattgtttga aacaaccaat cccaatcttg tttgaccaca    87540
gagttccatt atttctgctc aacagctgat aacatctgaa cacacgttgg gagatgccac    87600
cctcatttcc tgctttctag gaaatggcaa ggggagtcag agctgtgagg aacaccctct    87660
cgcagggatg agtggctcca cctctacaga aatcatctcc agtcatgtgc accatcgcta    87720
ggccattcct cctgttctca ccttccttgt ctgattcagc ccccacagcg gcctggagag    87780
gtcactagca tcaatgtctc catcatacag atgaggaaat tgaggttcac aaaggttaag    87840
tgggcacata gccagtaagt ggcagatccg gtagacaaac ccacagcttc tgattctaaa    87900
```

```
ccccacattc gttcttctgt atgttgactg gaaaagtaaa aatagatcct attctaacag   87960
gatcaatctt cccccatcat aggcttttaa aaaactcagg tatttttttt ttccggtagc   88020
attgaatgct ttaaaaactt aaaattttta ctatctttct tttgattact aaagcagtac   88080
gtgcttgtta tgtataaaac ttttcaaaca ttttgagttg aaaaatgaaa aaaaggcagg   88140
gcgcggtggc tcaagcctgc aatcccatca ctttgggagg ctgaggcggg cggatcacga   88200
ggtcaggaga tcgagaccat cctggctaac acagtgaaac cccgtctcta ctaaaaatac   88260
aaaaattagc caggcgtagt ggcgggcacc tgtagtccca gctactcgag aggctgaggc   88320
aggagaatgg cgtgaaccca ggaggcggag cttgcagtga gtcgattgc gccactgcac    88380 gccagcctgg gcgacagagc cagactccgt ctgaaaaaaa aaaaaaaag aaaagaaaag    88440 aaagaaaaa tgaaaaaaaa aaaaaaacag atctgcatag ccctacaaag tagccattag    88500
cttttaaatg aaaatactta aatgctatct aaatgaaaat agttaaaatg aataagata    88560 aaaaattcag ttcctcagtt acagtagcca cgtttcaagc gctcgggatt cacgtgcccc   88620
tggtggctac tgtgttgggc agcacagaca tgggacatta ctatcatcac agagaatcct   88680
acgggacggt gccgttctag attcttctta gacatatcct aacacctata caggttgatt   88740
atccctaatt caaaatccta aaatctgaaa tgctccaaaa tccaaaactt ttttagggcc   88800
aacatggtac tcaaggaaa tgctcattgg agaattttgg attttggact gaagtataat    88860
ccaactattc cgaaatctga caaaatcaga agtcctaaat ttgaatgctt ctggtcccag   88920
ccatcttggg taagggatgt tcaacctgta atgactgtta atgtgtggtt ttttttttg    88980 gagaccaggt cttgctctgt cgcccaagct agagtgcagt ggcacgatca tagttcactg   89040
cagccttcac ctcttgagct caagttatcc tcctgcctca gcctcccaaa gtgttgggat   89100
tacaggcggg agccgccatg ccccagccta ttgatattct tgttgaggtt ctcagacata   89160
tctgcatggc ctcacacatg gaggaaagag acccacagag gcaaaaacaa gacatggggt   89220
aaaaatagac tggaaggaaa cacaccgaat gatagtggtt ttttctgggt gttgagatta   89280
ccgagcttat ttttaaattt cttagatcct tcaggtgttc tacaacgtaa aatgcagaca   89340
gggtggggac gttggttgga gtcatgtttt ccctaatgtt cttactggtt ctaaaatctt   89400
caagctatgc tctcacccaa ggcttcactt attattattt taacactgtg gattcataaa   89460
gaatggaagc ccacacaagt ccagggaagg aaggaaggc agacagaggc ttattttcag    89520
gcctgggcag ttgcacaggg tcccttgctt agaagggcct catgcttggt ttcgtgttct   89580
gtggtcgctg tcctgaaatt cttactgatt tttgaacaag ggatcctgta ttttcatttt   89640
gcactgtgcc ctgaaaatca tgccgccgtc actagccctg ggattctccc caggacaggt   89700
ttcccttcag ctgctctaag ccttcgccct tgtccttgtc caaccacgga cgtggccatc   89760
cacggagccc tctacgtgcc tcagagcaag tgtgcttcgg ctgctcaggt gtgtgtctag   89820
agactgataa aaacagggct cgtgagtggg tgcgggaggc ccctgtggtc tctgttcaca   89880
cacgtaccta ccctcaaggc catgtctaca ctggcctatt tcagagaacc gccctgtgca   89940
tcatgggatg cttgtgccca catcacggcc cagcttggtt cagtcctgga gccctgtgtc   90000
ctgaagccat gaccaacccc aggcctggcc caccttcttc ctcagtctcc tctccctcaa   90060
gccctccaca ggacccataa accttccatc tccatgtaat ccttttgtgt gatccttctt   90120 ccatacccttt gccatgctg ttcactctgc ttgtaccagc aaggttcctt cctcccaga    90180 tctgcccttt ctagacccat ctcagattcc acccttccta gaaagacttc aggaagtatt   90240
```

```
tgagaagggc ctgaagatgc tgtggttgca tagaggagga tatgaatcac ctcgcttaga    90300
ggtatcgggg agggctccat ggaggtggtg ccctcaggcc aaggaagaga agatatcttc    90360
cgggcagaag ggagagtttg acgggctggt tgatgtcag acagaccaca ggatgactca     90420
aggtcctctt tcctcttctt aaacattagt tgcagcaagt cccaccatct gcctgagtct    90480
gttttcatct ccacaatgga ggtggtgatg cccagcacac ggagctgtga tgaggattta    90540
atggggaatc cagagcattt atggaagtgc caggaggcca agattctgca taggtaggaa    90600
ggacctaagc cagaggggtg tgggtggcca gaggagagag cctaccttag tagggcttgg    90660
taggctaagg tctgggctga atctcgaggc tctggagctt agaacagcat ctgcaactcc    90720
ctggctgtcg ggttcaggc aaggactgcc tcctctctga gtgtcagttt ccccatctat     90780
aaatggaaag ctgggacact gaaaaacact gggggggagg gtggttcctg aggcagtctc    90840
tctccacaca tcacaggaat gtggcgcccc agggagaagg catctttgtc cattgtgttc    90900
acttctgcat ctccagtgcc cagaacagtg cttgcatgca gtagatgctc aataaatgtt    90960
cattgaatga atcagcagca accaattcgc ccacctcaca tcctaagtcc gctggggacg    91020
taggcccacc tctccaggga aactgtctgc agattgggac cacacctcag gtcacaagca    91080
tttcctgagc acctactgta tgcatggctc tgcgcagccc ggggcagacc cttgctccac    91140
agcccgacag ggcagagcca aggaggcagg tgacagacac agtgatttgg gaagaagaac    91200
agagagcagg gtggccagca gggccttgcc tgggtgggag caggccgttc ccaggctgga    91260
gctcaggctg atgggagccc cagcttgcct gttcctggga gggtgggact gcctcttcct    91320
ctttctttct ctgaaaacaa aaattgtttt cccttaaatt tacaagtatt aaaagtttgg    91380
aaaatacaca ataatcaaaa gaatataaaa taaaggttac ctgccatcat ggcggaccac    91440
acagtattaa ctactatgga cttttcagtg tttccctcta gtcttttttc tgaggtggct    91500
ttgctctcag aggtggcttt ctctccccct gggaagggat atagctgctc tgtaggagat    91560
gtgggggcac caggctctct ccatgggctc tttatcactt ctgacttgga ggtcctttct    91620
ccaccccccc tggacctagc acctcttccc gagacacagg ggtgcgaaga gctgggggag    91680
gtacgtcagc aggcctcccc tcctgcccct gcttacccca cggaggtggg gtgggacaga    91740
actcaggctt gaggaaggag cactggaggc caagccacag gtgctggtcc tcagccctgg    91800
tgcccaggca agttgggttt gggaataggg gcatgaccaa aatggacccc tcctttcctc    91860
cccaccccctt tccactccat ccgccttttcc ctttgcgttc tccaagcgtt ccgtccccca    91920
gatgccctct gtttcctctg ctccagcctt ttaactcctc tcaacaaagg ccaaggaatc    91980
aggcagactg tggacactca ggtgtgcatg atgggaaggg acctgcattt acaaaagctc    92040
cccccccacag ggactgcatg tgctggtgga atctcagtca ccatgtccca cgttaagga     92100
tgtttggagg gggctgactt tggtcaccct tcaaatcata agttatatgc gtctgccctt    92160
tccgcccaca cgtaagtctg aaccttttgc caaaaacact tttcccagac tcgaaagaaa    92220
accccaaaga ggaacctaaa ccttcacgct gcctgcaccg attggaccgg agtgctcagg    92280
ctcgcgccaa caagtgtttc aaagaagaag ccagacagtg aaggggaag tgagggagaa     92340
gctgaaaaac tctcaggctg accaatcgtc agcccattca ttcgttcatc catccatcca    92400
tccatccatc catccatcca tccatccatc cattctttct ttctttcctc tatccattca    92460
gtgagaaggg ctgaatatca cctgtgagcc tgccctgct cccaagaaca ccctttggac     92520
acctgtgggg tgagtagtga ggggcagcaa tggcagagca cccccaccgc ctggagggga    92580
gaaagggaag ggctgggaag gctccccaag ggggcggcca tgaagctggg ccttgagaag    92640
```

```
acaggccagg gtttctcacc ttccacatcc tgcttagagt cagacagaag gcttttgcag   92700
aggaggagga acattaaata gtagtaattt ctggcattcc atgagggctt gtctgtgccg   92760
ggccctgtgc tgtgcacgtg atacacacta cctcattaaa cctacccaac atgccttgag   92820
ggggtgctat tcattttctc cattttacag gtaagaaaat gaaacacaga gaggtgaggc   92880
acctctccca acgccacaca gcgaggaagt ggcagagcct ggctgcagct gaggcttata   92940
gccgcatttt acattgcttt ctctccgaag agtgccttcc tttatccctg ggagccattg   93000
acaaggggtc tgacagtccc tctagtcttg tgcctgctca gccctctcta gccctgaaaa   93060
aaccagggct tggcgctgga gaaagagcag gagggtgaga tgtggaaaca tctgttgagt   93120
ggcaggggat cacgctggcg cagaggggcc cgagccgatc aggaggccgg cctgtgccag   93180
gccagtgctc cctgtgtacc aggtgccaca tgcgggctc agggtagggc cacagttgct   93240
cctcccaacc acccttgag gtcagtgtta ctagcccatt ttacagagga ggaaactgag   93300
accttaagag gtgaattaac atgtcaggtc acccagctac catgcagttt aagcctagat   93360
tgttctgact cctaaactgt gtgcaaggcg gatgattgga ccccagggag gcaaggaaag   93420
tcagttttcc tgctgctgaa ttcaatgttt tacaagacca cacacctctt tagacctcag   93480
tttcgtcatg tatgaaatga ggaggggaac tctctgcctc cgggctctga tatgctcctg   93540
gactgattca ctgttccttg ttcttgtgac ttctcaaagc aagaccagag tcccactccc   93600
agccctaggc ccgagattcc catccccact gtgtccaggg gcttcaggag gtgctatttt   93660
agggcagatg gcaaaggcct gggctgtaga tccactgagg gctaaaggca atctttcttc   93720 cctccaccc tcccttcctt ccttccttct ctttacttcc actaagcaag gtagggaact   93780
actcgctgag tctcagggca ggcccacgga ctgaagctca ggaggacagg gctccccagt   93840
ggctgcaggt gtcccagcac tgactcctag cagagggggt gtttgggttc agtctggaag   93900
attgggtgag attccccaac tacgggggt ggggcacac tctgggtggc agatttgagg   93960
aagagtctgc agataaggca tccccaggag atggcaataa gagctggtgt tggggctgcc   94020
ccactgaacc cagagcccag gcctgttttcc ccacccatgg aggagtccgg actggctcag   94080
tggcaaggcc ggggtcagag gctgccactc tcctcctgcc tctcacagcc cgctggaagg   94140
tcaggttttc aggctctgct tatccgtctc ccggcctcct ccctccaggt aaccgaggga   94200
gcctccgctt tgatgcggcc acctccaggc ccaggcgtca atgagccctc tatatgacca   94260
gtggggctgc tgggggcctc cagcccgcca gagtgggtgc ggtgaggcct ggacacacag   94320
tcccgctgtg tggggtcggc tcatgcctgc ctagaccctg tggcagtgg ggggctccta   94380 ggaatgcttt tccagcctgg ggggcacttt ggacaggcag ggtggtctgg ggagacgggt   94440
gtgtgcaggg cagcctcaga agccgccatc aaagggacct agcagacgtg gcgccaggca   94500
agcgccatag tgggcacgga agggctggcg gtcagtctgt tcctctccca gggatggcgg   94560 ggaggggag gccccatgga cacatgtgct caggtgacc agccatcagg ggttgcctgg   94620
gatgaagggg tttcctggga cgtggagctt tcagtgctaa aacagagagt cccctgttat   94680
tggaacttcc tggaccttcg gaaaggatac agtgactgac ctctctggtc tgggcagcct   94740
cctccctgtc cggtgacctc tgagtcagac catctcggcc agacctgccc agggccattt   94800
tgtccacccc ctgcctccac acaggcctgc ctcatacccca agagtccact ttccatttct   94860
cccaggcatc ttcaggggag gagctgccgg ccaactccaa ccactgctag ggggacctcg   94920
gccagaccca caccacgctc ccagccctcc ctgtggctcc cgagccagct catactttcc   94980
```

```
tgcttccaca cctttgccca ggacgttcct tctgcctgga acatcctttc cctgtctttg    95040
ttacctcttt acccttaggg acccagtttc caagtcactc ctccagagga cttgttctct    95100
ctttcccaag gctgggctag taccoctctt tgaactcaca gccctggttc ttctcccaaa    95160
aaacctttgt cacgcccag ggcaatttc tgttgaccca tcttttcta caccagatgg       95220 tgagctctta ggatggagat c                                              95241
```

<210> SEQ ID NO 54
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

```
tcctcttacc tatccctact tccccytccc aaagaagcct tagtagtgtt g             51
```

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

```
agtgagcaaa ctgaggcaca gagatrttac atcacctgta caagggtaca c             51
```

<210> SEQ ID NO 56
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

```
ctttccagag actggcttcc tacagkacag gcggggtcac aggatgtgtt c             51
```

<210> SEQ ID NO 57
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
tttaattta gccattcttc tgcctmatt cttaaaatta gagaattaag g                51
```

<210> SEQ ID NO 58
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

```
ttttcctgct tccagacatg aatcakgtca ctattcaatg ggatgcagta a             51
```

<210> SEQ ID NO 59
<211> LENGTH: 51
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 59
attgggatat taacagatc attccraact gggtaggttt ttgcagaatt t          51

<210> SEQ ID NO 60
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttatctagaa ataaaaaagc atacawttga taattcacca aattgtggag c          51

<210> SEQ ID NO 61
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aactctaact ctttatatag gaagtygttc aatgttgtca gttatgactg t          51

<210> SEQ ID NO 62
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ttagcttctc ctgataaact aattgyctca cattgtcact gcaaatcgac a          51

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
acacctaaac ttgggagaac attgtycccc agtgctgggg taggagagtc t          51

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccagtttctc cctcgctgtt tttatrgctt tcaaaagcag aagtaggagg c          51

<210> SEQ ID NO 65
<211> LENGTH: 51
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 65
cataagcctc gttatcccat gtgtcraaga agataggttc tgaaatgtgg a          51

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgcccttccc attttccttc agaagragag attcttctat gacctcattg g          51

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttaaagaaac tttttcgcga gggacrgttc aactgaaact tcgaaagcat c          51

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggtttctgga ggacttctag gaaaaygagg gaagagcagg aaaaggcgac a          51

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aacactgata tcaagatact ggattstatt atgagaaatt atcaaaatcc t          51

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcctggctcc aggccaaaag gaagcmcagg aaagctccca gcaggaacat c          51

<210> SEQ ID NO 71
<211> LENGTH: 51
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 71
ctcactatgc tcgatctttc ctacawcaac ttaaatgtgg ttggtaacga t                   51

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
acttgctcat tctcccttac acataytcaa cctaaccaag aataaaatct c                   51

<210> SEQ ID NO 73
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
gcatacttag actactacct cgatgrtatt attgacttat ttaattgttt g                   51

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
tgttctcaaa gtgattttgg gacaaycagc ctaaagtatt tagatctgag c                   51

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
ttgagggtaa aattcagtaa ggttgracct ctggtgagtt ctgataaaaa t                   51

<210> SEQ ID NO 76
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
tttccaatgt ggacactgaa gagacwaatt cttatccttt ttaacataat c                   51

<210> SEQ ID NO 77
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
agtgaagttg gcttctgctc aaatgycaga acttctgtag aaagttatga a           51

<210> SEQ ID NO 78
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggtttgtctg gtgggttaac catacrgagg tgactattcc ttacctggcc a           51

<210> SEQ ID NO 79
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aatgaaaaat tagaacaaca gaaacrtggt aagccacttc tatttcttta g           51

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aatcaaatgg cttgaatatc acagaygggg cattcctcaa cctaaaaaac c           51

<210> SEQ ID NO 81
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gtctggattt atcccttaat aggctsaagc acatcccaaa tgaagcattc c           51

<210> SEQ ID NO 82
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tgtgtgagtg gccggccccc agctcyacct ccacccactc cacttcatgg g           51

<210> SEQ ID NO 83
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 83
agctgaggtc cagggcctcc agtcgyggta gctccgtgaa tgagtgctcg t            51

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
agcaatagaa ccgatgtctt agcatkttct aaactaagat ttcgttgcat t            51

<210> SEQ ID NO 85
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agagttttca agtgaggcag ttggakagtt cttttaaaca actcgtctgt t            51

<210> SEQ ID NO 86
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gagatcagtt agaaaattaa atgcartatt tagttctcgt aaggccatca g            51

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aaatttttta attcacaggt acaccrgaat ggatttcttc ccgcatttag a            51
```

MATERIALS AND METHODS FOR DETERMINING CANCER RISK

CROSS-REFERENCE TO RELATED APPLICATIONS

This application claims the benefit of U.S. Provisional Application Ser. No. 61/392,342, filed Oct. 12, 2010. The disclosure of the prior application is considered part of (and is incorporated by reference in) the disclosure of this application.

BACKGROUND

1. Technical Field

This document relates to materials and methods involved in assessing inflammatory bowel disease patients at risk for developing cancer. For example, this document relates to materials and methods for monitoring colorectal cancer risk in ulcerative colitis patients.

2. Background Information

Inflammatory bowel disease (IBD) refers to chronic diseases that cause inflammation in the intestine. The major types of IBD are Crohn's disease and ulcerative colitis (UC). Crohn's disease and UC differ in the location and nature of the inflammation. Crohn's disease can affect any part of the gastrointestinal tract, though it most commonly affects the terminal ileum and parts of the large intestine. Ulcerative colitis is an idiopathic inflammatory bowel disease characterized by chronic, relapsing mucosal inflammation primarily limited to the colon and rectum. Patients with longstanding and extensive IBD are at increased risk to develop colorectal cancer (CRC). Because of this, patients with IBD are advised to undergo surveillance colonoscopy and biopsy, every one to two years, wherein biopsy samples are histologically evaluated for the presence of pre-cancerous changes (colorectal dysplasia) or CRC.

SUMMARY

This document provides methods and materials for assessing inflammatory bowel disease patients at risk for developing cancer. For example, this document provides materials and methods that can be used to monitor colorectal cancer risk in ulcerative colitis patients. As described herein, markers (e.g., nucleic acid markers, polypeptide markers, epigenetic markers, or combinations thereof) can be used to screen UC patients to determine risk for developing CRC. Detection of such markers may allow a physician to more closely monitor those patients deemed to be at a higher risk of developing CRC.

Patients with UC have an increased risk of developing CRC as compared with the general population (Ekbom et al., *N. Engl. J. Med.,* 323:1228-1233 (1990)). The exact mechanism by which the extent and duration of UC contribute to the pathogenesis of CRC is unclear, but studies measuring colonic inflammation and CRC risk have found a correlation between increased severity of histologic inflammation and risk for CRC (Rutter et al., *Gastroenterology,* 126(2):451-459 (2004) and Gupta et al., *Gastroenterology,* 133(4):1099-1105 (2007)). Rutter et al. assessed disease activity using a four-point grading scale ranging from 0 (inactive) to 3 (severely active) to quantify levels of neutrophil infiltration on hematoxylin and eosin-stained tissue sections (H&E).

This document is based, in part, on the discovery that hemotoxylin and eosin-stained tissue section (H&E) examinations alone may underestimate the level of disease activity present in the colonic tissue of patients with UC, and that patients with UC-CRC may have higher levels of disease activity at the tissue level even when they have what would currently be defined as inactive disease. For example, nucleic acid markers, epigenetic markers, polypeptide markers, or combinations of markers can be used to identify patients with higher levels of immune cell infiltrate associated with UC-CRC and can be detected even during what is currently defined as inactive disease (e.g., no neutrophil infiltration seen on H&E stained tissue slides). Measuring polypeptide levels of MPO (myeloperoxidase), and/or the methylation status of MINT1, COX-2, and/or RUNX3 nucleic acids in patient samples can provide useful information about the risk of developing colorectal cancer in inflammatory bowel disease patients. In some cases, genetic associations in TNF-alpha nucleic acids or in other biomolecules regulated by NFκB can provide additional useful information about cancer risk.

In general, one aspect of this document features a method for assessing a mammal diagnosed with inflammatory bowel disease for the presence of or an increased risk of developing colorectal cancer. The method comprises, or consists essentially of, determining whether or not the mammal comprises at least two markers from the group consisting of elevated MPO polypeptide levels, elevated RUNX3 methylation status, elevated MINT1 methylation status, and reduced COX-2 methylation status as compared to a normal control, wherein the presence of the at least two markers is indicative of an increased risk of developing colorectal cancer. The method can further comprise determining whether or not the mammal comprises at least one polymorphism in a TNF alpha nucleic acid, wherein the presence of the polymorphism is indicative of an increased risk of developing colorectal cancer. The inflammatory bowel disease can be ulcerative colitis. The determining step can comprise performing an immunoassay. The determining step can comprise performing methylation-specific PCR. The mammal can be a human.

In another aspect, this document features a method for assessing a mammal with histologically inactive inflammatory bowel disease for the presence of colorectal cancer or an increased risk of developing colorectal cancer. The method comprises, or consists essentially of, determining whether or not the mammal comprises the presence of at least two markers selected from a group consisting of the presence of at least one polymorphism in a TNF alpha nucleic acid, an elevated MPO polypeptide level, an elevated methylation level of a RUNX3 nucleic acid, an elevated methylation level of a MINT1 nucleic acid, and a reduced methylation level of a COX-2 nucleic acid as compared to a normal control, wherein the presence of the at least two markers is indicative of the presence of colorectal cancer or an increased risk of developing the colorectal cancer. The mammal can be assessed as having the increased risk of developing colorectal cancer and can be categorized as a mammal needing more frequent monitoring than a mammal assessed as not having the increased risk of developing colorectal cancer.

In another aspect, this document features a method for assessing a mammal diagnosed with inflammatory bowel disease for the presence of or an increased risk of developing colorectal cancer. The method comprises, or consists essentially of, (a) determining the methylation status in a RUNX3 nucleic acid and a COX-2 nucleic acid in the human, (b) classifying the human as having or as having an increased risk of developing the colorectal cancer if the RUNX3 nucleic acid methylation status is elevated and the COX-2 nucleic acid methylation status is reduced as compared to a normal control, and (c) classifying the human as not having or as not having at an increased risk of developing the colorectal cancer if the RUNX3 nucleic acid methylation status is not elevated and the COX-2 nucleic acid methylation status is not reduced. The inflammatory bowel disease can be histologically inactive. The method can further comprise determining the level of an MPO polypeptide in the mammal, wherein an elevated level of the MPO polypeptide is indicative of the presence of or an increased risk of developing colorectal cancer. The method can further comprise determining the methylation status of a MINT1 nucleic acid in the mammal, wherein an elevated level of the MINT1 nucleic acid methylation status is indicative of the presence of or an increased risk of developing the colorectal cancer. The method can further comprise determining whether or not the mammal contains a polymorphism in a nucleic acid encoding a TNF-alpha protein, wherein the presence of the polymorphism is associated with the presence of or an increased risk of the colorectal cancer. The polymorphism can be rs1800629.

In another aspect, this document features a method for assessing a biopsy sample from an ulcerative colitis patient having the presence of a polymorphism in a TNF-alpha nucleic acid. The method comprises, or consists essentially of, analyzing the biopsy sample for at least two markers selected from the group consisting of an MPO polypeptide level, methylation status of a RUNX3 nucleic acid, methylation status of a MINT1 nucleic acid, and methylation status of a COX-2 nucleic acid.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 contains a sequence listing of human TNF-alpha nucleic acid promoter region (GenBank Accession No. AB048818; GI No. 13365764; SEQ ID NO: 1).

FIG. 2 contains a sequence listing of a human clone MINT1 colon cancer differentially methylated CpG island genomic sequence (GenBank Accession No. AF135501; GI No: 4914684; SEQ ID NO: 51).

FIG. 3 contains a sequence listing of human cyclooxygenase nucleic acid, promoter region and exon 1 (GenBank Accession No. AF044206; GI: 3282785; SEQ ID NO: 52).

FIG. 4 contains the 3' end of human runt-related transcription factor 3 coding and non-coding regions and a CpG island, complete sequence. (GenBank Accession No. AL023096; GI: 3900882; SEQ ID NO: 53).

DETAILED DESCRIPTION

Figures 5, 6:
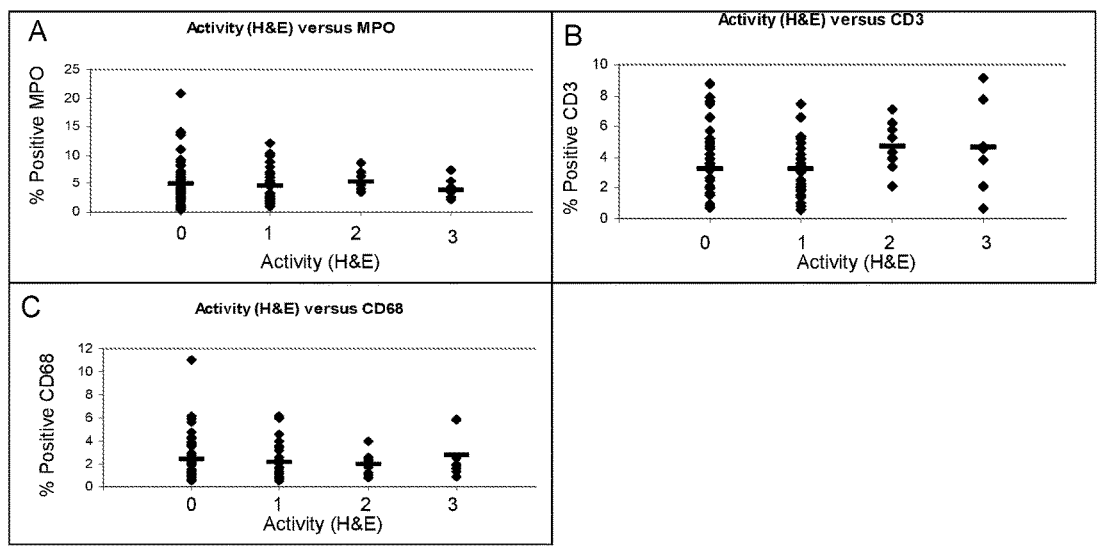
FIG. 5 contains a sequence listing of a human TNF-alpha nucleic acid promoter region (SEQ ID NO: 4). The underlined regions represent the area of the −308 and −238 SNP, respectively, and the parenthetic bases indicate the polymorphism sites.
FIG. 6 is a graph of histologic disease activity and cell surface marker levels.

This document provides materials and methods related to assessing inflammatory bowel disease patients at risk for developing cancer. For example, this document relates to materials and methods for monitoring colorectal cancer risk in ulcerative colitis patients.

In general, this document provides methods for determining the risk of inflammatory bowel disease patients of developing a cancer by determining the methylation status, genetic polymorphism status, or level of one or more biomolecules in a test sample from a mammal. The methylation status, genetic polymorphism status, or level of one or more biomolecules can be correlated with the presence of or the risk of developing cancer. Identifying cancers at an early stage can help a physician properly diagnose and treat a cancer patient. Typically, a properly diagnosed and treated cancer patient can experience an improvement in general health and survival.

As described herein, methods and materials to stratify risk of inflammatory bowel disease patients developing CRC have been identified that may identify patients at risk of developing CRC even in patients deemed to have histologically inactive disease (0 neutrophils on H&E). Patients found to have an increased risk of developing colorectal cancer may benefit from more intensive surveillance and/or different treatment strategies.

The term "biomolecule" as used herein refers to DNA, RNA, or polypeptides. This document provides methods for measuring biomolecules related to, without limitation, markers of immune cell infiltration into gastrointestinal tissue such as markers of neutrophil granulocytes (e.g., myeloperoxidase; MPO), T-cells (e.g., CD3), natural killer cells (e.g., CD16, CD56, CD8), B-cells (e.g., CD19, CD20), and macrophages (e.g., CD68). This document also provides methods for measuring biomolecules related to inflammatory markers (e.g., tumor necrosis factor alpha; TNF-alpha, cyclooxygenase 2; COX-2), runt-related transcription factors (e.g., RUNX3), and other factors such as Methylated-in-tumor 1 (MINT1). In some cases, this document provides methods for measuring biomolecules that are regulated by nuclear factor kappa beta (NFκB).

The term "marker level" as used herein refers to a test level of a biomolecule that is either altered or normal compared to a control level. The level of a particular biomolecule can be measured in a test sample from a mammal. The resulting test level then can be compared to a control level of the corresponding biomolecule. If a test level is altered compared to a control level, then the potential for the presence of or the risk of developing cancer in the mammal corresponding to that test sample can be classified as increased. For example, if the level of an MPO polypeptide measured in a colorectal biopsy sample from a patient is elevated compared to a control level of MPO polypeptide, then that patient can be classified as having an increased risk of developing colorectal cancer. In another example, if the methylation status of a MINT1 or RUNX3 nucleic acid measured in a colorectal tissue biopsy is elevated compared to a control level of MINT1 or RUNX3 methylation, then that patient can be classified as having an increased risk of developing colorectal cancer. In yet another example, if the methylation status of a COX-2 nucleic acid measured in a colorectal tissue biopsy is reduced compared to a control level of COX-2 methylation, then that patient can be classified as having an increased risk of developing colorectal cancer.

In some cases, if a test level is normal compared to a control level, then the risk of developing cancer in a patient corresponding to that test sample can be classified as decreased. For example, if the level of an MPO polypeptide measured in a colorectal biopsy sample is normal compared to a control level of MPO polypeptide, then the patient corresponding to that tissue biopsy sample can be classified as having a decreased risk of developing colorectal cancer.

In another embodiment, detecting the presence, absence, levels, or status of multiple biomarkers can be used to determine the risk for developing a cancer. In some cases, the presence of one or more polymorphisms in the promoter region of a TNF-alpha nucleic acid can be determined in combination with determining the methylation levels of one or more MINT1, COX-2, and RUNX3 nucleic acids and/or polypeptide levels of biomarkers associated with immune cell infiltration (e.g., MPO). In some cases, a combination of biomarkers that do not include TNF-alpha polymorphism detection can be used as described herein. For example, the presence of a polymorphism (e.g., −308G>A, −301G>A, −293C>T) in a TNF-alpha nucleic acid, an elevated level of an MPO polypeptide, and an elevated level of methylation in a RUNX3 nucleic acid in a sample or samples from a mammal can indicate that that mammal has an increased risk of developing colorectal cancer. In some cases, determining the presence or absence of a polymorphism in a nucleic acid of a biomolecule regulated by NFκB (e.g., IL1B) in combination with determining the methylation status of one or more MINT1, COX-2, and RUNX3 nucleic acids can be used to determine the risk for developing cancer. Other non-limiting examples of suitable combinations of markers include determining an MPO polypeptide level in a patient sample in combination with determining the methylation status of one or more RUNX3, MINT1, or COX-2 nucleic acids.

In some cases, the presence, absence, level, or status of one or more biomarkers can be determined prior to testing for the presence, absence, level, or status of additional biomarkers. For example, the presence of one or more polymorphisms in a promoter region of a TNF-alpha nucleic acid (or other biomarkers regulated by NFκB) can be determined in an initial screening assay from a patient with UC. Genomic screening tools such as single nucleotide polymorphism (SNP) analysis are particularly useful in inflammatory disease settings because these markers are not affected by disease activity and thus do not change over time. Patients determined to have a SNP present in a TNF alpha nucleic acid could then undergo additional testing to determine the status or levels of other biomarkers. For example, MPO polypeptide levels could be determined in a biopsy sample. In another example, methylation levels of one or more RUNX3, MINT1, and COX-2 nucleic acids can be determined in patients with a SNP present in a TNF alpha nucleic acid. Other non-limiting examples of suitable screening/reflex tests include determining MPO polypeptide levels in a blood or biopsy tissue sample followed by determining methylation status of one or more RUNX3, MINT1, and COX-2 nucleic acids in biopsy samples from patients with increased MPO polypeptide levels.

In some cases, it may be useful to determine the presence, absence, level, or status of one or more biomarkers in a patient that has previously been deemed to have histologically inactive disease (e.g., 0 neutrophils on H&E). For example, determining the presence or absence of a polymorphism in a nucleic acid of a biomolecule (e.g., TNF-alpha, IL1B), optionally in combination with determining the methylation status of one or more MINT1, COX-2, and RUNX3 nucleic acids in a biopsy sample from an inactive area of the colon (e.g., 0 neutrophils on H&E), can be used to determine the risk for developing cancer in a patient previously found to have histologically inactive disease. Other non-limiting examples of suitable combinations of markers include determining an MPO polypeptide level in a patient sample in combination with determining the methylation status of one or more RUNX3, MINT1, or COX-2 nucleic acids in a patient previously found to have histologically inactive disease.

Various types of samples can be used when measuring a biomolecule. Such samples include, without limitation, tissue samples, neoplastic tissue biopsies, non-neoplastic tissue biopsies, blood, plasma, serum, surgical waste, and whole organs. Biopsy specimens can be frozen, embedded, sectioned, and stained to identify regions of cellular infiltration. Samples can also include those that have been manipulated in any way after their procurement, such as by treatment with reagents, solubilization, or enrichment for certain components, such as polynucleotides or polypeptides.

Various appropriate methods can be used to measure a biomolecule level in a sample. Such methods can vary depending on the type of biomolecule measured. For example, methods for measuring polypeptide levels include, without limitation, ELISA, immunohistochemistry, and immunofluorescence-based techniques. Such methods typically involve using antibodies having specific binding affinity for a particular polypeptide.

The term "antibody" as used herein refers to intact antibodies as well as antibody fragments that retain some ability to bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid residues, amino acid-nucleic linkages) and usually have specific three dimensional structural characteristics as well as specific charge characteristics.

The antibodies provided herein can be any monoclonal or polyclonal antibody having specific binding affinity for an MPO polypeptide. "Specific binding affinity" refers to an antibody's ability to interact specifically with a particular polypeptide without significantly cross-reacting with other different polypeptides in the same environment. An antibody having specific binding affinity for MPO can interact with MPO polypeptides specifically in the presence of multiple different polypeptides, for example, multiple different markers expressed by neutrophils. MPO antibodies can have specific binding affinity for full-length or fragments of an MPO polypeptide from any suitable species, including, without limitation, mouse, rat, chimpanzee, and human. For example, MPO antibodies can have specific binding affinity for a full-length human MPO polypeptide or fragments of a human MPO polypeptide including.

Antibodies used for measuring polypeptide levels can include a detectable label. A detectably labeled antibody can refer to an antibody (or antibody fragment which retains binding specificity for a target polypeptide or epitope), having an attached detectable label. The detectable label is normally attached by-chemical conjugation, but where the label is a polypeptide, it could alternatively be attached by genetic engineering techniques. Methods for production of detectably labeled proteins are well known in the art. Detectable labels may be selected from a variety of such labels known in the art, including, but not limited to, radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. Antibodies: A Laboratory Manual (1988) Cold Spring Harbor Laboratory Press, Cold Spring Harbor, N.Y.).

MPO polypeptide levels in a colon tissue biopsy sample can, for example, be measured using a quantitative or semi-quantitative immunohistochemistry technique. For example, a section of a colorectal tissue biopsy sample can be treated with anti-MPO primary antibodies. Negative control sections can be incubated with pre-immune rabbit or mouse serum in lieu of primary antibodies. After antibody binding and subsequent washing, the primary antibodies can be detected with appropriate label-conjugated secondary antibodies (e.g., gold-conjugated or enzyme-conjugated antibodies). The label is then developed and quantitated using an image analysis system such as a computer-aided imaging system.

The resulting quantitated polypeptide levels can be correlated with the risk of having or developing colorectal cancer. Although samples can be processed individually, samples from different tissues or from a population of different patients can be processed simultaneously. Such processing methods include, without limitation, tissue microarrays as described elsewhere (Kononen et al., *Nat. Med.*, 4:844-847 (1998)).

Immunofluorescence techniques represent another approach to measuring the level of a polypeptide. For example, MPO and CD68 polypeptides can be localized in the same colon biopsy sample section using polyclonal and monoclonal antibodies against MPO and CD68. The bound antibodies can be detected using different fluorescently conjugated antibodies. The levels of MPO and CD68 fluorescence can be quantitated using an image analysis system, and the resulting quantitated levels correlated with the risk of having or developing cancer.

Suitable antibodies for ELISA-, immunohistochemistry- and immunofluorescence-based methods can be obtained using standard techniques. In addition, commercially available antibodies to polypeptides associated with immune cell infiltration can be used.

As used herein, a "methylated nucleic acid marker" is a mammalian nucleic acid sequence that is methylated (e.g., hypermethylated or hypomethylated) in certain conditions (e.g., pre-cancer, cancer) as compared to the methylation status of the same mammalian nucleic acid under normal conditions (e.g., in an individual that does not have pre-cancer or cancer). In some cases, hypermethylated DNA markers can be particularly useful for detecting colorectal dysplasia or colorectal cancer. Such hypermethylated DNA markers can include, for example, CpG sequences from a methylated-in-tumor 1 (MINT1) nucleic acid and a runt-related transcript factor 3 (RUNX3) nucleic acid. In some cases, hypomethylated DNA markers can be particularly useful for detecting colorectal dysplasia or colon cancer. Such hypomethylated DNA markers can include, for example, CpG sequences from a cyclooxygenase 2 (COX-2) nucleic acid.

DNA methylation does not alter the coding function of a DNA, but has the potential to alter gene expression and thus can have profound developmental and genetic consequences. DNA methylation occurs at target cytosine residues that are found within CpG dinucleotides. The methylation reaction involves flipping a target cytosine out of an intact double helix to allow the transfer of a methyl group from S-adenosylmethionine to form 5-methylcytosine (Klimasauskas et al., *Cell* 76:357-369 (1994)). Areas of the genome containing long repeats of CpG dinucleotides are referred to as "CpG islands" (Bird, *Nature* 321:209-213 (1986) and Gardiner-Garden et al., *J. Mol. Biol.*, 196:261-282 (1987)). CpG islands typically are between 0.2 to about 1 kb in length and are located upstream of many genes, but may also extend into gene coding regions.

Methylation of cytosine residues contained within CpG islands of certain genes typically correlates inversely with gene activity. For example, CpG islands of promotors are unmethylated if genes are expressed. Methylation can lead to decreased gene expression by a variety of mechanisms including, without limitation, disruption of local chromatin structure, inhibition of DNA binding by transcription factors, or by recruitment of proteins that interact specifically with methylated sequences and thus indirectly prevent transcription factor binding. Hypermethylation of CpG islands within tumor suppressor genes therefore can lead to progressive reduction of normal tumor suppressor expression, resulting in the selection of a population of cells having a selective growth advantage (i.e., neoplasm). Alterations in normal methylation processes also can be associated with genomic instability (see, e.g., Lengauer et al., *Proc. Natl. Acad. Sci. USA*, 94:2545-2550 (1997)). Such abnormal epigenetic changes may be found in many types of cancer and can therefore serve as potential markers for oncogenic transformation.

Any appropriate method can be used to detect a DNA methylation marker in a sample. Such methods can include isolating DNA from the sample, separating out one or more particular regions from the total DNA (e.g., CpG islands), subjecting the DNAs to bisulfite treatment, and determining whether the separated DNAs are abnormally methylated (e.g., hypermethylated). To analyze which residues within a DNA sample are methylated, the sequences of PCR products corresponding to samples treated with and without sodium bisulfite can be compared. The sequence from the untreated DNA will reveal the positions of all cytosine residues within the PCR product. Cytosines that were methylated will be converted to thymidine residues in the sequence of the bisulfite-treated DNA, while residues that were not methylated will be unaffected by bisulfite treatment.

In some cases, a test nucleic acid sample can be amplified with primers which amplify a sequence region known to include a CpG island region of interest. For example, primers specific for unmethylated and methylated nucleic acids such as those described in Example 1 can be used to amplify the sample DNA and determine the methylation status of the tested residues. In some cases, oligonucleotide primers can amplify a region of interest in a RUNX3, MINT1, or COX-2 nucleic acid. For example, the methylated primers of SEQ ID NO: 37 and SEQ ID NO: 38 amplify a 129 base pair fragment (SEQ ID NO: 45) and unmethylated primers of SEQ ID NO: 39 and SEQ ID NO: 40 can be used to amplify a 159 base pair fragment (SEQ ID NO 46) in the promoter region of a RUNX3 nucleic acid (Table 1). In some cases, alternate oligonucleotide primer sequences could be used to amplify all or part of the RUNX3 nucleic acid fragment of SEQ ID NO: 45 or SEQ ID NO: 46 or any fragment of SEQ ID NO: 53 (FIG. 4) that when amplified, can be analyzed to determine the methylation status of a RUNX3 nucleic acid. A patient diagnosed with IBD and containing a hypermethlated RUNX3 nucleic acid (e.g. elevated methylation status) can be classified as being at a higher risk of having or developing colorectal cancer as compared to a corresponding patient not containing a hypermethylated RUNX3 nucleic acid.

In another example, the methylated primers of SEQ ID NO: 29 and SEQ ID NO: 30 amplify a 81 base pair fragment (SEQ ID NO: 47) and unmethylated primers of SEQ ID NO: 32 and SEQ ID NO: 33 can be used to amplify a 112 base pair fragment (SEQ ID NO 48) in the promoter region of a MINT1 nucleic acid. In some cases, alternate oligonucleotide primer sequences could be used to amplify all or part of the MINT1 nucleic acid fragment of SEQ ID NO: 47 or SEQ ID NO: 48 or any fragment of SEQ ID NO: 51 (FIG. 2) that when amplified, can be analyzed to determine the methylation status of a MINT1 nucleic acid. A patient diagnosed with IBD and containing a hypermethlated MINT1 nucleic acid (e.g. elevated methylation status) can be classified as being at a higher risk of having or developing colorectal cancer as compared to a corresponding patient not containing a hypermethylated MINT1 nucleic acid.

In yet another example, the methylated primers of SEQ ID NO: 13 and SEQ ID NO: 14 amplify a 142 base pair fragment (SEQ ID NO: 49) and the unmethylated primers of SEQ ID NO: 15 and SEQ ID NO: 16 can be used to amplify a 138 base pair fragment (SEQ ID NO 50) in the promoter region of a COX-2 nucleic acid. In some cases, alternate oligonucleotide primer sequences could be used to amplify all or part of the COX-2 nucleic acid fragment of SEQ ID NO: 49 or SEQ ID NO: 50 or any fragment of SEQ ID NO: 52 (FIG. 3) that when amplified, can be analyzed to determine the methylation status of a COX-2 nucleic acid. In some cases, a patient diagnosed with IBD and containing a hypomethylated COX-2 nucleic acid (e.g. reduced methylation status) can be classified as being at a higher risk of having or developing colorectal cancer as compared to a corresponding patient not containing a hypomethylated COX-2 nucleic acid.

Other non-limiting examples of nucleic acids where analyzing the methylation status may be useful in determining the risk of developing colorectal cancer in IBD patients include p16, p14, e-cadherin, estrogen receptor and HPP1.

TABLE 1

Methylation Assay Amplification Products

| SEQ ID | Gene | Status | Nucleotide Sequence |
|---|---|---|---|
| 45 | RUNX3 | Methylated | CGTTTGCGTGGTTCGTTAGTACGTTTATTA TCGAGCGTATTTCGGGTCGGGCGCGTTTTT CGGGTTTTACGGTCGTTTGCGCGTTTAGCG CGTCGTTGTTTTCGTTTATTTTGTCGTCGT CGTCGTCGT |
| 46 | RUNX3 | Unmethylated | TTGGGTTTTATGGTTGTTTGTGTGTTTAGT GTGTTGTTGTTTTTGTTTATTTTGTTGTTG TTGTTGTTGTAGGGGAAGGTTGGGGAGGGA GGTGTGAAGTGGTGGTTGGTGTTTGGGTTT ATGGGAATATGTATAATAGTGGTTGTTAGG GTGTTGGGT |
| 47 | MINT1 | Methylated | TTTCGAAGCGTTTGTTTGGCGTTTAAGAGA GAGTAAGAGAGGGTTGGAGTGTAGGGGAGT TCGCGGGGTTGAGGTTT |
| 48 | MINT1 | Unmethylated | TGGAGAGTAGGGGAGTTTGTGGGGTTGAGG TTTTTTGTTAGTGTTTGTATTTTTTATGTT ATAATGTTTTTATTTAGTAAAAATTTTTTG GGTGTTTGTTGTGTGTTAGGTT |
| 49 | COX-2 | Methylated | AGGGGATTTTTTGCGTTTTCGGATTTTAGG GTCGTTTAGATTTTTGGAGAGGAAGTTAAG TGTTTTTTGTTTTTTTTCGGTATTTTATT TAAGGCGATTAGTTTTAGAATTGGTTTTCGG AAGCGTTCGGGTAAAGATTGCG |
| 50 | COX-2 | Unmethylated | GAGGGGATTTTTTGTGTTTTTGGATTTTAG GGTTGTTTAGATTTTTGGAGAGGAAGTTAA GTGTTTTTTGTTTTTTTTGGTATTTTAT TTAAGGTGATTAGTTTAGAATTGGTTTTTG GAAGTGTTTGGGTAAAGA |

It is noted that a single sample can be analyzed for one DNA methylation marker or for multiple DNA methylation markers. For example, a sample can be analyzed using assays that detect a panel of different DNA methylation markers. In addition, multiple samples can be collected from a single mammal and analyzed as described herein. In some cases, PCR techniques can be used to detect the presence or absence of a methylated mammalian nucleic acid marker. Cottrell et al describe appropriate methods of methylation-specific PCR (MSP) and other DNA methylation techniques (*Ann N Y Acad Sci* 2003 March; 983:120-30).

Purified nucleic acid fragments from a sample or samples can be analyzed to determine the presence or absence of one or more polymorphisms, such as single nucleotide polymorphisms (SNPs). For example, a sample can be analyzed to determine the presence or absence of a polymorphism identified as rs1800629 (−308G>A) which can be viewed in the single nucleotide polymorphism section of the NCBI website and the TNF-alpha sequences carrying the major alleles disclosed as SEQ ID NO:1 in the present document. It is noted that the minor allele (e.g. A) of this SNP is associated with higher risk of having or developing colorectal cancer, whereas the major allele (e.g. G) is associated with lower risk of developing colorectal cancer. In some cases, a test sample can be analyzed to determine the presence or absence of one or more polymorphisms such as −301G>A, and −293C>T in a TNF-alpha nucleic acid. The exact position of the aforementioned variants may vary from individual to individual or from species to species, e.g., by from 1 to about 10 base pairs. Further description of these and other TNF-alpha polymorphisms are provided elsewhere (Garrity-Park et al., *Am. J. Gastroenterol.*, 103:407-415 (2008)). In some cases, polymorphisms may occur in the promoter region of a TNF-alpha nucleic acid. In some cases, polymorphisms may occur in the coding or non-coding regions of a TNF-alpha nucleic acid.

A mammal diagnosed with IBD and containing one or more polymorphisms in a TNF-alpha nucleic acid can be classified as being at a higher risk of having or developing colorectal cancer as compared to a corresponding mammal containing wild-type TNF-alpha nucleic acid at one or both alleles. For example, detection of the rs1800629 polymorphism in a sample from an IBD patient indicates that the patient is at a higher risk of having or developing colorectal cancer. Detection of this polymorphism allows selection of a monitoring schedule or treatment plan that is most likely to be effective in early diagnosis and prevention of CRC.

In some embodiments, genomic DNA or mRNA can be used to detect polymorphisms. If mRNA is used, a cDNA copy may first be made. Genomic DNA or mRNA is typically extracted from a biological sample, such as a peripheral blood sample or a tissue sample. Standard methods can be used to extract genomic DNA or mRNA from a biological sample, such as phenol extraction. In some cases, genomic DNA or mRNA can be extracted using a commercially available kit (e.g., from Qiagen, Chatsworth, Calif.; Promega, Madison, Wis.; or Gentra Systems, Minneapolis, Minn.).

Any appropriate method of analysis can be used to detect a polymorphism in a nucleic acid. Methods of analysis can include conventional Sanger based sequencing, pyrosequencing, next generation sequencing, allele specific PCR, allele-specific restriction digests, microarrays, single molecule sequencing, sequencing by synthesis, single strand conformation polymorphism (SSCP) detection, restriction length polymorphism (RFLP) analysis, denaturing high performance liquid chromatography (DHPLC), and the like. The aforementioned techniques are well known in the art. Detailed description of these techniques can be found in a variety of publications, including, e.g., "Laboratory Methods for the Detection of Mutations and Polymorphisms in DNA" (1997) G. R. Taylor, ed., CRC Press, and references cited therein.

In some cases, a test nucleic acid sample can be amplified with primers which amplify a sequence region known to comprise the polymorphism(s) of interest. For example, oligonucleotide primers such as SEQ ID NO: 2 (ACCTG-GTCCCCA-AAAGA) and SEQ ID NO: 3 (CGGGGATTTGGAAAGTTG) can be used to amplify a region of interest in a TNF-alpha nucleic acid. The primers of SEQ ID NO: 2 and SEQ ID NO: 3 amplify a 186 base pair fragment (SEQ ID NO: 4) in the promoter region of a TNF-alpha nucleic acid. In some cases, alternate oligonucleotide primer sequences could be used to amplify all or part of the TNF-alpha nucleic acid fragment of SEQ ID NO: 4 (FIG. 5) or any fragment of SEQ ID NO: 1 that when amplified, can be analyzed for association with increased TNF-alpha expression levels. The reference TNF-alpha promoter region nucleic acid sequence is provided in GenBank (Accession No. AB048818; GI No. 13365764); a portion of this sequence is provided in FIG. 1 and SEQ ID NO: 1.

In another example, commercially available kits can be used to amplify a region of interest. For example, a commercially available kit, such as a SNP genotyping kit from Applied Biosystems, can be used to amplify of region of interest in an Interleukin 1B (IL1B) nucleic acid. In some cases alternate kits or methods could be used to amplify all or part of an IL1B nucleic acid fragment that when amplified, can be analyzed for the presence or absence of a polymorphism identified as rs1143627 (−31T>C) which can be viewed in the single nucleotide polymorphism section of the NCBI website. It is noted that the T allele of this SNP is associated with higher risk of having or developing ulcerative colitis associated-colorectal cancer, whereas the C allele is associated with lower risk of developing ulcerative colitis associated-colorectal cancer. The exact position of the aforementioned variants may vary from individual to individual or from species to species, e.g., by from 1 to about 10 base pairs. In some cases, polymorphisms may occur in the promoter region of an IL1B nucleic acid. In some cases, polymorphisms may occur in the coding or non-coding regions of an IL1B nucleic acid.

A mammal diagnosed with IBD and containing one or more polymorphisms in an IL1B nucleic acid can be classified as being at a higher risk of having or developing colorectal cancer as compared to a corresponding mammal containing wild-type IL1B nucleic acid at one or both alleles. For example, detection of the rs1143627 polymorphism in a sample from an IBD patient indicates that the patient is at a higher risk of developing colorectal cancer. Detection of this polymorphism allows selection of a monitoring schedule or treatment plan that is most likely to be effective in early diagnosis and treatment of CRC. Other non-limiting examples of polymorphisms associated with a higher risk of developing colorectal cancer include SNP's found in an Interleukin-23 Receptor (IL-23R) nucleic acid such as rs10889677 (2284C>A) and rs1884444 (94G>T).

Polymorphisms in promoter sequences may affect gene expression. In some cases, serum levels of one or more of a TNF-alpha, IL1B, or IL-23R polypeptide can be measured to determine whether or not an IBD patient has an increased risk of developing CRC. For example, an IBD patient with an increased serum level of a TNF-alpha polypeptide as compared to a normal control may have an increased likelihood of developing CRC. Detection of an increased level of a TNF-alpha polypeptide allows selection of a monitoring schedule or treatment plan that is most likely to be effective in early diagnosis and treatment of CRC. Any known method for measuring polypeptide levels can be used, such as denaturing high performance liquid chromatography (DHPLC, Underhill et al. (1997) *Genome Res.* 7:996-1005), infrared matrix-assisted laser desorption/ionization (IR-MALDI) mass spectrometry (WO 99/57318), and combinations of such methods. Other useful detection techniques include, but are not limited to surface-enhanced laser desorption/ionization (SELDI) mass spectrometry, immunoassays, and array-based technologies. Other non-limiting examples of increased polypeptide levels associated with a higher risk of developing CRC include increased IL-23R and IL1B polypeptide levels.

It is understood that the term "specifically amplifies" refers to the ability of an oligonucleotide primer to interact specifically with a particular nucleic acid without significantly cross-reacting with other different nucleic acids in the same environment and facilitate or promote the amplification of that particular nucleic acid. Likewise, the term "specifically hybridizes" refers to the ability of an oligonucleotide probe to interact specifically with a particular nucleic acid without significantly cross-reacting with other different nucleic acids in the same environment and facilitate or promote the detection of that particular nucleic acid.

The term "elevated level" as used herein with respect to the level of an MPO polypeptide is any level that is above a median polypeptide level in a sample from a random population of mammals (e.g., a random population of 10, 20, 30, 40, 50, 100, or 500 mammals) that do not have UC-CRC. Elevated MPO polypeptide levels can be any level provided that the level is greater than a corresponding reference level. For example, an elevated level of MPO polypeptide can be 0.5, 1, 2, 3, 4, 5, 6, 7, 8, 9, 10, or more fold greater than the reference level MPO polypeptide observed in a normal colon biopsy or blood sample. It is noted that a reference level can be any amount. For example, a reference level can be zero. In some cases, an elevated level of an MPO polypeptide can be any detectable level of an MPO polypeptide in a tissue biopsy sample.

The term "elevated level" as used herein with respect to the methylation status of MINT1 or RUNX3 nucleic acid is any methylation level that is above a median methylation level in a sample from a random population of mammals (e.g., a random population of 10, 20, 30, 40, 50, 100, or 500 mammals) that do not have UC-CRC. Elevated MINT1 or RUNX3 methylation levels can be any level provided that the level is greater than a corresponding reference level. For example, an elevated level of MINT1 or RUNX3 methylation can be 0.5, 1, 2, 3, 4, 5, 6, 7, 8, 9, 10, or more fold greater than the reference level methylation observed in a normal colon biopsy sample. It is noted that a reference level can be any amount.

The term "reduced level" as used herein with respect to the level of COX-2 methylation status is any level that is below a median methylation level in a sample from a random population of mammals (e.g., a random population of 10, 20, 30, 40, 50, 100, or 500 mammals) that do not have UC-CRC. Reduced COX-2 methylation levels can be any level provided that the level is lesser than a corresponding reference level. For example, a reduced level of COX-2 methylation can be 0.5, 1, 2, 3, 4, 5, 6, 7, 8, 9, 10, or more fold lesser than the reference level methylation observed in a normal colon biopsy sample. It is noted that a reference level can be any amount.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, includes any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

This document provides kits that can be used to determine the level of one or more biomolecules in a sample. Kits can contain an oligonucleotide primer pair that specifically amplifies all or a portion of a target region of a nucleic acid. For example, kits can contain oligonucleotide primers that specifically amplify a TNF-alpha, COX-2, MINT1, or a RUNX3 nucleic acid. Target regions can be defined at any place along a TNF-alpha, COX-2, MINT1, or RUNX3 nucleic acid. For example, a target region can be defined by nucleotides 1-500 of the 5' portion of a TNF-alpha nucleic acid. In this case, a kit of the invention can contain an oligonucleotide primer pair that specifically amplifies all 500 nucleotides defining that target region, or a portion (e.g., nucleotides 80-188) of that target region.

Components and methods for producing kits are well known. Kits can contain multiple oligonucleotide primer pairs that specifically amplify TNF-alpha, COX-2, MINT1, or RUNX3-related nucleic acids, or probes that specifically hybridize TNF-alpha, COX-2, MINT1, or RUNX3-related nucleic acids. In addition, kits can contain antibodies for detecting MPO-related polypeptides. The kits provided herein also can contain a reference chart that indicates a reference level or baseline for MPO polypeptides or TNF-alpha, COX-2, MINT1, or RUNX3 nucleic acids. Kits can be configured in any type of design (e.g., microtiter plate design) and can be made of any type of material (e.g., plastic).

In some cases, a human may have a family history of primary sclerosing cholangitis (PSC) or CRC. Family history or relatives with PSC or CRC can be identified by examining medical records or family tree history. The methods provided in this document can also be used to identify CRC risk in relatives of affected mammals likely to have IBD or UC. Thus, these methods can facilitate decisions regarding the course of evaluation and treatment in humans with and without altered methylation in MINT1, COX-2, or RUNX3 nucleic acids, with and without polymorphisms in a TNF-alpha nucleic acid, or with and without increased MPO polypeptide levels.

This document also provides materials and methods to assist a medical professional in determining the risk of having or developing colorectal cancer in a mammal. Such a medical professional can be, for example, a physician, a nurse, a medical laboratory technologist, or a pharmacist. A person can be assisted by (1) determining the presence or absence of a nucleic acid polymorphism in a nucleic acid such as a TNF-alpha nucleic acid, determining the methylation status of a nucleic acids such as a RUNX3 nucleic acid in a test sample, and/or determining the level of a polypeptide such as an MPO polypeptide, and (2) communicating information about the presence, absence, or level of that marker to that medical professional.

After the presence, absence, level, or status of a particular biomolecule or biomolecules is reported, a medical professional can take one or more actions that can affect patient care. For example, a medical professional can record the results in a patient's medical record. In some cases, a medical professional can record that a patient is at an increased risk of developing colorectal cancer, or otherwise transform the patient's medical record to reflect the patient's medical condition. In some cases, a medical professional can review and evaluate a patient's entire medical record and assess multiple strategies for clinical intervention of a patient's condition. In some cases, a medical professional can recommend a change in therapy or a change in frequency or type of surveillance.

Any appropriate method can be used to communicate information to another person. For example, information can be given directly or indirectly to a person. In addition, any type of communication can be used to communicate the information. For example, mail, e mail, telephone, and face-to-face interactions can be used. The information also can be communicated to a person by making that information electronically available to the person. For example, the information can be communicated to a person by placing the information on a computer database such that the person can access the information. In addition, the information can be communicated to a hospital, clinic, or research facility at which the person is located.

The invention will be further described in the following examples, which do not limit the scope of the invention described in the claims.

EXAMPLES

Example 1—Methylation Status of Genes in Non-Neoplastic Mucosa from Patients with Ulcerative Colitis-Associated Colorectal Cancer Patient Selection The Mayo Clinic Institutional Review Board approved this work. The UC-CRC cases and UC controls analyzed herein were described elsewhere (Garrity-Park et al., Am. J. Gastroenterol., (2008) and Garrity-Park et al., Gut (2009)). UC-CRC cases were selected from a review of 274 patients identified from the Mayo Clinic centralized diagnostic index of medical records (1976-2006). These patients had inflammatory bowel disease (either Crohn's or UC) and CRC. Patients with Crohn's disease were excluded. Medical records for the remaining UC-CRC patients were reviewed to establish a date of disease onset. For each case, pathology slides from the surgical resection were also recalled to confirm the diagnosis of UC and identify the best tumor and non-adjacent, non-neoplastic block for DNA extraction. Patients who did not have UC confirmed by review of the pathology or whose duration of disease was less than 10 years were excluded. After these exclusions, 114 UC-CRC cases were included.

Potential UC controls were identified through the Mayo pathology index (1994-2006), which indicated the patient age, gender, and extent of UC as well as the presence of other confounding pathologies such as dysplasia. The final pool of potential UC controls for this work included UC patients who did not develop CRC, who underwent either colectomy or colonoscopy with biopsy at the Mayo Clinic, and who did not have prior dysplasia. The Mayo Clinic centralized diagnostic index of medical records was used with these remaining controls to establish a date of diagnosis. Patients with less than ten years between the date of UC diagnosis and either colectomy or date of last biopsy were excluded as were patients with a prior dysplasia diagnosis. From the remaining list, 181 controls were selected that were most closely matched to the UC-CRC cases with regard to gender, age, ethnicity, duration, and extent of UC. The surgical resection or biopsy specimens from these 181 controls were re-reviewed to confirm histologically the diagnosis of UC. After final review, 114 UC controls were included.

DNA Extraction

All formalin-fixed, paraffin-embedded (FFPE) blocks and hematoxylin and eosin-stained (H&E) slides were reviewed on all cases and controls to determine the inflammatory activity level (as assessed by neutrophil infiltrates) for all non-neoplastic sections. Each section was scored as normal, inactive (0), mildly active (1), moderate (2), or severe (3). A total of three different DNA extractions were then completed: 1) UC control, 2) UC-CRC non-neoplastic, non-adjacent, and 3) UC-CRC tumor. For non-adjacent, non-neoplastic UC-CRC cases and UC controls, DNA was extracted from all non-neoplastic paraffin tissue sections that showed evidence of chronic disease (scores 0-3; n=1-6 blocks/patient). For the tumor DNA extraction, only the section with confirmed CRC was used. Any sections scored as "normal colon" or any dysplastic lesions located away from the CRC in UC-CRC cases were excluded from all extractions. DNA was extracted using Gentra Puregene Tissue kit (Qiagen, Valencia, Calif.). DNA pellets were suspended in TE (10 mM Tris, pH=7.5, 0.1 mM EDTA, Integrated DNA Technologies, Coralville, Iowa) and quantified using Quant-iT™ PicoGreen® (Invitrogen, Carlsbad, Calif.).

Bisulfite Treatment/Methylation Specific Polymerase Chain Reaction (MSP)

Methylation status of each gene was determined using MSP after bisulfite treatment of 500 ng of DNA using the EZ DNA Methylation-Gold Kit™ (Zymo Research, Orange, Calif.) following standard protocols. Primers were designed using Methyl Primer Express v1.0 software (Applied Biosystems, Foster City, Calif.) (Table 2). Most of the proposed genes have multiple methylation sites. Therefore, whenever possible, sites chosen for evaluation were selected based on published studies that indicated that methylation in that area altered protein expression in situ. Primers were designed for the following genes: p16, p14, cyclooxygenase-2 (COX-2), e-cadherin, estrogen receptor (ER), HPP1, methylated-in-tumor 1 (MINT1), MINT31, RUNX3, and sodium solute symporter family 5 member 8 protein (SLC5A8). Unmethylated and methylated PCR reactions were carried out in separate, 25 µL reactions.

Amplicons were run through ethidium-stained agarose gels and visualized using the BioRad Gel Doc™ (Bio-Rad, Hercules, Calif.). Positive and negative controls were included in each experimental set-up. A sample was considered positive if amplicon was produced using the methylated primer set. A sample was negative for methylation if amplicon was produced using only the unmethylated primer set. Samples that did not produce amplicons for either reaction were excluded from analyses. To ensure the specificity of each reaction and to validate the adequacy of the bisulfite modification, 25 methylated and 25 unmethylated amplicons were sequenced for each gene using the ABI PRISM™ (Applied Biosystems) after shrimp alkaline phosphatase (USB, Cleveland, Ohio) and exonuclease (USB) treatment of the amplicon. All of the MSP products demonstrated methylation of CpG sites. To test the sensitivity of each methylated/unmethylated assay, serial dilutions of positive control DNA (100% to 0%) were tested for each gene. All assays could detect a positive result with 5% positive control DNA.

TABLE 2

Methylation-specific PCR primers.

| Gene | Forward (5' → 3') | Reverse (5' → 3') | Size (bp) | Temp |
|---|---|---|---|---|
| p16 | | | | |
| Methylated | TGGGGCGGATCGCGT GCGTT (SEQ ID NO: 5) | CGACCCCGAACCGC GACGGT (SEQ ID NO: 6) | 140 | 60 |
| Unmethylated | TGGGGTGGATTGTGT GTGTTTGGT (SEQ ID NO: 7) | CCACCTCCAACAATA CCCATACCT (SEQ ID NO: 8) | 172 | 60 |
| p14 | | | | |
| Methylated | GGCGGCGAGAATATG GTGC (SEQ ID NO: 9) | ACGACGAACGGCCC TAACG (SEQ ID NO: 10) | 137 | 60 |
| Unmethylated | TTGGTGTTAAAGGGTG GT (SEQ ID NO: 11) | AAAAACCCTCACTC ACAA (SEQ ID NO: 12) | 126 | 60 |
| COX-2 | | | | |
| Methylated | AGGGGATTTTTTGCGT TTTC (SEQ ID NO: 13) | CGCAATCTTTACCCG AACGC (SEQ ID NO: 14) | 142 | 55 |
| Unmethylated | GAGGGGATTTTTTGTG TTTTT (SEQ ID NO: 15) | TCTTTACCCAAACAC TTCCAA (SEQ ID NO: 16) | 138 | 60 |
| E-cadherin | | | | |
| Methylated | TTAGAGGGTTATCGCG TTTATGC (SEQ ID NO: 17) | ACCAAATAAACCCC GAAACACGG (SEQ ID NO: 18) | 150 | 50 |
| Unmethylated | TAATTTTAGGTTAGAG GGTTATTGT (SEQ ID NO: 19) | CACAACCAATCAAC AACACA (SEQ ID NO: 20) | 97 | 63 |
| Estrogen receptor | | | | |
| Methylated | CGTTCGGTTTTATCGG ATTC (SEQ ID NO: 21) | AAAAACTCAAAAAC CGACGA (SEQ ID NO: 22) | 138 | 55 |
| Unmethylated | TGAGTTGGAGTTTTTG AATTGTTT (SEQ ID NO: 23) | ACACATTAACAACA ACCACA (SEQ ID NO: 24) | 149 | 60 |
| HPP1 | | | | |
| Methylated | TTTCGGCGTAGTTTTT TAGC (SEQ ID NO: 25) | ACTAAACATCCCGC GAACG (SEQ ID NO: 26) | 167 | 60 |
| Unmethylated | TGGTGTAGTTTTTTAG TGGATG (SEQ ID NO: 27) | ACAATAACAATAAC ACCCAACA (SEQ ID NO: 28) | 127 | 60 |
| MINT1 | | | | |
| Methylated | TTTCGAAGCGTTTGTT TGGC (SEQ ID NO: 29) | CAAAAAACCTCAAC CCCGGG (SEQ ID NO: 30) | 81 | 55 |
| Unmethylated | TGGAGAGTAGGGGAG TTTGT (SEQ ID NO: 31) | AACCTAACACACAA CAAACA (SEQ ID NO: 32) | 112 | 60 |
| MINT3 1 | | | | |
| Methylated | TATTCGATTTATTTCG TC (SEQ ID NO: 33) | CTACGAAAAATAAA CACG (SEQ ID NO: 34) | 105 | 55 |
| Unmethylated | GATTTAATTTTTTGT GGTGGT (SEQ ID NO: 35) | CTAAAACCATCACCC CTAAACA (SEQ ID NO: 36) | 95 | 60 |
| RUNX3 | | | | |
| Methylated | CGTTTGCGTGGTTCGT TAGTAC (SEQ ID NO: 37) | ACGACGACGACGAC GACA (SEQ ID NO: 38) | 129 | 60 |
| Unmethylated | TTGGGTTTTATGGTTG TTTGTGT (SEQ ID NO: 39) | ACCCAACACCCTAA CAACCAC (SEQ ID NO: 40) | 159 | 60 |
| SLC5A8 | | | | |
| Methylated | ACGGGGTATCGGTATT TTC (SEQ ID NO: 41) | TACGATCATTCTACG ACCG (SEQ ID NO: 42) | 151 | 55 |
| Unmethylated | GGTTATTTTGGTTGTT ATT (SEQ ID NO: 43) | CAAACACTACAATC ATTCTACA (SEQ ID NO: 44) | 104 | 55 | bp, base pairs (bases in bold indicate methylation sites); COX, cyclooxygenase; HPP, hyperplastic polyposis gene; MINT, methylated-in-tumor; RUNX, runt-related transcript factor; SLC5A8, sodium solute symporter family-5 member-8.

Inflammation Scoring

All H&E slides from each case or control were reviewed by a pathologist, and the histologic disease activity was scored as inactive, mild, moderate, or severe based on the percentage of neutrophils. Each histologic activity level was given a corresponding number, such that inactive sections were scored as 0 and mildly active, moderate, or severe sections were scored as 1, 2, or 3, respectively. To obtain the final inflammation score for each case or control extracted, the values for all sections included in the extraction were summed and then divided by the total number of sections used. For instance, if a non-adjacent, non-neoplastic extraction for a case had four sections that were inactive and two sections that were mildly active, the inflammation score would be 0.33. Scores were obtained for all non-adjacent, non-neoplastic extractions for cases and for all extractions for controls.

Statistics

For initial identification of potential genes, a univariate analysis using the Fisher's exact test was done to compare the prevalence of methylation for each gene in UC-CRC cases versus UC controls. For genes identified as significant, another Fisher's Exact test was performed to determine its significance when comparing non-neoplastic DNA from UC-CRC cases versus UC controls. A multivariable analysis was then done to test for interactions between the genes found to be significant in the non-neoplastic comparison. Finally, logistic regression modeling was performed to determine the additive effect of these significant genes.

Results

Patient Selection

The summary of patient characteristics is given in Table 3. There were no significant differences between cases and controls with regard to age, gender, family history of CRC, or duration/extent of UC. Because there were no significant differences in distribution of disease extent between cases and controls (p=0.07), all subsequent analyses involving extent therefore used the broad categorization of extensive versus non-extensive (left-sided and proctitis) disease for cases and controls. Primary sclerosing cholangitis (PSC) was more prevalent in UC-CRC cases (p<0.0001). All cases and controls were Caucasian.

TABLE 3

Demographic and clinical features of 114 UC-CRC cases and 114 UC controls.

| Demographic/clinical information | UC-CRC (n = 114) | UC, no CRC (n = 114) | P value |
|---|---|---|---|
| Mean age at index date, years (range)[a] | 47.8 (26-82) | 48.8 (24-77) | 0.35 |
| Gender, n (%) | | | |
| Female | 36 (32) | 36 (32) | |
| Male | 78 (68) | 78 (68) | 1.00 |
| Mean duration of UC at index date, years (range) | 20.3 (10-49) | 19.5 (10-45) | 0.37 |
| Maximal extent, n (%)[b] | | | |
| Proctitis | 8 (7.0) | 7 (6) | |
| Left-sided | 12 (10.5) | 25 (22) | |
| Extensive | 94 (82.5) | 82 (72) | 0.07[c] |
| PSC, n (% yes) | 31 (27.2) | 4 (3.5) | <0.0001 |
| Family history of CRC, n (%) | 19 (17) | 15 (13) | 0.58 |

[a]Index date for UC-CRC was the age at CRC and for UC controls was the age at colectomy or most recent biopsy.
[b]Extent based on histological assessment of involvement.
[c]$\chi^2$-Test, P value represents the comparison between cases and controls with extensive colitis vs. left-sided vs. proctitis.
Values in bold are significant.

DNA Extraction and Location

Sixty percent of UC-CRC non-adjacent, non-neoplastic DNA extractions included a tissue section that was from the same segment of the colon in which the tumor arose, i.e. the tumor was in the ascending colon, and a different block without neoplasia was also available from the ascending colon. The majority of UC-CRC non-neoplastic and UC control DNA extractions included tissues obtained from both the left and right side of the colon (69% versus 74%, p=0.57). Three cases and two controls had tissue available from the rectum only. The majority of tissues used for UC-CRC case and UC control (218/228) extractions were obtained from resected colons. The remaining 10 patients had only biopsy samples available.

UC-CRC DNA Versus UC Control DNA

Univariate Analyses

To identify targets to investigate in non-adjacent, non-neoplastic regions of the UC-CRC colon, initial univariate analyses focused on the level of gene methylation in DNA extracted from tumor sections only as compared to UC controls. The majority of DNA from UC controls (between 96 to 109) and UC-CRC tumors (between 83 to 100) were successfully amplified for each target. Table 4 summarizes the results of these analyses for all 10 genes included in this study. The prevalence of gene methylation for p16, RUNX3, MINT1, MINT31, and HPP1 was significantly increased in UC-CRC cases versus controls. Conversely, COX-2 and e-cadherin were more frequently methylated in controls as compared to cases. The difference in methylation for ER, p14, and SLC5A8 was not significantly different between cases and controls.

TABLE 4

Univariate analyses of gene methylation status in UC-CRC cases (tumor sections) vs. UC controls (a) Methylated in UC-CRC cases

| Gene (±for methylation) | UC-CRC (%) | UC controls (%) | P value [a] |
|---|---|---|---|
| p16 | | | |
| Negative | 72 (84.7) | 107 (100) | |
| Positive | 13 (15.3) | 0 (0) | <0.0001 |
| RUNX3 | | | |
| Negative | 46 (55.4) | 97 (93.3) | |
| Positive | 37 (44.6) | 7 (6.7) | <0.0001 |
| MINT1 | | | |
| Negative | 46 (49.5) | 87 (85.3) | |
| Positive | 47 (50.5) | 15 (14.7) | <0.0001 |
| MINT31 | | | |
| Negative | 39 (40.6) | 76 (79.2) | |
| Positive | 57 (59.4) | 20 (20.8) | <0.0001 |
| HPP1 | | | |
| Negative | 19 (21.3) | 53 (49.5) | |
| Positive | 70 (78.7) | 54 (50.5) | 0.0001 |
| ESR1 | | | |
| Negative | 10 (10.8) | 17 (15.9) | |
| Positive | 83 (89.2) | 90 (84.1) | 0.31 |
| p14 | | | |
| Negative | 75 (81.5) | 95 (88.0) | |
| Positive | 17 (18.5) | 13 (12.0) | 0.24 |
| SLC5A8 | | | |
| Negative | 14 (14.7) | 6 (5.8) | |
| Positive | 81 (85.3) | 97 (94.2) | 0.06 |

TABLE 4-continued

Univariate analyses of gene methylation status in
UC-CRC cases (tumor sections) vs. UC controls

(b) Methylated in UC controls

| Gene (±for methylation) | UC-CRC (%) | UC controls (%) | P value |
|---|---|---|---|
| COX-2 | | | |
| Negative | 64 (66.7) | 43 (39.4) | |
| Positive | 32 (33.3) | 66 (60.6) | 0.0001 |

(a) Methylated in UC-CRC cases

| Gene (±for methylation) | UC-CRC (%) | UC controls (%) | P value [a] |
|---|---|---|---|
| E-cadherin | | | |
| Negative | 64 (64.0) | 42 (38.9) | |
| Positive | 36 (36.0) | 66 (61.1) | 0.0003 |

COX, cyclooxygenase; CRC, colorectal cancer; HPP, hyperplastic polyposis gene; MINT, methylated-in-tumor; RUNX, runt-related transcript factor; SLC5A8, sodium solute symporter family-5 member-8; UC, ulcerative colitis.
[a] Calculated using Fisher's exact test.
Values in bold are significant.

UC-CRC Non-Neoplastic DNA Versus UC-Control DNA

Univariate Analyses

Only genes that were significantly different between tumor and UC controls were tested for significance in non-adjacent, non-neoplastic normal tissue. The majority of DNA from UC controls (between 96 to 109) and non-adjacent, non-neoplastic areas from UC-CRC patients (between 66 to 88) were successfully amplified for each target. RUNX3, p16, MINT1, MINT31, e-cadherin, and COX-2 remained significantly associated with UC-CRC. The association involving HPP1 was no longer significant (Table 5).

TABLE 5

Univariate analyses of gene methylation status in UC-CRC cases
(non-adjacent, non-neoplastic sections) vs. UC controls.

(a) Methylated in UC-CRC cases

| Gene (±for methylation) | UC-CRC (%) | UC controls (%) | P value [a] |
|---|---|---|---|
| p16 | | | |
| Negative | 53 (80.3) | 107 (100) | |
| Positive | 13 (19.7) | 0 (0) | <0.0001 |
| RUNX3 | | | |
| Negative | 37 (49.3) | 97 (93.3) | |
| Positive | 38 (50.7) | 7 (6.7) | <0.0001 |
| MINT1 | | | |
| Negative | 48 (54.5) | 87 (85.3) | |
| Positive | 40 (45.5) | 15 (14.7) | <0.0001 |
| MINT31 | | | |
| Negative | 47 (54.7) | 76 (79.2) | |
| Positive | 39 (45.3) | 20 (20.8) | 0.0005 |
| HPP1 | | | |
| Negative | 27 (36.0) | 53 (49.5) | |
| Positive | 48 (64.0) | 54 (50.5) | 0.09 |

(b) Methylated in UC controls

| Gene (±for methylation) | UC-CRC (%) | UC controls (%) | P value |
|---|---|---|---|
| COX-2 | | | |
| Negative | 54 (61.4) | 43 (39.4) | |
| Positive | 34 (38.6) | 66 (60.6) | 0.003 |
| E-cadherin | | | |
| Negative | 46 (55.4) | 42 (38.9) | |
| Positive | 37 (44.6) | 66 (61.1) | 0.03 |

COX, cyclooxygenase; CRC, colorectal cancer; HPP, hyperplastic polyposis gene; MINT, methylated-in-tumor; RUNX, runt-related transcript factor; SLC5A8, sodium solute symporter family-5 member-8; UC, ulcerative colitis.
[a] Calculated using Fisher's exact test.
Values in bold are significant.

Multivariable Analyses

Multivariable logistic regression was performed with the univariately significant genes (p16, RUNX3, MINT1, MINT31, e-cadherin, and COX-2) to determine if each gene was independently significant for UC-CRC. Table 6 indicates p-values and odds ratios for the three genes that remained significant in this analysis. Methylation of RUNX3 and MINT1 in non-neoplastic sections remained strongly associated with the presence of CRC. Conversely, unmethylated COX-2 was an indication of CRC.

TABLE 6

Multivariate analyses of UC-CRC (non-adjacent,
non-neoplastic sections) vs. UC controls.

| | Logistic regression | | |
|---|---|---|---|
| Gene (±for methylation) | Odds ratio | CI | P value |
| (a) Significantly methylated in UC-CRC cases | | | |
| RUNX3 | 12.6 | 4.4, 35.7 | <0.0001 |
| MINT1 | 9.0 | 3.4, 23.7 | <0.0001 |
| (b) Significantly methylated in UC controls | | | |
| COX-2 | 0.2 | 0.07, 0.4 | 0.0002 |

CI, confidence interval; COX, cyclooxygenase; CRC, colorectal cancer; HPP, hyperplastic polyposis gene; MINT, methylated-in-tumor; RUNX, runt-related transcript factor; UC, ulcerative colitis.
Values in bold are significant.

Given the association of methylation with inflammation (Kundu et al., *Mutat Res* (2008)), a multivariable logistic regression also was performed that included RUNX3, MINT1, COX-2, and the inflammation score to determine if the increased incidence of methylation merely reflected a higher inflammation score in cases versus controls. Table 7A summarizes these findings. The p-values and odds ratios all remained highly significant even when the degree of inflammation, as determined by H&E, was incorporated into the logistic regression. Interestingly, greater inflammation as determined by neutrophils on H&E was not associated with UC-CRC.

Because cases and controls varied with regard to the presence of PSC, logistic regression also was performed to ensure that the significance of RUNX3, MINT1, and COX-2 was independent of PSC (Table 7B). Although PSC remained highly associated with UC-CRC, the methylation status of these three genes was still significant in this analysis.

Given that for the majority of the UC-CRC cases (60%) the non-adjacent, non-neoplastic DNA sample included tissue procured from the same region in which the tumor arose, analysis was performed to determine whether proximity to the tumor affected methylation status. The presence or absence of a non-neoplastic section from within the corresponding tumor region did not affect the prevalence of methylation for RUNX3, COX-2, or MINT1 (P=0.17, 0.69, and 0.23, respectively).

Although there was no significant difference between the UC-CRC non-neoplastic and UC controls with regard to inclusion of tissue from both the right and the left colon (P=0.57), tests were performed to determine whether this could have affected the methylation status of a given gene. It was found that the prevalence of altered methylation was not significantly different between DNA samples containing tissue sections from both the left and the right side of the colon and those that did not (P=0.24, 0.87, and 0.48 for COX-2, MINT1, and RUNX3, respectively).

Finally, to interrogate whether these alterations in methylation were specific to UC, the prevalence of altered gene methylation in a cohort of non-UC patients described elsewhere (Garrity-Park et al., Gut, 58:1226-1233 (2009)) was assessed. In brief, this cohort included biopsies taken from 60 non-UC normal patients that are a part of the average risk CRC screening population at the Mayo Clinic. These were frequency matched for age to the UC patients (both CRC and non-CRC controls) in this study (average age for UC group, 48 years, vs. 49 years for non-UC patients). For RUNX3, COX-2, and MINT1, there was no significant difference between the UC controls and non-UC patients (P=0.53, 0.21, and 0.70, respectively), but there was a significance between the UC-CRC cases and non-UC patients (P<0.0001, 0.001, and <0.001, respectively).

TABLE 7

Effect of inclusion of inflammation and PSC in the multivariable model of UC-CRC risk

| | Odds ratio | CI | P value |
|---|---|---|---|
| (a) Inflammation | | | |
| Inflammation score | 0.3 | 0.1, 0.6 | 0.001 |
| RUNX3 | 11.9 | 3.9, 36.0 | <0.0001 |
| MINT1 | 9.7 | 3.4, 27.7 | <0.0001 |
| COX-2 | 0.2 | 0.1, 0.5 | 0.002 |
| (b) PSC | | | |
| PSC | 9 | 2.2, 37.8 | 0.003 |
| RUNX3 | 11.7 | 3.9, 35.3 | <0.0001 |
| MINT1 | 10.4 | 3.7, 28.8 | <0.0001 |
| COX-2 | 0.2 | 0.06, 0.4 | 0.0002 |

CI, confidence interval; COX, cyclooxygenase; CRC, colorectal cancer; MINT, methylated-in-tumor; PSC, primary sclerosing cholangitis; RUNX, runt-related transcript factor; UC, ulcerative colitis.
Values in bold are significant.

Diagnostic Modeling

Logistic regression modeling was undertaken to determine if RUNX3, MINT1, and COX-2 interacted to have an additive effect, i.e. did the odds of having a synchronous CRC increase as the number of genes altered increased (Table 8). These analyses indicated that having both RUNX3 methylated and COX-2 unmethylated greatly increased the likelihood of a CRC elsewhere in the colon. This also was true of the concurrent presence of MINT1 methylation and COX-2 unmethylation, although the increase was not as dramatic. Although informative, it is important to note that the number of samples available for this analysis was small, as reflected by the wide confidence intervals.

TABLE 8

Logistic regression model of gene methylation on UC-CRC.

| Gene combination (M = methylated; U = unmethylated) | Logistic regression Odds Ratio | 95% CI | Exact odds ratio CI estimation method (StatExact) [a] Exact | 95% CI |
|---|---|---|---|---|
| RUNX3 (M) + MINT1 (U) + COX-2 (M) | 1.0 | Referent | 1.0 | Referent |
| RUNX3 (M) + COX-2 (M) | 4.4 | 0.8, 23.2 | 4.2 | 0.5, 29.6 |
| MINT1 (M) + COX-2 (M) | 6.1 | 1.7, 21.4 | 5.9 | 1.5, 26.8 |
| RUNX3 (U) + MINT1 (U) + COX-2 (U) | 4.7 | 1.6, 14.0 | 4.6 | 1.4, 17.7 |
| RUNX3 (M) + MINT1 (M) + COX-2 (M) | [b] | [b] | [b] | 29.5, [b] |
| RUNX3 (M) + COX-2 (U) | 61.2 | 6.2, 608.5 | 53.5 | 5.4, 2, 833.0 |
| MINT1 (M) + COX-2 (U) | 17.6 | 2.5, 121.6 | 16.0 | 1.8, 219.4 |
| RUNX3 (M) + MINT1 (M) + COX-2 (U) | [b] | [b] | [b] | 19.6, [b] |

[a] Used to establish the lower confidence interval of the effect.
[b] Unable to calculate because there is a 0 in the control group.

Example 2—Myeloperoxidase as a Measure of Disease Activity in UC: Association with UC-CRC, TNF Polymorphism, and RUNX3

Patient Selection

The Mayo Clinic Institutional Review Board approved this work. Patients with UC for >10 years who developed CRC were identified from the Mayo Clinic centralized diagnostic index of medical records (1986-2006). For each case, pathology slides from the surgical resection were recalled to confirm the diagnosis of UC and to identify the best non-adjacent, non-neoplastic block for immunostaining Complete patient chart reviews were completed on all UC-CRC cases. Patients who did not have UC confirmed by review of the pathology or whose duration of disease was less than 10 years as documented in the clinical chart were excluded. A total of 50 UC-CRC cases, representing a subset of the UC-CRC cases described elsewhere (Garrity-Park et al., Gut., 58:1226-1233 (2009); Garrity-Park et al., Am. J. Gastroenterol., 103(2):407-15 (2008); and Garrity-Park et al., Am. J. Gastroenterol., 107(7):1610-9 (2010)), were examined in this study. UC controls were identified through the Mayo pathology index (1994-2006), which indicated the patient age, gender, and extent of UC as well as any other confounding pathologies such as dysplasia. Complete patient chart reviews were completed on all potential UC-controls. All potential UC-controls included UC patients who did not develop CRC, who had greater than 10 years of disease, who underwent either colectomy or colonoscopy with biopsy at the Mayo Clinic, and who did not have prior dysplasia. The final selection of UC-controls was based on frequency matching to UC-CRC cases for age, gender, extent, and duration of UC. A representative non-neoplastic section for each control was selected for analyses. A total of 50 UC-controls, a subset of the UC-control group described elsewhere (Garrity-Park et al., Gut., 58:1226-1233 (2009); Garrity-Park et al., Am. J. Gastroenterol., 103(2):407-15 (2008); and Garrity-Park et al., Am. J. Gastroenterol., 107 (7):1610-9 (2010)), were analyzed in this study.

H&E Scoring

A board certified pathologist reviewed and scored all sections. Histologic disease activity level was determined for the entire resection specimen using standard clinical methodologies utilizing H&E-stained sections. A disease activity score was assigned to each case or control using the following cut offs: 0 (inactive)—no neutrophils; 1 (mild)—rare neutrophils in crypt or surface epithelium; 2 (moderate)—neutrophils in up to 25% of crypts; and 3 (severe)—neutrophils in more than 25% of crypts.

For cases, slides from all available sections were examined to identify the best non-adjacent, non-neoplastic section for immunostaining. Whenever possible, this section was from an area distinct from where the tumor arose. Selection criteria also included 1) a well-oriented, full thickness section with generous amounts of mucosa for improved likelihood of informative IHC scoring and 2) a section reflective of overall disease state, i.e. if the patient had colitis to the hepatic flexure, sections were not chosen from the cecum.

For controls, slides from all available sections were examined to represent the best normal section for immunostaining. This included a well-oriented, full thickness section with generous amounts of mucosa that was reflective of the overall disease state.

Immunohistochemistry

Serial 4-micron sections were cut from each selected block. CD3 (DAKO, Carpinteria, Calif.), CD68 (DAKO), and MPO (Abcam, Cambridge, Mass.) antibodies were applied and developed using the DAKO Envision+system (DAKO) after heated antigen retrieval. Whole sections were then digitally scanned using the NanoZoomer (Hamamatsu, Bridgewater, N.J.). Scans were downloaded and analyzed using ImageJ software (available at http://rsbweb.nih.gov/ij/). Using 15 different tissue sections, optimal thresholding was established that accurately distinguished positive cellular area (stained brown) from negative area (stained purple). Once established, this threshold was used for all subsequent slides to avoid biasing results. A total of four to six areas of mucosa were measured to determine the % area positive (scans were analyzed at 5× magnification). The average of the areas was recorded and used for statistical analyses.

TNF-α Polymorphism and RUNX3 Data

Prior studies included runt-related transcription factor 3 (RUNX3) methylation status and single nucleotide polymorphism testing for TNF-α (Garrity-Park et al., *Am. J. Gastroenterol.*, 103(2):407-15 (2008); and Garrity-Park et al., *Am. J. Gastroenterol.*, 107(7):1610-9 (2010)). These previously derived data were used for associations in the current study. Cases and controls were selected without knowledge of TNF-α or RUNX3 status.

Statistical Analyses

Four statistical analyses were performed: 1) a Fisher exact test or Chi-square test was used to determine if the demographic/clinical selection criteria between UC-CRC and UC-control groups were appropriately matched; 2) a Fisher exact test was used to test for significant differences in % area between UC-CRC cases and UC-controls for CD3, CD68, and MPO, and for the association between the % area and the presence/absence of TNF-α SNP and RUNX3; 3) a Chi-square test was used to determine the association between case/control status and TNF-α SNP and RUNX3 methylation; and 4) logistic regression and receiver operating characteristic (ROC) analyses were performed to determine if the combination of any significant variables improved the prediction of case/control status.

Results

Patient and Sample Characteristics

UC-CRC cases and controls did not have any significant differences with regard to clinical characteristics (Table 9). Similarly, the UC-CRC or UC-control tissue sections selected for analyses were matched for location. However, UC-controls demonstrated significantly higher levels of histologic disease activity as determined by H&E than UC-CRC cases (Table 10).

TABLE 9

Characteristics of UC-CRC cases versus UC-controls.

| Characteristic | Cases (n = 50) | Controls (n = 50) | p-value |
|---|---|---|---|
| Average age, years (range) | 49.4 (26-80) | 50.8 (28-77) | 0.55 |
| Average duration of UC, years (range) | 20.6 (10-49) | 20.9 (10-45) | 0.86 |
| Extent of UC | | | |
| Extensive/pancolitis | 82% | 68% | |
| Left-sided | 18% | 32% | 0.11 |
| Gender | | | |
| Male | 68% | 66% | |
| Female | 32% | 34% | 0.83 |
| Ethnicity | | | |
| Caucasian | 100% | 100% | 1.00 |

TABLE 10

Pathological characteristics of UC-CRC cases versus UC-controls.

| Non-neoplastic tissue location | Cases (n = 50) | Controls (n = 50) | p-value* |
|---|---|---|---|
| Rectum | 21% | 26% | 0.12 |
| Sigmoid | 32% | 19% | |
| Descending | 15% | 33% | |
| Transverse | 9% | 14% | |
| Ascending | 9% | 5% | |
| Cecum | 15% | 2% | |
| Histologic disease activity level of non-neoplastic tissue section | | | |
| 0 | 66% | 41% | 0.01 |
| 1 | 26% | 35% | |
| 2 | 8% | 10% | |
| 3 | 0% | 14% | |

*p-value calculated using chi-square test.

Activity Level Determined Using Cell Surface Markers

Analysis of all cases and controls indicated detectable staining of all three cell surface markers, demonstrating that current H&E scoring, in general, underestimates cellular infiltrate (FIG. 6). Determination of the possible significance of a given cell surface marker in discriminating between UC-CRC cases and UC-controls is summarized in Table 11. For cases, MPO staining was significantly higher than that of UC-controls regardless of H&E activity level (p<0.0001). There were limited UC-CRC cases with active disease as measured by H&E so to facilitate subgroup analyses, cases and controls were pooled and categorized as either inactive (H&E=0) or active (H&E=1, 2 or 3). The significance of MPO was maintained in subgroup analyses of inactive cases and controls (H&E score of 0, p=0.002) as well as those classified as active (H&E score of 1-3, p=0.02). CD68 staining was slightly elevated in the overall analysis of UC-CRC cases versus controls (p=0.04), but this finding did not persist in subgroup analyses. CD3 staining did not vary between UC-CRC cases and UC-controls. The % area of positive staining for FOXP3, a marker of T-regulatory cells ($T_{reg}$) involved in suppression of inflammation (Kamikozuru et al., *Clin. Exp. Immunol.*, 156(2):320-327 (2009); Yu et al., *Inflamm. Bowel Dis.*, 13(2):191-199 (2007)), on a subset of cases and controls (n=25 for both) was subsequently investigated to see if this could account for the lack of difference in CD3. Analysis indicated that there was no significant difference (p=0.624, data not shown).

TABLE 11

Disease activity level versus cell surface markers in cases and controls.

| Activity Level | CD68 Cases | CD68 Controls | p-value | MPO Cases | MPO Controls | p-value | CD3 Cases | CD3 Controls | p-value |
|---|---|---|---|---|---|---|---|---|---|
| All | 2.668 | 2.031 | 0.04 | 6.06 | 3.41 | <0.0001 | 3.58 | 3.44 | 0.70 |
| 0 | 2.76 | 1.95 | 0.14 | 6.44 | 2.77 | 0.002 | 3.65 | 2.69 | 0.07 |
| 1-3 | 2.49 | 2.09 | 0.25 | 5.74 | 3.85 | 0.02 | 3.45 | 3.94 | 0.43 |

Values in bold are significant.

MPO Expression Associated with Genetic and Epigenetic Changes

Figure 7A:
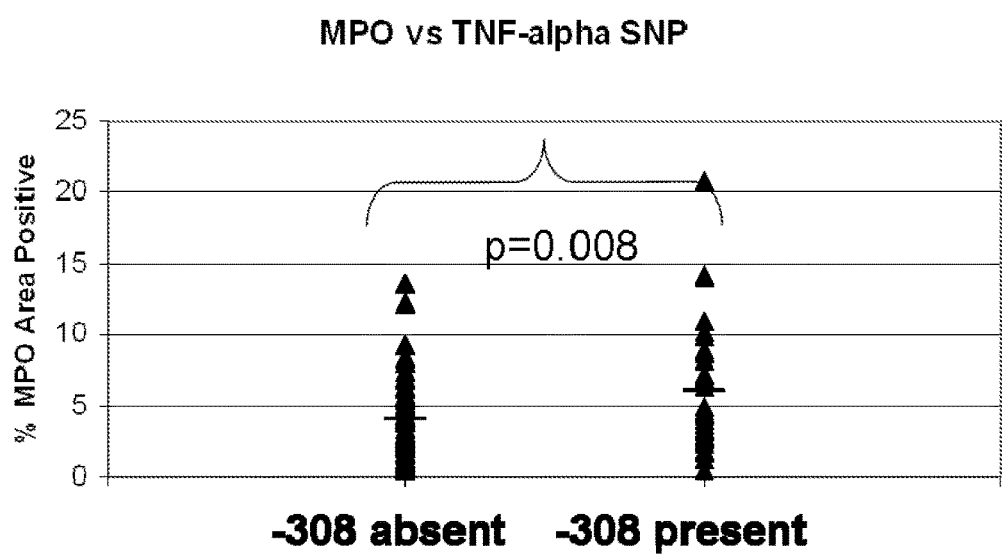
FIG. 7 contains data showing the association of MPO expression levels with a TNF-alpha polymorphism (FIG. 7A) and RUNX3 methylation status (FIG. 7B).
Figure 7B:
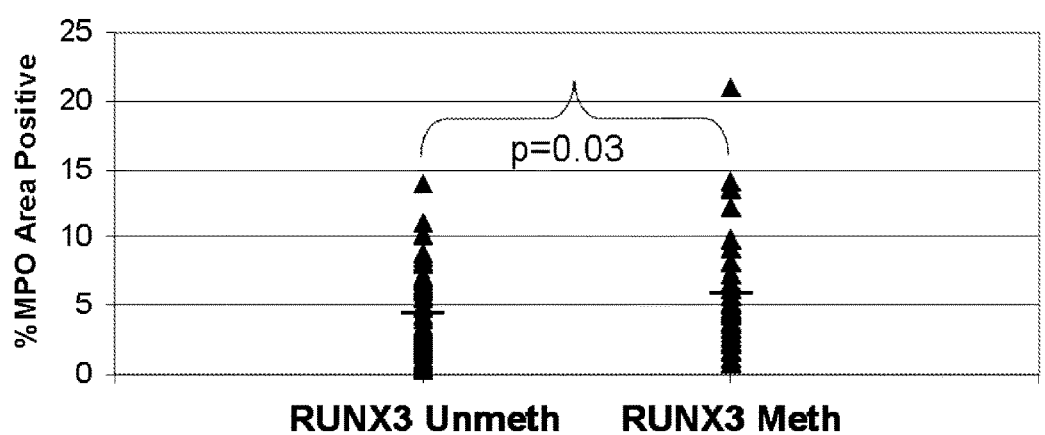
Figure 8:
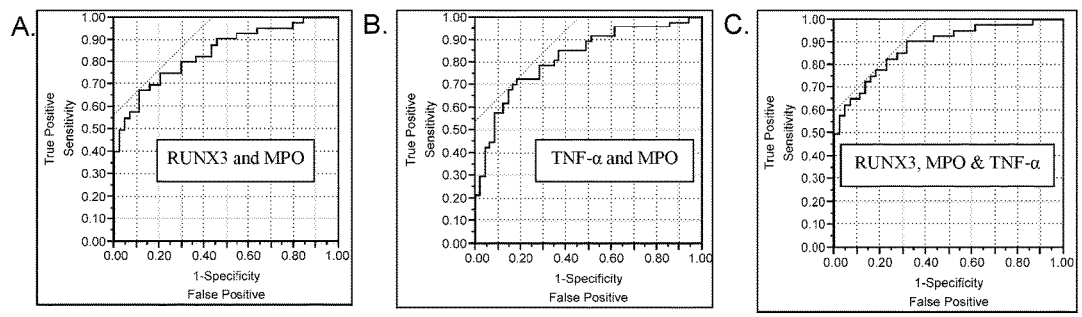
FIG. 8 contains Receiver operating characteristic (ROC) curves for combined markers. The area under the curve (AUC) for any combination of markers was higher than for TNF-α (72.0%), MPO (72.3%) or RUNX3 (66.9%) alone. The AUC for RUNX3 & MPO was 84.1, for TNF-α & MPO was 82.2% and for TNF-α, MPO & RUNX3 was 88.1%.

Increased MPO expression was significantly associated with the presence of the TNF-α-308 G>A SNP (5.95 vs 4.02, p=0.008) (FIG. 7A) as well as RUNX3 methylation (5.90 vs 4.30, p=0.03) (FIG. 7B). It is important to note that the RUNX3 methylation was detected in DNA extracted from non-adjacent, non-neoplastic of UC-CRC cases. Receiver operating characteristic (ROC) curves indicated that an analysis with combined markers was more informative than individual marker assessment (FIG. 7). The area under the curve (AUC) was higher for MPO combined with TNF-α and/or RUNX3. To further interrogate this association, logistic regression was performed. Odds ratios and p-values were either improved or remained highly significant in the presence of other variables (Table 12).

TABLE 12

Univariate and Multivariate analyses of variables.

| | Odds Ratio | CI* | p-value |
|---|---|---|---|
| Univariate | | | |
| MPO | 1.38 | 1.17, 1.67 | <0.0001 |
| RUNX3 methylated | 8.07 | 2.47, 36.58 | 0.0003 |
| TNF-α | 7.87 | 3.18, 21.36 | <0.0001 |
| Multivariate | | | |
| MPO&TNF-α | | | |
| MPO | 1.36 | 1.13, 1.69 | 0.0005 |
| TNF-α | 7.15 | 2.66, 21.06 | <0.0001 |
| MPO&RUNX3 | | | |
| MPO | 1.51 | 1.25, 1.90 | <0.0001 |
| RUNX3 | 15.90 | 4.20, 81.78 | <0.0001 |
| MPO, RUNX3 &TNF-α | | | |
| MPO | 1.46 | 1.19, 1.87 | <0.0001 |
| RUNX3 | 14.29 | 3.46, 80.00 | 0.0001 |
| TNF-α | 6.60 | 2.22, 21.63 | 0.0006 |

*Confidence interval
P-values in bold are significant.

Example 3—Nucleic Acid Markers and UC-CRC

Patient Selection

The Mayo Clinic Institutional Review Board approved this work. The UC-CRC cases and UC controls analyzed in this study have been described elsewhere (Garrity-Park et al., Am. J. Gastroenterol., 103(2):407-15 (2008); and Garrity-Park et al., Gut., 58:1226-1233 (2009)). UC-CRC cases were selected from a review of 274 patients identified from the Mayo Clinic centralized diagnostic index of medical records (1976-2006). These patients had inflammatory bowel disease (either Crohn's or UC) and CRC. Patients with Crohn's disease were excluded. Medical records for the remaining UC-CRC patients were reviewed to establish a date of disease onset. For each case, pathology slides from the surgical resection also were recalled to confirm the diagnosis of UC and identify the best block for DNA extraction. Patients who did not have UC confirmed by review of the pathology or whose duration of disease was less than 10 years were excluded. After these exclusions, 114 UC-CRC cases were included in the study. Potential UC controls were identified through the Mayo pathology index (1994-2006), which indicated the patient age, gender, and extent of UC as well as the presence of other confounding pathologies such as dysplasia. The final pool of potential UC controls for this study included UC patients who did not develop CRC, who underwent either colectomy or colonoscopy with biopsy at the Mayo Clinic, and who did not have prior dysplasia. The Mayo Clinic centralized diagnostic index of medical records was used with these remaining controls to establish a date of diagnosis. Patients with less than ten years between the date of UC diagnosis and either colectomy or date of last biopsy were excluded as were patients with a prior dysplasia diagnosis. From the remaining list, 181 controls were selected that were most closely matched to the UC-CRC cases with regard to gender, age, ethnicity, duration, and extent of UC. The surgical resection or biopsy specimens from these 181 controls were re-reviewed to histologically confirm the diagnosis of UC. After final review, 114 UC controls were included in this study.

DNA Extraction

DNA was extracted from formalin-fixed, paraffin-embedded tissues using a modified Gentra (Gentra Systems Inc., Minneapolis, Minn.) protocol, and DNA was suspended in TE (10 mM Tris/0.1 mM EDTA, Integrated DNA Technologies, Coralville, Iowa). Quantification of total DNA was performed using the Picogreen assay (Invitrogen, Portland, Oreg.).

Genotyping

Samples are interrogated for the presence of additional SNP's in the nucleic acid sequences outlined in Table 13 below. If possible, testing is completed using Taqman genotyping kits (Applied Biosystems; ABI) after optimization for use with formalin fixed, paraffin embedded DNA samples. The 7900HT real-time PCR system is used for evaluating each sample. If a kit is not available for a given SNP, testing is then completed using traditional PCR followed by sequencing as described elsewhere (Garrity-Park et al., Am. J. Gastroenterol., 103(2):407-15 (2008)).

Statistical Analysis

The ability of a SNP to delineate a case from a control is determined using either a Fisher Exact test or chi-square, as appropriate. Any significant SNP is further interrogated using logistic regression with all other significant SNPs and previously known clinical risk factors (i.e., PSC). Modeling is then performed to determine the best diagnostic paradigm for predicting CRC.

TABLE 13

Analysis of nucleic acid polymorphisms in UC-CRC cases vs. UC controls
(SEQ ID NOS 54-87, respectively, in order of appearance)

| Target | SNP(s) Identified | p-value | Context sequence (ABI) |
|---|---|---|---|
| IL-1 | | | |
| IL-6 | -174G>C (1800925) | | |
| IL-6 | -6337T>C | | |
| IL-10 | -1082G>A (1800896) | | TCCTCTTACCTATCCCTACTTCCCC[T/C]TCCC AAAGAAGCCTTAGTAGTGTTG |
| IL-10 | -819C.T (1800871) | | AGTGAGCAAACTGAGGCACAGAGAT[A/G]T TACATCACCTGTACAAGGGTACAC |
| IL-10 | -592 C>A (1800872) | | CTTTCCAGAGACTGGCTTCCTACAG[T/G]AC AGGCGGGGTCACAGGATGTGTTC |
| IL-10 | -627C>A | | |
| IL-15 | | | |
| IL-18 | | | |
| TGFB | | | |
| TNF-α | -308G>A (G19) | | |
| TNF-α | -238G>A (673) | | |
| TNF-α | -863C>A (1800630); | | |
| TNF-α | -857C>T | | |
| TNF-α | -301G>A | | |
| TNF-α | -293C>T | | |
| IL-12 | | | |
| IL-15 | | | |
| IL-23 | | | |
| IL-23R | 2284C>A (10889677) | >0.0001 | TTTAATTTTAGCCATTCTTCTGCCT[A/C]AT TTCTTAAAATTAGAGAATTAAGG |
| IL-23R | 94G>T (1884444) | =0.02 | TTTTCCTTGCTTCCAGACATGAATCA[G/T]GT CACTATTCAATGGGATGCAGTAA |
| IL-23R | 1142G>A (11209026) | | ATTGGGATATTTAACAGATCATTCC[A/G]AA CTGGGTAGGTTTTTGCAGAATTT |
| IL-7 | | | |
| NFKB | DelATTG | | |
| TLR1-10 | | | |
| IL-8 | -251T>A (4073) | | TTATCTAGAAATAAAAAAGCATACA[A/T]T TGATAATTCACCAAATTGTGGAGC |
| IL-8 | 2767A>T | | |
| IL-8 | 781C>T (2227306) | | AACTCTAACTCTTTATATAGGAAGT[C/T]G TTCAATGTTGTCAGTTATGACTGT |
| IFNG | | | |
| IL-4 | -168C>T (2070874) | | TTAGCTTCTCCTGATAAACTAATTG[C/T]CT CACATTGTCACTGCAAATCGACA |
| IL-4 | -590C>T | | |

TABLE 13-continued

Analysis of nucleic acid polymorphisms in UC-CRC cases vs. UC controls
(SEQ ID NOS 54-87, respectively, in order of appearance)

| Target | SNP(s) Identified | p-value | Context sequence (ABI) |
|---|---|---|---|
| IL-4 | -34C>T | | |
| IL-4 | -588C>T (2243250) | | ACACCTAAACTTGGGAGAACATTGT[C/T]C CCCAGTGCTGGGGTAGGAGAGTCT |
| IL-1β | -31T>C (1143627) | >0.0001 | CCAGTTTCTCCCTCGCTGTTTTTAT[G/A]GC TTTCAAAAGCAGAAGTAGGAGGC |
| IL-1β | -571C>T | | |
| IL-1β | 3953C>T (114634) | | CATAAGCCTCGTTATCCCATGTGTC[G/A]A AGAAGATAGGTTCTGAAATGTGGA |
| IL-1β | -511 C>T (3087258) | | |
| IL-21 | | | |
| IL-17 | -197G>A (2275913) | | TGCCCTTCCCATTTTCCTTCAGAAG[A/G]A GAGATTCTTCTATGACCTCATTGG |
| TREM1 | | | |
| MPO | | | |
| MIP-1α | | | |
| MDR1 | | | |
| P16 | | | |
| RUNX3 | | | |
| COX2 | | | |
| MINT1 | | | |
| HPP1 | | | |
| MINT31 | | | |
| PPARγ | 34C>G | | |
| PPARγ | 161C>T | | |
| IL-1RA | 86 bp repeat (Intron 2) | | |
| IL-13 | 2044 G>A (20541) | | TTAAAGAAACTTTTTCGCGAGGGAC[A/G]GT TCAACTGAAACTTCGAAAGCATC |
| IL-13 | -1112 C>T (1800925); | | GGTTTCTGGAGGACTTCTAGGAAAA[C/T]GA GGGAAGAGCAGGAAAAGGCGACA |
| IL-13 | -1512 A>C | | |
| TLR1 | R80T (5743611) | | AACACTGATATCAAGATACTGGATT[C/G]TA TTATGAGAAATTATCAAAATCCT |
| TLR1 | I602S (5743618) | | |
| TLR2 | R753Q (5743708); | | |
| TLR2 | GT repeat (Intron2); | | |
| TLR2 | P631H (5743704) | | GCCTGGCTCCAGGCCAAAAGGAAGC[A/C]C AGGAAAGCTCCCAGCAGGAACATC |
| TLR3 | N284I (5743316); | | CTCACTATGCTCGATCTTTCCTACA[A/T]CA ACTTAAATGTGGTTGGTAACGAT |

TABLE 13-continued

Analysis of nucleic acid polymorphisms in UC-CRC cases vs. UC controls
(SEQ ID NOS 54-87, respectively, in order of appearance)

| Target | SNP(s) Identified | p-value | Context sequence (ABI) |
|---|---|---|---|
| TLR3 | L412F (3775291); | | ACTTGCTCATTCTCCCTTACACATA[T/C]TC AACCTAACCAAGAATAAAATCTC |
| TLR3 | 908 T>C | | |
| TLR4 | D299G (4986790) | | GCATACTTAGACTACTACCTCGATG[A/G]TA TTATTGACTTATTTAATTGTTTG |
| TLR4 | T399I (4986791) | | TGTTCTCAAAGTGATTTTGGGACAA[C/T]C AGCCTAAAGTATTTAGATCTGAGC |
| TLR5 | R392* | | |
| TLR6 | S249P (5743810) | | TTGAGGGTAAAATTCAGTAAGGTTG[A/G]A CCTCTGGTGAGTTCTGATAAAAAT |
| TLR6 | -1401 A>G (5743795) | | |
| TLR7 | Q11L (179008); | | TTTCCAATGTGGACACTGAAGAGAC[A/T]A ATTCTTATCCTTTTTAACATAATC |
| TLR7 | A448V (5743781) | | AGTGAAGTTGGCTTCTGCTCAAATG[C/T]C AGAACTTCTGTAGAAAGTTATGAA |
| TLR7 | T801T (864058) | | GGTTTGTCTGGTGGGTTAACCATAC[A/G]G AGGTGACTATTCCTTACCTGGCCA |
| TLR8 | M1V (3764880); | | AATGAAAAATTAGAACAACAGAAAC[A/G]TG GTAAGCCACTTCTATTTCTTTAG |
| TLR8 | D118D (2159377) | | AATCAAATGGCTTGAATATCACAGA[C/T]G GGGCATTCCTCAACCTAAAAAACC |
| TLR8 | L651L (2407992) | | GTCTGGATTTATCCCTTAATAGGCT[C/G]A AGCACATCCCAAATGAAGCATTCC |
| TLR9 | 1174 G>A (352139); | | TGTGTGAGTGGCCGGCCCCCAGCTC[C/T]A CCTCCACCCACTCCACTTCATGGG |
| TLR9 | 1635 G>A (352140); | | AGCTGAGGTCCAGGGCCTCCAGTCG[C/T]G GTAGCTCCGTGAATGAGTGCTCGT |
| TLR9 | -1237 T>C (5743836) | | |
| TLR10 | N241H (11096957); | | AGCAATAGAACCGATGTCTTAGCAT[T/G]TT CTAAACTAAGATTTCGTTGCATT |
| TLR10 | I369L (11096955) | | AGAGTTTTCAAGTGAGGCAGTTGGA[T/G]A GTTCTTTTAAACAACTCGTCTGTT |
| TLR10 | I473T (11466657); | | GAGATCAGTTAGAAAATTAAATGCA[A/G]TA TTTAGTTCTCGTAAGGCCATCAG |
| TLR10 | R525W (11466658) | | AAATTTTTAATTCACAGGTACACC[A/G]GA ATGGATTTCTTCCCGCATTTAGA |

Example 4—Early Appearance of Nucleic Acid Markers in UC-CRC Pateints

Biopsies from 10 UC-CRC cases and 10 UC-controls obtained between 10 and 24 months prior to the index date analyzed in the work described in the above Examples were tested for methylation of RUNX3 and MINT1. RUNX3 was more frequently methylated in UC-CRC cases than controls (80% versus 10%). MINT1 was also more frequently methylated in UC-CRC cases than controls (60% versus 0%). These results demonstrate that the methylation changes apparent at the time of CRC (index date) actually occurred prior to overt neoplasm.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for conducting a beneficial colonoscopy and biopsy surveillance regimen on a human diagnosed with inflammatory bowel disease, wherein said method comprises:
   (a) detecting the presence of an adenosine at the polymorphic position of rs1800629 in a TNF alpha nucleic acid of said human,
   (b) detecting the presence of a thymine at the polymorphic position of rs1143627 in an IL-1 beta nucleic acid of said human,
   (c) detecting the presence of hypermethylated RUNX3 nucleic acid by performing a methylation specific polymerase chain reaction, using nucleic acid obtained from a colon sample of said human and treated with bisulfite,
   (d) detecting the presence of hypermethylated MINT1 nucleic acid by performing a methylation specific polymerase chain reaction, using nucleic acid obtained from a colon sample of said human and treated with bisulfite,
   (e) detecting the presence of hypomethylated COX-2 nucleic acid by performing a methylation specific polymerase chain reaction, using nucleic acid obtained from a colon sample of said human and treated with bisulfite, and
   (f) conducting more frequent colonoscopy and biopsy surveillance on said human than surveillance colonoscopy and biopsy every year based at least in part on said presence of said rs1800629 polymorphism, said presence of said rs1143627 polymorphism, said presence of said hypermethylated RUNX3 nucleic acid, said presence of said hypermethylated MINT1 nucleic acid, and said presence of said hypomethylated COX-2 nucleic acid.

2. The method of claim 1, wherein said inflammatory bowel disease is ulcerative colitis.

\* \* \* \* \*